(12) United States Patent
Ho et al.

(10) Patent No.: US 8,252,935 B2
(45) Date of Patent: Aug. 28, 2012

(54) PIPERIDINYL AND PIPERAZINYL MODULATORS OF γ-SECRETASE

(75) Inventors: Chih Yung Ho, Lansdale, PA (US); Yan Zhang, Fort Washington, PA (US); Umar S. M. Maharoof, North Wales, PA (US); Jeremy Major, Cambridge (GB); John Harrison, Cambridge (GB)

(73) Assignees: Janssen Pharmaceutica N.V., Beerse (BE); Cellzome Limited, Cambridge (GB)

( * ) Notice: Subject to any disclaimer, the term of this patent is extended or adjusted under 35 U.S.C. 154(b) by 710 days.

(21) Appl. No.: 12/251,521

(22) Filed: Oct. 15, 2008

(65) Prior Publication Data

US 2009/0105275 A1     Apr. 23, 2009

Related U.S. Application Data

(60) Provisional application No. 60/981,189, filed on Oct. 19, 2007.

(51) Int. Cl.
| C07D 211/08 | (2006.01) |
| C07D 237/00 | (2006.01) |
| A61K 31/497 | (2006.01) |
| A61K 31/445 | (2006.01) |

(52) U.S. Cl. ............... 546/192; 544/224; 514/252.12; 514/317

(58) Field of Classification Search .................. None
See application file for complete search history.

(56) References Cited

U.S. PATENT DOCUMENTS

| 3,876,636 | A * | 4/1975 | Fauran et al. ............ 544/122 |
| 4,013,768 | A | 3/1977 | Fauran et al. |
| 4,252,951 | A | 2/1981 | Jackson et al. |
| 5,391,817 | A | 2/1995 | Springer et al. |
| 5,877,399 | A | 3/1999 | Hsiao et al. |
| 7,825,160 | B2 | 11/2010 | Wilson et al. |
| 7,897,643 | B2 | 3/2011 | Ho |
| 7,951,843 | B2 | 5/2011 | Ho |
| 7,968,725 | B2 | 6/2011 | Lu |
| 2002/0128319 | A1 | 9/2002 | Koo et al. |
| 2009/0105288 | A1 | 4/2009 | Ho |
| 2009/0105300 | A1 | 4/2009 | Ho |
| 2009/0306392 | A1 | 12/2009 | Ho |

FOREIGN PATENT DOCUMENTS

| CN | 101903347 | | 12/2010 |
| EP | 1650183 | | 4/2006 |
| EP | 2212287 | | 8/2010 |
| EP | 2215043 | | 8/2010 |
| WO | WO 01/78721 | A1 | 10/2001 |
| WO | WO 03/008635 | | 1/2003 |
| WO | WO 2006/004555 | | 1/2006 |
| WO | WO 2006/005554 | | 1/2006 |
| WO | WO 2006/008558 | | 1/2006 |
| WO | WO 2006/045554 | | 5/2006 |
| WO | WO 2007/124351 | | 11/2007 |
| WO | WO 2007/124394 | | 11/2007 |
| WO | WO 2007/146838 | A2 | 12/2007 |
| WO | WO 2009-052126 | | 4/2009 |
| WO | WO 2009/052334 | | 4/2009 |

OTHER PUBLICATIONS

Vippagunta, S. Adv. Drug Deliv. Rev. 2001, vol. 48, pp. 3-26.*
Silverman, R. "The Organic Chemistry of Drug Design and Drug Action," 2004, Elsevier, pp. 29-32.*
CAPLUS 1973:124623.*
Buchwald, H., et al. "Long-Term, Continuous Intravenous Heparin Administration by an Implantable Infusion Pump in Ambulatory Patients with Recurrent Venous Thrombosis", Surgery 88, p. 507 (1980).
During, M., et al. "Controlled Release of Dopamine from a Polymeric Brain Implant: In Vivo Characterization", Ann. Neurol. 25, p. 351 (1989).
Eriksen, J., et al. "NSAIDs and Enanatiomers of Flurbiprofen Target Gamma-Secretase and Lower A-beta-42 in vivo", Journal of Clinical Investigation, New York, NY US vol. 112, No. 3, (2003), XP002311406.
Frautschy, S., et al. "Microglial Response to Amyloid Plaques in APPsw Transgenic Mice", Am. J. of Pathology, Vl. 52, No. 1 p. 307 (1998).
Howard, M., et al. "Acute Subdural Hematomas: An Age-Dependent Clinical Entity", J. Neurosurgery, vol. 71, p. 858 (1989). Huffman (Thompson), et al. "The Conversion of Phenols to the Corresponding Aryl Halides Under Mild Conditions", Synthesis No. 4, p. 0547 (2005).
Hsiao, K., et al. "Correlative Memory Deficits, Aβ Elevation and Amyloid Plaques in Transgenic Mice", Science 274, p. 99 (1996).
Ida, N., et al. "Analysis of Heterogeneous βA4 Peptides in Human Cerebrospinal Fluid and Blood by a Newly Developed Sensitive (Continued)

*Primary Examiner* — Janet Andres
*Assistant Examiner* — Heidi Reese
(74) *Attorney, Agent, or Firm* — Woodcock Washburn LLP

(57) ABSTRACT

The present invention relates to compounds of Formula I as shown below, wherein the definitions of Het, $R^0$, $R^1$ $R^2$, $R^3$, $R^4$, $R^5$, $R^6$, $R^7$, $R^8$, and $R^9$ are provided in the specification. Compounds of Formula I are useful for the treatment of diseases associated with γ-secretase activity, including Alzheimer's disease.

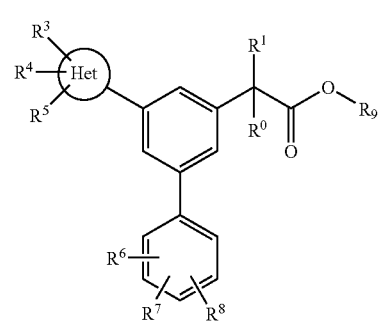

7 Claims, No Drawings

OTHER PUBLICATIONS

Western Blot Assay", J. Biol. Chem. 271, p. 22908 (1996).
Irizarry, M., et al. "APP$_{sw}$ Transgenic Mice Develop Age-Related Aβ Deposits and Neuropil Abnormalities, but no Neuronal Loss in CA1", J. of Neuropathology and Experimental Neurology, vol. 56(9), p. 965 (1997).
Jensen, M., et al. "Quantification of Alzheimer Amyloid Peptides Ending at Residues 40 and 42 by Novel ELISA Systems", Mol. Med. 6 p. 291 (2000).
Kawarabayahsi, T., et al. "Age-Dependent Changes in Brain, CSF, and Plasma Amyloid β Protein in the Tg2576 Transgenic Mouse Model of Alzheimer's Disease", J. Neurosci. 21 p. 372 (2001).
Langer, R., "New Methods of Drug Delivery", Science 249, p. 1527 (1990).
Langer and Peppas "Chemical and Physical Structure of Polymers as Carriers for Controlled Release of Bioactive Agents: A Review", Macromol. Chem. Phys. C23(1), 61-126 (1983).
Larner, A., "Secretases as Therapeutic Targets in Alzheimer's Disease: Patents 2000-2004", Exp. Opinion Ther. Patents 14, p. 1403 (2004).
Lehman, J., et al. "Alterations in β-Amyloid Production and Deposition in Brain Regions of Two Transgenic Models", Neurobiol. Aging 24, p. 645 (2003).
Levy, R., et al. "Inhibition of Calcification of Bioprosthetic Heart Valves by Local Controlled Release Diphosphonate", Science 228, p. 190 (1985).
Lim, G., et al. "Ibuprofen Effects on Alzheimer Pathology and Open Field Activity in APPsw Transgenic Mice", Neuroibol. Aging 22, p. 645 (2001).
Lim, G., et al. "Ibuprofen Suppresses Plaque Pathology and Open Field Activity in APPsw Transgenic Mice", Journal of Neuroscience, vol. 20(15), p. 5709 (2000).
Marjaux, E., et al. "γ-Secretase Inhibitors: Still in the Running as Alzheimer's Therapeutics", Drug Discovery Today: Therapeutics Strategies 1, p. 1 (2004).
Morihara, T., et al. "Selective Inhibition of Aβ42 Production b NSAID R-Enantiomer", J., Neurochem. 83, p. 1009 (2002).
Myers, A., et al. "Use of Pseudo Ephedrine as a Practical Chiral Auxiliary for Asymmetric Synthesis", Journal of American Chemical Society, 116 (20), p. 9361 (1994).
Nesmeyanov, E., et al. "Immediate Cyanization of Ferricinium Salts", Department for Organic Chemistry of the Moscow State University (Jul. 1960).
Peretto, D., et al. "Synthesis and Biological Activity of Fluriprofen Analogues as Selective Inhibitors of β-Amylid 1-42 Secretion", J. Med. Chem. 48 p. 5705 (2005).
Saudek, C., et al. "A Preliminary Trial of the Programmable Implantable Medication System for Insulin Delivery", N. Engl. J. Med. p. 321 (1989).
Schweisguth, F., et al. Regulation of Notch Signaling Activity, Curr. Biol. 14, p. R129 (2004).
Sefton, M., "Implantable Pumps", CRC Crit. Ref. Biomed. Eng. 14, p. 201 (1987).
Shimizu, K., et al. "Binding of Delta1, Jagged1, and Jagged2 to Notch2 Rapidly Induces Cleavage, Nuclear Translocation, and Hyperphosphorylation of Notch2", Mol. Cell. Biol. 20, p. 6913 (2000).
Steiner, H., "Uncovering γ-Sucretase", Curr. Alzheimer Research 1(3), p. 175 (2004).
Thompson(Huffman), et al. "The Conversion of Phenols to the Corresponding Aryl Halides Under Mild Conditions", Synthesis No. 4, p. 0547 (2005).
Vassar, R., et al. "β-Secretese Cleavage of Alzheimer's Amyloid Precursor Protein by the Transmembrane Aspartic Protease BACE", science 286, p. 735 (1999).
Wang, R., et al. "The Profile of Soluble Amyloid β Protein in Cultured Cell Media", J. Biol. Chem. 271 p. 31894 (1996).
Weggen, S., et al. "A Subset of NSAIDs Lower Amylidogenic Aβ42 Independently of Cyclooxygenase Activity", Nature 414, p. 212 (2001).
Yan, R., et al. "Membrane Anchored Aspartyl Protease with Alzheimer's Disease β Secretase Activity", Nature 402, p. 533 (1999).
Yan, Q., et al. "Anti-Inflammatory Drug Therapy Alters β-Amyloid Processing and Deposition in an Animal Model of Alzheimer's Disease", Journal of Neuroscience 23(20), p. 7504 (2003).
Xia, W., et al. "Preseilin 1 Regulates the Processing of β-Amyloid Precursor Protein C-Terminal Fragments and the Generation of Amyloid β-Protein in Endoplasmic Reticulum and Golgi", Biochemistry 3, 16465 (1998).
International Patent Application No. PCT/US2008/079905: International Search Report dated Aug. 1, 2009, 2 pages.
Braga, et al., "Making crystals from crystals: a green route to crystal engineering and polymorphism", Chem. Comm., Apr. 2005, 3635-3645.
Criton, et al., "Mutant Presenilins of Alzheimer's Disease increase production of 42-Residue Amyloid β-protein in both transfected cells and transgenic mice", Nature Medicine, Jan. 1997, 3(1), 67-72.
Curtis, et al., "1, 6, 13, 8, 25, 30-Hexaoxa [6.6.6.](1, 3, 5) cyclophane. Attempted synthesis of a [4] Cyptand", Journal of the Chemical Society, Perkin Transactions 1: Organic and Bio-Organic Chemistry, 1977, 7, 785-788 (XP-002508187).
Evans, et al., "Synthesis of Diaryl Ethers through the copper-promoted arylation of Phenols with Arylbornic Acids. An expedient synthesis of Thyroxine", Tetrahedron Letters, Jan. 1998, 39, 2937-2940.
Goodson, J., "Medical Applications of Controlled Release", 1984, vol. II, Chapter 6, 115-138.
Hendrickson, et al., "A new synthesis of Depsidones. Diploicin and Gangaleoidin", Journal of the American Chemical Society, 1972, 94(19), 6834-6843 (XP-002508189).
International Patent Application No. PCT/US2008/080241: International Search Report dated Feb. 20, 2009, 2 pages.
Kaminski, et al., "Side-chain retention during lithiation of 4-Picoline and 3,4-Lutidine: Easy access to molecular diversity in Pyridine Series", European J. of Organic Chemistry, Oct. 2003, 19, 3855-3860.
Krivun, et al., "Pyrylium salts from pyrones and some organometallic compounds", Chemistry of Heterocyclic Compounds, Oct. 1973, 9(10), 1191-1194 (XP-002544092).
Krivun, et al., "Pyrylium salts from pyrones and some organometallic compounds", HCAPLUS, 2009, Accession No. 1974:47782, 2 pages (Abstract).
Lin, et al., "Structure-Activity studies on a novel series of cholinergic channel activators based on a Heteroaryl Ether framework", Bioorganic & Medicinal Chemistry Letters, Aug. 1999, 9, 2747-2752.
Patani, et al., "Bioisosterism: A rational approach in drug design", Chem. Rev., May 1996, 96(8), 3147-3176.
Shih, et al., "Notch signaling, gamma-secretase inhibitors, and cancer therapy", Cancer Research, Mar. 2007, vol. 67, pp. 1879-1882.
Silverman, Richard B., "The Organic Chemistry of Drug Design and Drug Action", Academic Press, Inc., 1992, Chapter 2: Drug Discovery, Design, and Development, 15-22.
Suh, et al., "Novel potent antagonists of transient receptor potential channel, vanilloid subfamily member 1: Structure-Activity relationship of 1,2-Diarylalkyl Thioureas possessing new vanilloid equivalents", Journal of Medicinal Chemistry, Sep. 2005, 48, 5823-5836.
Tagat, et al., "Synthetic inhibitors of Interleukin-6 II: 3,5-Diaryl Pyridines and Meta-Terphenyls", Bioorganic & Medicinal Chemistry Letters, Sep. 1995, 5(18), 2143-2146.
Tanzi, et al., "Twenty years of the Alzheimer's Disease Amyloid Hypothesis: A Genetic Perspective", Cell, Feb. 2005, 120, 545-555.
Vu, et al., "A Practical method for the preparation of 2-Arylbenzofurans and the synthesis of Moracin A and B", Liebigs Ann. Chem., 1984, 734-741 (XP-002508188) (English Abstract).
West, Anthony R., "Solid state chemistry and its applications", Wiley, New York, Mar. 1988, 358 and 365.
Wilson, et al., "Preparation of tephenylcarboxylates for treatment of Alzheimer's disease", CAPLUS, 2010, Accession No. 2007:1201441, 3 pages.

* cited by examiner

PIPERIDINYL AND PIPERAZINYL MODULATORS OF γ-SECRETASE

CROSS REFERENCE TO RELATED APPLICATIONS

This application claims priority of the benefits of the filing of U.S. Provisional Application Ser. No. 60/981,189, filed Oct. 19, 2007. The complete disclosures of the aforementioned related U.S. patent application is hereby incorporated herein by reference for all purposes.

FIELD OF THE INVENTION

The present invention relates the use of compounds having the general Formula I, wherein the definitions or Het, $R^0$, $R^1$ $R^2$, $R^3$, $R^4$, $R^5$, $R^6$, $R^7$, $R^8$, and $R^9$ are provided in the specification. Compounds of Formula I are useful for the treatment of diseases associated with γ-secretase activity, including Alzheimer's disease.

BACKGROUND OF THE INVENTION

Alzheimer's Disease (AD) is a progressive neurodegenerative disorder marked by loss of memory, cognition, and behavioral stability. AD afflicts 6-10% of the population over age 65 and up to 50% over age 85. It is the leading cause of dementia and the third leading cause of death after cardiovascular disease and cancer. There is currently no effective treatment for AD. The total net cost related to AD in the U.S. exceeds $100 billion annually.

AD does not have a simple etiology, however, it has been associated with certain risk factors including (1) age, (2) family history (3) and head trauma; other factors include environmental toxins and low level of education. Specific neuropathological lesions in the limbic and cerebral cortices include intracellular neurofibrillary tangles consisting of hyperphosphorylated tau protein and the extracellular deposition of fibrillar aggregates of amyloid beta peptides (amyloid plaques). The major component of amyloid plaques are the amyloid beta (A-beta, Abeta or Aβ) peptides of various lengths. A variant thereof, which is the Aβ1-42-peptide (Abeta-42), is believed to be the major causative agent for amyloid formation. Another variant is the Aβ1-40-peptide (Abeta-40). Amyloid beta is the proteolytic product of a precursor protein, beta amyloid precursor protein (beta-APP or APP).

Familial, early onset autosomal dominant forms of AD have been linked to missense mutations in the β-amyloid precursor protein (β-APP or APP) and in the presenilin proteins 1 and 2. In some patients, late onset forms of AD have been correlated with a specific allele of the apolipoprotein E (ApoE) gene, and, more recently, the finding of a mutation in alpha2-macroglobulin, which may be linked to at least 30% of the AD population. Despite this heterogeneity, all forms of AD exhibit similar pathological findings. Genetic analysis has provided the best clues for a logical therapeutic approach to AD. All mutations, found to date, affect the quantitative or qualitative production of the amyloidogenic peptides known as Abeta-peptides (Aβ), specifically Aβ42, and have given strong support to the "amyloid cascade hypothesis" of AD (Tanzi and Bertram, 2005, Cell 120, 545). The likely link between Aβ peptide generation and AD pathology emphasizes the need for a better understanding of the mechanisms of Aβ production and strongly warrants a therapeutic approach at modulating Aβ levels.

The release of Aβ peptides is modulated by at least two proteolytic activities referred to as β-and γ-secretase cleaving at the N-terminus (Met-Asp bond) and the C-terminus (residues 37-42) of the Aβ peptide, respectively. In the secretory pathway, there is evidence that β-secretase cleaves first, leading to the secretion of S-APPβ (sβ) and the retention of a 11 kDa membrane-bound carboxy terminal fragment (CTF). The latter is believed to give rise to Aβ peptides following cleavage by γ-secretase. The amount of the longer isoform, Aβ42, is selectively increased in patients carrying certain mutations in a particular protein (presenilin), and these mutations have been correlated with early-onset familial Alzheimer's disease. Therefore, Aβ42 is believed by many researchers to be the main culprit of the pathogenesis of Alzheimer's disease.

It has now become clear that the γ-secretase activity cannot be ascribed to a single particular protein, but is in fact associated with an assembly of different proteins.

The gamma-secretase activity resides within a multiprotein complex containing at least four components: the presenilin (PS) heterodimer, nicastrin, aph-1 and pen-2. The PS heterodimer consists of the amino-and carboxyterminal PS fragments generated by endoproteolysis of the precursor protein. The two aspartates of the catalytic site are at the interface of this heterodimer. It has recently been suggested that nicastrin serves as a gamma-secretase-substrate receptor. The functions of the other members of gamma-secretase are unknown, but they are all required for activity (Steiner, 2004. Curr. Alzheimer Research 1(3): 175-181).

Thus, although the molecular mechanism of the second cleavage-step has remained elusive until present, the γ-secretase-complex has become one of the prime targets in the search for compounds for the treatment of Alzheimer's disease.

Various strategies have been proposed for targeting gamma-secretase in Alzheimer's disease, ranging from targeting the catalytic site directly, developing substrate-specific inhibitors and modulators of gamma-secretase activity (Marjaux et al., 2004. Drug Discovery Today: Therapeutic Strategies, Volume 1, 1-6). Accordingly, a variety of compounds were described that have secretases as targets (Lamer, 2004. Secretases as therapeutics targets in Alzheimer's disease: patents 2000-2004. Expert Opin. Ther. Patents 14, 1403-1420.)

Indeed, this finding was recently supported by biochemical studies in which an effect of certain NSAIDs on γ-secretase was shown (Weggen et al (2001) Nature 414, 6860, 212 and WO 01/78721 and US 2002/0128319; Morihara et al (2002) J. Neurochem. 83, 1009; Eriksen (2003) J. Clin. Invest. 112, 440). Potential limitations for the use of NSAIDs to prevent or treat AD are their inhibition activity of Cox enzymes, which can lead to unwanted side effects, and their low CNS penetration (Peretto et al., 2005, J. Med. Chem. 48, 5705-5720).

Thus, there is a strong need for novel compounds which modulate γ-secretase activity thereby opening new avenues for the treatment of Alzheimer's disease.

The object of the present invention is to provide such compounds.

SUMMARY OF THE INVENTION

The invention comprises compounds having the general Formula (I)

I

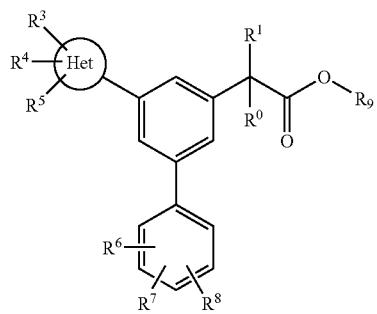

wherein

is:

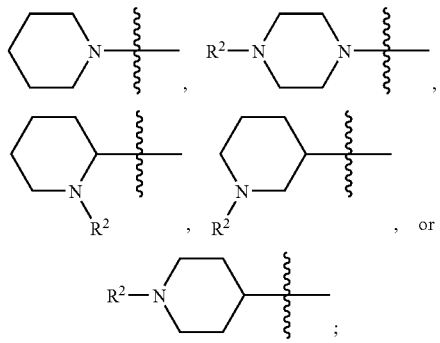

$R^0$ is H or F;

$R^1$ is selected from the group consisting of H, F, alkyl selected from the group $CH_3$, $C_2H_5$, i-$C_3H_7$, n-$C_3H_7$, i-$C_4H_9$, n-$C_4H_9$, sec-$C_4H_9$, tert-$C_4H_9$; alkenyl selected from $C_2H_3$, i-$C_3H_5$, n-$C_3H_5$, n-$C_4H_7$, i-$C_4H_7$, sec-$C_4H_7$; wherein said alkyl and alkenyl groups are optionally substituted with one, two, or three substituents independently selected from the group consisting of F, Cl, Br, I and $CF_3$;

$R^2$ is selected from the group consisting of H, cyclohexyl,

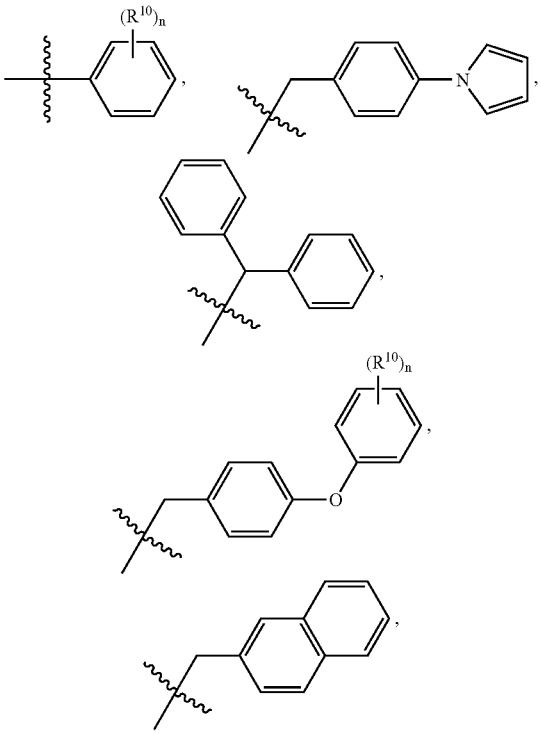

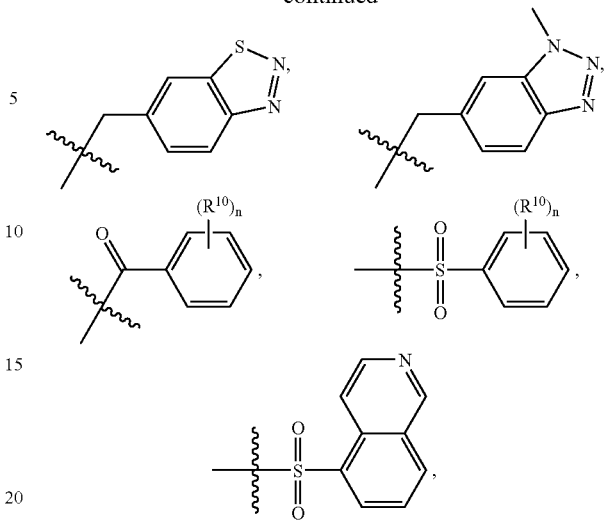

$SO_2CH_3$, alkyl selected from the group consisting of $CH_3$, $C_2H_5$, i-$C_3H_7$, n-$C_3H_7$, i-$C_4H_9$, n-$C_4H_9$, sec-$C_4H_9$, tert-$C_4H_9$, $CH_2CH_2CH(CH_3)_2$, $CH_2CH_2CH_2CH(CH_3)_2$, $CH_2CH_2C(CH_3)_3$, $CH(CH_2CH_3)_2$, and $C(O)CH_2CH(CH_3)_2$; alkenyl selected from the group consisting of $C_2H_3$, i-$C_3H_5$, n-$C_3H_5$, n-$C_4H_7$, i-$C_4H_7$, sec-$C_4H_7$, and $CH_2CH=CHCH(CH_3)_2$; wherein said alkyl and alkenyl groups are optionally substituted with F, Cl, Br, I, $CF_3$, -heteroaryl-$(R^{10})_n$, or

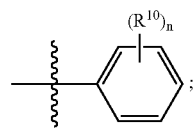

wherein $R^{10}$ is $CF_3$, $OCF_3$, H, F, Cl, $OCH_3$, $C_{(1-4)}$alkyl, or CN; and n is 1, 2, or 3; alternatively, $R^2$ can be two $C_{(1-4)}$alkyl groups, so that their attached nitrogen is quaternized;

$R^3$ is H,

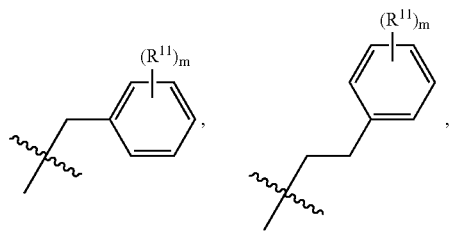

or $C_{(1-4)}$alkyl-$R^{11}$; wherein $R^{11}$ is $CF_3$, $OCF_3$, H, F, Cl, $OCH_3$, $C_{(1-4)}$alkyl, or CN; and m is 1, 2, or 3;

$R^6$ is selected from the group consisting of H, F, Cl, Br, I, CN, OH, $C(O)N(C_{(1-4)}alkyl)_2$, $S(O)_2C_{(1-4)}alkyl$, $SO_2N(C_{(1-4)}alkyl)_2$, $S(O)N(C_{(1-4)}alkyl)_2$, $N(C_{(1-4)}alkyl)S(O)_2C_{(1-4)}alkyl$, $N(C_{(1-4)}alkyl)S(O)C_{(1-4)}alkyl$, $S(O)_2C_{(1-4)}alkyl$, $N(C_{(1-4)}alkyl)S(O)_2N(C_{(1-4)}alkyl)_2$, $SC_{(1-4)}alkyl$, $N(C_{(1-4)}alkyl)_2$, $N(C_{(1-4)}alkyl)C(O)C_{(1-4)}alkyl$, $N(C_{(1-4)}alkyl)C(O)N(C_{(1-4)}alkyl)_2$, $N(C_{(1-4)}alkyl)C(O)OC_{(1-4)}alkyl$, $OC(O)N(C_{(1-4)}alkyl)_2$, $C(O)C_{(1-4)}alkyl$, $C_1$-$C_4$- alkyl, and $C_1$-$C_4$ alkoxy; wherein said alkyl and alkoxy are optionally substituted with one, two, or three substituents selected from the group consisting of F, Cl, Br, and I;

$R^4$, $R^5$, $R^7$, and $R^8$ are independently selected from the group consisting of $CF_3$, H, F, Cl, $OCH_3$, $C_{(1-4)}$alkyl, and CN;

$R^9$ is selected from the group consisting of H, alkyl selected from the group $CH_3$, $C_2H_5$, i-$C_3H_7$, n-$C_3H_7$, i-$C_4H_9$, n-$C_4H_9$, sec-$C_4H_9$, tert-$C_4H_9$; alkenyl selected from $C_2H_3$, i-$C_3H_5$, n-$C_3H_5$, n-$C_4H_7$, i-$C_4H_7$, sec-$C_4H_7$; wherein said alkyl and alkenyl groups are optionally substituted with one, two, or three substituents independently selected from the group consisting of F, Cl, Br, I and $CF_3$;

and solvates, hydrates, esters, and pharmaceutically acceptable salts thereof.

DETAILED DESCRIPTION OF THE INVENTION

The invention comprises compounds having the general Formula (I)

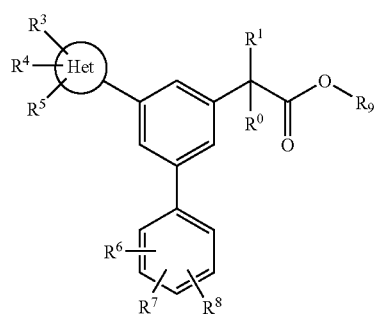

wherein

is:

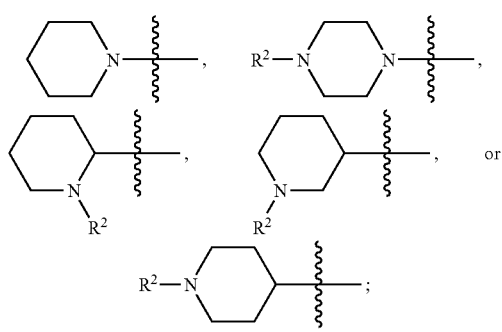

$R^0$ is H or F;
$R^1$ is selected from the group consisting of H, F, alkyl selected from the group $CH_3$, $C_2H_5$, i-$C_3H_7$, n-$C_3H_7$, i-$C_4H_9$, n-$C_4H_9$, sec-$C_4H_9$, tert-$C_4H_9$; alkenyl selected from $C_2H_3$, i-$C_3H_5$, n-$C_3H_5$, n-$C_4H_7$, i-$C_4H_7$, sec-$C_4H_7$; wherein said alkyl and alkenyl groups are optionally substituted with one, two, or three substituents independently selected from the group consisting of F, Cl, Br, I and $CF_3$;

$R^2$ is selected from the group consisting of H, cyclohexyl,

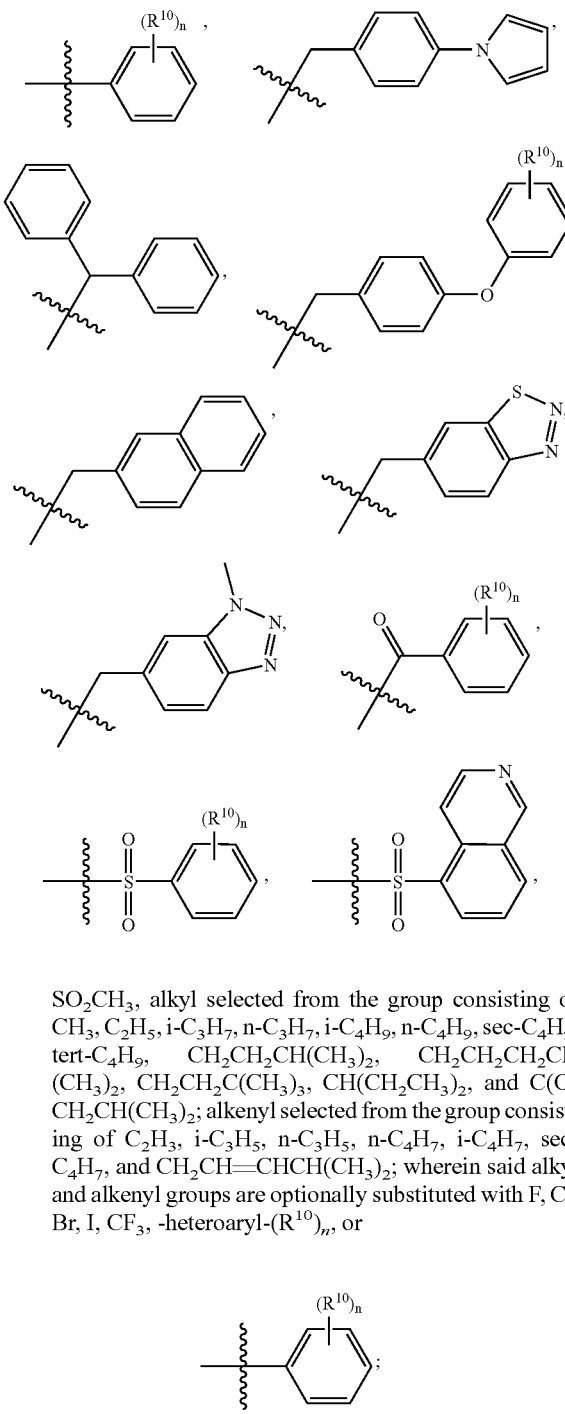

$SO_2CH_3$, alkyl selected from the group consisting of $CH_3$, $C_2H_5$, i-$C_3H_7$, n-$C_3H_7$, i-$C_4H_9$, n-$C_4H_9$, sec-$C_4H_9$, tert-$C_4H_9$, $CH_2CH_2CH(CH_3)_2$, $CH_2CH_2CH_2CH(CH_3)_2$, $CH_2CH_2C(CH_3)_3$, $CH(CH_2CH_3)_2$, and $C(O)CH_2CH(CH_3)_2$; alkenyl selected from the group consisting of $C_2H_3$, i-$C_3H_5$, n-$C_3H_5$, n-$C_4H_7$, i-$C_4H_7$, sec-$C_4H_7$, and $CH_2CH=CHCH(CH_3)_2$; wherein said alkyl and alkenyl groups are optionally substituted with F, Cl, Br, I, $CF_3$, -heteroaryl-$(R^{10})_n$, or

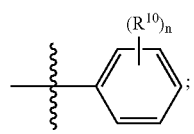

wherein $R^{10}$ is $CF_3$, $OCF_3$, H, F, Cl, $OCH_3$, $C_{(1-4)}$alkyl, or CN; and n is 1, 2, or 3;alternatively, $R^2$ can be two $C_{(1-4)}$alkyl groups, so that their attached nitrogen is quaternized;

R³ is H,

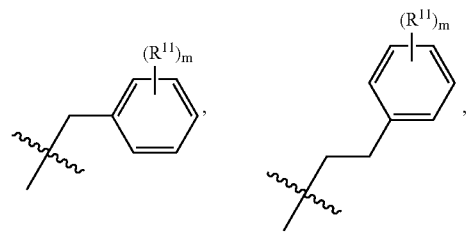

or C$_{(1-4)}$alkyl-R¹¹; wherein R¹¹ is CF$_3$, OCF$_3$, H, F, Cl, OCH$_3$, C$_{(1-4)}$alkyl, or CN; and m is 1, 2, or 3;

R⁶ is selected from the group consisting of H, F, Cl, Br, I, CN, OH, C(O)N(C$_{(1-4)}$alkyl)$_2$, S(O)$_2$C$_{(1-4)}$alkyl, SO$_2$N(C$_{(1-4)}$alkyl)$_2$, S(O)N(C(1-4)alkyl)$_2$, N(C$_{(1-4)}$alkyl)S(O)$_2$C$_{(1-4)}$alkyl, N(C$_{(1-4)}$alkyl)S(O)C$_{(1-4)}$alkyl, S(O)$_2$C$_{(1-4)}$alkyl, N(C$_{(1-4)}$alkyl)S(O)$_2$N(C$_{(1-4)}$alkyl)$_2$, SC$_{(1-4)}$alkyl, N(C$_{(1-4)}$alkyl)$_2$, N(C$_{(1-4)}$alkyl)C(O)C$_{(1-4)}$alkyl, N(C$_{(1-4)}$alkyl)C(O)N(C$_{(1-4)}$alkyl)$_2$, N(C$_{(1-4)}$alkyl)C(O)OC$_{(1-4)}$alkyl, OC(O) N(C$_{(1-4)}$alkyl)$_2$, C(O)C$_{(1-4)}$alkyl, C$_1$-C$_4$-alkyl, and C$_1$-C$_4$alkoxy; wherein said alkyl and alkoxy are optionally substituted with one, two, or three substituents selected from the group consisting of F, Cl, Br, and I;

R⁴, R⁵, R⁷, and R⁸ are independently selected from the group consisting of CF$_3$, H, F, Cl, OCH$_3$, C$_{(1-4)}$alkyl, and CN;

R⁹ is selected from the group consisting of H, alkyl selected from the group CH$_3$, C$_2$H$_5$, i-C$_3$H$_7$, n-C$_3$H$_7$, i-C$_4$H$_9$, n-C$_4$H$_9$, sec-C$_4$H$_9$, tert-C$_4$H$_9$; alkenyl selected from C$_2$H$_3$, i-C$_3$H$_5$, n-C$_3$H$_5$, n-C$_4$H$_7$, i-C$_4$H$_7$, sec-C$_4$H$_7$; wherein said alkyl and alkenyl groups are optionally substituted with one, two, or three substituents independently selected from the group consisting of F, Cl, Br, I and CF$_3$;

and solvates, hydrates, esters, and pharmaceutically acceptable salts thereof.

In another embodiment of the invention

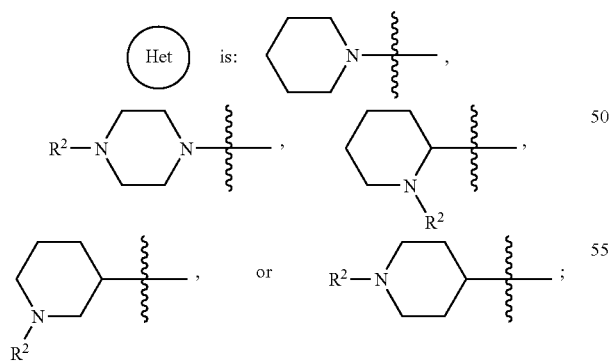

R⁰ is H or F;

R¹ is selected from the group consisting of H, F, alkyl selected from the group CH$_3$, C$_2$H$_5$, i-C$_3$H$_7$, n-C$_3$H$_7$, i-C$_4$H$_9$, n-C$_4$H$_9$, sec-C$_4$H$_9$, and tert-C$_4$H$_9$; and alkenyl selected from C$_2$H$_3$, i-C$_3$H$_5$, n-C$_3$H$_5$, n-C$_4$H$_7$, i-C$_4$H$_7$, and sec-C$_4$H$_7$;

R² is selected from the group consisting of H, cyclohexyl,

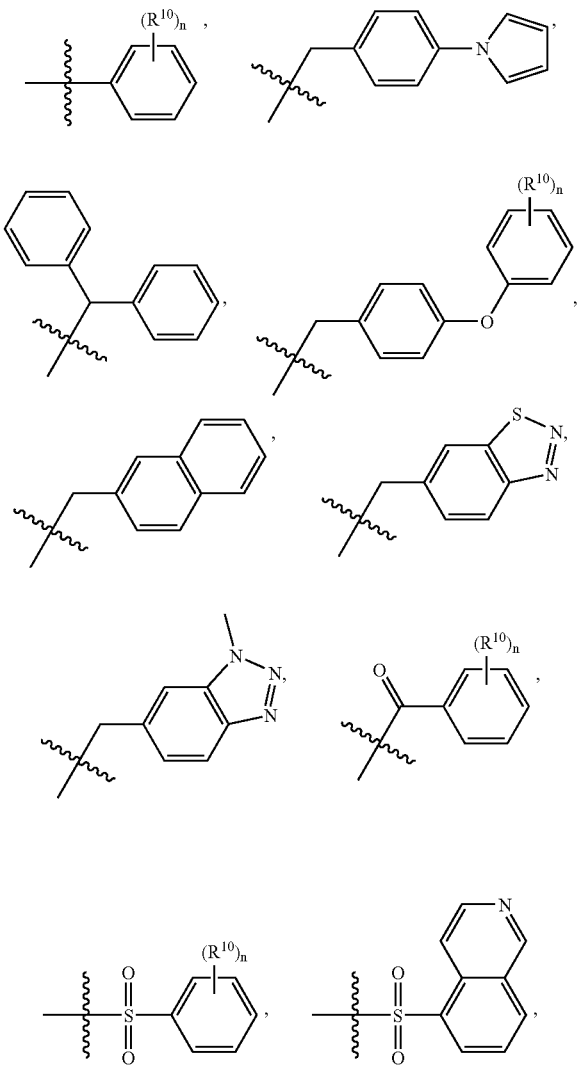

SO$_2$CH$_3$, alkyl selected from the group consisting of CH$_3$, C$_2$H$_5$, i-C$_3$H$_7$, n-C$_3$H$_7$, i-C$_4$H$_9$, n-C$_4$H$_9$, sec-C$_4$H$_9$, tert-C$_4$H$_9$, CH$_2$CH$_2$CH(CH$_3$)$_2$, CH$_2$CH$_2$CH$_2$CH (CH$_3$)$_2$, CH$_2$CH$_2$C(CH$_3$)$_3$, CH(CH$_2$CH$_3$)$_2$, and C(O) CH$_2$CH(CH$_3$)$_2$; alkenyl selected from the group consisting of C$_2$H$_3$, i-C$_3$H$_5$, n-C$_3$H$_5$, n-C$_4$H$_7$, i-C$_4$H$_7$, sec-C$_4$H$_7$, and CH$_2$CH=CHCH(CH$_3$)$_2$; wherein said alkyl and alkenyl groups are optionally substituted with F, Cl, Br, I, CF$_3$, wherein R¹⁰ is CF$_3$, OCF$_3$, H, F, Cl, OCH$_3$, C$_{(1-4)}$alkyl, or CN; and n is 1, 2, or 3; alternatively, R² can be two C$_{(1-4)}$alkyl groups, so that their attached nitrogen is quaternized;

$R^3$ is H,

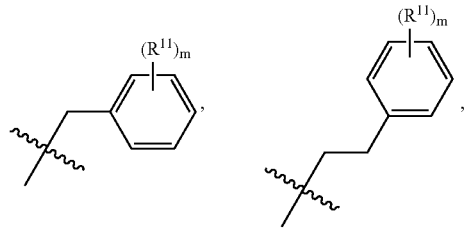

or $C_{(1-4)}$alkyl-$R^{11}$; wherein $R^{11}$ is $CF_3$, $OCF_3$, H, F, Cl, $OCH_3$, $C_{(1-4)}$alkyl, or CN; and m is 1, 2, or 3;

$R^6$ is selected from the group consisting of H, F, Cl, Br, I, CN, OH, $C(O)N(C_{(1-4)}alkyl)_2$, $S(O)_2C_{(1-4)}$alkyl, $SO_2N(C_{(1-4)}alkyl)_2$, $S(O)N(C_{(1-4)}alkyl)_2$, $N(C_{(1-4)}alkyl)S(O)_2C_{(1-4)}$alkyl, $N(C_{(1-4)}alkyl)S(O)C_{(1-4)}$alkyl, $S(O)_2C_{(1-4)}$alkyl, $N(C_{(1-4)}alkyl)S(O)_2N(C_{(1-4)}alkyl)_2$, $SC_{(1-4)}$alkyl, $N(C_{(1-4)}alkyl)_2$, $N(C_{(1-4)}alkyl)C(O)C_{(1-4)}$alkyl, $N(C_{(1-4)}alkyl)C(O)N(C_{(1-4)}alkyl)_2$, $N(C_{(1-4)}alkyl)C(O)OC_{(1-4)}$alkyl, $OC(O)N(C_{(1-4)}alkyl)_2$, $C(O)C_{(1-4)}$alkyl, $C_1$-$C_4$-alkyl, and $C_1$-$C_4$alkoxy; wherein said alkyl and alkoxy are optionally substituted with one, two, or three substituents selected from the group consisting of F, Cl, Br, and I;

$R^4$, $R^5$, $R^6$, $R^7$, and $R^8$ are independently selected from the group consisting of $CF_3$, H, F, Cl, $OCH_3$, $C_{(1-4)}$alkyl, and CN;

$R^9$ is selected from the group consisting of H, alkyl selected from the group $CH_3$, $C_2H_5$, i-$C_3H_7$, n-$C_3H_7$, i-$C_4H_9$, n-$C_4H_9$, sec-$C_4H_9$, and tert-$C_4H_9$;

and solvates, hydrates, esters, and pharmaceutically acceptable salts thereof.

In another embodiment of the invention

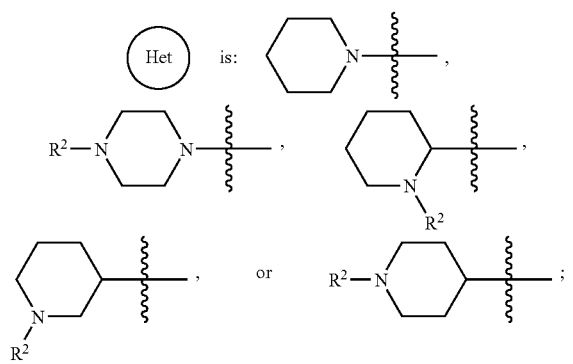

$R^0$ is H or F;

$R^1$ is selected from the group consisting of H, F, alkyl selected from the group $CH_3$, $C_2H_5$, i-$C_3H_7$, n-$C_3H_7$, i-$C_4H_9$, n-$C_4H_9$, sec-$C_4H_9$, and alkenyl selected from $C_2H_3$, i-$C_3H_5$, n-$C_3H_5$, n-$C_4H_7$, i-$C_4H_7$, and sec-$C_4H_7$;

$R^2$ is selected from the group consisting of H, cyclohexyl,

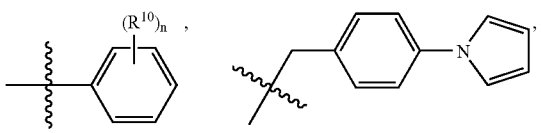

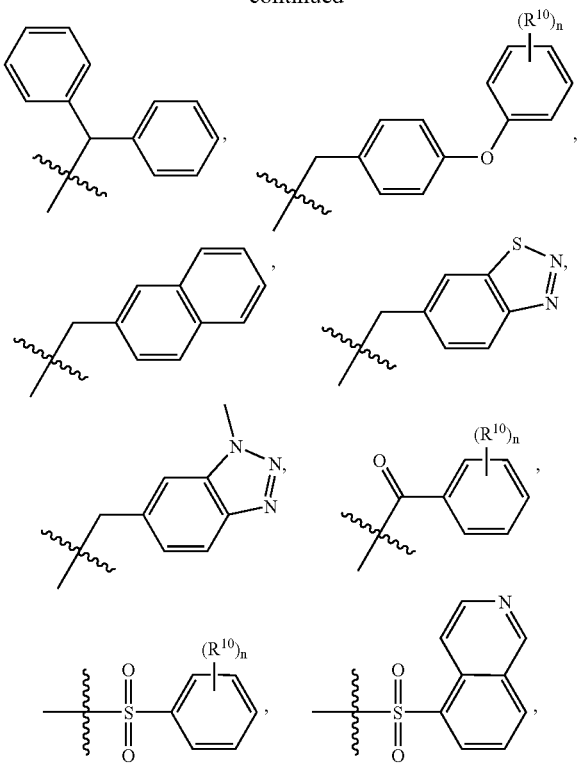

$SO_2CH_3$, alkyl selected from the group consisting of $CH_3$, $C_2H_5$, i-$C_3H_7$, n-$C_3H_7$, i-$C_4H_9$, n-$C_4H_9$, sec-$C_4H_9$, tert-$C_4H_9$; $CH_2CH_2CH(CH_3)_2$, $CH_2CH_2CH_2CH(CH_3)_2$, $CH_2CH_2C(CH_3)_3$, $CH(CH_2CH_3)_2$, and $C(O)CH_2CH(CH_3)_2$; alkenyl selected from the group consisting of $C_2H_3$, i-$C_3H_5$, n-$C_3H_5$, n-$C_4H_7$, i-$C_4H_7$, sec-$C_4H_7$, and $CH_2CH=CHCH(CH_3)_2$; wherein said alkyl and alkenyl groups are optionally substituted with F, Cl, Br, I, $CF_3$,

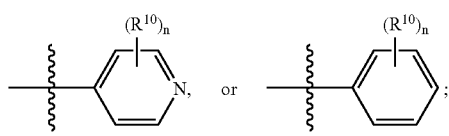

wherein $R^{10}$ is $CF_3$, $OCF_3$, H, F, Cl, $OCH_3$, $C_{(1-4)}$alkyl, or CN; and n is 1, 2, or 3; alternatively, $R^2$ can be two $C_{(1-4)}$alkyl groups, so that their attached nitrogen is quaternized;

$R^3$ is H,

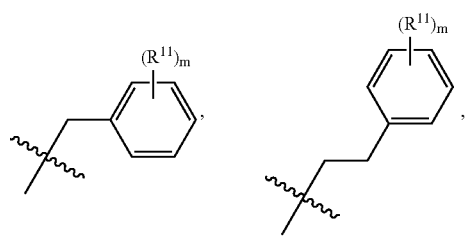

or $C_{(1-4)}$alkyl-$R^{11}$; wherein $R^{11}$ is $CF_3$, $OCF_3$, H, F, Cl, $OCH_3$, $C_{(1-4)}$alkyl, or CN; and m is 1, 2, or 3;

$R^4$, $R^5$, $R^6$, $R^7$, and $R^8$ are H, $CF_3$, Cl, and F;

$R^9$ is selected from the group consisting of H, alkyl selected from the group $CH_3$, $C_2H_5$, $i$-$C_3H_7$, $n$-$C_3H_7$, $i$-$C_4H_9$, $n$-$C_4H_9$, sec-$C_4H_9$, and tert-$C_4H_9$;

and solvates, hydrates, esters, and pharmaceutically acceptable salts thereof.

In another embodiment of the invention

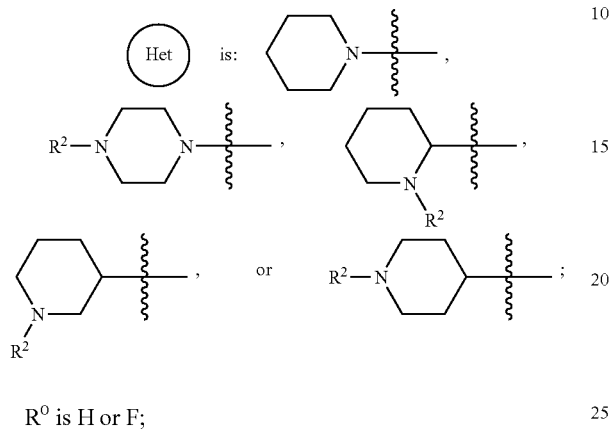

$R^0$ is H or F;

$R^1$ is selected from the group consisting of H, F, alkyl selected from the group $CH_3$, $C_2H_5$, $i$-$C_3H_7$, $n$-$C_3H_7$, $i$-$C_4H_9$, $n$-$C_4H_9$, sec-$C_4H_9$, and tert-$C_4H_9$; and alkenyl selected from $C_2H_3$, $i$-$C_3H_5$, $n$-$C_3H_5$, $n$-$C_4H_7$, $i$-$C_4H_7$, and sec-$C_4H_7$;

$R^2$ is selected from the group consisting of H, cyclohexyl,

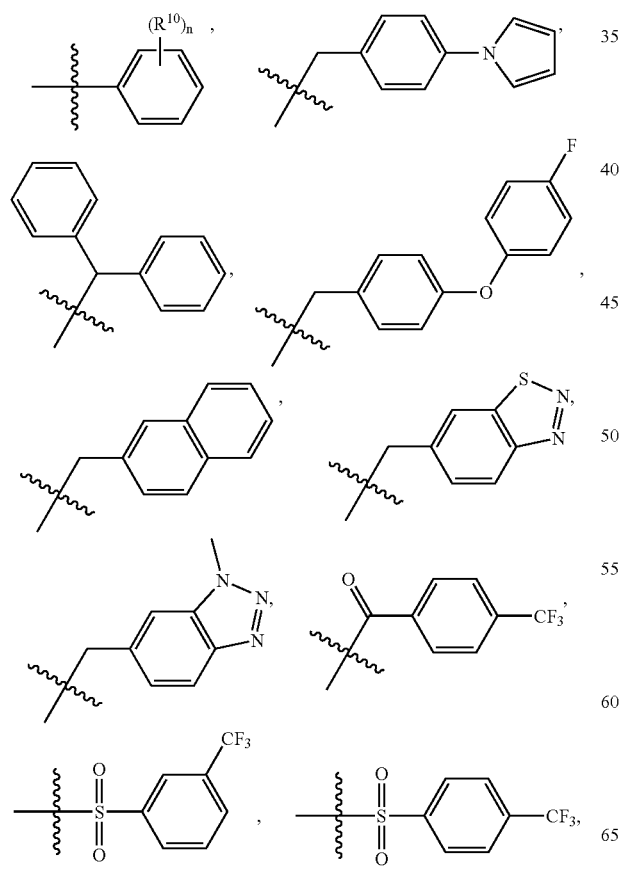

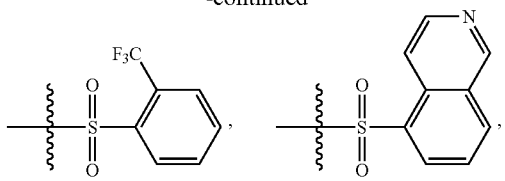

$SO_2CH_3$, alkyl selected from the group consisting of $CH_3$, $C_2H_5$, $i$-$C_3H_7$, $n$-$C_3H_7$, $i$-$C_4H_9$, $n$-$C_4H_9$, sec-$C_4H_9$, tert-$C_4H_9$, $CH_2CH_2CH(CH_3)_2$, $CH_2CH_2CH_2CH(CH_3)_2$, $CH_2CH_2C(CH_3)_3$, $CH(CH_2CH_3)_2$, and $C(O)CH_2CH(CH_3)_2$; alkenyl selected from the group consisting of $C_2H_3$, $i$-$C_3H_5$, $n$-$C_3H_5$, $n$-$C_4H_7$, $i$-$C_4H_7$, sec-$C_4H_7$, and $CH_2CH=CHCH(CH_3)_2$; wherein said alkyl and alkenyl groups are optionally substituted with F, Cl, Br, I, $CF_3$,

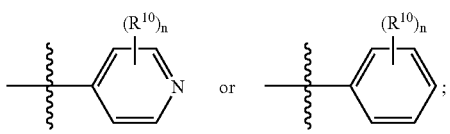

wherein $R^{10}$ is $CF_3$, $OCF_3$, H, F, Cl, $OCH_3$, $C_{(1-4)}$alkyl, or CN; and n is 1, 2, or 3; alternatively, $R^2$ can be two $C_{(1-4)}$alkyl groups, so that their attached nitrogen is quaternized;

$R^3$ is H,

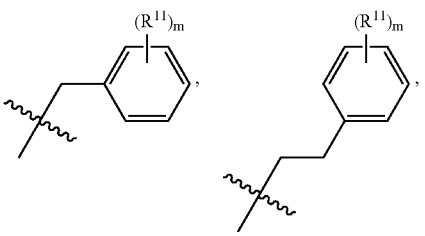

or $C_{(1-4)}$alkyl-$R^{11}$; wherein $R^{11}$ is $CF_3$, $OCF_3$, H, F, Cl, $OCH_3$, $C_{(1-4)}$alkyl, or CN; and m is 1, 2, or 3;

$R^4$, $R^5$, $R^6$, $R^7$, and $R^8$ are H, $CF_3$, Cl, and F;

$R^9$ is H;

and solvates, hydrates, esters, and pharmaceutically acceptable salts thereof.

In another embodiment of the invention

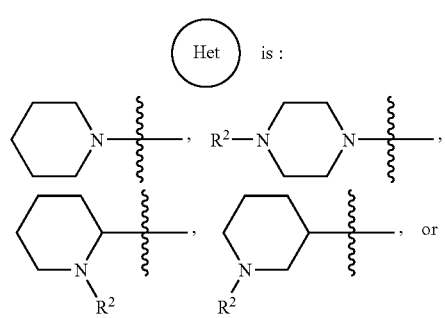

-continued

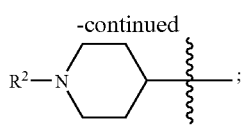

R⁰ is H or F;
R¹ is H, F, or CH₂CH(CH₃)₂;
R² is selected from the group consisting of H, cyclohexyl,

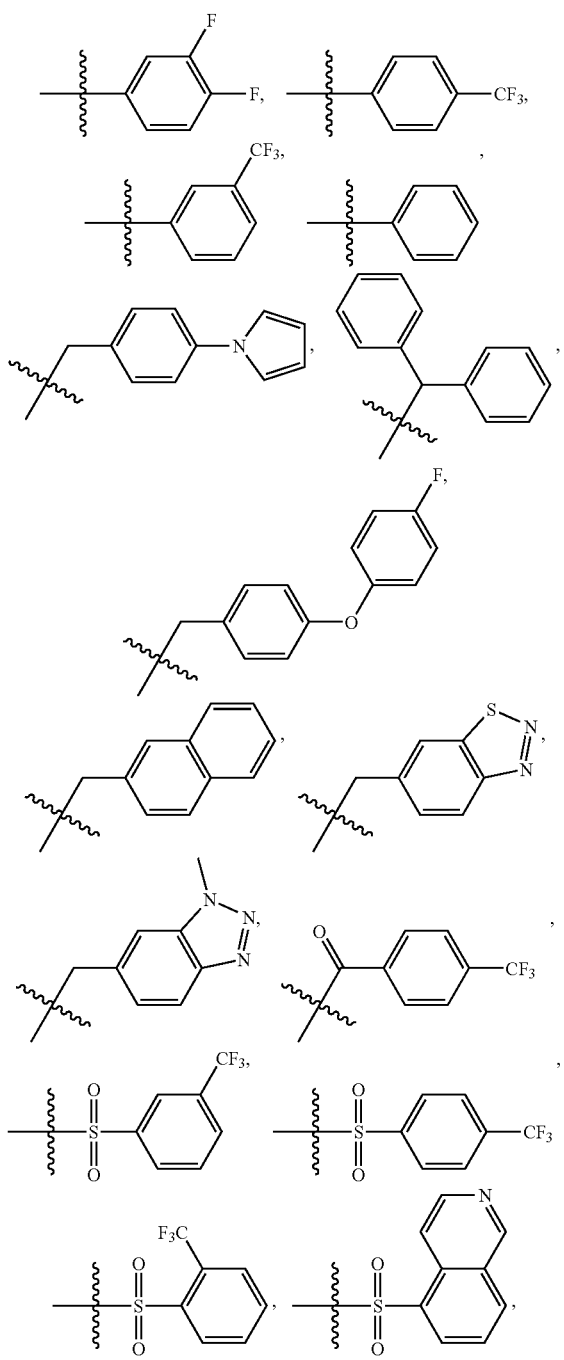

SO₂CH₃, CH₂CH=CHCH(CH₃)₂, alkyl selected from the group consisting of CH₃, C₂H₅, i-C₃H₇, n-C₃H₇, i-C₄H₉, n-C₄H₉, sec-C₄H₉, tert-C₄H₉, CH₂CH₂CH(CH₃)₂, CH₂CH₂CH₂CH(CH₃)₂, CH₂CH₂C(CH₃)₃, and CH(CH₂CH₃)₂; wherein said alkyl is optionally substituted with F, Cl, Br, I, CF₃,

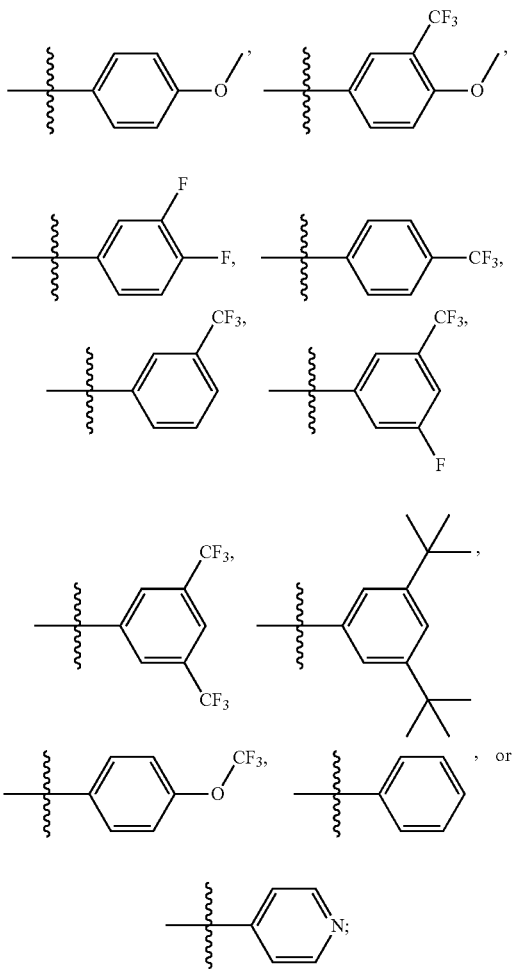

alternatively, R² can be two C₍₁₋₄₎alkyl groups, so that their attached nitrogen is quaternized;
R³ is H,

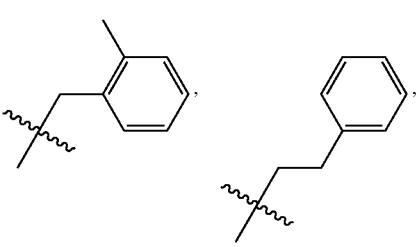

CF₃, CH₃, CH₂CH₃, CH₂CH₂CH₃, or (CH₂)₃OCH₃;
R⁴ and R⁵ are H;
R⁶ is CF₃;
R⁷ and R⁸ are H;
R⁹ is H;
and solvates, hydrates, esters, and pharmaceutically acceptable salts thereof.-

Another embodiment of the invention comprises a compound selected from the group consisting of:
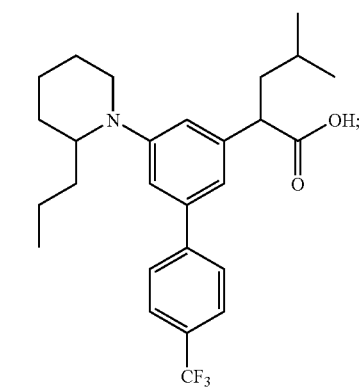
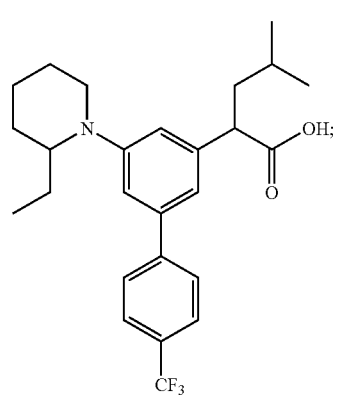
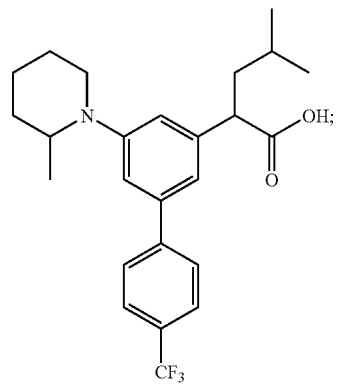
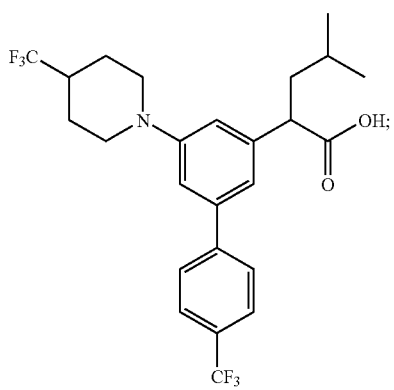
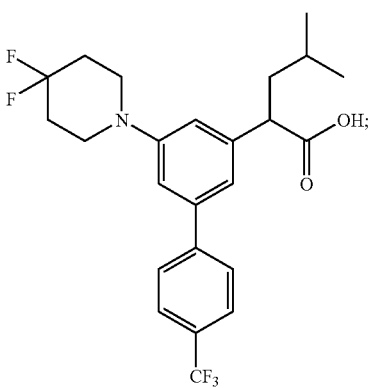
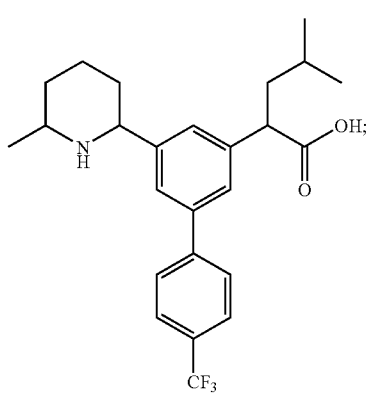
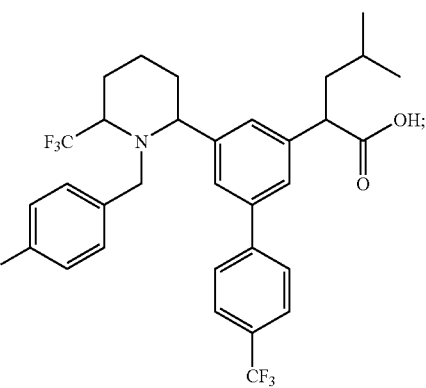
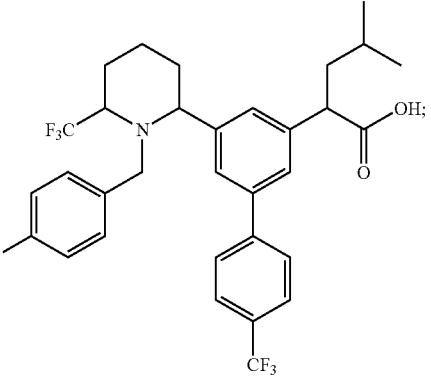

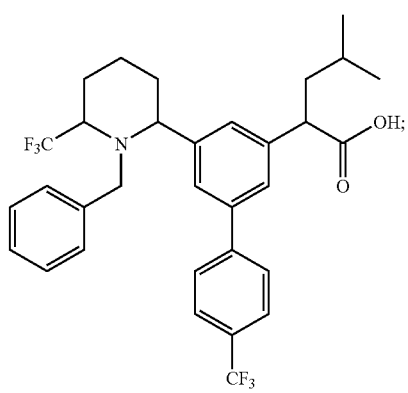
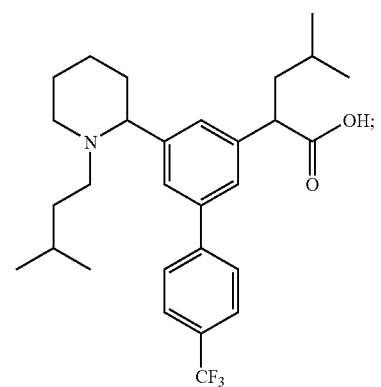
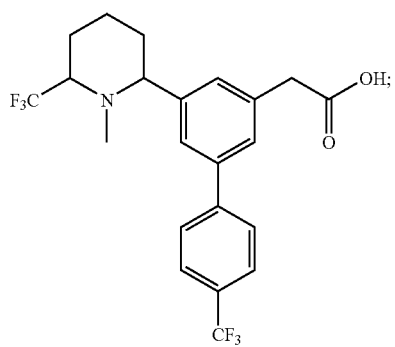
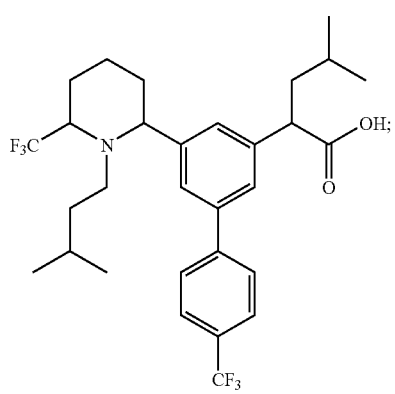
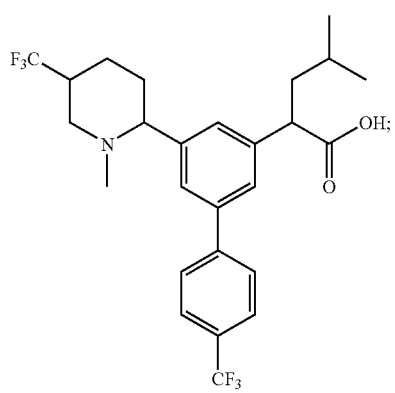
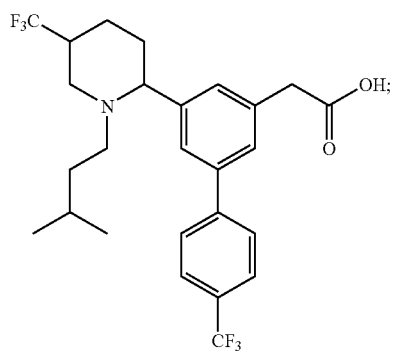
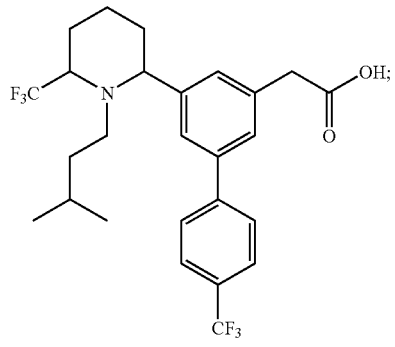
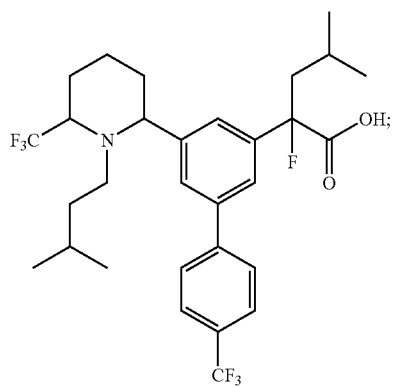

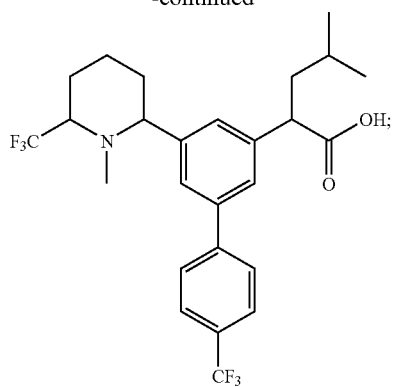
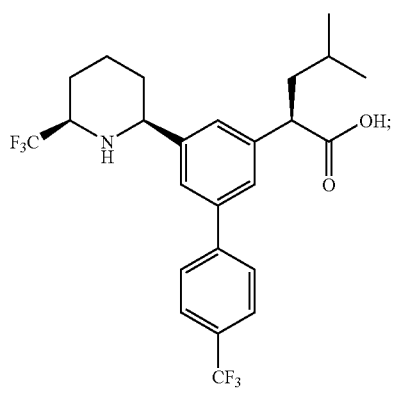
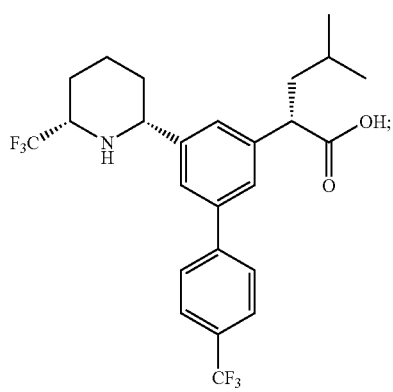
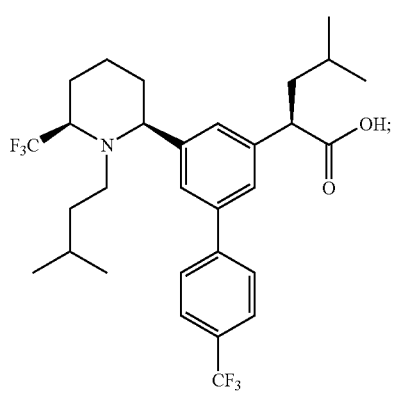
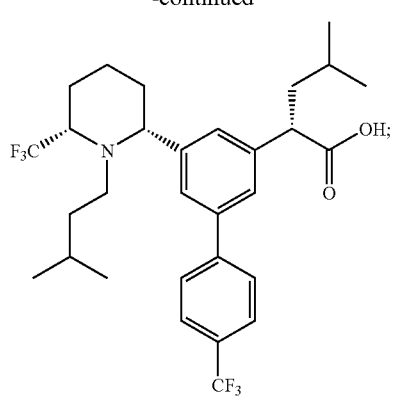
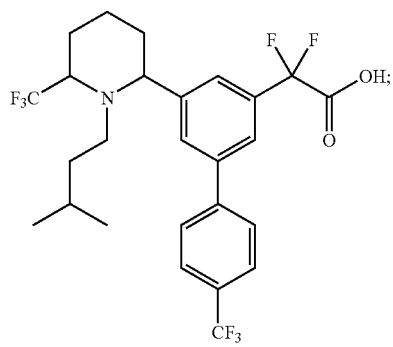
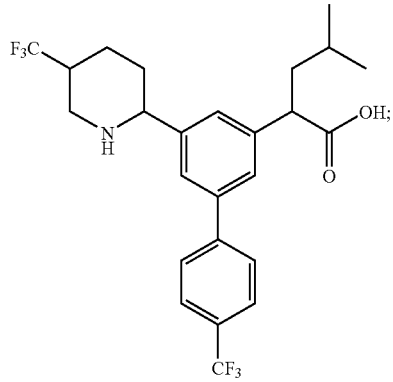
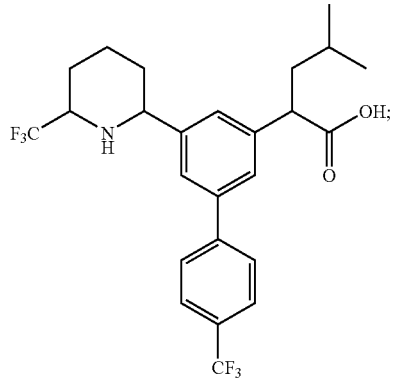

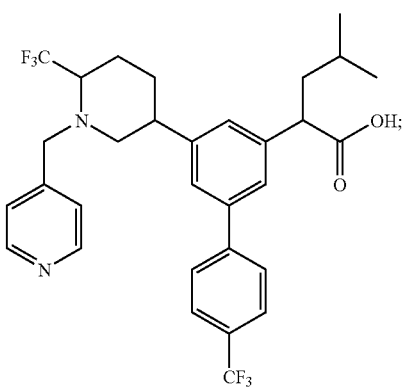
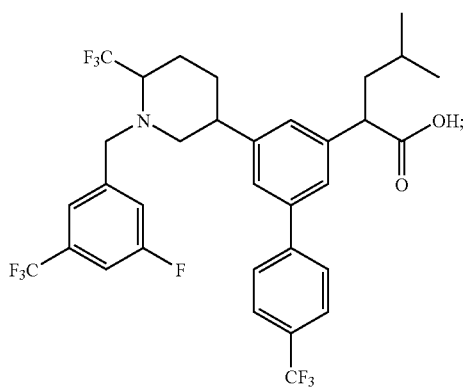
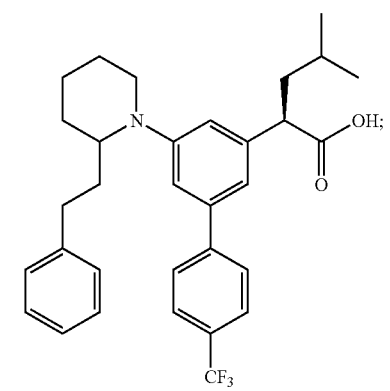
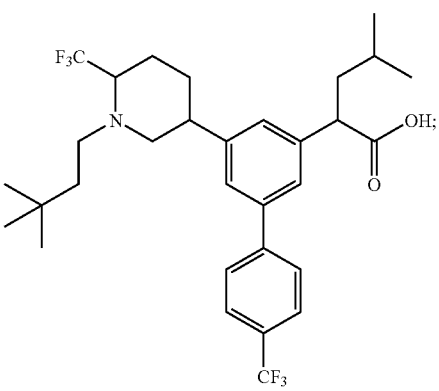
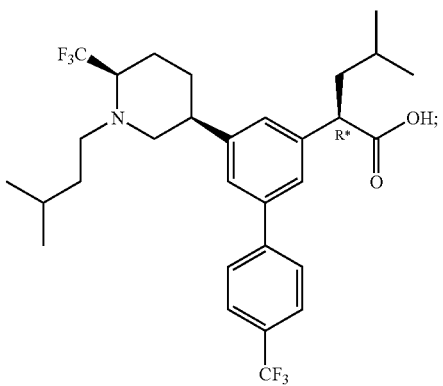
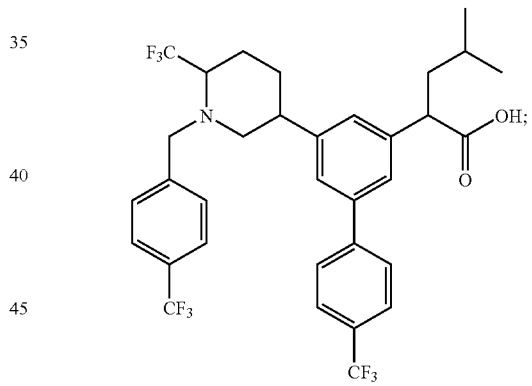
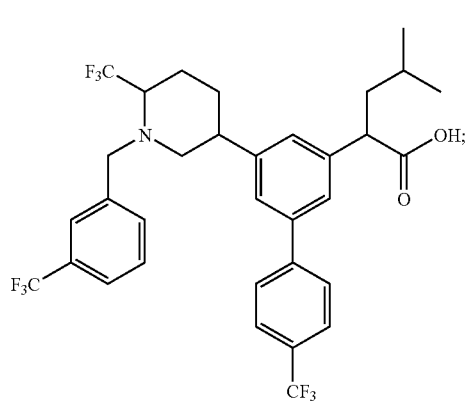
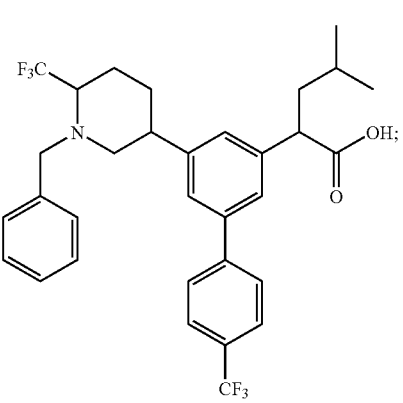

23
-continued
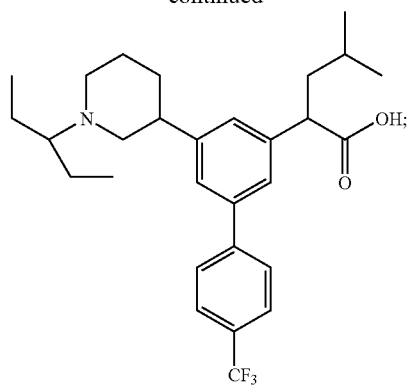
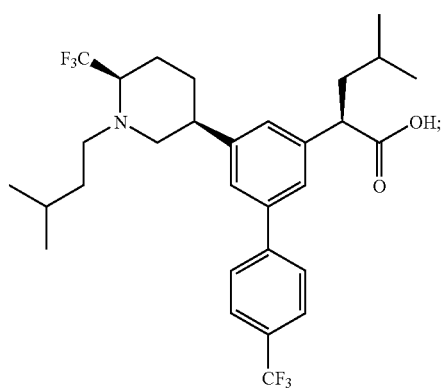
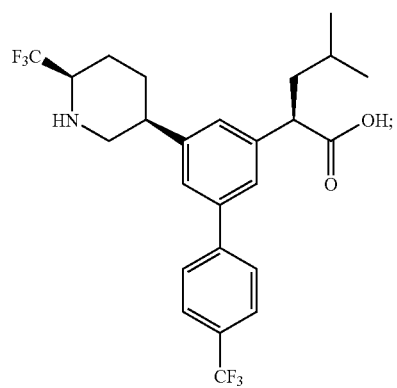
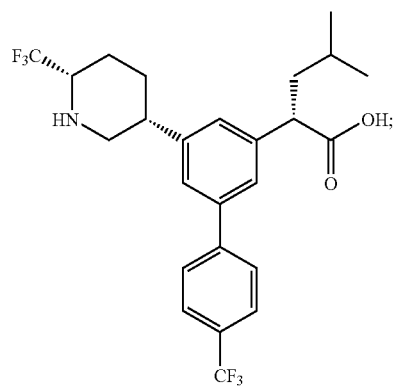
24
-continued
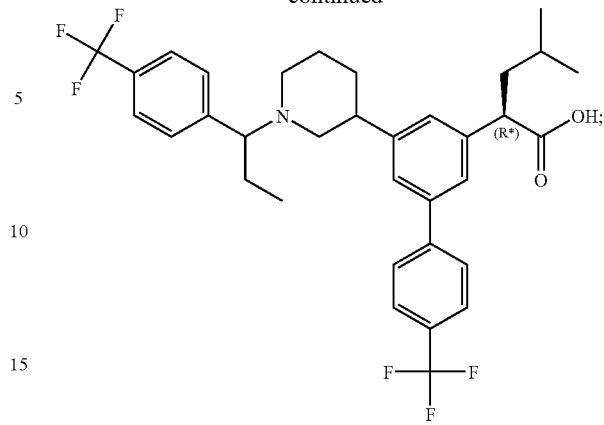
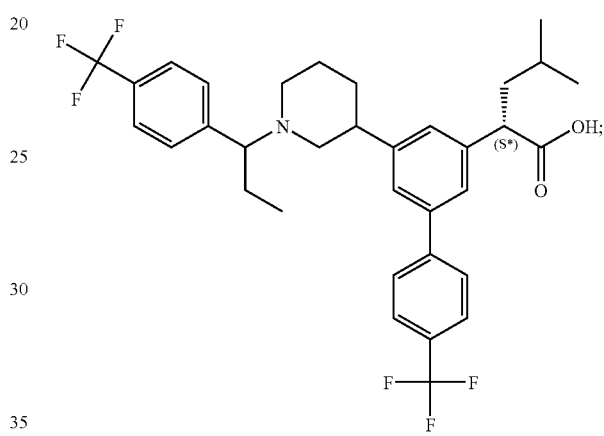
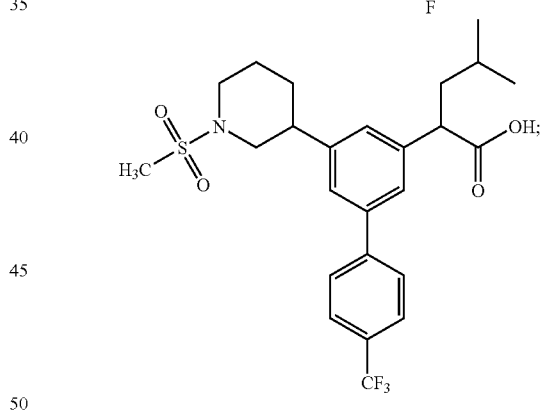
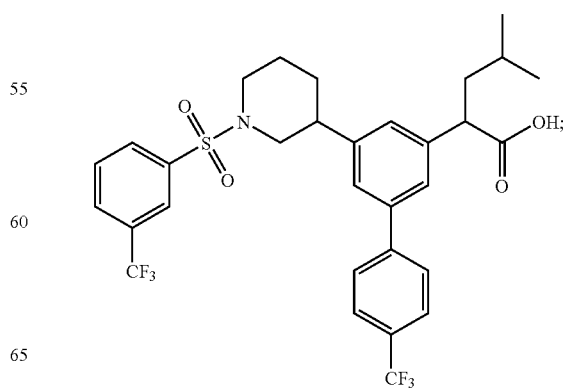

25
-continued
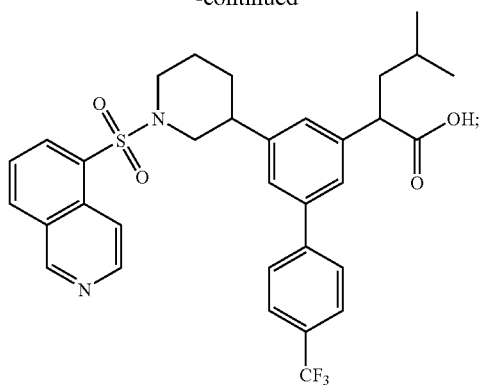
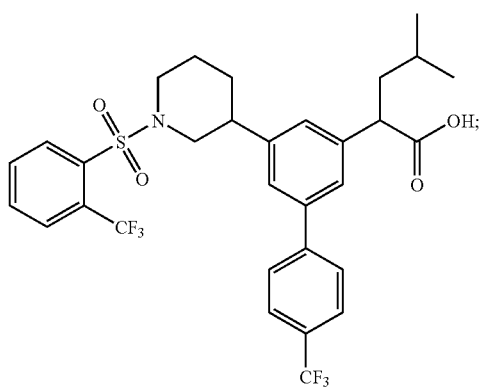
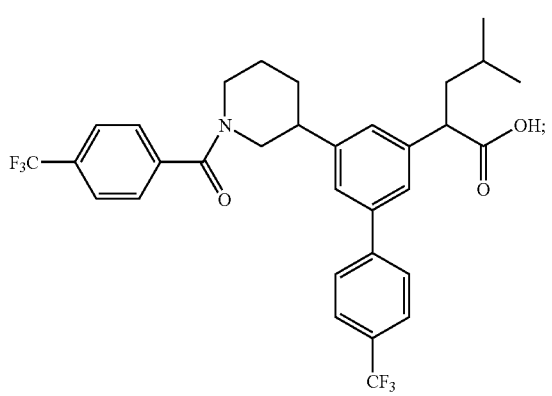
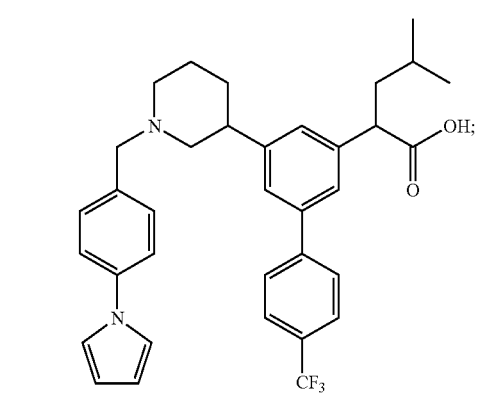
26
-continued
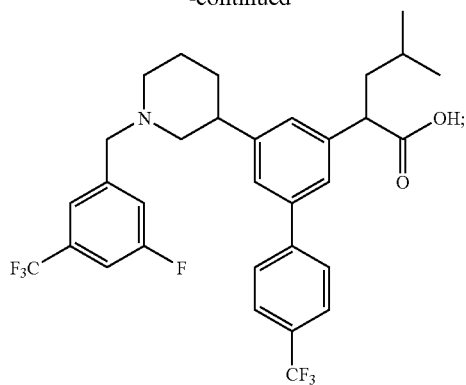
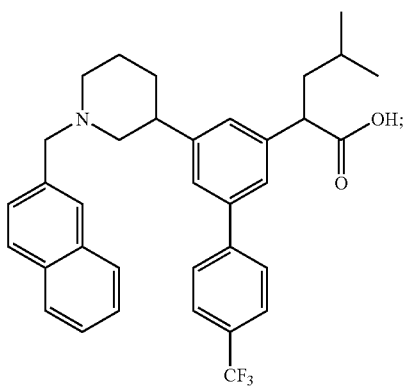
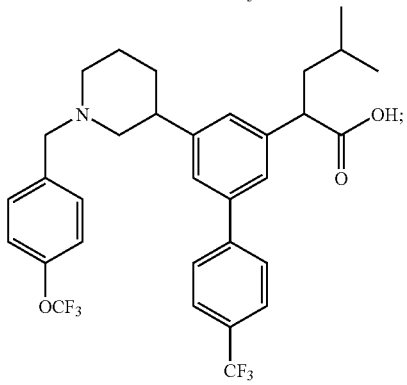
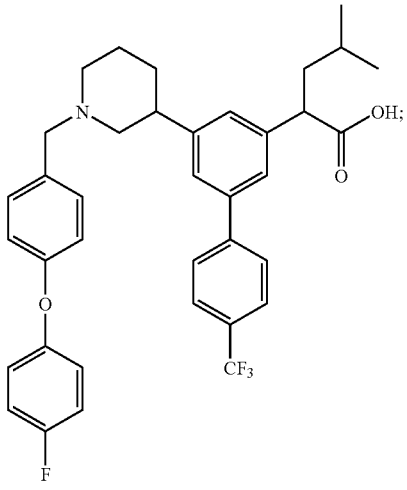

-continued
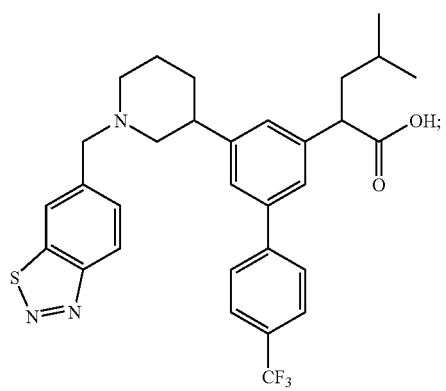
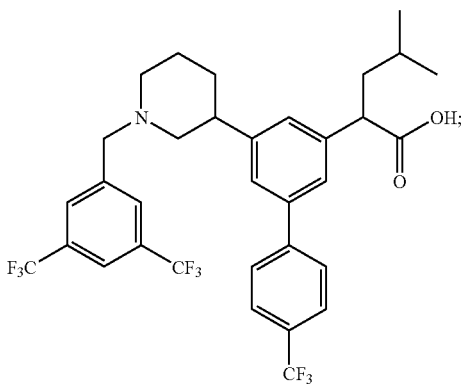
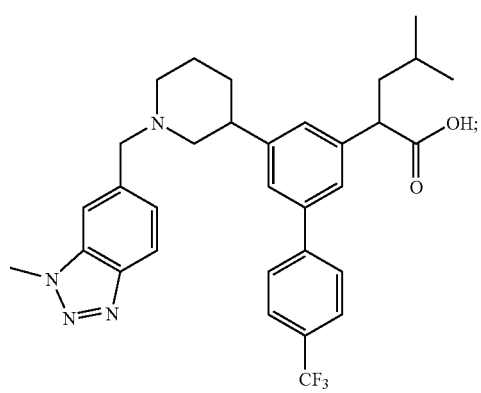
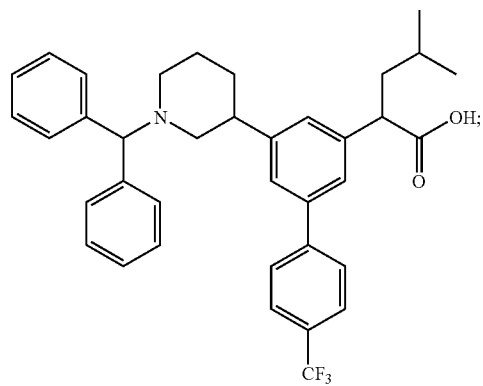
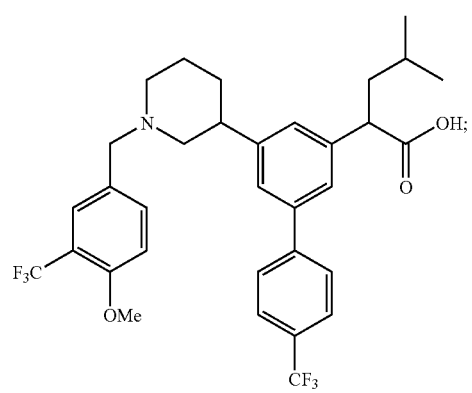
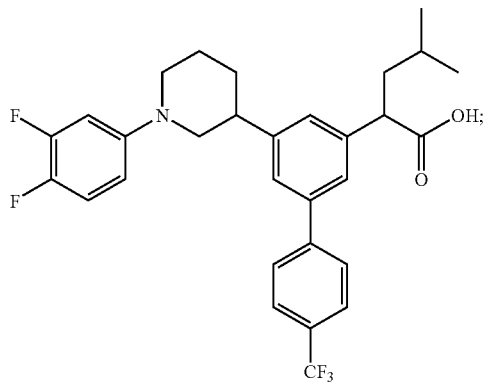
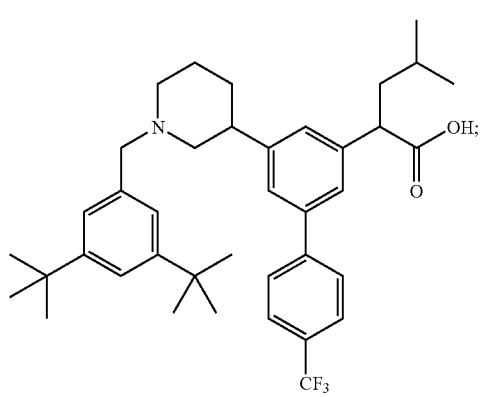
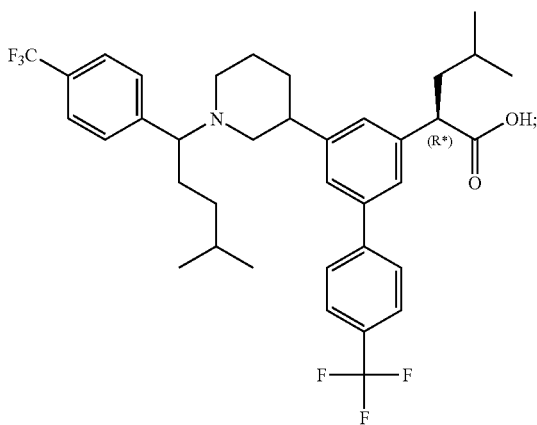

29
-continued
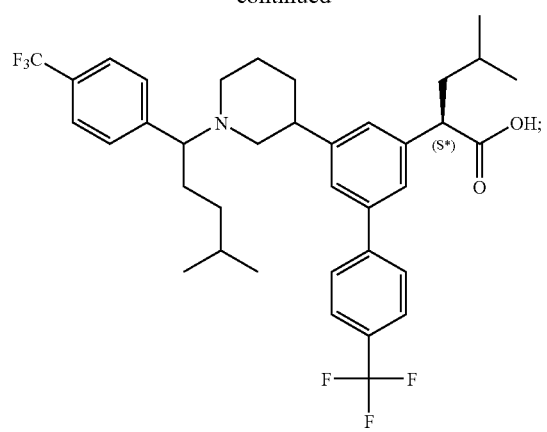
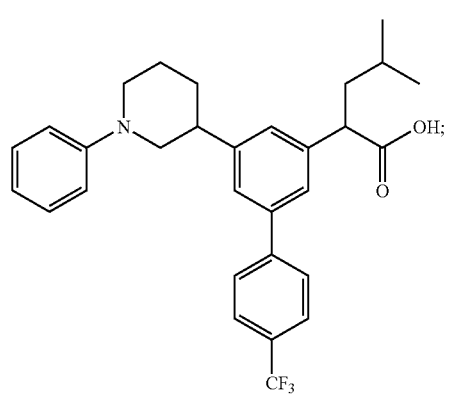
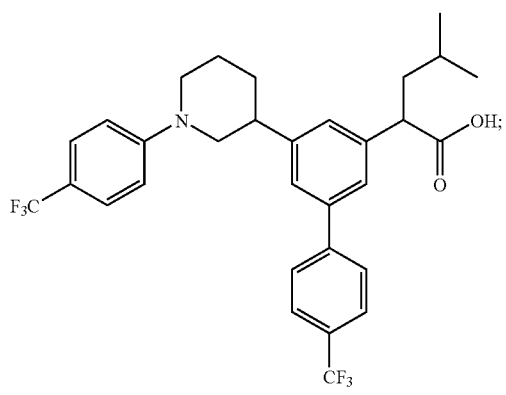
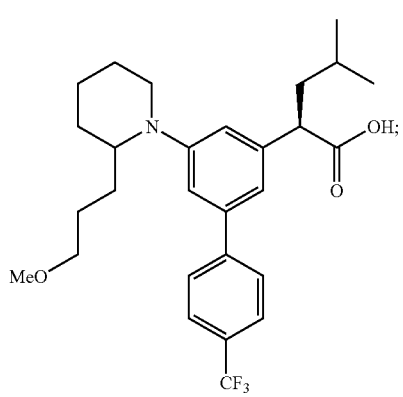
30
-continued
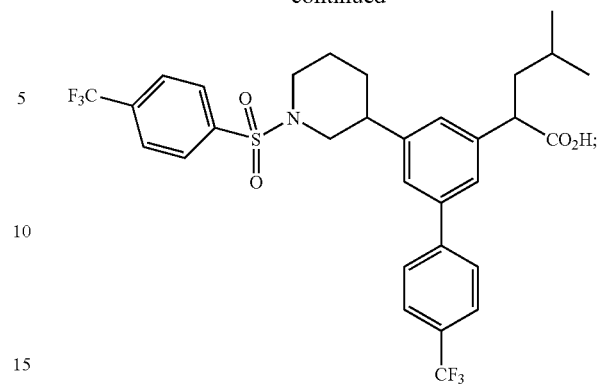
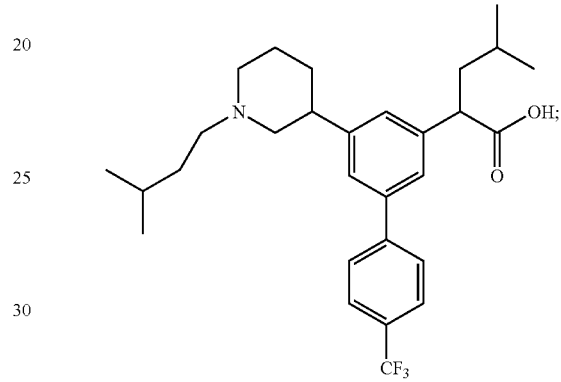
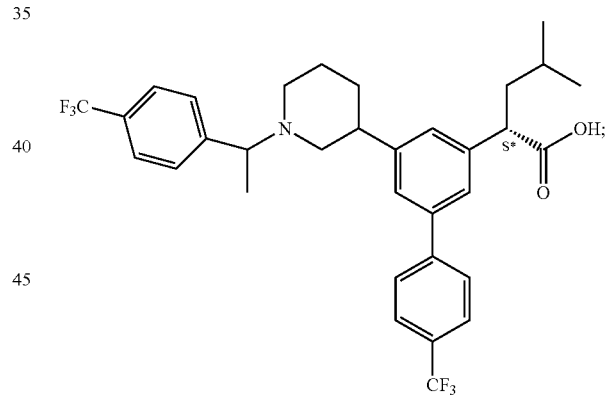
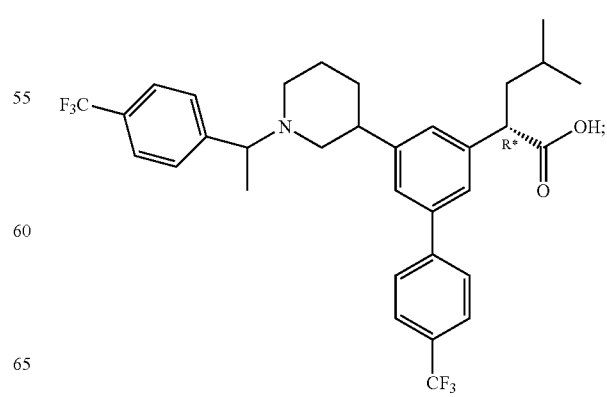

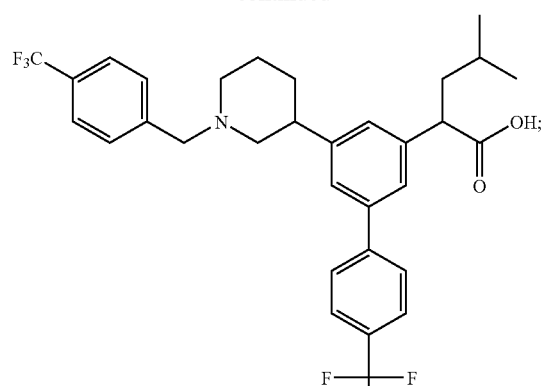
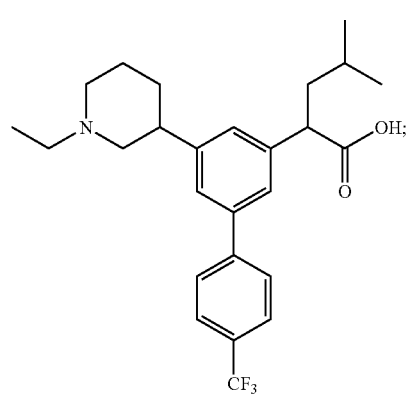
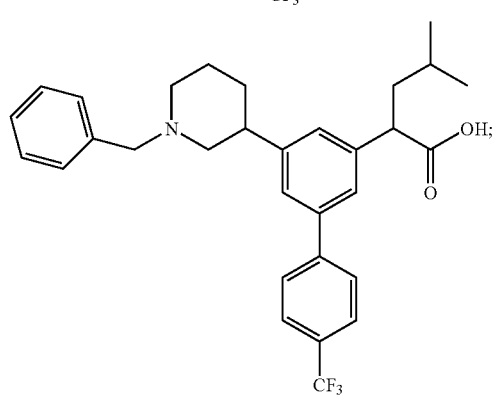
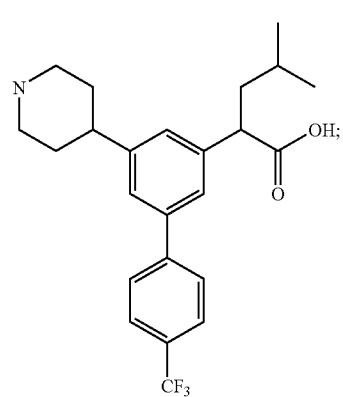
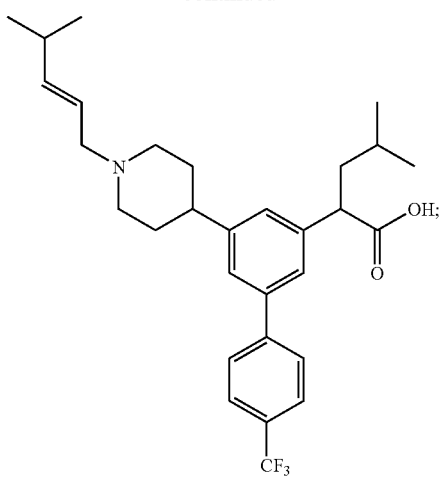
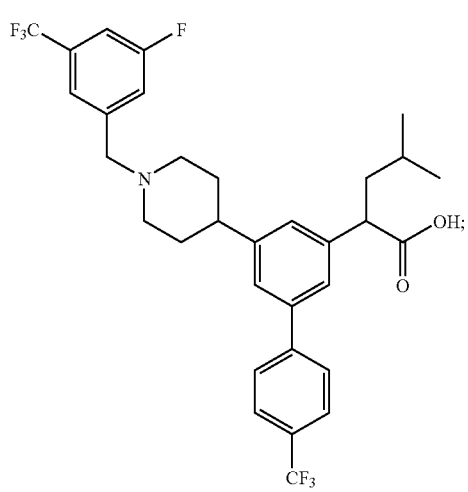
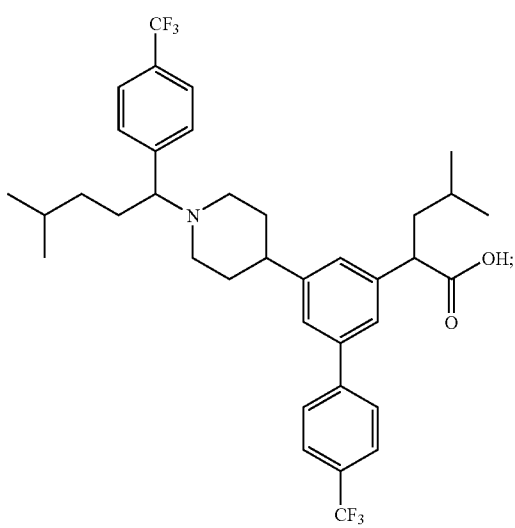

33
-continued
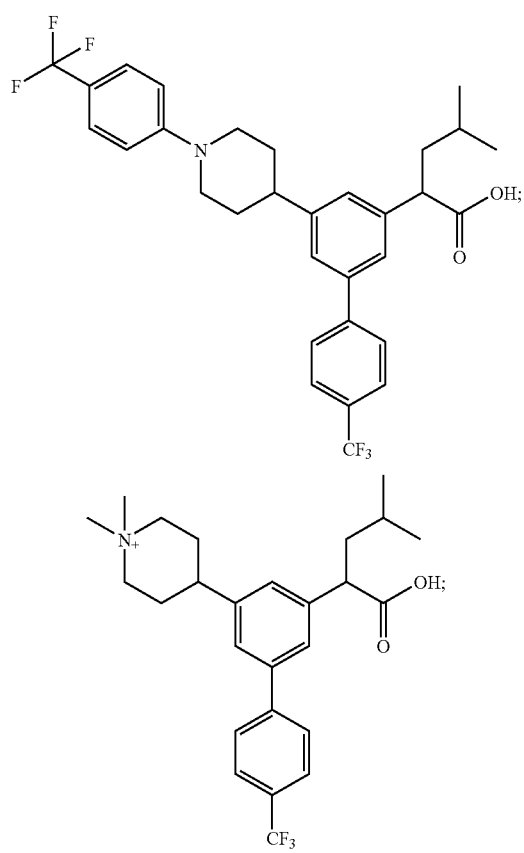
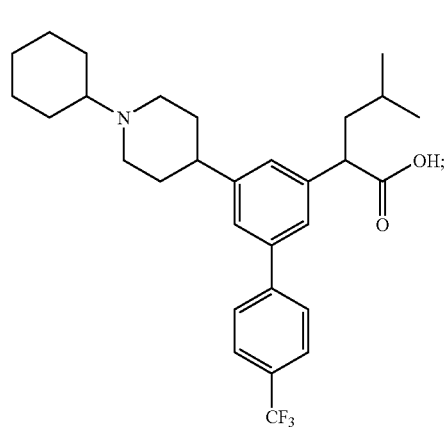
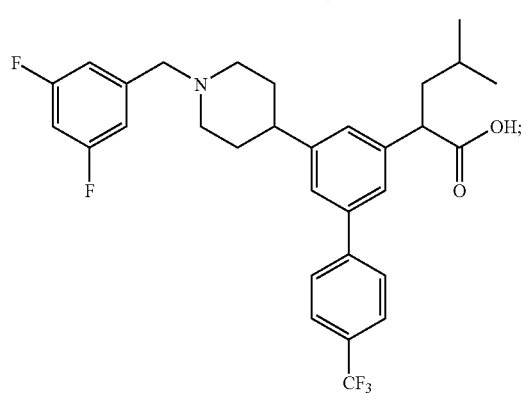
34
-continued
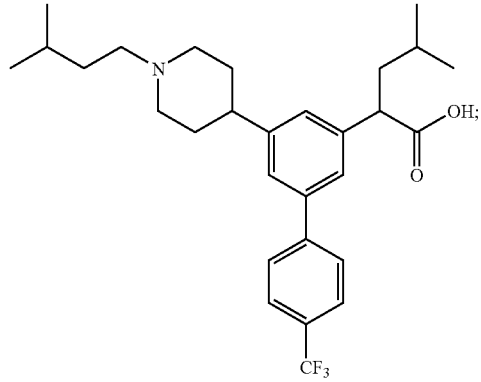
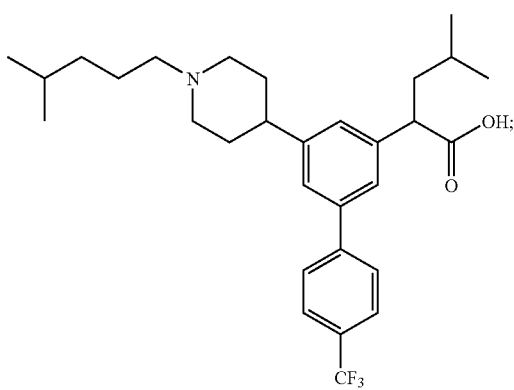
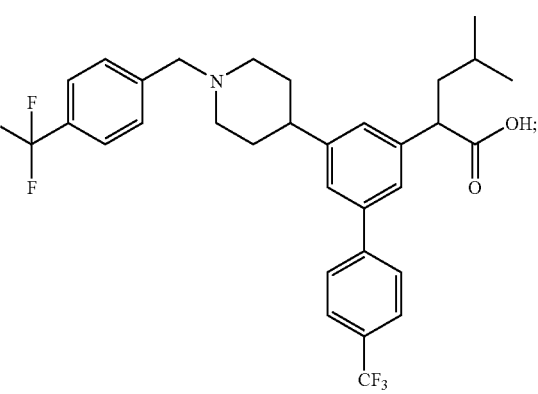
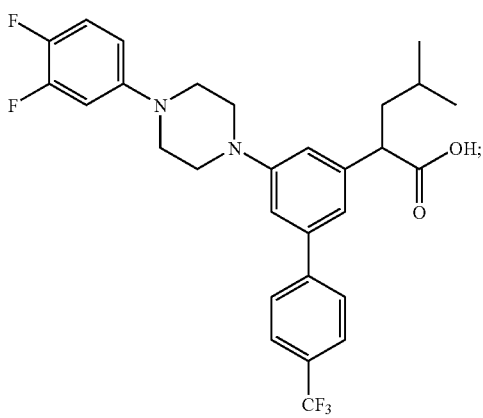

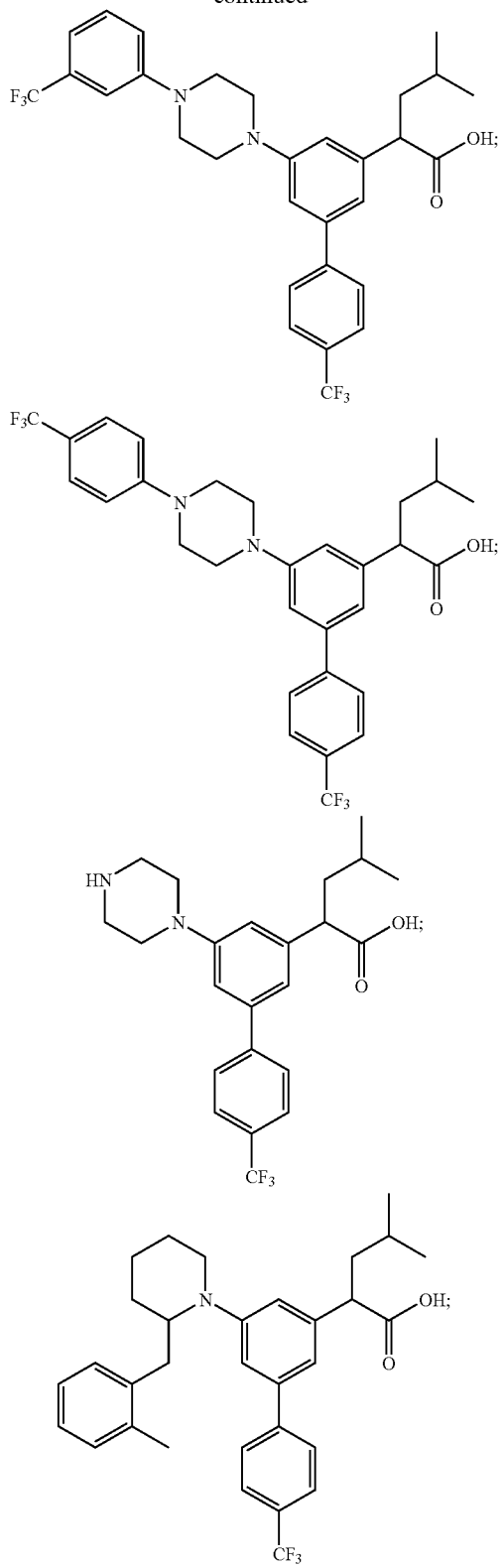

and solvates, hydrates, esters, and pharmaceutically acceptable salts thereof.

In another embodiment, the invention relates to a compound as described in the above examples or Formula I for use as a medicament.

In another embodiment, the invention relates to the use of a compound according to the above examples or Formula I for the preparation of a medicament for the modulation of γ-secretase.

In another embodiment, the invention relates to the use of a compound according to the above examples or Formula I for the preparation of a medicament for the treatment of a disease associated with an elevated level of Aβ42-production.

In another embodiment, the invention relates to the use of a compound according to the above examples or Formula I for the preparation of a medicament for the treatment of Alzheimer's disease.

In another embodiment, the invention relates to a method of treating a mammal for the modulation of γ-secretase, wherein said method comprises administering to the mammal a therapeutically effective amount of a compound of Formula I.

In another embodiment, the invention relates to a method of treating in a mammal a disease associated with an elevated level of Aβ42-production, wherein said method comprises administering to the mammal a therapeutically effective amount of a compound of Formula I.

One skilled in the art will recognize that the compounds of Formula I may have one or more asymmetric carbon atoms in their structure. It is intended that the present invention include within its scope single enantiomer forms of the compounds, racemic mixtures, and mixtures of enantiomers in which an enantiomeric excess is present.

Some of the compounds of the inventions and/or salts or esters thereof will exist in different stereoisomeric forms. All of these forms are subjects of the invention.

Described below are exemplary salts of the compounds according to the invention which are included herein. The list of the different salts stated below is not meant to be complete and limiting.

Compounds according to the invention which contain one or more acidic groups can be used according to the invention, e.g. as their alkali metal salts, alkaline earth metal salts or ammonium salts. More precise examples of such salts include sodium salts, potassium salts, calcium salts, magnesium salts or salts with ammonia or organic amines such as, e.g. ethylamine, ethanolamine, triethanolamine or amino acids.

The term "pharmaceutically acceptable" means approved by a regulatory agency such as the EMEA (Europe) and/or the FDA (US) and/or any other national regulatory agency for use in animals, preferably in humans.

The respective salts of the compounds according to the invention can be obtained by customary methods which are known to the person skilled in the art, for example by contacting these with an organic or inorganic base in a solvent or dispersant, or by cation exchange with other salts.

Furthermore, the invention includes all salts of the compounds according to the invention which, owing to low physiological compatibility, are not directly suitable for use in pharmaceuticals but which can be used, for example, as intermediates for chemical reactions or for the preparation of pharmaceutically acceptable salts or which might be suitable for studying γ-secretase modulating activity of a compound according of the invention in any suitable manner, such as any suitable in vitro assay.

The invention is considered to include prodrugs, i.e., derivatives of an acting drug that possess superior delivery capabilities and therapeutic value as compared to the acting drug. Prodrugs are transformed into active drugs by in vivo enzymatic or chemical processes.

The present invention furthermore includes all solvates of the compounds according to the invention.

The present invention furthermore includes derivatives/prodrugs (including the salts thereof) of the compounds according to the invention which contain physiologically tolerable and cleavable groups and which are metabolized in animals, preferably mammals, most preferably humans into a compound according to the invention. The present invention furthermore includes the metabolites of the compounds according to the invention.

The term "metabolites" refers to all molecules derived from any of the compounds according to the invention in a cell or organism, preferably mammal.

Preferably the term "metabolites" relates to molecules which differ from any molecule which is present in any such cell or organism under physiological conditions.

The structure of the metabolites of the compounds according to the invention will be obvious to any person skilled in the art, using the various appropriate methods.

The invention also relates to compounds of the invention for use as medicaments. The compounds are as defined above, furthermore with respect to the medicaments the embodiments as described below with respect to the use of the invention, e.g. formulation, application and combination, also apply to this aspect of the invention.

In particular the compounds according to the invention are suitable for the treatment of Alzheimer's disease.

Details relating to said use are further disclosed below.

The compounds can be used for modulation of γ-secretase activity.

As used herein, the term "modulation of γ-secretase activity" refers to an effect on the processing of APP by the γ-secretase-complex. Preferably it refers to an effect in which the overall rate of processing of APP remains essentially as without the application of said compounds, but in which the relative quantities of the processed products are changed, more preferably in such a way that the amount of the Aβ42-peptide produced is reduced. For example a different Abeta species can be produced (e.g. Abeta-38 or other Abeta peptide species of shorter amino acid sequence instead of Abeta-42) or the relative quantities of the products are different (e.g. the ratio of Abeta-40 to Abeta-42 is changed, preferably increased).

Gamma secretase activity can e.g. be measured by determining APP processing, e.g. by determining the levels of Abeta peptide species produced, most importantly levels of Abeta-42 (see Example section, infra).

It has been previously shown that the γ-secretase complex is also involved in the processing of the Notch-protein. Notch is a signaling protein which plays a crucial role in developmental processes (e.g. reviewed in Schweisguth F (2004) Curr. Biol. 14, R129). With respect to the use of said compounds for the modulation of γ-secretase activity in therapy, it seems particularly advantageous not to interfere with the Notch-processing activity of the γ-secretase activity in order to avoid putative undesired side-effects.

Thus, compounds are preferred which do not show an effect on the Notch-processing activity of the γ-secretase-complex.

Within the meaning of the invention, "effect on the Notch processing activity" includes both an inhibition or an activation of the Notch-processing activity by a certain factor.

A compound is defined as not having an effect on the Notch processing activity, if said factor is smaller than 20, preferably smaller than 10, more preferably smaller than 5, most preferably smaller than 2 in the respective assay as described in Shimizu et al (2000) Mol. Cell. Biol, 20: 6913 at a concentration of 30 μM.

Such a γ-secretase modulation can be carried out, e.g. in animals such as mammals. Exemplary mammals are mice, rats, guinea pigs, monkeys, dogs, cats. The modulation can also be carried out in humans. In a particular embodiment of the invention, said modulation is performed in vitro or in cell culture. As known to the person skilled in the art, several in vitro and cell culture assays are available.

Exemplary assays useful for measuring the production of C-terminal APP fragments in cell lines or transgenic animals by Western blot analysis include but are not limited to those described in Yan et al., 1999, Nature 402, 533-537.

An example of an in vitro γ-secretase assay is described in WO-03/008635. In this assay a suitable peptide substrate is contacted with a γ-secretase preparation and the ability to cleave the substrate is measured.

Concentrations of the various products of the γ-secretase cleavage (the Aβ-peptides) can be determined by various methods known to a person skilled in the art. Examples for such methods include determination of the peptides by mass-spectrometry or detection by antibodies.

Exemplary assays useful for the characterization of the profile of soluble Aβ peptides in cultured cell media and biological fluids include but are not limited to those described by Wang et al., 1996, J. Biol. Chem. 271, 31894-31902. In this assay a combination of immunoprecipitation of Abeta-peptides with specific antibodies and detection and quantification of the peptide species with matrix-assisted laser desorption ionization time-of-flight mass spectrometry is used.

Exemplary assays useful for measuring the production of Abeta-40 and Abeta-42 peptides by ELISA include but are not limited to those described in Vassar et al, 1999, Science 286, 735-741. Further information is disclosed for example in N. Ida et al. (1996) J. Biol. Chem. 271, 22908, and M. Jensen et al. (2000) Mol. Med. 6, 291. Suitable antibodies are available for example from The Genetics Company, Inc., Switzerland. Antibody-based kits are also available from Innogenetics, Belgium.

Cells which can be employed in such assays include cells which endogenously express the γ-secretase complex and transfected cells which transiently or stably express some or all interactors of the γ-secretase complex. Numerous available cell lines suitable for such assays are known to the skilled person. Cells and cell lines of neuronal or glial origin are particularly suitable. Furthermore, cells and tissues of the brain as well as homogenates and membrane preparations thereof may be used (Xia et al., 1998, Biochemistry 37, 16465-16471).

Such assays might be carried out for example to study the effect of the compounds according to the invention in different experimental conditions and configurations.

Furthermore, such assays might be carried out as part of functional studies on the γ-secretase complex.

For example, either one or more interactors (either in their wild-type form or carrying certain mutations and/or modifications) of the γ-secretase complex of an animal, preferably a mammal, more preferably humans, might be expressed in certain cell lines and the effect of the compounds according to the invention might be studied.

Mutated forms of the interactor(s) used can either be mutated forms which have been described in certain animals, preferably mammals, more preferably humans or mutated forms which have not previously been described in said animals.

Modifications of the interactors of the γ-secretase complex include both any physiological modification of said interactors and other modifications which have been described as modifications of proteins in a biological system.

Examples of such modifications include, but are not limited to, glycosylation, phosphorylation, prenylation, myristylation and farnesylation.

Furthermore, the compounds according to the invention can be used for the preparation of a medicament for the modulation of γ-secretase activity.

The activity of the γ-secretase can be modulated in different ways, i.e. resulting in different profiles of the various Aβ-peptides.

Respective dosages, routes of administration, formulations etc are disclosed further below.

The invention further relates to the use of the compounds of Formula I for the treatment of a disease associated with an elevated level of Aβ42-production. The disease with elevated levels of Abeta peptide production and deposition in the brain is typically Alzheimer's disease (AD), cerebral amyloid angiopathy, multi-infarct dementia, dementia pugilistica or Down syndrome, preferably AD.

As used herein, the term "treatment" is intended to refer to all processes, wherein there may be a slowing, interrupting, arresting, or stopping of the progression of a disease, but does not necessarily indicate a total elimination of all symptoms.

As used herein, the term "elevated level of Aβ42-production" refers to a condition in which the rate of production of Aβ42-peptide is increased due to an overall increase in the processing of APP or, preferably, it refers to a condition in which the production of the Aβ42 peptide is increased due to a modification of the APP-processing profile in comparison to the wild-type APP and non-pathological situation.

As outlined above, such an elevated Aβ42-level is a hallmark of patients developing or suffering from Alzheimer's disease.

One advantage of the compounds or a part of the compounds of the present invention may lie in their enhanced CNS-penetration.

Furthermore the invention relates to a pharmaceutical composition comprising a compound of Formula I in a mixture with an inert carrier.

Modulators of γ-secretase derived from compounds of Formula I can be formulated into pharmaceutical compositions comprising a compound of Formula I in a mixture with an inert carrier, where said inert carrier is a pharmaceutical carrier.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water is a preferred carrier when the pharmaceutical composition is administered orally.

Saline and aqueous dextrose are preferred carriers when the pharmaceutical composition is administered intravenously. Saline solutions and aqueous dextrose and glycerol solutions are preferably employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

The compounds according to the invention and their pharmaceutically acceptable salts, optionally in combination with other pharmaceutically active compounds are suitable to treat or prevent Alzheimer's disease or the symptons thereof. Such additional compounds include cognition-enhancing drugs such as acetylcholinesterase inhibitors (e.g. Donepezil, Tacrine, Galantamine, Rivastigmin), NMDA antagonists (e.g. Memantine) PDE4 inhibitors (e.g. Ariflo) or any other drug known to a person skilled in the art suitable to treat or prevent Alzheimer's disease. Such compounds also include cholesterol-lowering drugs such as statins (e.g. simvastatin). These compounds can be administered to animals, preferably to mammals, and in particular humans, as pharmaceuticals by themselves, in mixtures with one anther or in the form of pharmaceutical preparations.

Preservatives and other additives can also be present, such as, for example, antimicrobials, antioxidants, chelating agents, inert gases and the like. All carriers can be mixed as needed with disintegrants, diluents, granulating agents, lubricants, binders and the like using conventional techniques known in the art.

This invention further provides a method of treating a subject having a condition ameliorated by modulation of γ-secretase activity, which comprises administering to the subject a therapeutically effective dose of the instant pharmaceutical composition.

As used herein, the term "subject" includes, without limitation, any animal or artificially modified animal having a disorder ameliorated by modulation of γ-secretase activity. In a preferred embodiment, the subject is a human.

As used herein, a "therapeutically effective dose" of a pharmaceutical composition is an amount sufficient to stop, reverse or reduce the progression of a disorder. A "prophylactically effective dose" of a pharmaceutical composition is an amount sufficient to prevent a disorder, i.e., eliminate, ameliorate and/or delay the disorder's onset. Methods are known in the art for determining therapeutically and prophylactically effective doses for the instant pharmaceutical composition. The effective dose for administering the pharmaceutical composition to a human, for example, can be determined mathematically from the results of animal studies.

Various delivery systems are known and can be used to administer a compound of the invention for the treatment of Alzheimer's disease or for the modulation of the γ-secretase activity, e.g. encapsulation in liposomes, microparticles, and microcapsules: If not delivered directly to the central nervous system, preferably the brain, it is advantageous to select and/or modify methods of administration in such a way as to allow the pharmaceutical compound to cross the blood-brain barrier.

Methods of introduction include, but are not limited to, intradermal, intramuscular, intraperitoneal, intravenous, subcutaneous, intranasal, epidural, and oral routes.

The compounds may be administered by any convenient route, for example by infusion, by bolus injection, by absorption through epithelial or mucocutaneous linings and may be administered together with other biologically active agents.

Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g. by use of an inhaler or nebulizer, and formulation with an aerosolizing agent.

Modulators of γ-secretase derived from compounds of Formula I can be delivered in a vesicle, in particular a liposome (Langer (1990) Science 249, 1527.

Modulators of γ-secretase derived from compounds of Formula I can be delivered via a controlled release system. In one embodiment, a pump may be used (Sefton (1987) CRC Crit. Ref. Biomed. Eng. 14, 201; Buchwald et al. (1980) Surgery 88, 507; Saudek et al. (1989) N. Engl. J. Med. 321, 574). In another embodiment, polymeric materials can be used (Ranger and Peppas (1983) Macromol. Sci. Rev. Macromol. Chem. 23, 61; Levy et al. (1985) Science 228, 190; During et al. (1989) Ann. Neurol. 25, 351; Howard et al. (1989) J. Neurosurg. 71, 858). In yet another embodiment, a controlled release system can be placed in proximity of the therapeutic target, i.e., the brain, thus requiring only a fraction of the systemic dose (e.g. Goodson, 1984, In: Medical Applications of Controlled Release, supra, Vol. 2, 115). Other controlled release systems are discussed in the review by Langer (1990, Science 249, 1527).

In order to select an appropriate way of administration, the person skilled in the art will also consider routes of administration which have been selected for other known Anti-Alzheimer-drugs.

For example, Aricept/Donepezil and Cognex/Tacrine (all acetylcholinesterase-inhibitors) are being taken orally, Axura/Memantine (an NMDA-receptor antagonist) has been launched both as tablets/liquid and as an i.v.-solution.

Furthermore, the skilled person in the art will take into account the available data with respect to routes of administration of members of the NSAID-family in clinical trials and other studies investigating their effect on Alzheimer's disease.

In order to select the appropriate dosage, the person skilled in the art will choose a dosage which has been shown to be not toxic in preclinical and/or clinical studies and which can be in accordance with the values given beforehand, or which may deviate from these.

The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 mg/kg body weight to 1 mg/kg body weight. Effective doses may be extrapolated from dose-response curves derived from in vitro or animal model test systems.

An exemplary animal model is the transgenic mouse strain "Tg2576" containing an APP695-form with the double mutation KM670/671NL. For reference see e.g. patent U.S. Pat. No. 5,877,399 and Hsiao et al. (1996) Science 274, 99 and also Kawarabayahsi T (2001) J. Neurosci. 21, 372; Frautschy et al. (1998) Am. J. Pathol. 152, 307; Irizarry et al. (1997) J. Neuropathol. Exp. Neurol. 56, 965; Lehman et al. (2003) Neurobiol. Aging 24, 645.

Substantial data from several studies are available to the skilled person in the art, which are instructive to the skilled person to select the appropriate dosage for the chosen therapeutic regimen.

Numerous studies have been published in which the effects of molecules on the γ-secretase activity are described. Exemplary studies are Lim et al. (2001) Neurobiol. Aging 22, 983; Lim et al. (2000) J Neurosci. 20, 5709; Weggen et al. (2001) Nature 414, 212; Eriksen et al. (2003) J Clin Invest. 112, 440; Yan et al. (2003) J Neurosci. 23, 7504.

Definitions:

The term "alkenyl," whether used alone or as part of a substituent group, for example, "$C_{1-4}$alkenyl(aryl)," refers to a partially unsaturated branched or straight chain monovalent hydrocarbon radical having at least one carbon—carbon double bond, whereby the double bond is derived by the removal of one hydrogen atom from each of two adjacent carbon atoms of a parent alkyl molecule and the radical is derived by the removal of one hydrogen atom from a single carbon atom. Atoms may be oriented about the double bond in either the cis (Z) or trans (E) conformation. Typical alkenyl radicals include, but are not limited to, ethenyl, propenyl, allyl(2-propenyl), butenyl and the like. Examples include $C_{2-8}$alkenyl or $C_{2-4}$alkenyl groups.

The term "$C_{a-b}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{1-4}$ denotes a radical containing 1, 2, 3 or 4 carbon atoms.

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, n-butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl.

The term "heteroaryl" refers to 5-to 7-membered mono-or 8-to 10-membered bicyclic aromatic ring systems, any ring of which may consist of from one to four heteroatoms selected from N, O or S where the nitrogen and sulfur atoms can exist in any allowed oxidation state. Examples include benzimidazolyl, benzothiazolyl, benzothienyl, benzoxazolyl, furyl, imidazolyl, isothiazolyl, isoxazolyl, oxazolyl, pyrazinyl, pyrazolyl, pyridyl, pyrimidinyl, pyrrolyl, quinolinyl, thiazolyl and thienyl.

The term "heterocyclyl" refers to a saturated or partially unsaturated monocyclic ring radical derived by the removal of one hydrogen atom from a single carbon or nitrogen ring atom. Typical heterocyclyl radicals include 2H-pyrrolyl, 2-pyrrolinyl, 3-pyrrolinyl, pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolyl, piperidinyl, 1,4-dioxanyl, morpholinyl, 1,4-dithianyl, thiomorpholinyl, piperazinyl, azepanyl, hexahydro-1,4-diazepinyl and the like.

The term "substituted," refers to a core molecule on which one or more hydrogen atoms have been replaced with one or more functional radical moieties. Substitution is not limited to a core molecule, but may also occur on a substituent radical, whereby the substituent radical becomes a linking group.

General Synthesis Description

The following general description is for illustrative purposes only and is in no way meant to limit the invention.

Compounds of Formula I wherein Het, $R^0$, $R^1$ $R^2$, $R^3$, $R^4$, $R^5$, $R^6$, $R^7$ and $R^8$ are defined as in Formula I, and $R^9$ is H, may be obtained by hydrolysis of esters II under standard acidic or basic hydrolysis conditions, including reaction with NaOH, at room temperature, for several hours, in an appropriate solvent mixture, such as water, tetrahydrofuran (THF), and methanol or ethanol. For illustrative purposes, esters II are shown with $R^9$ as alkyl, but those skilled in the art will recognize that ester hydrolysis will work for all $R^9$ as defined in Formula I.

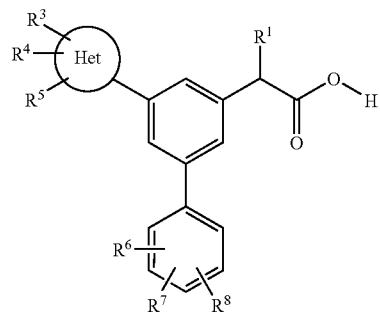

Wherein

is represented by the following formula:

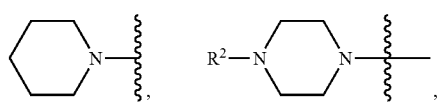

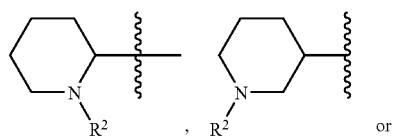

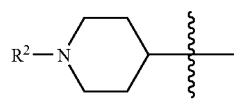

Compounds of Formula IIa may be obtained by coupling reactions of compound IIIa or IIIb with commercially available piperidines and piperazines or synthetically prepared piperidines and piperazines under typical Buckwald or Hartwig conditions, e.g. in toluene, dioxane or THF in the presence of potassium t-butoxide and a catalyst, e.g. palladium (II) acetate (Pd(OAc)$_2$) or Palladium (0) trans, trans-dibenzylideneacetone at elevated temperature (80-180° C.) or the reaction may be performed in a microwave reactor. The aforementioned reaction products from piperazine can be subsequently alkylated with alkyl halides or mesylates in the presence of base such as cesium carbonate or potasssium carbonate or reductivly alkylated with alkyl carboxyadehydes for installing an $R^2$ group on the amine functionality to provide compounds IIa.

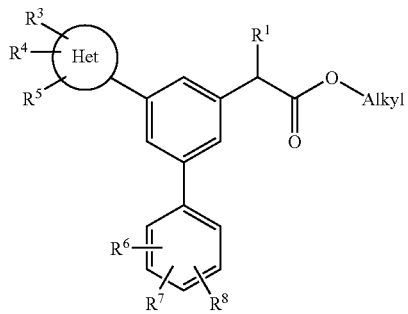

IIA Where

is represented by

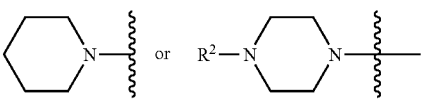

IIb Where

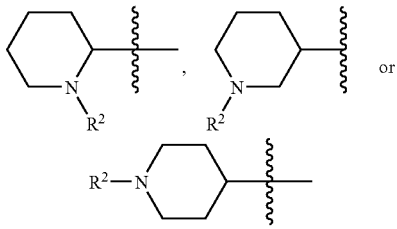

is represented by

Compounds IIIa may be obtained from the reaction of phenols IV with trifluoromethanesulfonic anhydride in DCM in the presence of a base such as pyridine, or triethylamine at 0° C. Compounds IIIb can be obtained from reactions of phenols IV with concentrated HCl, or HBr, or HI at elevated temperature (25 to 120° C.). Alternatively, compounds IIIb can be obtained under mild conditions by treatment of the corresponding triflates IIIa with pinacoborane in dioxane in the presence of triethylamine catalyzed with PdCl$_2$ to give pinacol boronate esters which are then treated with copper (II) halide in methanol-water, procedure described by Nesmejanow et al. (Chem Ber. 1960, 2729). The aforementioned pinacolboronate ester could also be reacted with NaI in aqueous THF in the presence of chloramines-T to give aryl iodide described by J. W. Huffman et. al.(Synthesis, 2005, 547).

Alternatively, compounds of Formula IIa can be obtained from compounds IIIc by ring closure reactions via double reductive amination with pentanedial or ring closure reactions with dichloropentanes or bischloroethylamines.

Compounds IIIc can be obtained from compounds IIIa or IIIb by reaction with benzophenone imine in an aprotic solvent such as DMF, toluene or THF in the presence of a catalytic amount of tetrakistriphenylphosphine palladium (0) and triphenylphosphine, followed by aqueous basic hydrolysis of the imine intermediate.

III

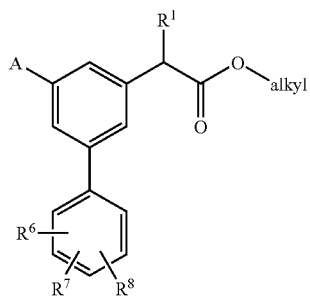

wherein:
IIIa, A is OTf
IIIb, A is Br, Cl, I
IIIc, A is NH$_2$

IIId, A is 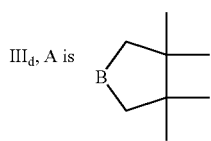

IV

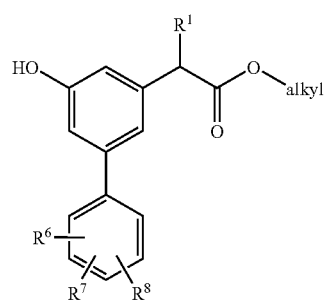

Compounds IV may be prepared by debenzylation of compounds V by hydrogenation in alcohol, e.g. MeOH or EtOH in the presence of Pd—C. Debenzylation can also be achieved with other methods, such as BBr$_3$ in DCM, NaCN in DMSO/120-200° C. or LiCl in DMF/120-200° C.

V

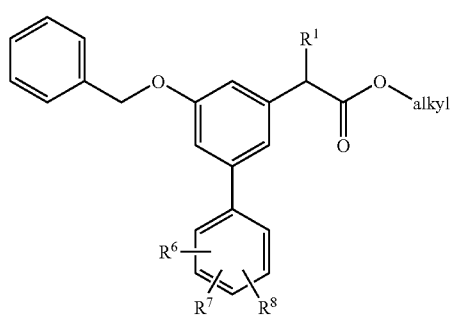

Compounds V may be prepared from the alkylation of compounds VI with either alkyl or alkenyl halides. Treatment of compounds VI in THF or other aprotic solvent with a base, e.g. lithium bis(trimethylsilyl)amide, sodium bis(trimethylsilyl)amide, or lithium diisopropylamide at −78° C., followed by the addition of electrophiles, e.g. alkyl or alkenyl halides, will give alkylated V.

VI

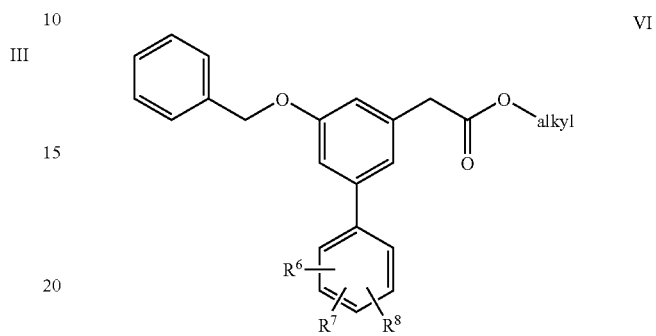

Compounds VI may be prepared from compounds VIIa through a coupling reaction with arylboronic acids under Suzuki conditions of aqueous sodium carbonate in DME in the presence of Pd(PPh$_3$)$_4$. Similarly, the triflates can be converted to boronate esters VIIb under the conditions described above (Nesmejanow et. al., Chem Ber. 1960, 2729; J. W. Huffman et. al., Synthesis, 2005, 547) which can be coupled with aryl bromides or aryl chlorides to give compound VI.

VIIa

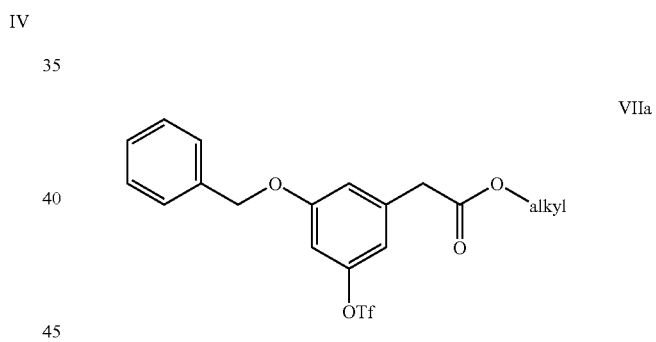

VIIb

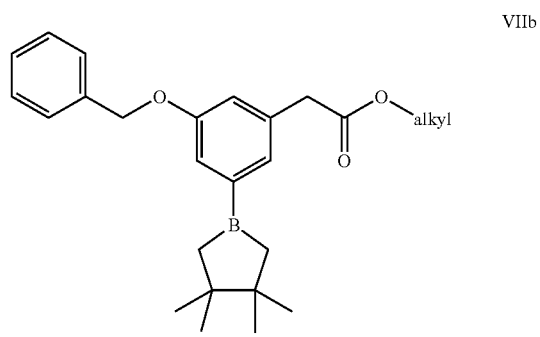

Intermediate triflate compound VII may be prepared from phenolic compound VIII with trifluoromethanesulfonic anhydride in DCM in the presence of one equivalent of pyridine at 0° C.

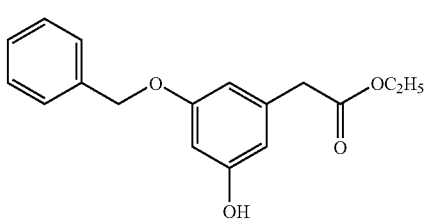

VIII

Intermediate compound VIII can be prepared from the mono-debenzylation of compound IX. Selective mono-debenzylation of compound IX can be achieved by selective hydrogenolysis of compound IX in ethanol or methanol with an addition of 1.1 equivalents of base, e.g. sodium hydroxide or potassium hydroxide in the presence of Pd—C catalyst in a Parr shaker. The reaction is allowed to proceed until one equivalent of hydrogen is consumed

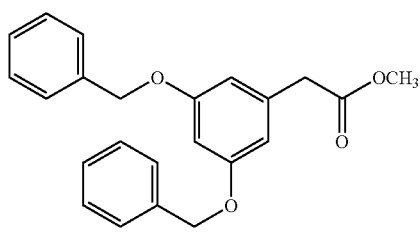

IX

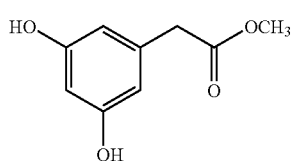

X

Intermediate IX can be readily prepared from reaction of 3,5-dihydroxyphenyl acetic acid methyl ester, compound X, (commercially available) with benzyl bromide and potassium carbonate in DMF at room temperature.

Compounds of Formula IIb can be obtained from the alkylation of compounds XI with alkyl halides or alkylate mesylates in the presence of a base such as potassium carbonate for introducing $R^2$ group on the amino group functionality. Alternatively, compounds IIb can be obtained via the reductive amination of compounds XI via conditions aforementioned for installing $R^2$ group on the amino group functionality. Compounds XI may be obtained by hydrogenation of the corresponding pyridines XII with platium oxide or palladium-carbon in acidic medium such as methanol or ethanol.

Compounds XII can be obtained by coupling of compounds IIa or IIb with pyridine boronic acids under the typical Suzuki coupling conditions, e.g. in DME, dioxane or THF in the presence of aqueous sodium carbonate solution and catalyst, e.g. tetrakis(triphenylphosphine)palladium(0) at elevated temperature (range from 60-180 degrees C.).

Alternatively, compounds XII can be prepared from the coupling reactions of pinacol boronate esters IIId with pyridine bromides or chlorides under the Suzuki conditions as aforementioned.

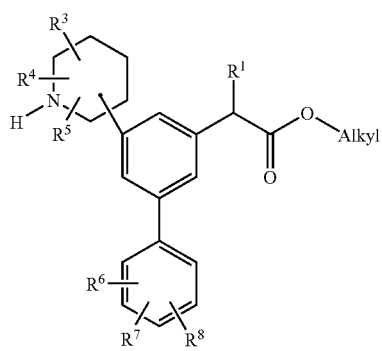

XI

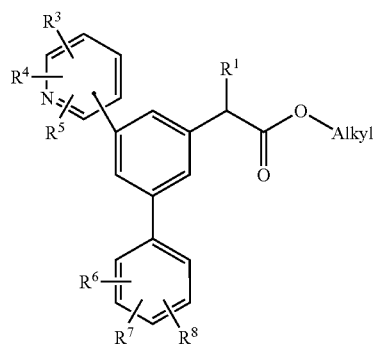

XII

Compounds of Formula I have a chiral center α to the carboxylic group, and can exist as one of two enantiomers (or a mixture threof, wherein an enantiomeric excess may or may not be present). The enantiomers Ia (R enantiomer) and Ib (S enantiomer) are shown. The pure enantiomers Ia and Ib may be obtained by chiral separation using chiral columns. The enantiomers Ia and Ib may also be separated by resolutions through forming chiral amine salts by fractional recrystallizations. The enantiomers Ia and Ib also may be obtained from kinetic resolution of the racemates of corresponding esters using lipase enzymes, e.g. Amano lipase Ak, Amano lipase PS, Amano lipaseA, Amano lipase M, Amano lipase F-15 Amano lipase G (from Biocatalytics Inc) in aqueous organic solvents, e.g. aqueous DMF, DMSO, t-butyl-ethyl ether or triton X-100 aqueous solutions.

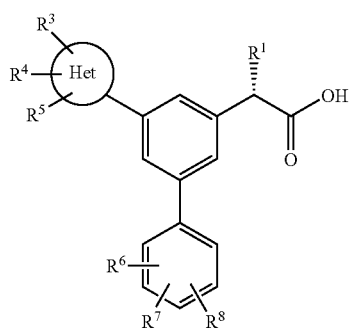

Ia

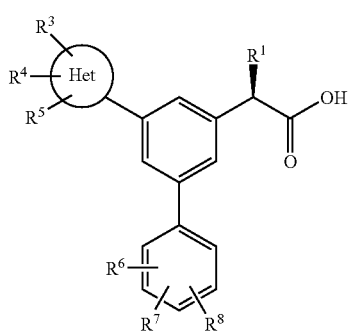

Ib

Alternatively, both enantiomers of compound Ia and Ib may be prepared from chiral syntheses. Compounds Ia and Ib may be obtained from reactions starting with chiral phenol compounds IVa and IVb with the reactions as described above.

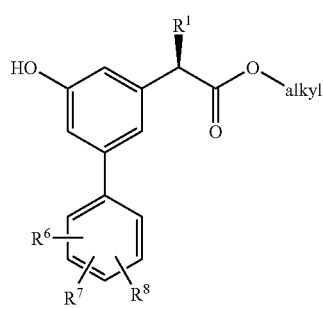

IVa

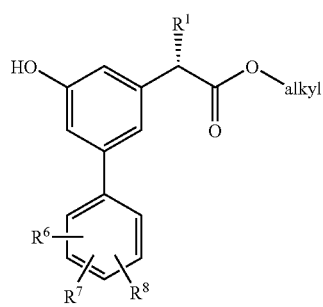

IVb

Chiral compounds IVa and IVb may be obtained from the removal of chiral auxiliary groups from compounds XIIIa and XIIIb respectively, with lithium hydroxide/hydrogen peroxide in aqueous THF, followed by esterification

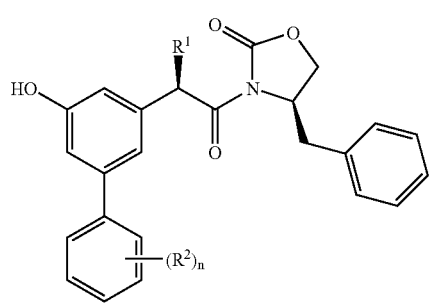

XIIIa

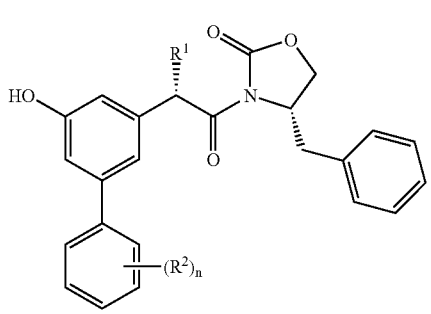

XIIIb

Compounds XIIIa and XIIIb may be prepared from debenzylation of compounds XIVa and XIVb respectively by hydrogenation in an alcohol solvent, e.g. MeOH or EtOH, in the presence of Pd—C.

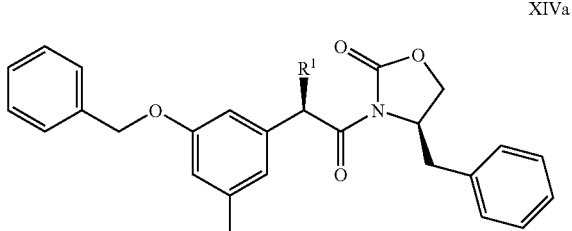

XIVa

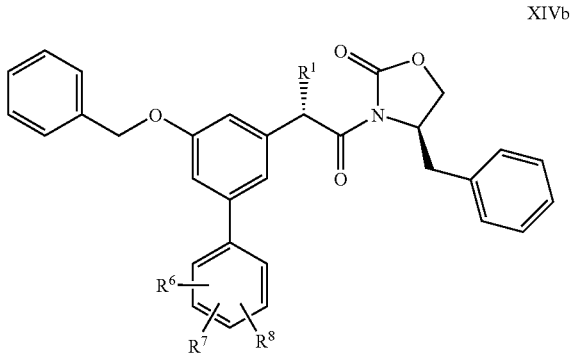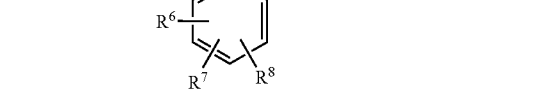

XIVb

Compounds XIVa and XIVb may be prepared from the alkylation of compounds XVa and XVb respectively with an appropriate alkyl bromide, including sec-butyl bromide or sec-butenyl bromide for introducing the $R^1$ group on the carbon a to the carboxylic group. For examples, treatments of compounds XVa and XVb in THF or other aprotic solvents with bases, e.g. lithium bis(trimethylsilyl)amide, sodium bis(trimethylsilyl)amide, or lithium diisopropylamide at −78° C., followed by the addition of electrophiles, sec-butyl bromide or sec-butenyl bromide gives alkylated compounds XIVa and XIVb respectively.

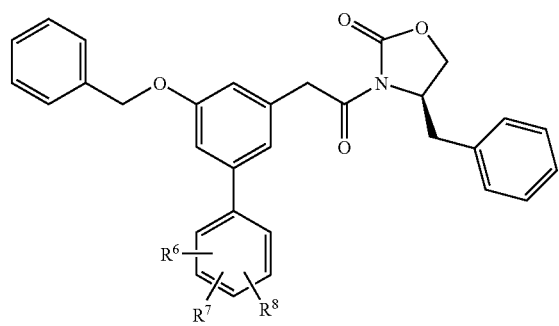
XVa

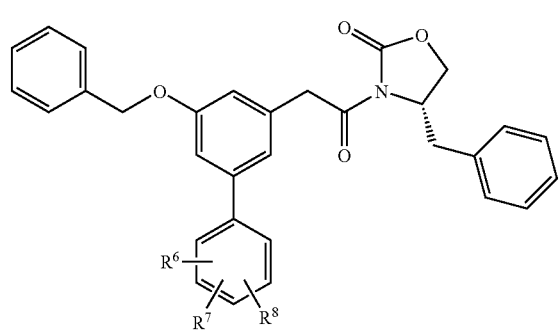
XVb

Compounds XVa and XVb may be prepared from intermediate XVI by coupling either the R-isomer of 4-benzyl-oxazolidin-one (XVIIa) or the S-isomer of 4-benzyl-oxazolidin-one (XVIIb) via Evans's procedures. Intermediates XVI may be reacted with pivaloyl chloride, oxalyl chloride or isopropyl chloroformate in THF in the presence of a base, e.g. triethylamine or N-methylmorpholine, to generate the mix anhydrides or acid chlorides which then are reacted with the lithium salt of XVIIa or XVIIb in THF.

Alternatively, other chiral auxiliary groups may also be used for the chiral syntheses of compound IVa and IVb, e.g. pseudoephedrine via the A. G. Myers conditions (J. Am. Chem. Soc. 1994, 116, 9361-9362). Treatment of either the carboxylic acid chlorides or anhydrides with pseudoephedrine will give amide derivatives such as compounds XVIIIa and XVIIIb. The amides are then treated with a strong base, e.g. lithium diisopropyl amide in the presence of lithium chloride, followed by the addition of alkylating agents to yield the corresponding alkylated products XIXa and XIXb. Chiral phenolic compounds IVa and IVb can be obtained from compounds XIXa and XIXb by removal of the chiral auxiliary pseudoephedrine in aqueous sulfuric acid solution, followed by BBr$_3$/DCM or hydrogenolysis with Pd—C in methanol or ethanol to remove the protecting benzyl group.

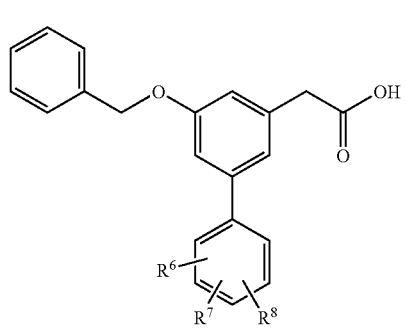
XVI

XVIIa

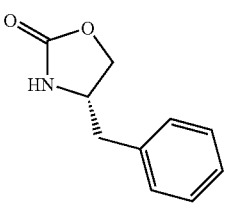
XVIIb

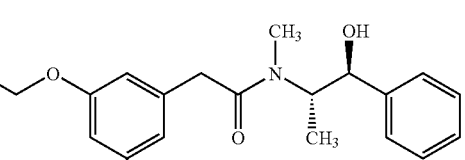
XVIIIa

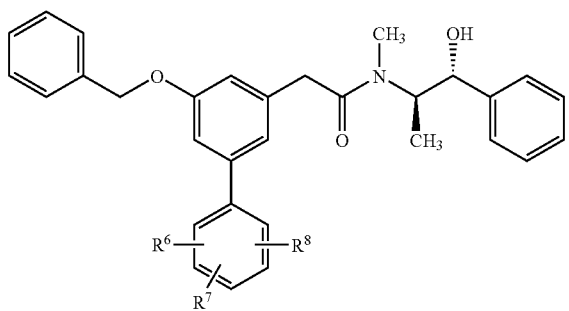
XVIIIb

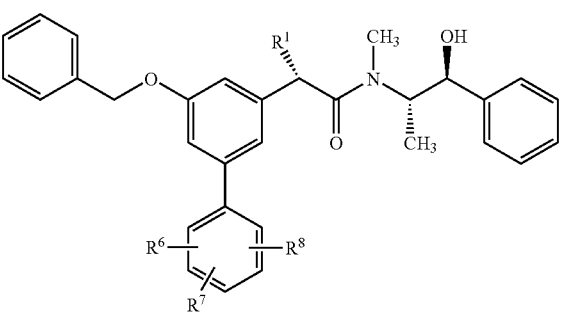
XIXa

-continued

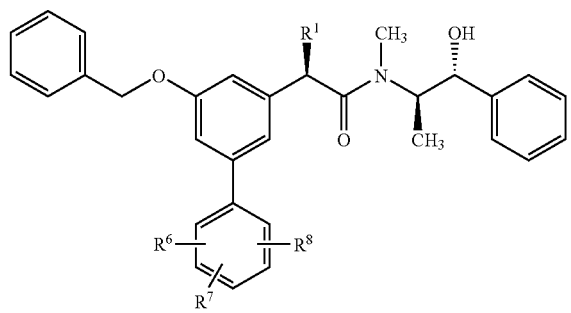
XIXb

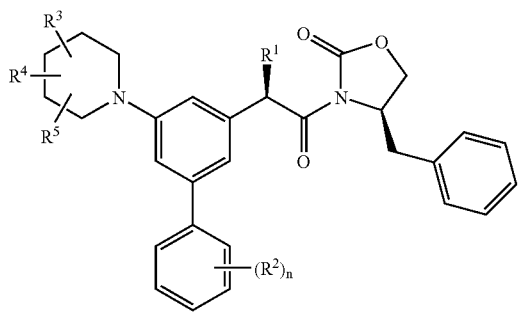
XXIa

Alternatively, the chiral phenolic compounds XIIIa, XIIIb, XXa and XXb can serve as chiral intermediates for preparing chiral compounds Ia and Ib. The chiral auxiliary groups are then removed at the later stage of synthesis under the conditions described above.

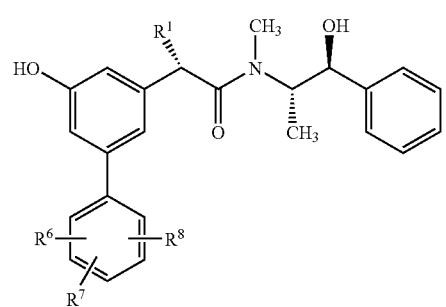
XXa

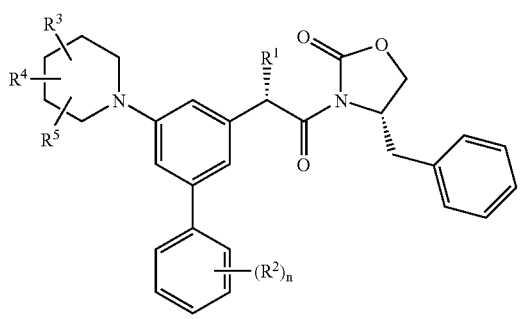
XXIb

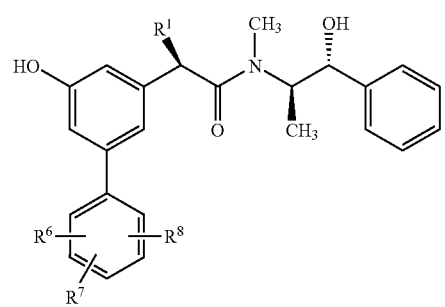
XXb

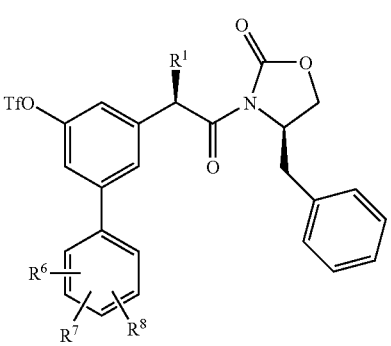
XXIIa

For example, compounds XXIa and XXIb can be prepared from chiral phenolic compounds XIIIa and XIIIb under similar conditions to those described above. The triflate compounds XXIIa and XXIIb, prepared from phenolic compounds XIIIa and XIIIb by reacting with trifluoromethylsulfonyl anhydride in pyridine-methylene chloride solution, can then give compounds XXIa and XXIb through Buckwald or Hartwig coupling conditions as described above. The final compounds of Formula Ia and Ib can be obtained after removing the chiral auxiliary groups from compounds XXIa nd XXIb with the conditions aforementioned.

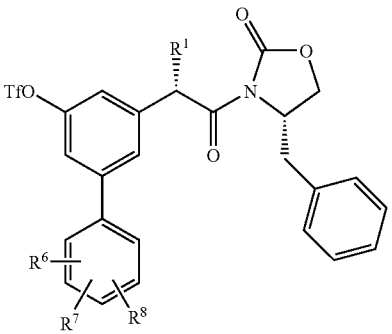
XXIIb

Synthetic Procedures

All reactions were carried out under inert atmosphere unless otherwise stated. NMR spectra were obtained on a Bruker dpx400. LCMS was carried out on an Agilent 1100 using a ZORBAX® SB-C18, 4.6×75 mm, 3.5 micron column for method A. Column flow was 1 ml/min and solvents used were water and acetonitrile (0.1% TFA) with an injection volume of 10 ul. Wavelengths were 254 and 210 nm. Methods are described below:

| Method | Flow Rate | Solvent |
|---|---|---|
| A | 1 ml/min | 0-1.5-95% MeCN |
|  |  | 1.5-6 min 95% |
|  |  | 4.5-5 min 95%-5% MeCN |

Abbreviations

| | |
|---|---|
| Ac | Acetyl |
| d | Doublet |
| DCM | Dichloromethane |
| DME | 1,2-dimethoxyethane |
| DMF | N,N-dimethylformamide |
| DMSO | Dimethyl sulfoxide |
| e.e. | enantiomeric excess |
| Eq | Equivalents |
| Et | Ethyl |
| EtOAc | ethyl acetate |
| g | Gram |
| h | Hour |
| HPLC | high pressure liquid chromatography |
| $K_2CO_3$ | Potassium carbonate |
| l | Liter |
| LCMS | liquid chromatography - mass spectrometry |
| LDA | lithium diisopropylamide |
| M | Molar |
| m | Multiplet |
| Me | Methyl |
| min | Minute |
| mol | Mole |
| NMR | nuclear magnetic resonance |
| q | Quartet |
| RT | Retention time |
| s | Singlet |
| sat | Saturated |
| t | Triplet |
| TFA | Trifluoroacetic acid |
| THF | Tetrahydrofuran |

EXAMPLE 1

4-Methyl-2-[5-(2-propyl-piperidin-1-yl)-4'-trifluoromethyl-biphenyl-3-yl]-pentanoic acid

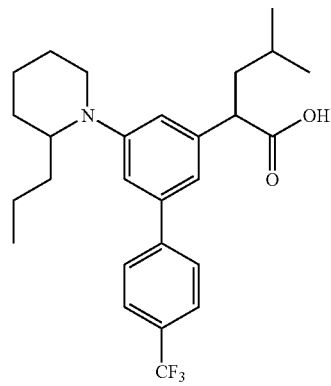

a) (3,5-Bis-benzyloxy-phenyl)-acetic acid methyl ester

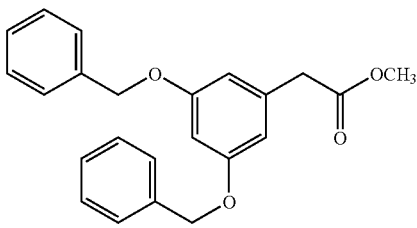

A mixture of (3,5-dihydroxy-phenyl)-acetic acid methyl ester (from Aldrich, 70 g, 0.385 mol), benzylbromide (137 mL, 1.16 mol), potassium carbonate (160 g, 1.16 mol) and DMF (1.5 L) under $N_2$ was mechanically stirred at room temperature overnight. The resulting reaction mixture was poured into a mixture of 1.5 L of ice-water with stirring. The precipitate was obtained by filtration and washed with heptane successively to remove benzyl bromide to give the title compounds (123.7 g) as a brown solid which was air dried for the next reaction. $^1$H-NMR(CDCl$_3$): δ 3.60 (s, 2H), 3.71(s, 3H), 5.05 (s, 4H), 6.60 (s, 3H), 7.35-7.50 (m, 10H); Calcd for C23H22O4 (M+H) 363.15, Found 363.

b) 3-Benzyloxy-5-hydroxy-phenyl)-acetic acid ethyl ester

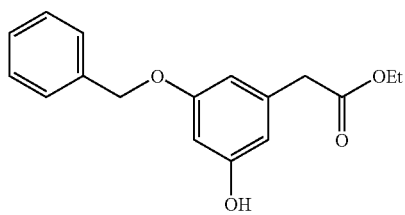

A solution of 3,5-Bis-benzyloxy-phenyl)-acetic acid methyl ester (50 g, 1.38 mol) and NaOH (6.6 g, 1.65 mole) in 1 L of EtOH in the presence of 10% of Pd—C was hydrogenated in a Parr shaker until one equivalent of hydrogen was consumed. The mixture was acidified with concentrated HCl and then the catalyst and solvent were removed to give an oil residue. The crude product was purified by ISCO silica gel column chromatography (ISCO) using EtOAC-heptane as eluents (gradient from 10% to 75% of EtOAc) to give 25 g of (65% yield) the title compound. $^1$H-NMR (CDCl$_3$): δ 1.15-1.20 (t, 3H), 3.4-(s,2H), 4.05-4.1 (q, 2H),4.9(s, 2H), 5.5(s, 1H), 6.4(s, 2H), 6.5(s, 1H), 7.207.35(m, 5H); Calcd for C17H18O4 (M+H) 287.3, Found 287.

c) (3-Benzyloxy-5-trifluoromethanesulfonyloxy-phenyl)-acetic acid ethyl ester

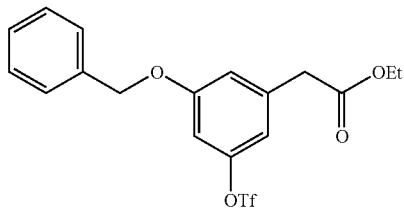

To a solution of 3-(benzyloxy-5-hydroxy-phenyl)-acetic acid ethyl ester (74.4 g, 0.26 mol) in dichloromethane (700 mL) was added pyridine (62.5 mL, 0.78 mol). The mixture was cooled to 0° C. To this cold solution was added trifluoromethanesulfonic anhydride (65.6 mL, 0.39 mol), over 1.5 h, maintaining the internal temperature below 5° C. and stirred for an additional 0.5 h at 0° C. This reaction mixture was poured to a mixture of 1 N HCl (420 mL), and wet-ice (105 g) and stirred for 0.5 h. The aqueous layer was extracted with dichloromethane (2×100 mL). Combined fractions were washed with water (2×100 mL), saturated aqueous NaHCO$_3$ solution (2×100 mL), and brine (2×100 mL). The organics were dried (MgSO$_4$) and concentrated in vacuo to receive a reddish liquid (108 g) which was carried on to the next step without further purification. Calcd for C18H17F3O6S (M+H) 419.07, Found 419.1.

d) (5-Benzyloxy-4'-trifluoromethyl-biphenyl-3-yl)-acetic acid ethyl ester

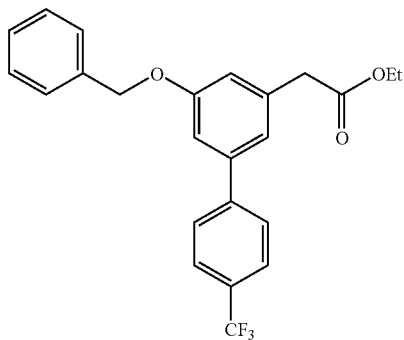

A mixture of (3-benzyloxy-5-trifluoromethanesulfonyloxy-phenyl)-acetic acid ethyl ester (108 g, 0.26 mol), 4-(trifluoromethyl)phenylboronic acid (55.6 g, 0.29 mol), 1,2-dimethoxyethane (1.1 L) and aqueous Na$_2$CO$_3$ (2 M, 129 mL, 0.26 mol) was mechanically stirred while purging N$_2$ at room temperature for 10 min. To this system was added Pd(Ph$_3$)$_4$ (480 mg, 0.42 mmol) and heated to reflux (95° C.) for 2.5 h. The red-brown mixture was diluted with EtOAc (0.5 L) and washed with saturated aqueous NaHCO$_3$ solution (3×200 mL) and brine (2×200 mL). The organic fraction was dried (Na$_2$SO$_4$) and concentrated in vacuo. The crude mixture was purified by ISCO column chromatography to obtain (5-benzyloxy-4'-trifluoromethyl-biphenyl-3-yl)-acetic acid ethyl ester (107 g, 100%).

$^1$H-NMR (CDCl$_3$): δ 1.26 (t, 3H), 3.66 (s, 2H), 4.17 (q, 2H), 5.12 (s, 2H), 6.99 (s, 1H), 7.12 (s, 2H), 7.34-7.49 (m, 5H), 7.67 (s, 4H); Calcd for C24H21F3O3 (M+H) 415.14, Found 415.2.

e) 2-(5-Benzyloxy-4'-trifluoromethyl-biphenyl-3-yl)-4-methyl-pent-4-enoic acid ethyl ester

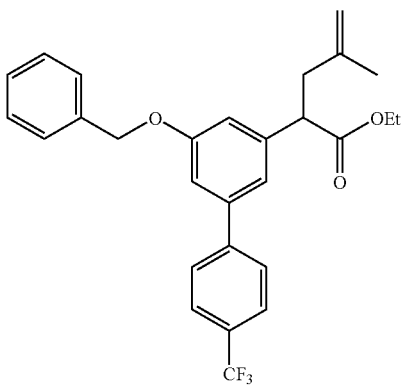

To a solution of compound 1d (4.9 g, 11.8 mmol) in THF (50 mL) at −78° C. was added Li[N(SiMe$_3$)$_2$] (1N in THF, 14.2 mL, 14.2 mmol) dropwise. The reaction mixture was stirred for 1 h at −78° C. and then 3-bromo-2-methyl-propene (1.25 mL, 12.4 mmol) was added dropwise. The solution was slowly warmed up to −35° C. and stirred at −35° C. for 0.5 h. The reaction was quenched with NH$_4$Cl saturated solution and extracted with EtOAc. The organic extracts was dried (Na$_2$SO$_4$), concentrated and purified by column chromatography give compound 1e (5.1 g, 92%) as a clear oil; $^1$H NMR (400 MHz, CHLOROFORM-D) δ ppm 1.19-1.29 (m, 3 H), 1.74 (s, 3 H), 2.47 (m, 1 H), 2.85 (m, 1 H), 3.83 (m, 1 H), 4.11 (m, 2 H), 4.72 (s, 1 H), 4.77 (s, 1 H), 5.12 (s, 2 H), 7.03 (s, 1 H), 7.10 (s, 1 H), 7.15 (s, 1 H), 7.35-7.48 (m, 5 H), 7.67 (s, 4 H); Calcd for C28H27F3O3 (M+H) 469.19, Found 469.

f) 2-(5-Hydroxy-4'-trifluoromethyl-biphenyl-3-yl)-4-methyl-pentanoic acid ethyl ester

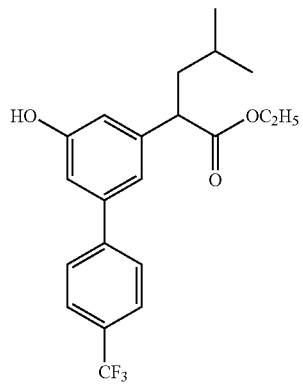

A mixture of compound 1e (5.1 g, 10.9 mmol), 10% Pd/C (500 mg) in EtOH (50 mL) was hydrogenated under H$_2$ (40 psi) in par-shaker for 20 h. The resulting reaction mixture was filtered through a celite pad and the filtrate was concentrated to give the title compound (4.2 g, 100%) as a clear oil; 1H NMR (300 MHz, CHLOROFORM-D) δ ppm 0.92 (d, J=6.6 Hz, 6 H), 1.25 (m, 3 H), 1.49-1.61 (m, 1 H), 1.65-1.70 (m, 1 H), 1.95-2.05 (m, 1 H), 3.67 (t, J=7.7 Hz, 1 H), 4.10-4.29 (m, 2 H), 6.91 (s, 1 H), 6.97 (t, J=2.0 Hz, 1 H), 7.08 (s, 1 H), 7.65 (s, 4 H); Calcd for C21H23F3O3 (M+H) 381.16, Found 381.

g) 4-Methyl-2-(5-trifluoromethanesulfonyloxy-4'-trifluoromethyl-biphenyl-3-yl)-pentanoic acid ethyl ester

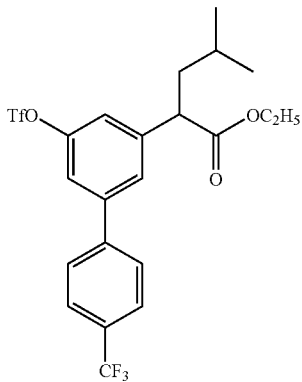

To a solution of compound 1f, 2-(5-Hydroxy-4'-trifluoromethyl-biphenyl-3-yl)-4-methyl-pentanoic acid ethyl ester, 2.8 g, 7.36 mmol) and N-phenyl-bis-(trifluoromethanesulfonimide) (3.16 g, 8.83 mmol) in THF (30 mL) under $N_2$ was added Et$_3$N (2.05 mL, 14.7 mmol). The reaction mixture was heated to reflux overnight. After cooling to room temperature, the solution was concentrated and purified by column chromatography to give the title compound (3.7 g, 98%) as a colorless thick oil; $^1$H NMR (400 MHz, CHLOROFORM-D) δ ppm 0.94 (dd, J=6.60, 1.47 Hz, 6 H), 1.22-1.28 (m, 3 H), 1.46-1.52 (m, 1 H), 1.69 (ddd, J=13.82, 7.09, 6.97 Hz, 1 H), 1.98-2.06 (m, 1 H), 3.75 (t, J=7.83 Hz, 1 H), 4.10-4.21 (m, 2 H), 7.31 (s, 1 H), 7.38 (s, 1 H), 7.57 (s, 1 H), 7.65-7.75 (m, 4 H); Calcd for C22H22F6O5S (M+H) 513.11, Found 513.

h) 4-Methyl-2-[5-(2-propyl-piperidin-1-yl)-4'-trifluoromethyl-biphenyl-3-yl]-pentanoic acid ethyl ester

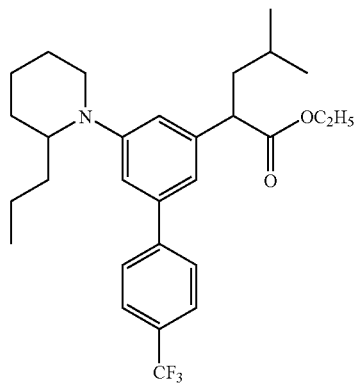

To a solution of 4-methyl-2-(5-trifluoromethanesulfonyloxy-4'-trifluoromethyl-biphenyl-3-yl)-pentanoic acid ethyl ester, 1 g (250 mg, 0.49 mmol) in toluene (5 mL) in a sealed tube was added racemic-2-(di-t-butylphosphino)-1,1'-binaphthyl (59 mg, 0.15 mmol), Pd(OAc)$_2$ (110 mg, 0.49 mmol), 2-propyl-piperidine hydrogen bromide (152 mg, 0.73 mmol). The system was flushed with nitrogen. To this was added NaO$^t$Bu (118 mg, 1.23 mmol) and heated to 100° C. for 3 h. The system was cooled to room temperature and quenched by slow addition of water. The mixture was extracted with EtOAc (3×20 mL). The organic phase was washed with saturated NaHCO$_3$ solution and brine. The organic fraction was dried (MgSO$_4$) and concentrated in vacuo. The crude mixture was purified by ISCO column chromatography to obtain 4-methyl-2-[5-(2-propyl-piperidin-1-yl)-4'-trifluoromethyl-biphenyl-3-yl]-pentanoic acid ethyl ester. Calcd for C29H38F3NO2 (M+H) 490.61, Found 490.4.

i) 4-Methyl-2-[5-(2-propyl-piperidin-1-yl)-4'-trifluoromethyl-biphenyl-3-yl]-pentanoic acid To a solution of 4-methyl-2-[5-(2-propyl-piperidin-1-yl)-4'-trifluoromethyl-biphenyl-3-yl]-pentanoic acid ethyl ester (24 mg, 0.05 mmol) in MeOH (1 mL) was added 3N NaOH (0.200 mL) and heated to 60° C. for 2 h. The reaction was concentrated in vacuo to remove MeOH. The thick liquid was acidified to pH 2 by 2N HCl. The resulting acidic solution was extracted with EtOAc. The organic fraction was dried (MgSO$_4$) and concentrated in vacuo. The crude mixture was purified by Gilson reverse phase column chromatography to obtain 4-methyl-2-[5-(2-propyl-piperidin-1-yl)-4'-trifluoromethyl-biphenyl-3-yl]-pentanoic acid.

$^1$H-NMR (CDCl3): δ 0.73 (m, 3H), 0.92 (m, 6H), 1.09 (m, 1H), 1.32 (m, 2H), 1.48 (m, 1H), 1.57-1.72 (m, 3H), 1.88 (t, 1H), 1.97-2.06 (m, 3H), 2.12-2.28 (m, 2H), 3.26 (q, 1H), 3.36 (t, 1H), 3.67-3.81 (m, 2H), 7.58-7.73 (m, 7H); Calcd for C27H34F3NO2 (M+H) 462.56, Found 462.3

EXAMPLE 2

2-[5-(2-Ethyl-piperidin-1-yl)-4'-trifluoromethyl-biphenyl-3-yl]-4-methyl-pentanoic acid

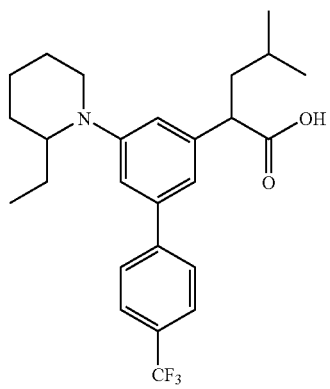

a) 2-[5-(2-Ethyl-piperidin-1-yl)-4'-trifluoromethyl-biphenyl-3-yl]-4-methyl-pentanoic acid ethyl ester

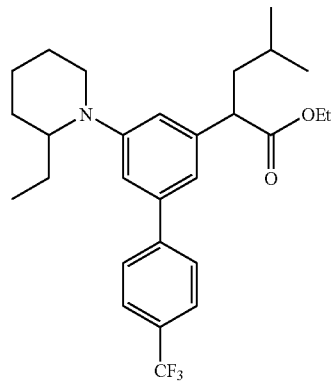

To a solution of 4-methyl-2-(5-trifluoromethanesulfonyloxy-4'-trifluoromethyl-biphenyl-3-yl)-pentanoic acid ethyl ester, 1g (250 mg, 0.49 mmol) in toluene (5 mL) in a sealed tube was added racemic-2-(di-t-butylphosphino)-1,1'-binaphthyl (59 mg, 0.15 mmol), Pd(OAc)$_2$ (110 mg, 0.49 mmol), 2-ethyl-piperidine (83 mg, 0.73 mmol). The system was flushed with nitrogen. To this was added NaO$^t$Bu (70 mg, 0.73 mmol) and heated to 100° C. for 3 h. The system was cooled to room temperature and quenched by slow addition of water. The mixture was extracted with EtOAc (3×20 mL). The organic phase was washed with saturated NaHCO$_3$ solution and brine. The organic fraction was dried (MgSO$_4$) and concentrated in vacuo. The crude mixture was purified by ISCO column chromatography to obtain 2-[5-(2-ethyl-piperidin-1-yl)-4'-trifluoromethyl-biphenyl-3-yl]-4-methyl-pentanoic acid ethyl ester. Calcd for C28H36F3NO2 (M+H) 476.59, Found 476.38.

b) 2-[5-(2-Ethyl-piperidin-1-yl)-4'-trifluoromethyl-biphenyl-3-yl]-4-methyl-pentanoic acid To a solution of 2-[5-(2-ethyl-piperidin-1-yl)-4'-trifluoromethyl-biphenyl-3-yl]-4-methyl-pentanoic acid ethyl ester (12 mg, 0.03 mmol) in MeOH (1 mL) was added 3N NaOH (0.200 mL) and heated to 60° C. for 2 h. The reaction was concentrated in vacuo to remove MeOH. The thick liquid was acidified to pH=2 by 2N HCl. The resulting acidic solution was extracted with EtOAc. The organic fraction was dried (MgSO$_4$) and concentrated in vacuo. The crude mixture was purified by Gilson reverse phase column chromatography to obtain 2-[5-(2-ethyl-piperidin-1-yl)-4'-trifluoromethyl-biphenyl-3-yl]-4-methyl-pentanoic acid. $^1$H-NMR (CDCl3): δ 0.80 (t, 3H), 0.92 (d, 6H), 1.44 (m, 1H), 1.50 (q, 1H), 1.58-1.69 (m, 3H), 1.89 (m, 1H), 2.02 (m, 2H), 2.14-2.26 (m, 2H), 3.29 (m, 2H), 3.68-3.81 (m, 2H), 7.59-7.73 (m, 7H); Calcd for C26H32F3NO2 (M+H) 448.53, Found 448.34

EXAMPLE 3

4-Methyl-2-[5-(2-methyl-piperidin-1-yl)-4'-trifluoromethyl-biphenyl-3-yl]-pentanoic acid

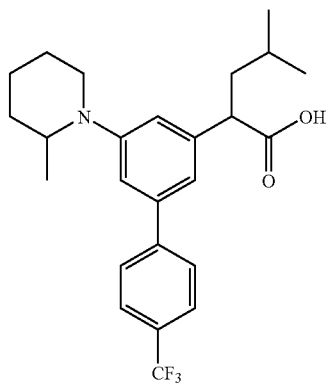

a) 4-Methyl-2-[5-(2-methyl-piperidin-1-yl)-4'-trifluoromethyl-biphenyl-3-yl]-pentanoic acid ethyl ester

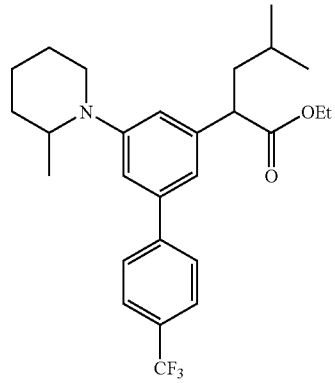

To a solution of 4-methyl-2-(5-trifluoromethanesulfonyloxy-4'-trifluoromethyl-biphenyl-3-yl)-pentanoic acid ethyl ester, 1g (63 mg, 0.12 mmol) in toluene (1 mL) in a sealed tube was added racemic-2-(di-t-butylphosphino)-1,1'-binaphthyl (48 mg, 0.12 mmol), Pd(O AC)$_2$ (27 mg, 0.12 mmol), 2-methyl-piperidine (0.020 mL, 0.17 mmol). The system was flushed with nitrogen. To this was added NaO$^t$Bu (14 mg, 0.14 mmol) and heated to 100° C. for 10 minutes. The reaction was cooled to room temperature. To this was added another portion of Pd(OAC)$_2$ (27 mg, 0.12 mmol), 2-methyl-piperidine (0. 020 mL, 0.17 mmol) and NaO$^t$Bu (14 mg, 0.14 mmol). The system was heated to 100° C. for 5 minutes, cooled to room temperature and quenched by slow addition of water. The mixture was extracted with EtOAc (3×20 mL). The organic phase was washed with saturated NaHCO$_3$ solution and brine. The organic fraction was dried (MgSO$_4$) and concentrated in vacuo. The crude mixture was purified by ISCO column chromatography to obtain 4-methyl-2-[5-(2- methyl-piperidin-1-yl)-4'-trifluoromethyl-biphenyl-3-yl]-pentanoic acid ethyl ester. Calcd for C27H34F3NO2 (M+H) 462.56, Found 462.3.

b) 4-Methyl-2-[5-(2-methyl-piperidin-1-yl)-4'-trifluoromethyl-biphenyl-3-yl]-pentanoic acid To a solution of 4-methyl-2-[5-(2-methyl-piperidin-1-yl)-4'-trifluoromethyl-biphenyl-3-yl]-pentanoic acid ethyl ester (18 mg, 0.04 mmol) in MeOH (1 mL) was added 3N NaOH (0.200 mL) and heated to 60° C. for 2 h. The reaction was concentrated in vacuo to remove MeOH. The thick liquid was acidified to pH 2 by 2N HCl. The resulting acidic solution was extracted with EtOAc. The organic fraction was dried (MgSO$_4$) and concentrated in vacuo. The crude mixture was purified by Gilson reverse phase column chromatography to obtain 4-methyl-2-[5-(2-methyl-piperidin-1-yl)-4'-trifluoromethyl-biphenyl-3-yl]-pentanoic acid. $^1$H-NMR (MeOD-d$_4$): δ 0.96 (m, 6H), 1.10 (dd, 3H), 1.51 (m, 1H), 1.76 (m, 1H), 1.82 (m, 2H), 1.96-2.10 (m, 4H), 2.19 (d, 1H), 3.73 (m, 2H), 3.89 (t, 1H), 3.95 (m, 1H), 7.68 (s, 1H), 7.80-7.89 (m, 6H); Calcd for C25H30F3NO2 (M+H) 434.51, Found 434.2

EXAMPLE 4

4-methyl-2-(4'-(trifluoromethyl)-5-(4-(trifluoromethyl)piperidin-1-yl)biphenyl-3-yl)pentanoic acid

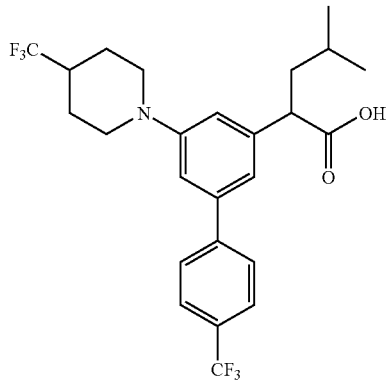

a) 4-methyl-2-(4'-(trifluoromethyl)-5-(4-(trifluoromethyl)piperidin-1-yl)biphenyl-3-yl) pentanoic acid ethyl ester

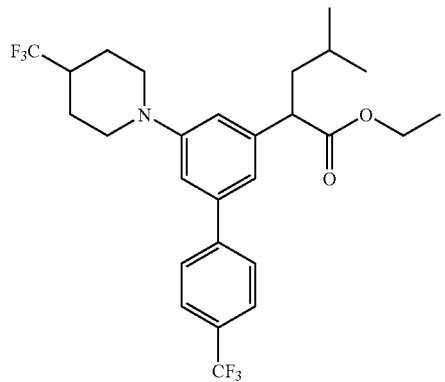

A solution of Pd(OAc)$_2$ (6 mg, 0.025 mmol) and rac-BINAP (56 mg, 0.09 mmol) in THF (2.0 mL) was stirred under nitrogen for 10 min. Cs$_2$CO$_3$ (182 mg, 0.58 mmol), 4-methyl-2-(5-trifluoromethanesulfonyloxy-4'-trifluoromethyl-biphenyl-3-yl)-pentanoic acid methyl ester, compound 1g (100 mg, 0.21 mmol) and 4-(triflurormethyl)piperidine.hydrochloride (0.041 mg, 0.25 mmol) were added and the reaction mixture was stirred under nitrogen at 65° C. for 48 h. The solution was then partitioned between EtOAc (10 mL) and H$_2$O (10 mL). The aqueous layer was extracted with EtOAc (2×10 mL). The organic layers were washed with brine, dried (MgSO$_4$) and concentrated to yield an oil. The residue was purified by flash chromatography (0 to 10% EtOAc in petroleum ether) to give the title compound. The resulting oil was used crude in the next step.

b) 4-methyl-2-(4'-(trifluoromethyl)-5-(4-(trifluoromethyl)piperidin-1-yl)biphenyl-3-yl) pentanoic acid A solution of 2-[5-(2,3-dihydro-indol-1-yl)-4'-trifluoromethyl-biphenyl-3-yl]-4-methyl-pentanoic acid methyl ester, MeOH (1 mL), THF (1 mL) and 10% aq. LiOH solution (0.2 mL) was stirred at 40° C. for 18 h. The solution was then acidified with aq. 2M HCl and extracted with DCM (3×1 mL). The organic layers were filtered through PTFE filter and concentrated to yield an oil. The residue was purified using reverse phase preparative HPLC (H$_2$O: MeCN) to give the title product in 8% yield as a colourless oil.

$^1$H-NMR (400 MHz, CD$_3$Cl): δ 7.55 (d, 2H), 7.51 (d, 2H), 7.02-6.84 (m, 3H), 3.60-3.56 (m, 1H), 3.33-3.30 (m, 3H), 3.23-3.21 (m, 1H), 2.12-2.03 (m, 3H), 1.93-1.85 (m, 1H), 1.60-1.53 (m, 2H), 1.45-1.39 (m, 1H), 1.33-1.29 (m, 1H), 0.81 (d, 6H); RT=4.07 min

EXAMPLE 5

2-(5-(4,4-difluoropiperidin-1-yl)-4'-(trifluoromethyl)biphenyl-3-yl)-4-methylpentanoic acid

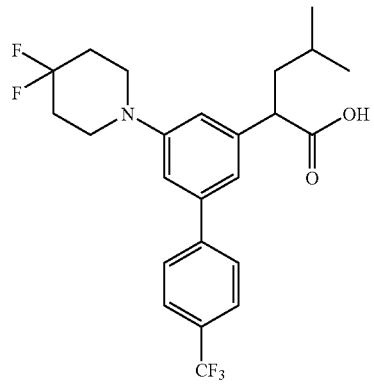

The title compound was prepared in 18% yield using 4,4-difluoropiperidine under the conditions described in Example 4.

$^1$H-NMR (400 MHz, CD$_3$Cl): δ 7.61 (d, 2H), 7.58 (d, 2H), 7.19-7.05 (m, 3H), 3.76-3.73 (m, 2H), 3.67-3.61 (m, 1H), 3.90-2.78 (m, 1H), 2.26-2.11 (m, 1H), 2.02-1.89 (m, 3H), 1.66-1.59 (m, 1H), 1.25-1.13 (m, 3H), 0.86 (d, 6H); Mass spectrum (ESI, m/z): 456 (M+H), RT=3.5 min.

EXAMPLE 6

4-Methyl-2-[5-(6-methyl-piperidin-2-yl)-4'-trifluoromethyl-biphenyl-3-yl]-pentanoic acid

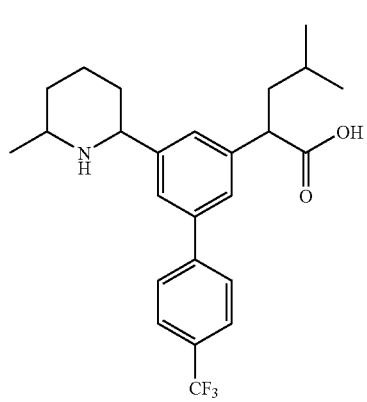

a) 4-Methyl-2-[5-(4,4,5,5-tetramethyl-[1,3,2]dioxaborolan-2-yl)-4'-trifluoromethyl-biphenyl-3-yl]-pentanoic acid ethyl ester

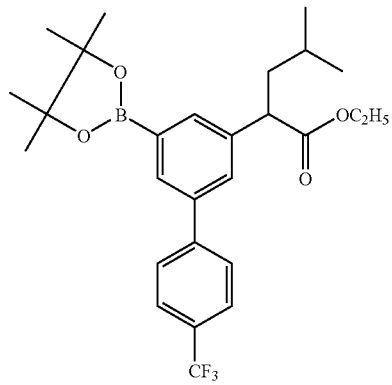

To a solution of 4-Methyl-2-(5-trifluoromethanesulfonyloxy-4'-trifluoromethyl-biphenyl-3-yl)-pentanoic acid ethyl ester, compound 1g (101 mg, 0.20 mmol) and Dichloro[1,1'-bis(diphenylphosphino)ferrocene]palladium (II) dichloromethane adduct (44.0 mg, 0.06 mmol) in dioxane (1 mL), degassed under N$_2$, was added Et$_3$N (82.2 µl, 0.59 mmol) and bis)pinacolato)diboron (150.0 mg, 0.059 mmol). The reaction mixture was degassed and heated to reflux overnight. After cooling to room temperature, the solution was quenched with water, extracted with dichloromethane (3×) and dried over magnesium sulfate, concentrated and purified by column chromatography to give the title compound (32 mg, 33%) as a clear oil; 1H NMR (300 MHz, CHLOROFORM-D) α ppm 0.93 (d, J=6.78 Hz, 6 H) 1.19-1.27 (m, 3 H) 1.33-1.39 (m, 12 H) 1.52 (dt, J=13.28, 6.73 Hz, 1 H) 1.68 (dt, J=13.66, 6.92 Hz, 1 H) 2.06 (ddd, J=13.56, 8.67, 6.78 Hz, 1 H) 3.75 (dd, J=8.67, 6.78 Hz, 1 H) 4.05-4.20 (m, 2 H) 7.65-7.75 (m, 5 H) 7.76 (s, 1 H) 7.94 (s, 1 H); Calcd for C27H34BF3O4 (M+H) 490.36, Found 490.4.

b) 4-Methyl-2-[5-(6-methyl-pyridin-2-yl)-4'-trifluoromethyl-biphenyl-3-yl]-pentanoic acid ethyl ester

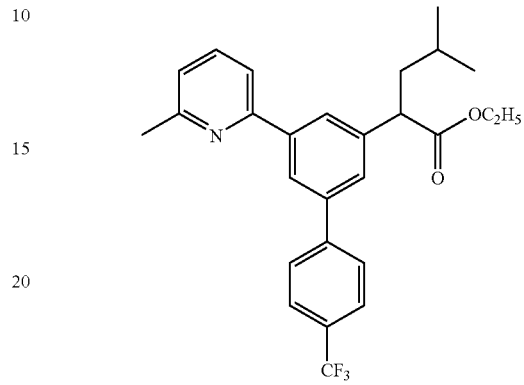

To 4-Methyl-2-[5-(4,4,5,5-tetramethyl-[1,3,2]dioxaborolan-2-yl)-4'-trifluoromethyl-biphenyl-3-yl-pentanoic acid ethyl ester, compound 6a (797 mg, 1.63 mmol) in dimethoxyethane (11 mL), was added 2-Bromo-6-methylpyridine (560 mg, 3.25 mmol), and 2M Na$_2$CO$_3$ (2.5 mL, 4.82 mmol). The mixture was degassed, tetrakis(triphenylphosphine)palladium (0) (377 mg, 0.326 mmol) was added and the mixture was degassed, and then heated to 80° C. After 2 hours, additional 2-Bromo-6-methylpyridine (560 mg, 3.25 mmol), 2M Na$_2$CO$_3$ (2.5 mL, 4.82 mmol). And tetrakis(triphenylphosphine)palladium (0) (377 mg, 0.326 mmol) was added. The reaction continued at 65° C. over 72 hours. The reaction was cooled to room temperature, diluted with EtOAc and washed with NaHCO$_3$ and brine. Purification by column chromatography to gave the title compound (172 mg, 23%). Calcd for C27H28F3NO4 (M+H) 455.51, Found 456.3.

c) 4-Methyl-2-[5-(6-methyl-piperidin-2-yl)-4'-trifluoromethyl-biphenyl-3-yl]-pentanoic acid ethyl ester

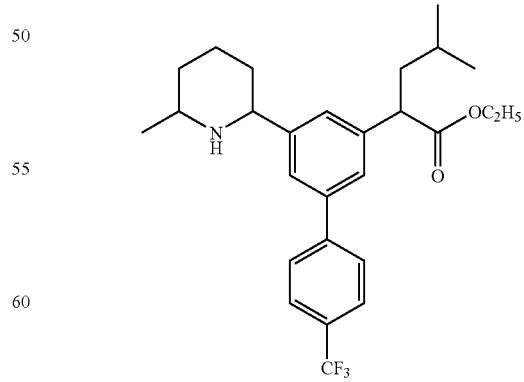

A solution of 4-Methyl-2-[5-(6-methyl-pyridin-2-yl)-4'-trifluoromethyl-biphenyl-3-yl]-pentanoic acid ethyl ester, compound 6b (161 mg, 0.35 mmol) in MeOH (12 mL), platinum oxide (8.0 mg, 0.35 mmol) and 4N HCl/dioxane (97.3 µL) was hydrogenated at 40 psi for 6 hours. The reaction mixture was filtered through celite, washed with MeOH and concentrated in vacuo. The residue was partitioned between dichloromethane/Na$_2$CO$_3$ and extracted 3×, dried over MgSO$_4$, filtered and concentrated to give the product as a pink oil (202 mg, quant.) (M+H) 461.56, Found 462.3.

d) 4-Methyl-2-[5-(6-methyl-piperidin-2-yl)-4'-trifluoromethyl-biphenyl-3-yl]-pentanoic acid To 4-Methyl-2-[5-(6-methyl-piperidin-2-yl)-4'-trifluoromethyl-biphenyl-3-yl]-pentanoic acid ethyl ester, compounds 6c in EtOH (4 mL) was added 2M KOH (162 µL, 0.324 mmol). The reaction was heated to 80° C. for 2 hours, cooled to room temperature, and concentrated in vacuo. Purification via Gilson HPLC, followed by salt exchange with aqueous 1N HCl gave the product as a white solid. 1H NMR (300 MHz, MeOD) δ ppm 0.96 (dd, J=6.59, 1.70 Hz, 6 H) 1.39 (d, J=6.41 Hz, 3 H) 1.49-1.63 (m, 2 H) 1.65-1.80 (m, 1 H) 1.85 (d, J=4.14 Hz, 1 H) 2.06 (dt, J=13.56, 7.72 Hz, 5 H) 3.35-3.49 (m, 1 H) 3.83 (t, J=7.72 Hz, 1 H) 4.36 (dd, J=12.06, 2.64 Hz, 1 H) 7.53-7.57 (m, 1 H) 7.73 (s, 2 H) 7.76-7.88 (m, 4 H) Calcd for C25H30F3NO2 (M+H) 433.51, Found 434.2.

EXAMPLE 7

2-{5-[1-(4-Methoxy-benzyl)-6-trifluoromethyl-piperidin-2-yl]-4'-trifluoromethyl-biphenyl-3-yl}-4-methyl-pentanoic acid

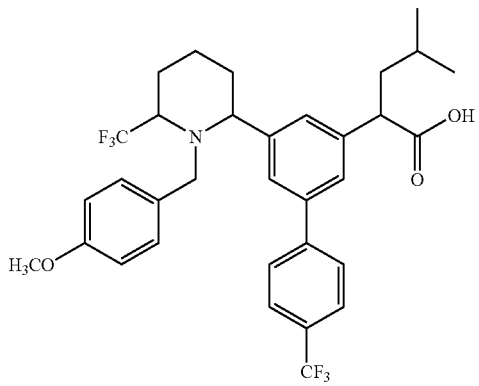

a) 4-Methyl-2-[4'-trifluoromethyl-5-(6-trifluoromethyl-pyridin-2-yl)-biphenyl-3-yl]-pentanoic acid ethyl ester

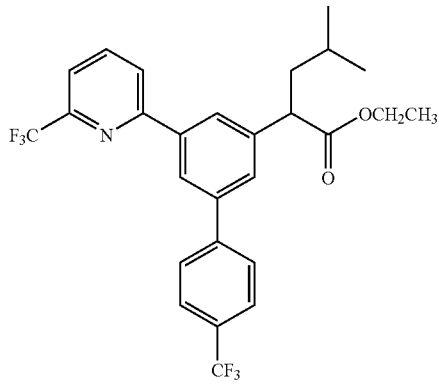

To 4-Methyl-2-(5-trifluoromethanesulfonyloxy-4'-trifluoromethyl-biphenyl-3-yl)-pentanoic acid ethyl ester, compound 1g (1.09 mg, 2.13 mmol) in dimethoxyethane (15 ml), was added 6-(Trifluoromethyl)pyridine-2-boronic acid pinacol ester (750 mg, 2.56 mmol), and 2M Na$_2$CO$_3$ (2.1 mL, 4.26 mmol). The mixture was degassed, tetrakis(triphenylphosphine)palladium (0) (490 mg, 0.426 mmol) was added and the mixture was degassed, and then heated to 80° C. After 1 hr, the reaction was cooled to room temperature, diluted with EtOAc and washed with NaHCO$_3$ and brine. Purification by column chromatography gave the title compound (987 mg, 91%). Calcd for C27H25F6NO2 (M+H) 509.44, Found 510.3.

b) 4-Methyl-2-[4'-trifluoromethyl-5-(6-trifluoromethyl-piperidin-2-yl)-biphenyl-3-yl]-pentanoic acid ethyl ester

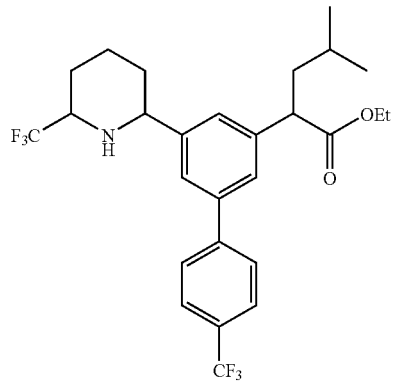

A solution of 4-Methyl-2-[4'-trifluoromethyl-5-(6-trifluoromethyl-pyridin-2-yl)-biphenyl-3-yl]-pentanoic acid ethyl ester, compound 7a (865 mg, 1.7mmol) in MeOH (50 mL), platinum oxide (39.0 mg, 0. 17 mmol) and 4N HCl/dioxane (500 µl) was hydrogenated at 20 psi for 4 hours. The reaction mixture was filtered through celite, washed with MeOH and concentrated in vacuo. The residue was partitioned between dichloromethane and Na$_2$CO$_3$ to give the free base. Purification by silica gel chromatography gave the desired product (813 mg, 93%) (M+H) 515.53, Found 516.3.

c) 2-{5-[1-(4-Methoxy-benzyl)-6-trifluoromethyl-piperidin-2-yl]-4'-trifluoromethyl-biphenyl-3-yl}-4-methyl-pentanoic acid ethyl ester

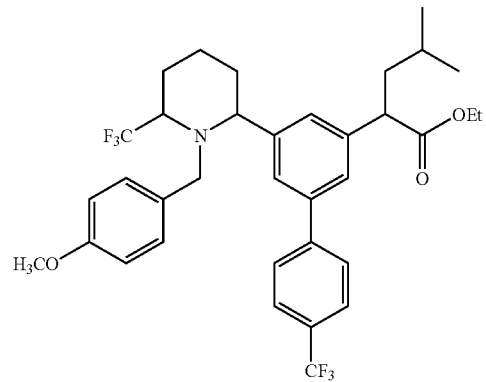

4-Methyl-2-[4'-trifluoromethyl-5-(6-trifluoromethyl-piperidin-2-yl)-biphenyl-3-yl]-pentanoic acid ethyl ester, compound 7b (47 mg, 0.092 mmol), 4-Methoxybenzyl bromide (66 μl, 0.46 mmol), DIEA (160 μl, 0.919), and tetrabutylammonium iodide (TBAI)(36 mg, 0.096 mmol) were combined and heated to 80° C. After overnight, no product was formed. Cesium carbonate (30 mg, 0.46 mmol) was added and after 5.5 hours ~30% product was obtained. Additional Cesium carbonate (30 mg), bromide (66 ml) and TBAI were added and the reaction continued 72 hours. Little change in product formation. Reaction was purified directly by silica gel chromatography to give 21.3 mg, 36% as a clear oil. (M+H) 635.38, Found 636.4.

d) 2-{5-[1-(4-Methoxy-benzyl)-6-trifluoromethyl-piperidin-2-yl]-4'-trifluoromethyl-biphenyl-3-yl}-4-methyl-pentanoic acid To 2-{5-[1-(4-Methoxy-benzyl)-6-trifluoromethyl-piperidin-2-yl]-4'-trifluoromethyl-biphenyl-3-yl}-4-methyl-pentanoic acid ethyl ester, compound 7c (21.3 mg, 0.034 mmol) in EtOH (2 mL) was added 2M KOH (67 μl, 0.134 mmol). The reaction was heated to 78° C. for 5 hours, cooled to room temperature, and concentrated in vacuo. Purification via Gilson HPLC, followed by salt exchange with aqueous 1N HCl and subsequent lyophilization, gave the title compound as a white solid. (13 mg, 61%) 1H NMR (300 MHz, MeOD) δ ppm 0.89-0.99 (m, 6 H) 1.53 (dd, J=13.38, 6.59 Hz, 1 H) 1.68 (ddd, J=13.75, 7.16, 6.97 Hz, 1 H) 1.74-1.89 (m, 4 H) 1.92-2.07 (m, 3 H) 3.50-3.58 (m, 1H) 3.68 (s, 3 H) 3.67-3.82 (m, 4 H) 6.70 (d, J=8.67 Hz, 2 H) 7.01 (d, J=7.16 Hz, 2 H) 7.41-7.54 (m, 3 H) 7.68-7.77 (m, 4 H) Calcd for C33H35F6NO3 (M+H) 607.63, Found 608.4.

EXAMPLE 8

4-Methyl-2-{4'-trifluoromethyl-5-[6-trifluoromethyl-1-(4-trifluoromethyl-benzyl)-piperidin-2-yl]-biphenyl-3-yl}-pentanoic acid

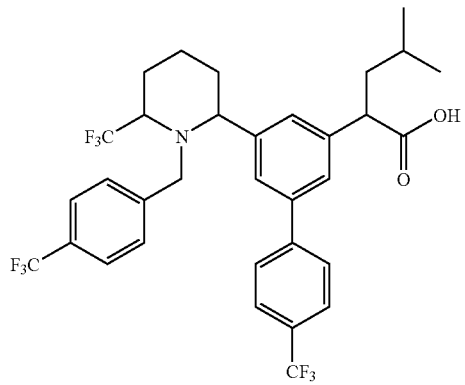

a) 4-Methyl-2-{4'-trifluoromethyl-5-[6-trifluoromethyl-1-(4-trifluoromethyl-benzyl)-piperidin-2-yl]-biphenyl-3-yl}-pentanoic acid ethyl ester

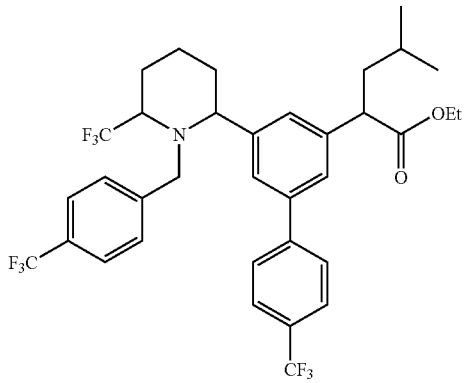

4-Methyl-2-[4'-trifluoromethyl-5-(6-trifluoromethyl-piperidin-2-yl)-biphenyl-3-yl]-pentanoic acid ethyl ester 7b (37 mg, 0.072 mmol), 4-trifluoromethylbenzyl bromide (86 mg, 0.36 mmol), DIEA (125 μl, 0.72), and tetrabutylammonium iodide (TBAI)(10 mg, 0.096 mmol) were combined and heated under microwave conditions to 150° C. After several additions of the starting materials and ~90 minutes under microwave, ~50% product was formed. The reaction was diluted with EtOAc, washed with brine, sat. NaHCO₃, and brine, dried over magnesium sulfate and filtered. Purification by silica gel chromatography gave the product as yellow oil. (25 mg, 52%) (M+H) 73.65, Found 674.4 b) 4-Methyl-2-{4'-trifluoromethyl-5-[6-trifluoromethyl-1-(4-trifluoromethyl-benzyl)-piperidin-2-yl]-biphenyl-3-yl}-pentanoic acid To a solution of 4-methyl-2-{4'-trifluoromethyl-5-[6-trifluoromethyl-1-(4-trifluoromethyl-benzyl)-piperidin-2-yl]-biphenyl-3-yl}-pentanoic acid ethyl ester, compound 8a (25 mg, 0.037 mmol), in EtOH (2 mL) was added 2M KOH (74 μl, 0.148 mmol). The reaction was heated to 78° C. for 5 hours, cooled to room temperature, and concentrated in vacuo. Purification via Gilson HPLC, followed by salt exchange with aqueous 1N HCl gave the product as a white solid. (2.1 mg, 9%) 1H NMR (300 MHz, MeOD) δ ppm 0.86-0.96 (m, 6 H) 1.43-1.50 (m, 1 H) 1.54-1.64 (m, J=13.52, 6.97, 6.83, 3.58 Hz, 2 H) 1.83-1.98 (m, 5 H) 2.10-2.30 (m, 1 H) 3.58-3.73 (m, 2 H) 3.98 (d, J=17.71 Hz, 3 H) 7.18-7.26 (m, 2 H) 7.35 (d, J=8.67 Hz, 3 H) 7.44-7.49 (m, 2 H) 7.60-7.65 (m, 2 H) 7.68-7.74 (m, 2 H) Calcd for C33H32F9NO2 (M+H) 645.60, Found 646.3.

EXAMPLE 9

2-[5-(1-Benzyl-6-trifluoromethyl-piperidin-2-yl)-4'-trifluoromethyl-biphenyl-3-yl]-4-methyl-pentanoic acid

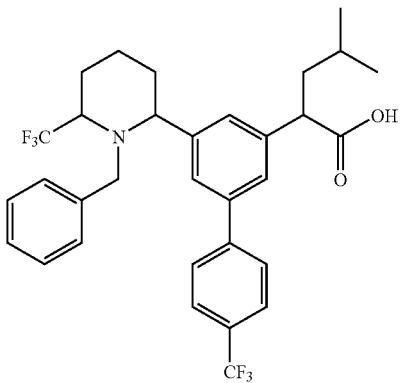

a) 2-[5-(1-Benzyl-6-trifluoromethyl-piperidin-2-yl)-4'-trifluoromethyl-biphenyl-3-yl]-4-methyl-pentanoic acid ethyl ester

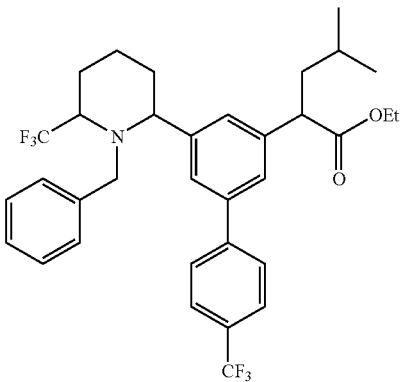

4-Methyl-2-[4'-trifluoromethyl-5-(6-trifluoromethyl-piperidin-2-yl)-biphenyl-3-yl]-pentanoic acid ethyl ester, compound 7b (32 mg, 0.062 mmol), Benzyl bromide (55 μl, 0.46 mmol), DIEA (110 μl, 0.62), and tetrabutylammonium iodide (TBAI)(10 mg) in acetonitrile (0.5 mL) were combined and heated under microwave conditions 150° C. for 30 minutes. The reaction was diluted with EtOAc, washed with brine, sat. NaHCO$_3$, and brine, dried over magnesium sulfate and filtered. Purification by silica gel chromatography gave the product as yellow oil. (56 mg, quant.) (M+H) 605.65, Found 606.2 b) 2-[5-(1-Benzyl-6-trifluoromethyl-piperidin-2-yl)-4'-trifluoromethyl-biphenyl-3-yl]-4-methyl-pentanoic acid To a solution of 2-[5-(1-Benzyl-6-trifluoromethyl-piperidin-2-yl)-4'-trifluoromethyl-biphenyl-3-yl]-4-methyl-pentanoic acid ethyl ester, compound 8a (38 mg, 0.062 mmol), in EtOH (3 mL) was added 2M KOH (310 μl, 0.62 mmol). The reaction was heated to 78° C. for 1.5 hours, cooled to room temperature, and concentrated in vacuo. Purification via Gilson HPLC, followed by salt exchange with aqueous 1N HCl gave the product as a light yellow solid. (18.6 mg, 52%) 1H NMR (300 MHz, MeOD) δ ppm 0.81-0.88 (m, 6 H) 1.42 (dd, J=13.38, 6.59 Hz, 1 H) 1.55 (dd, J=13.56, 7.16 Hz, 2 H) 1.63-1.76 (m, 4 H) 1.82-1.97 (m, 2 H) 3.39-3.49 (m, 1 H) 3.61 (td, J=7.82, 2.83 Hz, 1 H) 3.68-3.77 (m, 3 H) 6.96-7.09 (m, 5 H) 7.29-7.37 (m, 2 H) 7.43 (s, 1 H) 7.58-7.66 (m, 4 H) Calcd for C32H33F6NO2 (M+H) 577.60, Found 578.4.

EXAMPLE 10

4-Methyl-2-{5-[1-(3-methyl-butyl)-piperidin-2-yl]-4'-trifluoromethyl-biphenyl-3-yl}-pentanoic acid

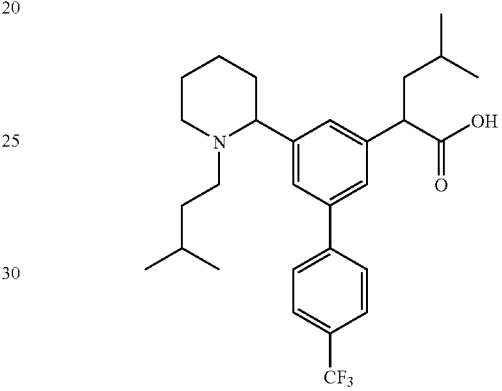

a) 4-Methyl-2-(5-pyridin-2-yl-4'-trifluoromethyl-biphenyl-3-yl)-pentanoic acid ethyl ester

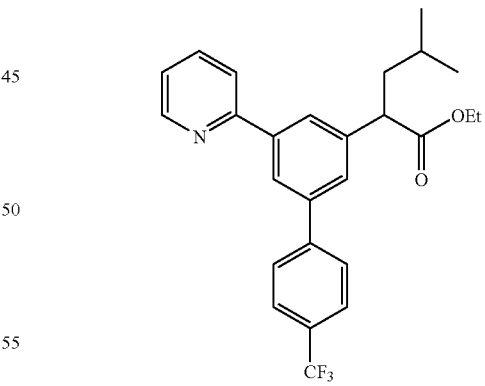

To a solution of 4-Methyl-2-(5-trifluoromethanesulfonyloxy-4'-trifluoromethyl-biphenyl-3-yl)-pentanoic acid ethyl ester, compound 1g (105 mg, 0.205 mmol) in dimethoxyethane (1.4 mL), was added 2-pyridine boronic acid pinacol ester adduct (169 mg, 0.41 mmol), and 2M Na$_2$CO$_3$ (0.31 ml, 0.614 mmol). The mixture was degassed, tetrakis(triphenylphosphine)palladium (0) (24.0 mg, 0.02 mmol) was added and the mixture was degassed again, and then heated to 80° C. overnight. The reaction was cooled to room temperature, diluted with EtOAc and washed with NaHCO$_3$ and brine. Purification by column chromatography gave the title compound (30 mg, 33%). Calcd for C26H26F3NO2 (M+H) 441.49, Found 442.2.

b) 4-Methyl-2-(5-piperidin-2-yl-4'-trifluoromethyl-biphenyl-3-yl)-pentanoic acid ethyl ester

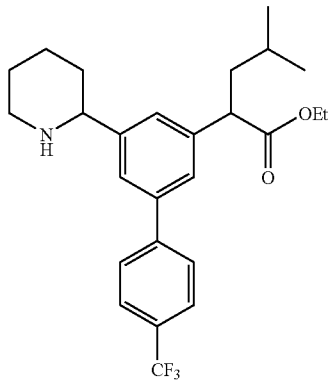

A solution of 4-Methyl-2-(5-pyridin-2-yl-4'-trifluoromethyl-biphenyl-3-yl)-pentanoic acid ethyl ester, compound 10a (30 mg, 0.068 mmol) in MeOH (2.3 mL), platinum oxide (1.55 mg, 0.007 mmol) and 4N HCl/dioxane (19 µl) was hydrogenated at 30 psi for 3 hours. The reaction mixture was filtered through celite, washed with MeOH and concentrated in vacuo. The residue was partitioned between dichloromethane and Na$_2$CO$_3$ to give the free base; (30 mg, 99%). Calculated for C26H32F3NO2 (M+H) 447.53, Found 448.4 c) 4-Methyl-2-{5-[1-(3-methyl-butyl)-piperidin-2-yl]-4'-trifluoromethyl-biphenyl-3-yl}-pentanoic acid ethyl ester To a solution of 4-Methyl-2-(5-piperidin-2-yl-4'-trifluoromethyl-biphenyl-3-yl)-pentanoic acid ethyl ester, compound 10b (30.0 mg, 0.067 mmol) in CH$_3$CN (0.5 mL) was added 1-iodo-3methylbutane (16.0 mg, 0.08 mmol) and cesium carbonate (44.0 mg, 0.134 mmol). The reaction was heated to 78° C. overnight. The reaction was cooled to room temperature, concentrated in vacuo, diluted with EtOAc, washed with NaHCO$_3$, and brine. The solution was filtered, and concentrated, then purified via Gilson HPLC to give the compound as a light yellow oil. (31.8 mg, 92%) Calculated for C31H42F3NO2 (M+H) 517.67, Found 518.4.

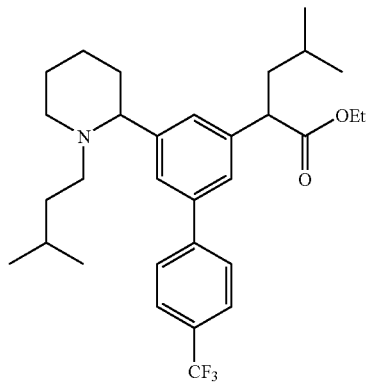

d) 4-Methyl-2-{5-[1-(3-methyl-butyl)-piperidin-2-yl]-4'-trifluoromethyl-biphenyl-3-yl}-pentanoic acid To a solution of 4-Methyl-2-{5-[1-(3-methyl-butyl)-piperidin-2-yl]-4'-trifluoromethyl-biphenyl-3-yl}-pentanoic acid ethyl ester, compound 10c (32.0 mg, 0.06 mmol)in EtOH (3 mL) was added 2M KOH (130 µl, 0.25 mmol). The reaction was heated to 78° C. for 2 hours, cooled to room temperature, and concentrated in vacuo. Purification via Gilson HPLC, followed by salt exchange with aqueous 1N HCl, followed by lyophilization gave the title compound as a white solid. (12.0 mg, 40%) 1H NMR (300 MHz, MeOD) δ ppm 0.70-0.77 (m, 6 H) 0.90-0.98 (m, 6 H) 1.32 (dt, J=11.59, 5.70 Hz, 1 H) 1.46-1.55 (m, 1 H) 1.63 (td, J=11.59, 6.22 Hz, 1 H) 1.71-1.87 (m, 2 H) 1.98-2.11 (m, 4 H) 2.13-2.18 (m, 1 H) 2.81-2.97 (m, 2 H) 3.22 (td, J=12.15, 3.96 Hz, 1 H) 3.71-3.87 (m, 2 H) 4.32-4.42 (m, 1 H) 7.54-7.60 (m, 1 H) 7.75-7.89 (m, 6 H) Calcd for C29H38F3NO2 (M+H) 489.61, Found 490.0.

EXAMPLE 11

[5-(1-Methyl-6-trifluoromethyl-piperidin-2-yl)-4'-trifluoromethyl-biphenyl-3-yl]-acetic acid

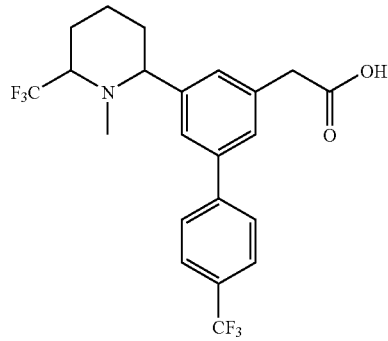

a) (3,5-Bis-trifluoromethanesulfonyloxy-phenyl)-acetic acid ethyl ester

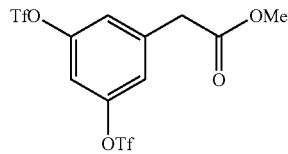

To a solution of (3,5-Dihydroxy-phenyl)-acetic acid, methyl ester (2.0 g, 11 mmol) and N-phenyl-bis-(trifluoromethanesulfonimide) (8.6 g, 24.2 mmol) in THF (100 mL) under N$_2$ was added Et$_3$N (6.1 mL, 44 mmol). The reaction mixture was heated to 50° C. for 2 days. After cooling to room temperature, the solution was concentrated and purified by column chromatography to give the title compound 11a (5.2 g) as a colorless thick oil;

b) (5-Trifluoromethanesulfonyloxy-4'-trifluoromethyl-biphenyl-3-yl)-acetic acid methyl ester

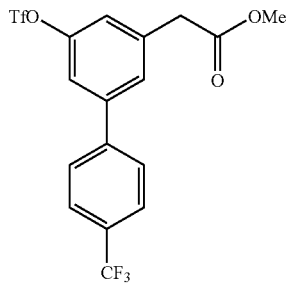

A mixture of compound 11a (4.5 g, 10.1 mmol), 4-trifluoromethyl-phenylboronic acid (1.92 g, 10.1 mmol), Pd(PPh$_3$)$_4$ (1.1 g, 1.01 mmol) and Na$_2$CO$_3$ (2N in H$_2$O, 10.1 mL, 20.2 mmol) in DME (1 mL) was heated to 85° C. for 17 h. After cooling to room temperature, the solution was partitioned between EtOAc and H$_2$O. The organic layer was dried (Na$_2$SO$_4$), concentrated and purified by column chromatography to give 3.0 g (65%) of compound 11b as a colorless thick oil; 1H NMR (400 MHz, CHLOROFORM-D) δ ppm 3.75 (s, 5 H) 7.20-7.70 (m, 7 H).

c) [4'-Trifluoromethyl-5-(6-trifluoromethyl-pyridin-2-yl)-biphenyl-3-yl]-acetic acid methyl ester

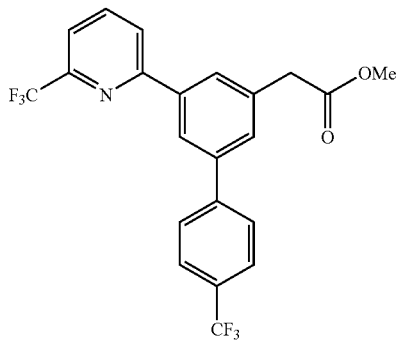

Replacing 4-trifluoromethyl-phenylboronic acid with 6-(trifluoromethyl)pyridine-2-boronic acid pinacol ester following the same Suzuki coupling procedure as in the preparation of 11b gave compound 11c.

d) [4'-Trifluoromethyl-5-(6-trifluoromethyl-piperidin-2-yl)-biphenyl-3-yl]-acetic acid methyl ester

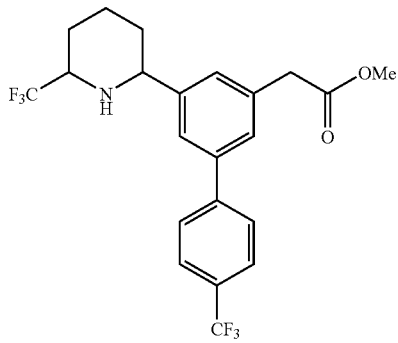

A mixture of compound 11c (150 mg, 0.341 mmol), PtO$_2$ (15 mg, 0.066 mmol) and 4N HCl/dioxane (0.1 mL, 0.4 mmol) in MeOH (5 mL) was hydrogenated under H$_2$ (45 psi) in par-shaker for 2 h. The resulting reaction mixture was filtered through celite and the filtrate was concentrated and purified by column chromatography to give compound 11d (100 mg, 49%) as a white solid; 1H NMR (400 MHz, CHLOROFORM-D) δ ppm 0.80-0.92 (m, 1 H), 1.20-1.32 (m, 1 H), 1.47-1.58 (m, 1 H), 1.81-1.91 (m, 2 H), 1.95-2.06 (m, 2 H), 3.31 (td, J=6.66, 3.30 Hz, 1 H), 3.67-3.77 (m, 5 H), 7.35 (s, 1 H) 7.42 (s, 1 H) 7.54 (s, 1 H) 7.64-7.71 (m, 4 H); Calcd for C22H21F6NO2 (M+H) 446.15, Found 446.

e) [5-(1-Methyl-6-trifluoromethyl-piperidin-2-yl)-4'-trifluoromethyl-biphenyl-3-yl]-acetic acid To a solution of compound 11d (40 mg, 0.088 mmol) in acetonitrile (1 mL) was added MeI (0.049 mL, 0.78 mmol) and Cs$_2$CO$_3$ (74 mg, 0.228 mmol). The mixture was heated to 85° C. in sealed tube for 17 h. After cooling to room temperature, the solution was partitioned between EtOAc and H$_2$O. The organic layer was dried (Na$_2$SO$_4$), concentrated and purified by column chromatography to give an ester intermediate.

A mixture of the above intermediate and NaOH solution (2N in H$_2$O, 0.114 mL, 0.228 mmol) in THF-MeOH (0.6 mL-0.6 mL) was stirred for 18 h and concentrated. CH$_2$Cl$_2$ and water were added, and the mixture was acidified with 1N HCl. The organic phase was separated and the aqueous phase was extracted with CH$_2$Cl$_2$. The combined organic layers were dried, concentrated, and purified by column chromatography to give 20 mg (51%, 2 steps) of the title compound 11 as a white solid; 1H NMR (300 MHz, CHLOROFORM-D) δ ppm 1.67-1.85 (m, 1 H), 1.92-2.18 (m, 5 H), 2.52 (s, 3 H), 3.67 (s, 2 H), 3.90-4.05 (m, 1 H), 4.20-4.32 (m, 1 H), 7.38 (s, 1 H) 7.46 (s, 1 H), 7.55 (s, 1 H), 7.60-7.73 (m, 4 H); Calcd for C22H21F6NO2 (M+H) 446.15, Found 446.

EXAMPLE 12

4-Methyl-2-{5-[1-(3-methyl-butyl)-6-trifluoromethyl-piperidin-2-yl]-4'-trifluoromethyl-biphenyl-3-yl}-pentanoic acid

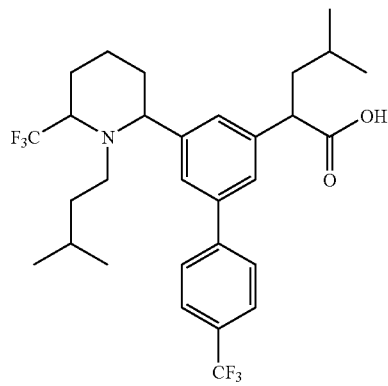

a) 4-Methyl-2-[4'-trifluoromethyl-5-(6-trifluoromethyl-pyridin-2-yl)-biphenyl-3-yl]-pentanoic acid ethyl ester

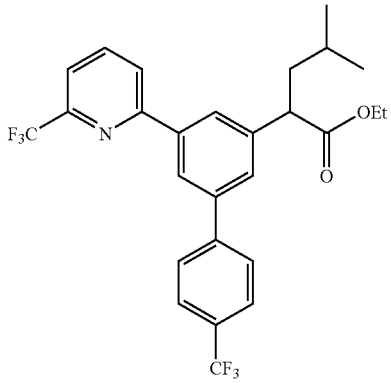

A mixture of compound 1g (150 mg, 0.293 mmol), 6-trifluoromethyl-pyridine-boronic acid pinacol ester (104 mg, 0.38 mmol), Pd(PPh$_3$)$_4$ (34 mg, 0.025 mmol) and Na$_2$CO$_3$ (2N in H$_2$O, 0.293 mL, 0.59 mmol) in DME (3 mL) was heated to 85° C. for 1 h. After cooling to room temperature, the solution was partitioned between EtOAc and H$_2$O. The organic layer was dried (Na$_2$SO$_4$), concentrated and purified by column chromatography to give 3.0 g (65%) of compound 12a as a white solid; 1H NMR (400 MHz, CHLOROFORM-D) δ 0.79-0.90 (m, 6 H), 1.11-1.22 (m, 3 H), 1.42-1.52 (m, 1 H), 1.60-1.72 (m, 1 H), 1.95-2.05 (m, 1 H), 3.76 (t, J=7.70 Hz, 1 H), 4.02-4.13 (m, 2 H), 7.57-7.62 (m, 3 H), 7.64-7.71 (m, 4 H), 7.86-7.98 (m, 3 H); Calcd for C27H25F6NO2 (M+H) 510.18, Found 510.

a) 4-Methyl-2-[4'-trifluoromethyl-5-(6-trifluoromethyl-piperidin-2-yl)-biphenyl-3-yl]-pentanoic acid ethyl ester

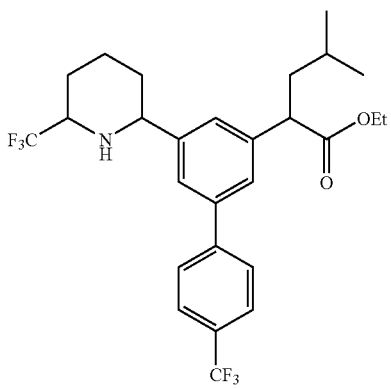

A mixture of compound 12a (970 mg, 1.9 mmol), PtO$_2$ (43 mg, 0.19 mmol) and 4N HCl/dioxane (0.524 mL, 2.17 mmol) in EtOH (10 mL) was hydrogenated under H$_2$ (20 psi) in par-shaker for 1 h. The resulting reaction mixture was filtered through celite and the filtrate was concentrated to give compound 12b (971 mg, 99%) as a white solid; 1H NMR (300 MHz, CHLOROFORM-D) δ 0.81-0.96 (m, 6 H), 1.19-1.33 (m, 4 H), 1.46-1.60 (m, 3 H), 1.67 (dt, J=13.66, 6.92 Hz, 1 H), 1.85-1.92 (m, 1 H), 1.95 (s, 1 H), 1.99-2.06 (m, 2 H), 3.25-3.39 (m, 1 H), 3.63-3.78 (m, 2 H), 4.06-4.22 (m, 2 H), 7.36 (s, 1 H), 7.42-7.56 (m, 2 H), 7.66-7.76 (m, 4 H); Calcd for C27H31F6NO2 (M+H) 516.23, Found 516.

c) 4-Methyl-2-{5-[1-(3-methyl-butyl)-6-trifluoromethyl-piperidin-2-yl]-4'-trifluoromethyl-biphenyl-3-yl}-pentanoic acid A mixture of 12b (240 mg, 0.465 mmol) and isovaleraldehyde (0.15 mL, 1.4 mmol) in THF (4 mL) was stirred for 1 h followed by addition of NaBH(OAc)$_3$ (297 mg, 1.4 mmol). The reaction mixture was stirred for 2 days and partitioned between EtOAc and saturated NaHCO$_3$ solution. The organic layer was dried (Na$_2$SO$_4$), concentrated and purified by column chromatography to give 180 mg (69%) of an ester intermediate.

The above intermediate was hydrolyzed following the same hydrolyzation procedure as in Example 11 to give Example 12; 1H NMR (400 MHz, CHLOROFORM-D) δ 0.54-0.60 (m, 3 H), 0.62-0.67 (m, 3 H), 0.86-0.94 (m, 6 H), 1.17-1.28 (m, 4 H), 1.41-1.54 (m, 2 H), 1.69-1.77 (m, 4 H), 1.95-2.06 (m, 2 H), 2.40-2.51 (m, 1 H), 2.56-2.67 (m, 1 H), 3.24 (ddd, J=9.17, 6.97, 4.16 Hz, 1 H), 3.63 (dd, J=11.37, 3.06 Hz, 1 H), 3.73 (td, J=7.83, 3.67 Hz, 1 H), 7.34 (d, J=5.38 Hz, 1 H), 7.42 (d, J=1.71 Hz, 1 H), 7.53 (d, J=1.96 Hz, 1 H), 7.65-7.72 (m, 4 H); Calcd for C30H37F6NO2 (M+H) 558.27, Found 558.2.

EXAMPLE 13

4-Methyl-2-[5-(1-methyl-5-trifluoromethyl-piperidin-2-yl)-4'-trifluoromethyl-biphenyl-3-yl]-pentanoic acid

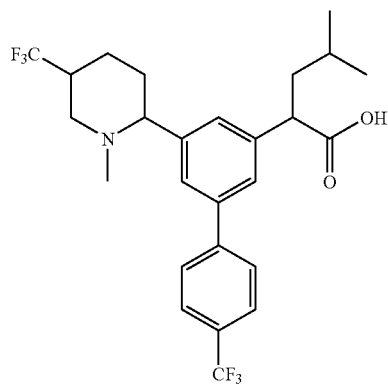

a) 4-Methyl-2-[4'-trifluoromethyl-5-(5-trifluoromethyl-piperidin-2-yl)-biphenyl-3-yl]-pentanoic acid ethyl ester

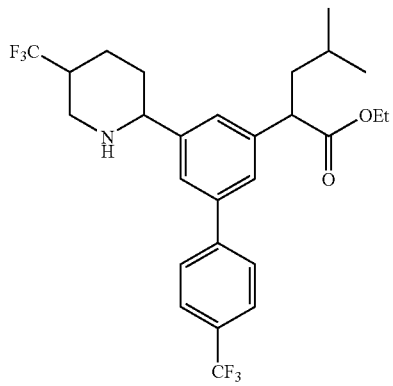

Replacing 6-trifluoromethyl-pyridine-boronic ester pinacol ester with 5-trifluoromethyl-pyridine-boronic ester pinacol ester following the same Suzuki-coupling and hydrogenation procedure as in the preparation of 12b gave compound 13a.

b) 4-Methyl-2-[5-(1-methyl-5-trifluoromethyl-piperidin-2-yl)-4'-trifluoromethyl-biphenyl-3-yl]-pentanoic acid Replacing compound 11d with compound 13a and following the same methylation and saponification procedure as in Example 11 gave the title compound; 1H NMR (400 MHz, MeOD) δ ppm 0.85 (dd, J=6.60, 3.18 Hz, 6 H), 1.44 (dd, J=6.72, 3.06 Hz, 1 H), 1.53-1.64 (m, 2 H), 1.86-1.97 (m, 7 H), 2.31-2.50 (m, 2 H), 2.52-2.95 (m, 2 H), 3.58-3.62 (m, 1 H), 7.29 (s, 1 H), 7.40 (s, 1 H), 7.48 (s, 1 H), 7.62-7.66 (m, 2 H), 7.68-7.72 (m, 2 H); Calcd for C26H29F6NO2 (M+H) 502.21, Found 502.2.

EXAMPLE 14

{5-[1-(3-Methyl-butyl)-5-trifluoromethyl-piperidin-2-yl]-4'-trifluoromethyl-biphenyl-3-yl}-acetic acid

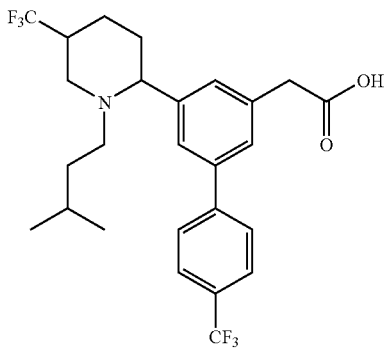

a) [4'-Trifluoromethyl-5-(5-trifluoromethyl-piperidin-2-yl)-biphenyl-3-yl]-acetic acid methyl ester

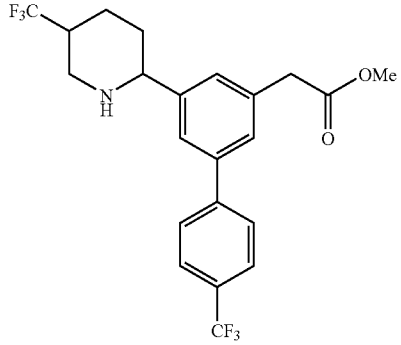

Replacing 6-trifluoromethyl-pyridine-boronic ester pinacol ester with 5-trifluoromethyl-pyridine-boronic ester pinacol ester following the same Suzuki-coupling (from 11b) and hydrogenation procedure as in the preparation of compound 11d gave compound 14a.

b) {5-[1-(3-Methyl-butyl)-5-trifluoromethyl-piperidin-2-yl]-4'-trifluoromethyl-biphenyl-3-yl}-acetic acid Replacing compound 12b with compound 14a following the same reductive-amination and saponification procedure as in Example 12 gave the title compound; 1H NMR (400 MHz, MeOD) δ ppm 0.78-0.84 (d, J=6.60 Hz, 3 H), 0.88 (d, J=6.60 Hz, 3 H), 1.43-1.54 (m, 1 H), 1.54-1.65 (m, 1 H), 1.67-1.75 (m, 1 H), 2.20-2.45 (m, 4 H), 3.00-3.25 (m, 3 H), 3.63-3.74 (m, 1 H) 3.83 (s, 2 H), 3.85-3.93 (m, 1 H), 4.53-4.62 (m, 1 H), 7.52 (s, 1 H), 7.76-7.84 (m, 4 H), 7.87-7.98 (m, 2 H); Calcd for C26H29F6NO2 (M+H) 502.21, Found 502.2.

EXAMPLE 15

{5-[1-(3-Methyl-butyl)-6-trifluoromethyl-piperidin-2-yl]-4'-trifluoromethyl-biphenyl-3-yl}-acetic acid

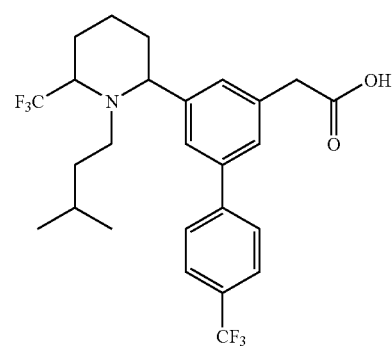

Replacing compound 12b with compound 11d following the same reductive-amination and saponification procedure as in Example 12 gave the title compound; 1H NMR (400 MHz, MeOD) δ ppm 0.54 (d, J=6.60 Hz, 3 H), 0.66 (d, J=6.60 Hz, 3 H), 1.40-1.70 (m, 2 H), 1.75-1.90 (m, 2 H), 1.99-2.40 (m, 4 H), 2.50-2.82 (m, 1 H), 2.90-3.12 (m, 2 H), 3.71 (s, 2 H), 4.50-4.62 (m, 2 H), 7.51 (s, 1 H), 7.67-7.72 (m, 3 H), 7.76-7.83 (m, 3 H); Calcd for C26H29F6NO2 (M+H) 502.21, Found 502.2.

EXAMPLE 16

2-Fluoro-4-methyl-2-{5-[1-(3-methyl-butyl)-6-trifluoromethyl-piperidin-2-yl]-4'-trifluoromethyl-biphenyl-3-yl}-pentanoic acid

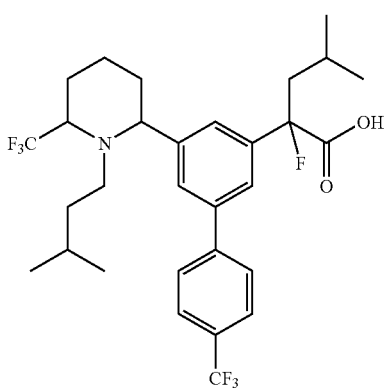

A mixture of compound 12b (240 mg, 0.465 mmol) and isovaleraldehyde (0.15 mL, 1.4 mmol) in THF (4 mL) was stirred for 1 h followed by addition of NaB(OAc)3H (297 mg, 1.4 mmol). The reaction mixture was stirred for 2 days and partitioned between EtOAc and saturated NaHCO3 solution. The organic layer was dried (Na2SO4), concentrated and purified by column chromatography to give 180 mg (69%) of an ester intermediate.

To a solution of the above intermediate (71 mg, 0.121 mmol) in THF (1 mL) at −78° C. was added K[N(SiMe3)2] (0.5N in THF, 0.364 mL, 0.182 mmol) dropwise. The reaction mixture was stirred for 30 min at −78° C. and then N-fluorobenzene-sulfonimide (57.4 mg, 0.182 mmol) in THF (0.5 mL) was added dropwise. The solution was slowly warmed up to room temperature and stirred at room temperature for 17 h. The reaction was quenched with NH4Cl saturated solution and extracted with EtOAc. The organic extracts was dried (Na2SO4), concentrated and purified by column chromatography give a white solid intermediate.

The above intermediate was hydrolyzed following the same hydrolyzation procedure as in Example 11 to give the title compound; 1H NMR (400 MHz, MeOD) δ ppm 0.47-0.51 (m, 3 H), 0.55-0.59 (m, 3 H), 0.87 (dd, J=13.08, 6.72 Hz, 6 H), 1.14-1.30 (m, 4 H), 1.47-1.78 (m, 6 H), 1.93-2.04 (m, 2 H), 2.11-2.21 (m, 1 H), 2.40-2.65 (m, 2 H), 3.62-3.67 (m, 1 H), 7.55-7.59 (m, 2 H), 7.63-7.73 (m, 5 H); Calcd for C30H36F7NO2 (M+H) 576.26, Found 576.2.

EXAMPLE 17

4-Methyl-2-[5-(1-methyl-6-trifluoromethyl-piperidin-2-yl)-4'-trifluoromethyl-biphenyl-3-yl]-pentanoic acid

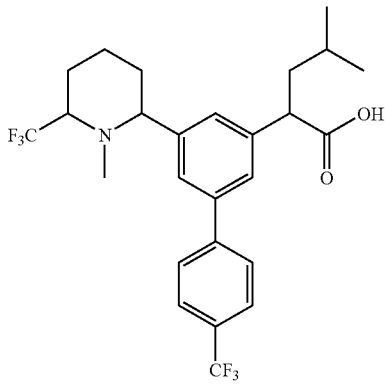

Replacing compound 11d with compound 12b and following the same methylation and saponification procedure as in Example 11 gave the title compound; 1H NMR (400 MHz, MeOD) δ ppm 0.85 (dd, J=6.60, 3.67 Hz, 6 H), 1.38-1.63 (m, 6 H), 1.69 (d, J=2.93 Hz, 1 H), 1.80-1.98 (m, 3 H), 2.09 (s, 3 H), 2.80-2.89 (m, 1 H), 3.65 (t, J=7.70 Hz, 1 H), 7.30-7.32 (m, 1 H), 7.43 (s, 1 H), 7.47 (d, J=1.22 Hz, 1 H), 7.63-7.67 (m, 2 H), 7.69-7.72 (m, 2 H); Calcd for C26H29F6NO2 (M+H) 502.21, Found 502.2.

EXAMPLE 18

(R) 4-Methyl-2-[4'-trifluoromethyl-5-(6-trifluoromethyl-piperidin-2-yl)-biphenyl-3-yl]-pentanoic acid

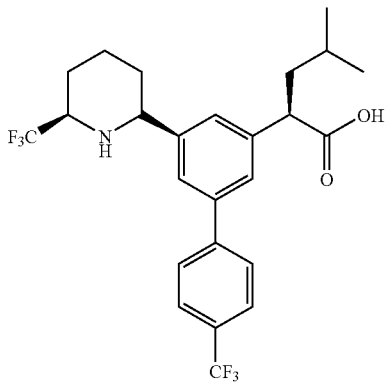

a) 5-Benzyloxy-4'-trifluoromethyl-biphenyl-3-yl)-acetic acid

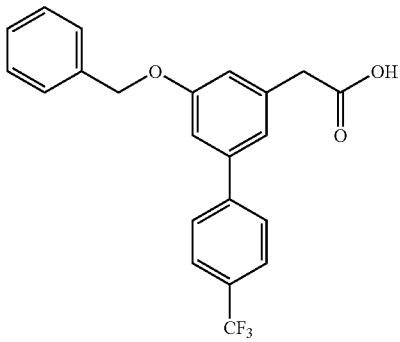

To a solution of (5-benzyloxy-4'-trifluoromethyl-biphenyl-3-yl)-acetic acid ethyl ester (compound 1d, 120 g, 0.29 mol) in THF (1.2 L) was added water (240 mL), LiOH.H2O (16 g, 0.32 mol) and the resulting mixture was stirred at room temperature for 16 h. The solution was filtered and concentrated in vacuo to remove THF. The resulting thick liquid was acidified to pH 2 by adding 2N aqueous HCl solution and the white suspension was mechanically stirred for 1 h at room temperature. The wet white product was recovered after filtration and dissolved in EtOAc (500 mL). The organic layer was separated from water, dried (MgSO$_4$) and concentrated in vacuo to obtain (5-benzyloxy-4'-trifluoromethyl-biphenyl-3-yl)-acetic acid (105 g, 94%).

$^1$H-NMR (d$_6$-DMSO): δ 3.64 (s, 2H), 5.18 (s, 2H), 7.02 (s, 1H), 7.24 (d, 2H), 7.34-7.50 (m, 5H), 7.81 (d, 2H), 7.89 (d, 2H), 12.25 (bs, 0.6H); Calcd for C22H17F3O3 (M+H) 387.11, Found 387.1.

b) 4-Benzyl-3-[2-(5-benzyloxy-4'-trifluoromethyl-biphenyl-3-yl)-acetyl]-oxazolidin-2-one

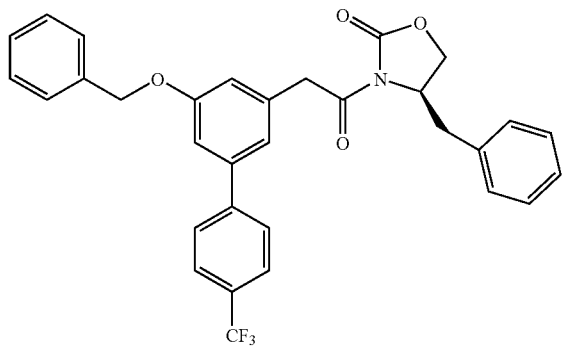

To a mechanically stirred solution of (5-benzyloxy-4'-trifluoromethyl-biphenyl-3-yl)-acetic acid from the previous step (20 g, 52 mmol) in THF (104 mL) at −78° C. was added N-methyl morpholine (NMM) (6.3 mL, 57 mmol) and trimethylacetyl chloride (7.0 mL, 57 mmol) maintaining the internal temperature below −70° C. This mixture was stirred at −78° C. for 15 minutes and at 0° C. for 1 h. The white solid was filtered off and the filtrate containing the mixed anhydride cooled back to −78° C. for the subsequent reaction. In a separate flask, to a solution of (R)-(+)-4-benzyl-2-oxazolidinone (9.6 g, 54.4 mmol) in THF (109 mL) at −78° C. was added nBuLi (1.6M in hexanes, 34 mL, 54.4 mol), drop-wise, maintaining the internal temperature below −70° C. and stirred for 45 min. This metalated chiral auxiliary was cannulated to add to a reaction flask containing the anhydride solution at −78° C. The reaction was stirred and allowed to warm to 0° C. over 1.5 h. The resulting mixture was stirred further at 0° C. for 30 minute and quenched by adding excess saturated aqueous NH$_4$Cl solution. The solution was diluted with EtOAc (200 mL) and the organic phase was washed with saturated aqueous NaHCO$_3$ solution (3×100 mL) and brine (2×100 mL). The solution was dried over MgSO$_4$ and the solvent was removed in vacuo. The crude material was purified by ISCO silica gel column chromatography to yield 20.3 g (72%) of 4-benzyl-3-[2-(5-benzyloxy-4'-trifluoromethyl-biphenyl-3-yl)-acetyl]-oxazolidin-2-one as a white solid.

$^1$H-NMR (CDCl$_3$): δ 2.76 (dd, 1H), 3.26 (dd, 1H), 4.19 (m, 2H), 4.35 (q, 2H), 4.69 (m, 1H), 5.13 (s, 2H), 7.04-7.46 (m, 13H), 7.67 (s, 4H); Calcd for C32H26F3NO4 (M+H) 546.18, Found 546.3.

c) 4-Benzyl-3-[2-(5-benzyloxy-4'-trifluoromethyl-biphenyl-3-yl)-4-methyl-pent-4-enoyl]-oxazolidin-2-one

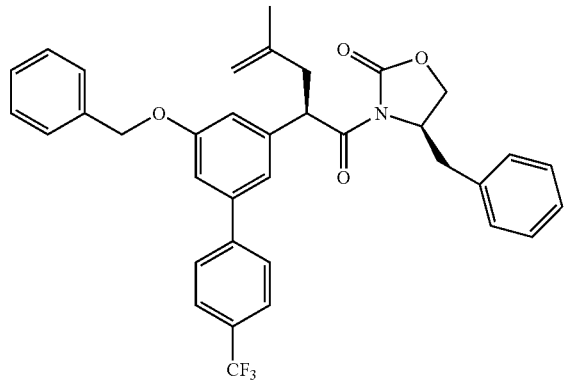

To a colorless solution of 4-benzyl-3-[2-(5-benzyloxy-4'-trifluoromethyl-biphenyl-3-yl)-acetyl]-oxazolidin-2-one from the previous step (6.0 g, 11.00 mmol) in dry THF (22 mL) at −78° C. was added sodium bis(trimethylsiyl)amide (NaHMDS) (1 M in THF solution, 12.11 mL, 12.11 mmol), drop-wise, maintaining the internal temperature below −75° C. The resulting red solution was stirred at −78° C. for 30 minutes. To this was added 3-bromo-2-methyl propene (4.44 mL, 44 mmol) maintaining the temperature below −75° C. When the addition was near completion, the reaction mixture turned green. At this point the dry-ice bath was quickly removed and replaced with water-ice bath, and the addition was completed. The reaction mixture was stirred at 0° C. for an additional 30 min and quenched with saturated aqueous NH$_4$Cl solution. The system was diluted with EtOAC (100 mL) and the organic phase was washed with saturated aqueous NaHCO$_3$ solution (3×50 mL) and dried (MgSO$_4$). Solvent was removed in vacuo and the crude mixture was purified by ISCO silica gel column to yield 4-benzyl-3-[2-(5-benzyloxy-4'-trifluoromethyl-biphenyl-3-yl)-4-methyl-pent-4-enoyl]-oxazolidin-2-one (6.3 g, 95%).

$^1$H-NMR (CDCl$_3$): δ 1.80 (s, 3H), 2.46 (dd, 1H), 2.75 (dd, 1H), 3.05 (dd, 1H), 3.32 (dd, 1H), 4.08 (m, 2H), 4.59 (m, 1H), 4.80 (d, 2H), 5.13 (s, 2H), 5.48 (dd, 1H), 7.11 (d, 2H), 7.21-7.49 (m, 11H), 7.67 (s, 4H); Calcd for C36H32F3NO4 (M+H) 600.23, Found 600.3.

d) 4-Benzyl-3-[2-(5-hydroxy-4'-trifluoromethyl-biphenyl-3-yl)-4-methyl-pentanoyl]-oxazolidin-2-one

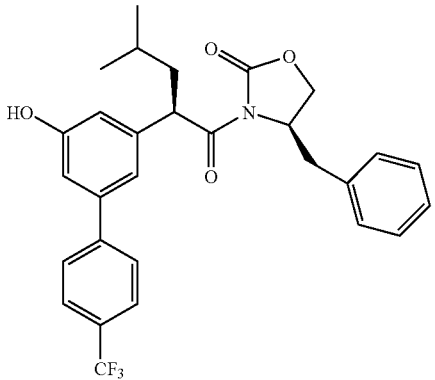

To a solution of 4-benzyl-3-[2-(5-benzyloxy-4'-trifluoromethyl-biphenyl-3-yl)-4-methyl-pent-4-enoyl]-oxazolidin-2-one from the previous step (6.7 g, 1 1.2 mmol) in MeOH (150 mL) was added 10% Pd/C (670 mg, 10 w %). The black suspension was hydrogenated at 5-50 psi overnight. The mixture was filtered through a celite pad and the solvent was removed in vacuo to obtain relatively pure 4-benzyl-3-[2-(5-hydroxy-4'-trifluoromethyl-biphenyl-3-yl)-4-methyl-pentanoyl]-oxazolidin-2-one (5.4 g, 93%).

$^1$H-NMR (CDCl$_3$): δ 0.94 (d, 3H), 0.98 (d, 3H), 1.54 (m, 1H), 1.74 (m, 1H), 2.12 (m, 1H), 2.79 (dd, 1H), 3.36 (dd, 1H), 4.11 (m, 2H), 4.62 (m, 1H), 5.25 (t, 1H), 6.97 (m, 2H), 7.21-7.37 (m, 6H), 7.67 (s, 4H); Calcd for C29H28F3NO4 (M+H) 512.20, Found 512.3.

e) Trifluoro-methanesulfonic acid 5-[1-(4-benzyl-2-oxo-oxazolidine-3-carbonyl)-3-methyl-butyl]-4'-trifluoromethyl-biphenyl-3-yl ester

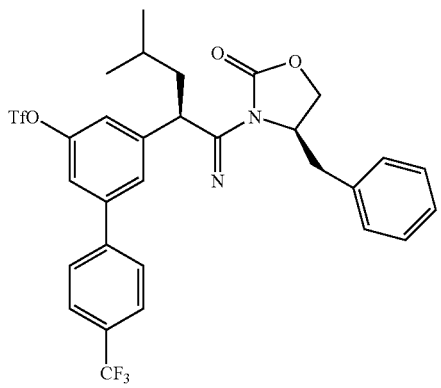

Compound 18e was prepared via the same procedure as described in Example 1, step (g) using compound 18d as the starting material.

f) 4-Benzyl-3-{4-methyl-2-[4'-trifluoromethyl-5-(6-trifluoromethyl-piperidin-2-yl)-biphenyl-3-yl]-pentanoyl}-oxazolidin-2-one

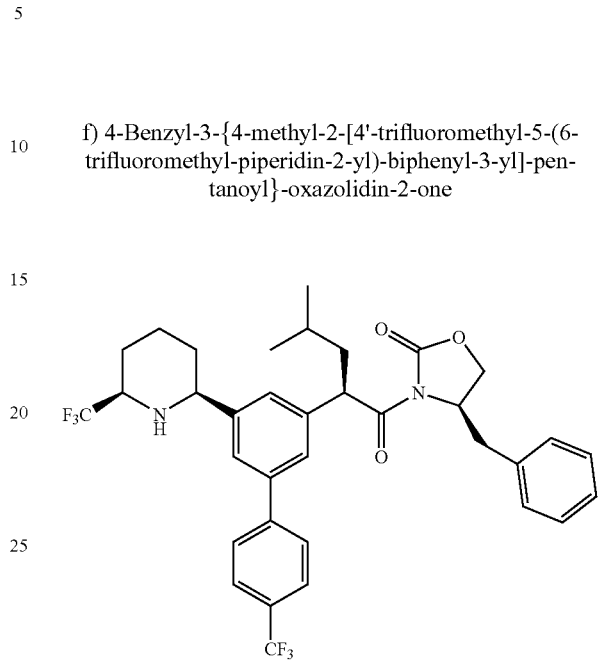

Replacing 1g with 18f following the same Suzuki-coupling and hydrogenation procedure as in the preparation of compound 12b, Example 12, steps (a) and (b) gave the title compound.

g) 4-Methyl-2-[4'-trifluoromethyl-5-(6-trifluoromethyl-piperidin-2-yl)-biphenyl-3-yl]-pentanoic acid To a solution of compound 18f from above (0.4 g) in THF (10 mL) was added water (3.5 mL). The system was cooled to 0° C. To this cold solution was added LiOH.H2O (0.028 g, 0.67 mmol) and 30% H$_2$O$_2$ (3.04 mL, 2.68 mmol), drop-wise, maintaining the internal temperature below 5° C. The resulting cloudy solution was stirred at 0° C. for 20 min. The excess H$_2$O$_2$ was quenched by adding 1.5 M aqueous Na$_2$SO$_3$ solution (1.79 mL, 2.68 mmol) and stirred at room temperature for 5 min. The organic solvent was removed in vacuo. The resulting liquid was acidified to pH 2 by adding 1 N aqueous HCl solution. The aqueous layer was extracted with EtOAc (3×25 mL) and dried (MgSO$_4$). The mixture was concentrated in vacuo and then purified by ISCO silica gel column chromatography to give the title compound; 1H NMR (400 MHz, MeOD) δ ppm 0.87 (d, J=6.36 Hz, 6 H), 1.39-1.50 (m, 1 H), 1.58-1.68 (m, 1 H), 1.78-1.89 (m, 2 H), 1.97 (ddd, J=13.57, 7.70, 7.58 Hz, 1 H), 2.05-2.25 (m, 4 H), 3.75 (t, J=7.70 Hz, 1 H), 4.28-4.38 (m, 1 H), 4.45-4.52 (m, 1 H), 7.54 (d, J=1.96 Hz, 1 H), 7.67 (d, J=8.31 Hz, 2 H), 7.70 (s, 1 H), 7.74-7.79 (m, 3 H); Calcd for C25H27F6NO2 (M+H) 488.19, Found 488.1.

EXAMPLE 19

(S) 4-Methyl-2-[4'-trifluoromethyl-5-(6-trifluoromethyl-piperidin-2-yl)-biphenyl-3-yl]-pentanoic acid

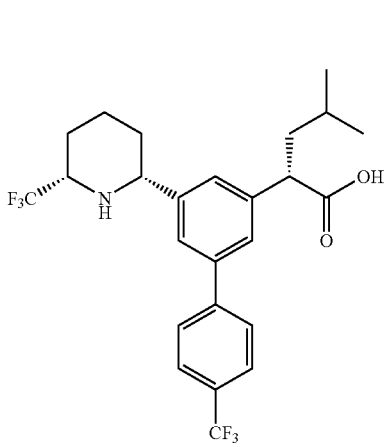

a) Trifluoro-methanesulfonic acid 5-[1-(4-benzyl-2-oxo-oxazolidine-3-carbonyl)-3-methyl-butyl]-4'-trifluoromethyl-biphenyl-3-yl ester

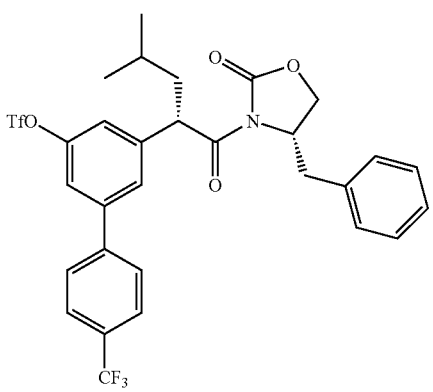

The intermediate compound 19a was prepared from 4-benzyl-3-[2-(5-benzyloxy-4'-trifluoromethyl-biphenyl-3-yl)-4-methyl-pent-4-enoyl]-oxazolidin-2-one following the same procedure as for the synthesis of Example 18, steps (a)-(e) using (S)-(−)-4-benzyl-2-oxazolidinone for a chiral auxiliary group.

d) 4-Methyl-2-[4'-trifluoromethyl-5-(6-trifluoromethyl-piperidin-2-yl)-biphenyl-3-yl]-pentanoic acid

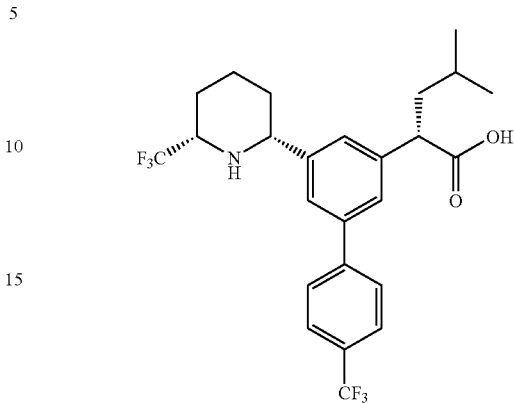

Replacing compound 1g with compound 19a following the same Suzuki-coupling and hydrogenation procedure as in the preparation of compound 12b gave an intermediate, same procedure as Example 18, steps (a-f).

The above intermediate was hydrolyzed to remove the chiral auxiliary group following the same procedure as in Example 18, step (g) to give the title compound; 1H NMR (400 MHz, MeOD) δ ppm 0.87 (d, J=6.36 Hz, 6 H), 1.39-1.50 (m, 1 H), 1.58-1.68 (m, 1 H), 1.78-1.89 (m, 2 H), 1.97 (ddd, J=13.57, 7.70, 7.58 Hz, 1 H), 2.05-2.25 (m, 4 H), 3.75 (t, J=7.70 Hz, 1 H), 4.28-4.38 (m, 1 H), 4.45-4.52 (m, 1 H), 7.54 (d, J=1.96 Hz, 1 H), 7.67 (d, J=8.31 Hz, 2 H), 7.70 (s, 1 H), 7.74-7.79 (m, 3 H); Calcd for C25H27F6NO2 (M+H) 488.19, Found 488.1.

EXAMPLE 20

(R) 4-Methyl-2-{5-[1-(3-methyl-butyl)-6-trifluoromethyl-piperidin-2-yl]-4'-trifluoromethyl-biphenyl-3-yl}-pentanoic acid

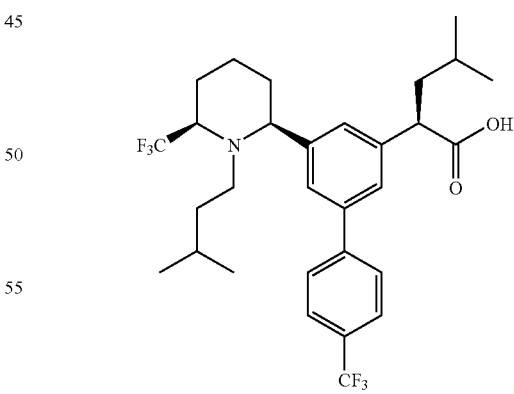

Replacing compound 1g with compound 18f following the same procedure as in the preparation of Example 12 gave the title compound; 1H NMR (400 MHz, MeOD) δ ppm 0.62 (dd, J=6.60, 2.93 Hz, 3 H), 0.72 (d, J=6.60 Hz, 3 H), 0.96 (td, J=4.34, 2.08 Hz, 6 H), 1.22-1.31 (m, 1 H), 1.35-1.45 (m, 2 H), 1.48-1.56 (m, 1 H), 1.69-1.81 (m, 2 H), 1.962.07 (m, 5 H), 2.23-2.32 (m, 1 H), 2.85-3.05 (m, 2 H), 3.81 (td, J=7.70, 1.96

Hz, 1 H), 4.08-4.20 (m, 1 H), 4.29-4.35 (m, 1 H), 7.59 (s, 1 H), 7.69 (s, 1 H), 7.76-7.85 (m, 5 H); Calcd for C30H37F6NO2 (M+H) 558.27, Found 558.2.

EXAMPLE 21

(S) 4-Methyl-2-{5-[1-(3-methyl-butyl)-6-trifluoromethyl-piperidin-2-yl]-4'-trifluoromethyl-biphenyl-3-yl}-pentanoic acid

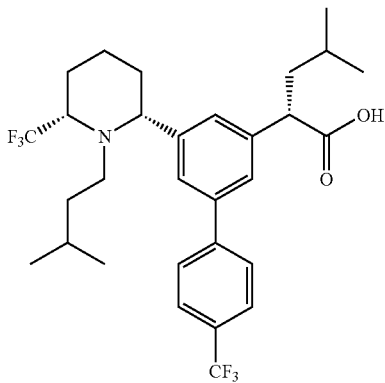

Replacing compound 1g with compound 19a following the same procedure as in the preparation of Example 12 gave the title compound; 1H NMR (400 MHz, MeOD) δ ppm 0.63 (dd, J=6.60, 2.93 Hz, 3 H), 0.73 (dd, J=6.60, 1.71 Hz, 3 H), 0.96 (td, J=4.34, 2.08 Hz, 6 H), 1.28-1.35 (m, 1 H), 1.43-1.54 (m, 3 H), 1.69-1.88 (m, 2 H), 2.00-2.11 (m, 4 H), 2.15-2.40 (m, 2 H), 2.92-3.03 (m, 1 H), 3.03-3.15 (m, 1 H), 3.83 (td, J=7.76, 2.32 Hz, 1 H), 4.37 (m, 1 H), 4.51 (d, J=1 1.49 Hz, 1 H), 7.64 (s, 1 H), 7.73-7.80 (m, 3 H), 7.84 (d, J=8.07 Hz, 3 H); Calcd for C30H37F6NO2 (M+H) 558.27, Found 558.2.

EXAMPLE 22

Difluoro-{5-[1-(3-methyl-butyl)-6-trifluoromethyl-piperidin-2-yl]-4'-trifluoromethyl-biphenyl-3-yl}-acetic acid

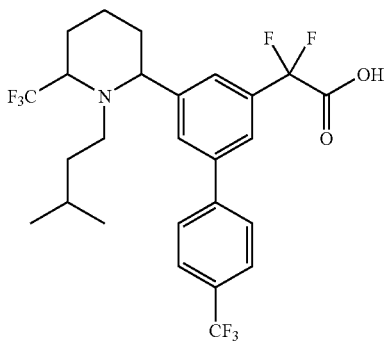

Reductive amination of compound 11d following the same procedure as in Example 12 gave an ester intermediate.

To a solution of the above intermediate (43 mg, 0.083 mmol) in THF (1 mL) at −78° C. was added Li[N(SiMe3)2] (1N in THF, 0.183 mL, 0.183 mmol) dropwise. The reaction mixture was stirred for 30 min at −78° C. and then N-fluorobenzene-sulfonimide (52.3 mg, 0.166 mmol) in THF (0.5 mL) was added dropwise. The solution was slowly warmed up to room temperature and stirred at room temperature for 1 h. The reaction was quenched with NH4Cl saturated solution and extracted with EtOAc. The organic extracts was dried (Na2SO4), concentrated and purified by preparative TLC to give 20 mg (45% ) of the title compound; as a white solid; 1H NMR (300 MHz, MeOD) δ ppm 0.51 (d, J=6.41 Hz, 3 H), 0.61 (d, J=6.78 Hz, 3 H), 1.12-1.21 (m, 1 H), 1.29 (td, J=11.12, 5.65 Hz, 2 H), 1.59-1.73 (m, 1 H), 1.80-1.95 (m, 4 H), 2.10-2.21 (m, 1 H), 2.63-2.75 (m, 1 H), 2.78-2.91 (m, 1 H), 3.88-4.00 (m, 1 H), 4.23 (dd, J=9.23, 5.09 Hz, 1 H), 7.68-7.79 (m, 5 H), 7.82 (s, 1 H), 7.93 (s, 1 H); Calcd for C26H27F8NO2 (M+H) 538.19, Found 538.2.

EXAMPLE 23

4-Methyl-2-[4'-trifluoromethyl-5-(5-trifluoromethyl-piperidin-2-yl)-biphenyl-3-yl]-pentanoic acid

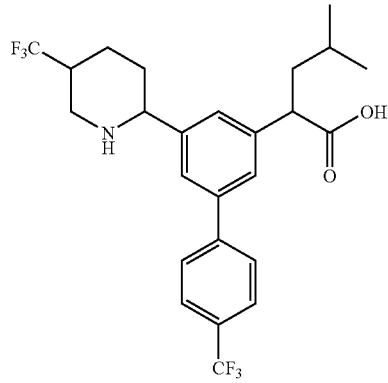

A mixture of compound 13a (30 mg, 0.058 mmol) and NaOH solution (2N in H2O, 0.114 mL, 0.228 mmol) in THF-MeOH (0.6 mL-0.6 mL) was stirred for 18 h and concentrated. CH2Cl2 and water were added, and the mixture was acidified with 1N HCl. The organic phase was separated and the aqueous phase was extracted with CH2Cl2. The combined organic layers were dried, concentrated, and purified by column chromatography to give 25 mg (88%) of the title compound 23 as a white solid; 1H NMR (300 MHz, MeOD) δ ppm 0.89-1.01 (m, 6 H), 1.50-1.63 (m, 1 H), 1.74 (dt, J=13.66, 6.92 Hz, 1 H), 1.99-2.45 (m, 5 H), 2.95-3.10 (m, 1 H), 3.65-3.70 (m, 2 H), 3.86 (t, J=7.72 Hz, 1 H), 4.55-4.65 (m, 1 H), 7.55 (d, J=1.51 Hz, 1 H), 7.76-7.90 (m, 6 H); Calcd for C25H27F6NO2 (M+H) 488.19, Found 488.1.

EXAMPLE 24

4-Methyl-2-[4'-trifluoromethyl-5-(6-trifluoromethyl-piperidin-2-yl)-biphenyl-3-yl]-pentanoic acid

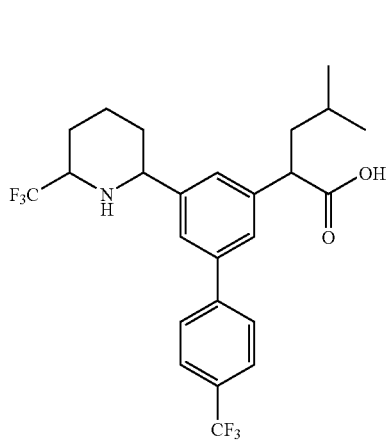

Replacing compound 13a with compound 12b following the same saponification procedure as in the preparation of Example 23 gave the title compound;; 1H NMR (300 MHz, MeOD) δ ppm 0.79-0.89 (m, 6 H), 1.45 (dt, J=12.90, 6.55 Hz, 1 H), 1.55-1.69 (m, 1 H), 1.76-2.24 (m, 7 H), 3.75 (t, J=7.72 Hz, 1 H), 4.26-4.40 (m, 1 H), 4.42-4.52 (m, 1 H), 7.54 (s, 1 H), 7.66 (s, 1 H), 7.67-7.81 (m, 5 H); Calcd for C25H27F6NO2 (M+H) 488.19, Found 488.1.

EXAMPLE 25

4-Methyl-2-[5-(1-pyridin-4-ylmethyl-6-trifluoromethyl-piperidin-3-yl)-4'-trifluoromethyl-biphenyl-3-yl]-pentanoic acid

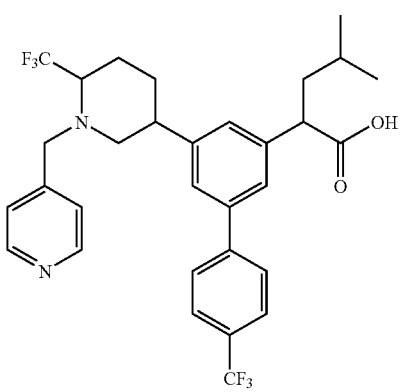

a) 4-Methyl-2-[4'-trifluoromethyl-5-(6-trifluoromethyl-piperidin-3-yl)-biphenyl-3-yl]-pentanoic acid ethyl ester

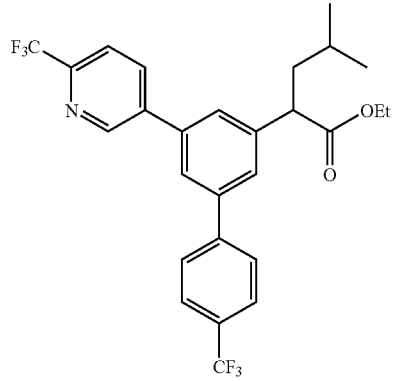

A mixture of compound compound 1g (302 mg, 0.59 mmol), 6-trifluoromethyl-pyridine-3-boronic acid (124 mg, 0.65 mmol), Pd(PPh$_3$)$_4$ (136 mg, 0.118 mmol) and Na$_2$CO$_3$ (2N in H$_2$O, 0.59 mL, 1.18 mmol) in DME (3 mL) was heated at 85° C. for 3 h. After cooling to room temperature, the solution was partitioned between EtOAc and H$_2$O. The organic layer was dried (Na$_2$SO$_4$), concentrated and purified by column chromatography to give 250 mg (83%) of compound 25a as a white solid.

b) 4-Methyl-2-[4'-trifluoromethyl-5-(6-trifluoromethyl-piperidin-3-yl)-biphenyl-3-yl]-pentanoic acid ethyl ester

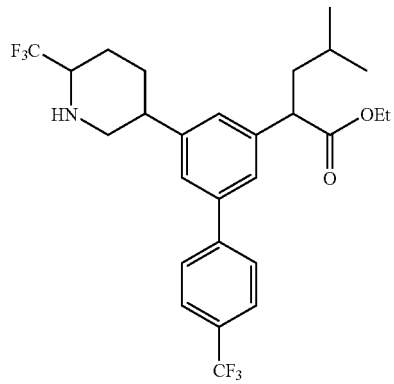

A mixture of compound 25a (250 mg, 0.49 mmol), PtO$_2$ (22 mg, 0.098 mmol) and 4N HCl/dioxane (0.245 mL, 0.98 mmol) in EtOH (10 mL) was hydrogenated under H$_2$ (50 psi) in par-shaker for 5 h. The resulting reaction mixture was filtered through celite and the filtrate was concentrated and purified by column chromatography to give compound two diasteromers, compound 25b-1 (lower Rf, 210 mg, 83%) and compound 25b-2 (higher Rf, 15 mg, 6%).

c) 4-Methyl-2-[5-(1-pyridin-4-ylmethyl-6-trifluoromethyl-piperidin-3-yl)-4'-trifluoromethyl-biphenyl-3-yl]-pentanoic acid A mixture of compound 25b-1 (30 mg, 0.058 mmol), 4-bromomethyl-pyridine hydrogen chloride (44 mg, 0.174 mmol) and K₂CO₃ (24 mg, 0.174 mmol) in DMF (1 mL) was heated under microwave irradiation (150° C., 300 W, 250 psi) for 30 min. After cooling to room temperature, the solution was partitioned between EtOAc and H₂O. The organic layer was dried (Na₂SO₄), concentrated and purified by column chromatography to give an ester intermediate.

The above intermediate was hydrolyzed following the same hydrolyzation procedure as in Example 11 to give the title compound;; 1H NMR (400 MHz, MeOD) δ ppm 0.79-0.85 (m, 6 H), 1.36-1.49 (m, 1 H), 1.50-1.58 (m, 1 H), 1.80-1.90 (m, 3 H), 2.03-2.10 (m, 2 H), 2.61-2.67 (m, 1 H), 2.90-2.98 (m, 2 H), 3.39-3.48 (m, 1 H), 3.60 (t, J=7.70 Hz, 1 H), 3.86-3.92 (m, 1 H), 4.07-4.13 (m, 1 H), 7.13 (s, 1 H), 7.25 (s, 1 H), 7.32-7.40 (m, 3 H), 7.61-7.67 (m, 4 H), 8.31-8.40 (m, 2 H); Calcd for C31H32F6N2O2 (M+H) 579.24, Found 579.2.

EXAMPLE 26

(R)-4-Methyl-2-[5-(2-phenethyl-piperidin-1-yl)-4'-trifluoromethyl-biphenyl-3-yl]-pentanoic acid

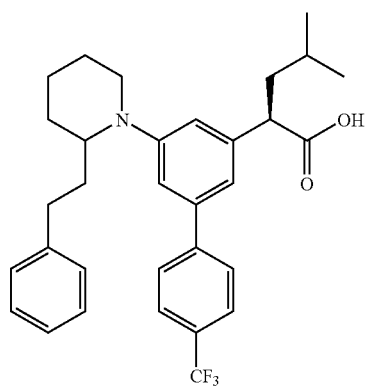

a) (R)-4-Methyl-2-[5-(2-phenethyl-piperidin-1-yl)-4'-trifluoromethyl-biphenyl-3-yl]-pentanoic acid methyl ester

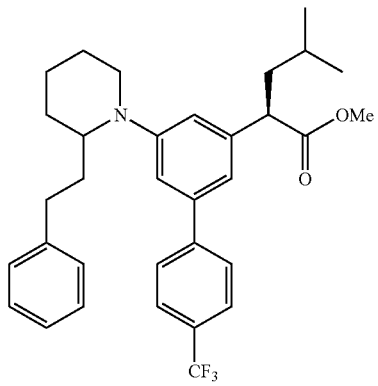

To a solution of (R)-4-methyl-2-(5-trifluoromethanesulfonyloxy-4'-trifluoromethyl-biphenyl-3-yl)-pentanoic acid methyl ester (1g-methyl ester) (215 mg, 0.43 mmol) in 1,2-dimethoxyethane (4 mL) in a sealed tube was added racemic-2-(di-t-butylphosphino)-1,1'-binaphthyl (17 mg, 0.04 mmol), Pd(OAc)₂ (10 mg, 0.04 mmol), 2-phenethyl-piperidine (98 mg, 0.52 mmol). The system was flushed with nitrogen. To this was added KO^tBu (1 M in THF, 0.430 mL, 0.43 mmol) and heated to 110° C. for 20 h. The reaction was cooled to room temperature and quenched by slow addition of water. The mixture was extracted with EtOAc (3×20 mL). The organic phase was washed with saturated NaHCO₃ solution and brine. The organic fraction was dried (MgSO₄) and concentrated in vacuo. The crude mixture was purified by ISCO column chromatography to obtain (R)-4-methyl-2-[5-(2-phenethyl-piperidin-1-yl)-4'-trifluoromethyl-biphenyl-3-yl]-pentanoic acid methyl ester. Calcd for C33H38F3NO2 (M+H) 537.66, Found 538.3.

EXAMPLE 27

4-Methyl-2-{5-[1-(3-methyl-butyl)-6-trifluoromethyl-piperidin-3-yl]-4'-trifluoromethyl-biphenyl-3-yl}-pentanoic acid

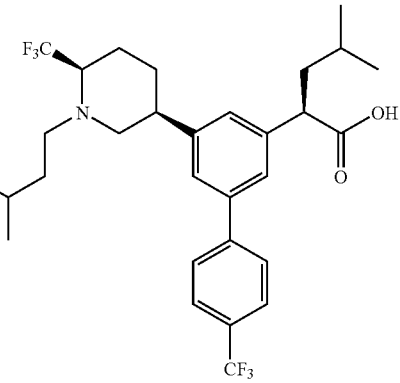

Replacing compound 12b with compound 25b-2 following the same reductive-amination and saponification procedure as in the preparation of Example 12 the title compound (structure tentatively assigned as shown); 1H NMR (400 MHz, MeOD) δ ppm 0.83 (ddd, J=19.32, 6.60, 2.93 Hz, 12 H), 1.31-1.46 (m, 2 H), 1.55-1.65 (m, 3 H), 1.87-2.02 (m, 3 H), 2.46-2.91 (m, 5 H), 2.97-3.15 (m, 2 H), 3.65 (t, J=7.70 Hz, 1 H), 4.45-4.55 (m, 1 H), 7.21 (d, J=1.47 Hz, 1 H), 7.37-7.40 (m, 2 H), 7.62-7.66 (m, 2 H), 7.68-7.72 (m, 2 H); Calcd for C30H37F6NO2 (M+H) 558.27, Found 558.2.

EXAMPLE 28

4-Methyl-2-{4'-trifluoromethyl-5-[6-trifluoromethyl-1-(3-trifluoromethyl-benzyl)-piperidin-3-yl]-biphenyl-3-yl}-pentanoic acid

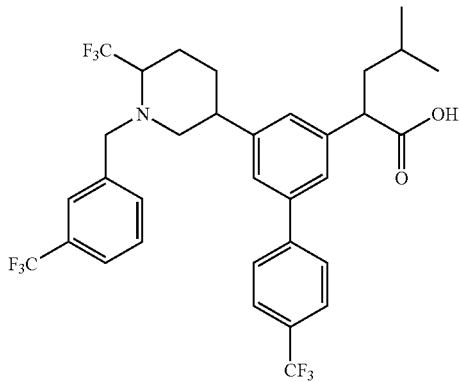

Replacing 4-bromomethyl-pyridine hydrogen chloride with 1-bromomethyl-3-trifluoromethyl-benzene following the same alkylation and saponification procedure as in the preparation of Example 25 gave the title compound; 1H NMR (400 MHz, MeOD) δ ppm 0.82-0.85 (m, 6 H), 1.39 (dt, J=13.21, 6.60 Hz, 1 H), 1.51-1.59 (m, 1 H), 1.82-1.92 (m, 3 H), 2.10-2.20 (m, 2 H), 2.82-2.90 (m, 1 H), 3.02-3.11 (m, 2 H), 3.59-3.70 (m, 2 H), 4.14-4.21 (m, 1 H), 4.26-4.33 (m, 1 H), 7.14 (s, 1 H), 7.28 (s, 1 H), 7.39 (d, J=1.22 Hz, 1 H), 7.45-7.56 (m, 2 H), 7.61-7.72 (m, 6 H); Calcd for C33H32F9NO2 (M+H) 646.23, Found 646.2.

EXAMPLE 29

2-{5-[1-(3-Fluoro-5-trifluoromethyl-benzyl)-6-trifluoromethyl-piperidin-3-yl]-4'-trifluoromethyl-biphenyl-3-yl}-4-methyl-pentanoic acid

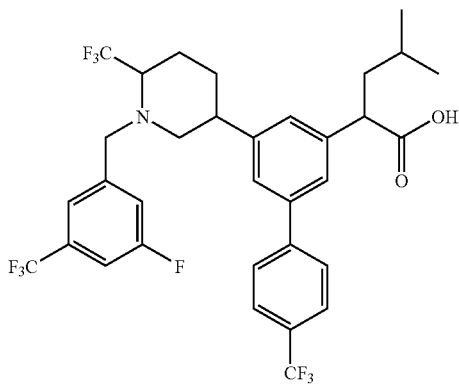

Replacing 4-bromomethyl-pyridine hydrogen chloride with 1-bromomethyl-5-fluoro-3-trifluoromethyl-benzene following the same alkylation and saponification procedure as in Example 25 gave the title compound; 1H NMR (400 MHz, MeOD) δ ppm 0.79-0.86 (m, 6 H), 1.39 (dt, J=13.27, 6.69 Hz, 1 H), 1.51-1.59 (m, 1 H), 1.81-1.92 (m, 3 H), 2.03-2.12 (m, 2 H), 2.64-2.75 (m, 1 H), 2.91-3.03 (m, 2 H), 3.44-3.53 (m, 1 H), 3.61 (t, J=7.70 Hz, 1 H), 3.99-4.05 (m, 1 H), 4.13-4.19 (m, 1 H), 7.12 (s, 1 H), 7.23-7.28 (m, 2 H), 7.35-7.41 (m, 2 H), 7.49 (s, 1 H), 7.61-7.67 (m, 4 H); Calcd for C33H31F10NO2 (M+H) 664.22, Found 664.2.

EXAMPLE 30

2-{5-[1-(3,3-Dimethyl-butyl)-6-trifluoromethyl-piperidin-3-yl]-4'-trifluoromethyl-biphenyl-3-yl}-4-methyl-pentanoic acid

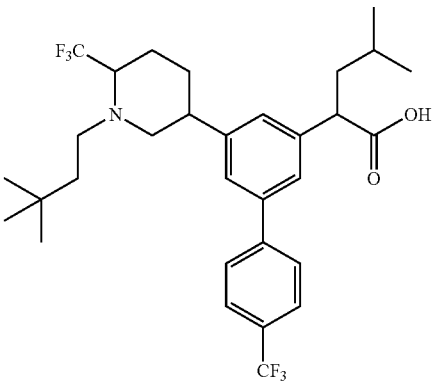

Replacing isovaleraldehyde with 3,3-dimethyl-butyraldehyde following the same reductive-amination and saponification procedure as in the preparation of Example 27 gave the title compound; 1H NMR (400 MHz, MeOD) δ ppm 0.80-0.88 (m, 6 H), 0.92 (s, 9 H), 1.41-1.50 (m, 1 H), 1.58-1.79 (m, 3 H), 1.91-2.06 (m, 3 H), 2.32 (d, J=3.91 Hz, 2 H), 3.35-3.59 (m, 5 H), 3.70 (t, J=7.70 Hz, 1 H), 4.45-4.58 (m, 1 H), 7.25 (s, 1 H), 7.41 (s, 1 H), 7.49 (s, 1 H), 7.64-7.74 (m, 2 H); Calcd for C31H39F6NO2 (M+H) 572.29, Found 572.3.

EXAMPLE 31

4-Methyl-2-{4'-trifluoromethyl-5-[6-trifluoromethyl-1-(4-trifluoromethyl-benzyl)-piperidin-3-yl]-biphenyl-3-yl}-pentanoic acid

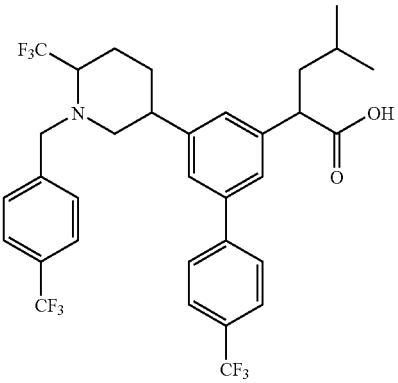

Replacing 4-bromomethyl-pyridine hydrogen chloride with 1-bromomethyl-4-trifluoromethyl-benzene following the same alkylation and saponification procedure as in Example 25 gave the title compound; 1H NMR (400 MHz, MeOD) δ ppm 0.88-0.95 (m, 6 H), 1.43-1.53 (m, 1 H), 1.64 (dt, J=13.76, 6.94 Hz, 1 H), 1.88-1.98 (m, 3 H), 2.05-2.15 (m, 2 H), 2.74 (d, J=9.29 Hz, 1 H), 2.93-3.05 (m, 2 H), 3.42-3.52 (m, 1 H), 3.70 (t, J=7.70 Hz, 1 H), 3.96-4.03 (m, 1 H), 4.07-4.18 (m, 1 H), 7.21 (s, 1 H), 7.34 (s, 1 H), 7.45 (s, 1 H), 7.55-7.64 (m, 4 H), 7.69-7.76 (m, 4 H); Calcd for C33H32F9NO2 (M+H) 646.23, Found 646.2.

EXAMPLE 32

2-[5-(1-Benzyl-6-trifluoromethyl-piperidin-3-yl)-4'-trifluoromethyl-biphenyl-3-yl]-4-methyl-pentanoic acid

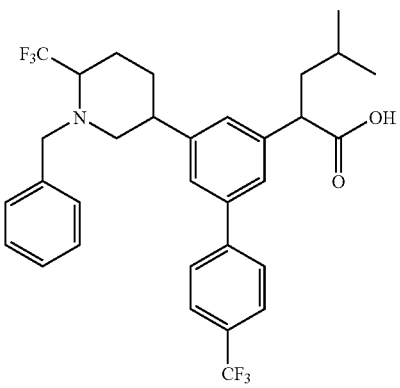

Replacing 4-bromomethyl-pyridine hydrogen chloride with benzyl bromide following the same alkylation and saponification procedure as in Example 25 gave the title compound; 1H NMR (400 MHz, MeOD) δ ppm 0.92 (d, J=6.11 Hz, 6 H), 1.43-1.54 (m, 1 H), 1.64 (ddd, J=13.63, 7.09, 6.91 Hz, 1 H), 1.87-1.99 (m, 3 H), 2.03-2.10 (m, 2 H), 2.77 (d, J=8.80 Hz, 1 H), 2.95 (s, 2 H), 3.38-3.48 (m, 1 H), 3.70 (t, J=7.83 Hz, 1 H), 3.86-3.94 (m, 1 H), 4.01-4.11 (m, 1 H), 7.19-7.25 (m, 2 H), 7.28-7.38 (m, 5 H), 7.44 (s, 1 H), 7.68-7.74 (m, 4 H); Calcd for C32H33F6NO2 (M+H) 578.24, Found 578.1.

EXAMPLE 33

2-{5-[1-(1-Ethyl-propyl)-piperidin-3-yl]-4'-trifluoromethyl-biphenyl-3-yl}-4-methyl-pentanoic acid

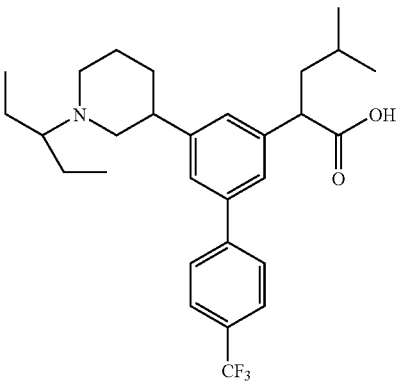

a) 4-Methyl-2-(5-pyridin-3-yl-4'-trifluoromethyl-biphenyl-3-yl)-pentanoic acid ethyl ester

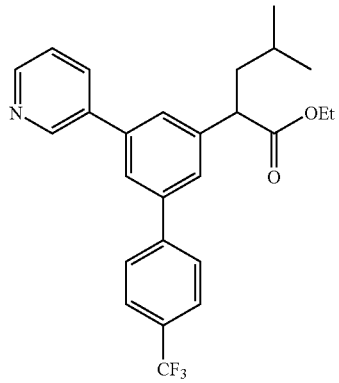

To compound 1g, 4-Methyl-2-(5-trifluoromethanesulfonyloxy-4'-trifluoromethyl-biphenyl-3-yl)-pentanoic acid ethyl ester (42 mg, 0.093 mmol) in dimethoxythane (16 ml), was added 3-Pyridine boronic acid (600 mg, 4.9 mmol), and 2M Na2CO3 (3.7 ml, 7.4 mmol) The mixture was degassed, tetrakis(triphenylphosphine)palladium (0) (280 mg, 0.25 mmol) was added and the mixture was degassed, and then heated to 80° C. for 2 hours. The reaction was cooled to room temperature, diluted with EtOAc and washed with NaHCO3 and brine. Purification by column chromatography gave the title compound (1.0 g, 92% ). Calcd for C26H26F3NO2 (M+H) 441.49, Found 442.3.

b) 4-Methyl-2-(5-piperidin-3-yl-4'-trifluoromethyl-biphenyl-3-yl)-pentanoic acid ethyl ester

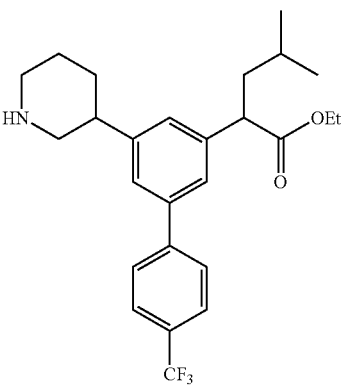

A solution of 4-Methyl-2-(5-pyridin-3-yl-4'-trifluoromethyl-biphenyl-3-yl)-pentanoic acid ethyl ester, compound 33a (1.0 g, 2.27 mmol) in MeOH (75 ml), platinum oxide (51 mg, 0.97 mmol) and 4N HCl/dioxane (0.62 ml) was hydrogenated at 40 psi for 5.5 hours. The reaction mixture was filtered through celite, washed with MeOH and concentrated in vacuo. The residue was partitioned between dichloromethane and Na$_2$CO$_3$ to give the free base, (977 mg, 97%).
Calculated for C26H32F3NO2 (M+H) 447.53, Found 448.3 c) 2-{5-[1-(1-Ethyl-propyl)-piperidin-3-yl]-4'-trifluoromethyl-biphenyl-3-yl}-4-methyl-pentanoic acid ethyl ester

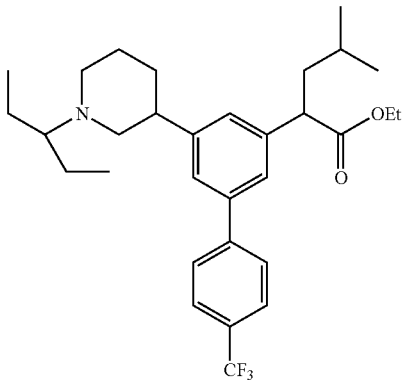

To a solution of compound 33b, 4-Methyl-2-(5-piperidin-3-yl-4'-trifluoromethyl-biphenyl-3-yl)-pentanoic acid ethyl ester (42 mg, 0.093 mmol) in CH$_3$CN (0.5 ml) was added 1-iodo-3-Bromopentane (21.0 mg, 0.14 mmol) and cesium carbonate (61.0 mg, 0.186 mmol). The reaction was heated to 78° C. overnight. The subsequent addition of the reactants as described above and allowing the reaction to continue over a second night, resulted in ~75% product: starting material. The reaction was cooled to room temperature, concentrated in vacuo, diluted with EtOAc, washed with NaHCO$_3$, and brine. The solution was filtered, and concentrated, then purified via silica gel chromatography to give the product as a clear oil. (32.7 mg, 68%) Calculated for C31H42F3NO2 (M+H) 517.67, Found 518.4.

d) 2-{5-[1-(1-Ethyl-propyl)-piperidin-3-yl]-4'-trifluoromethyl-biphenyl-3-yl}-4-methyl-pentanoic acid To a solution of compound 33c, 2-{5-[1-(1-Ethyl-propyl)-piperidin-3-yl]-4'-trifluoromethyl-biphenyl-3-yl}-4-methyl-pentanoic acid ethyl ester (30.7 mg, 59.3 μmol) in EtOH (3 ml) was added 2M KOH (119 μl, 0.24 mmol). The reaction was heated to 78° C. for 2.5 hours, cooled to room temperature, and concentrated in vacuo. Purification via Gilson HPLC, followed by salt exchange with aqueous 1N HCl, gave the product as a white solid. (10.2 mg, 35%) 1H NMR (300 MHz, MeOD) δ ppm 0.85 (d, J=6.78 Hz, 6 H) 0.99 (td, J=7.35, 3.77 Hz, 6 H) 1.35-1.49 (m, 1 H) 1.56-1.70 (m, 3 H) 1.79-1.93 (m, 4 H) 1.94-2.08 (m, 4H) 2.99 (dd, J=7.91, 4.14 Hz, 1 H) 3.05-3.15 (m, 2 H) 3.41 (s, 2 H) 3.68 (t, J=7.72 Hz, 1 H) 7.27 (s, 1 H) 7.47 (d, J=9.80 Hz, 2 H) 7.64-7.75 (m, 4 H) Calcd for C29H38F3NO2 (M+H) 489.61, Found 490.4.

EXAMPLE 34

4-Methyl-2-{5-[1-(3-methyl-butyl)-6-trifluoromethyl-piperidin-3-yl]-4'-trifluoromethyl-biphenyl-3-yl}-pentanoic acid

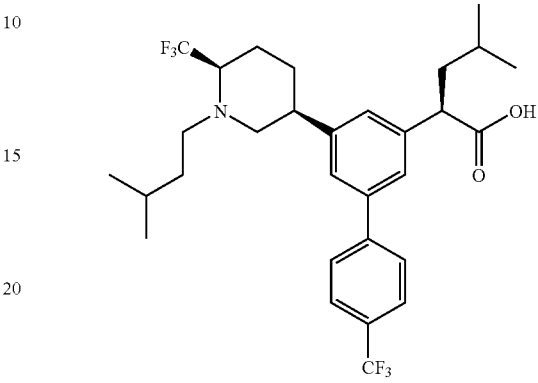

Replacing compound 25b-2 with compound 25b-1 following the same reductive-amination and saponification procedure as in Example 27 gave the title compound (Stereochemistry was tentatively assigned); 1H NMR (400 MHz, MeOD) δ ppm 0.93 (ddd, J=12.72, 6.60, 2.93 Hz, 12 H), 1.34-1.45 (m, 2 H), 1.52 (dt, J=13.27, 6.69 Hz, 1 H), 1.60-1.71 (m, 2 H), 1.86 (s, 2 H), 1.94-2.06 (m, 3 H), 2.78-2.90 (m, 3 H), 2.91-2.96 (m, 2 H), 3.35-3.45 (m, 1 H), 3.73 (t, J=7.70 Hz, 1 H), 7.26 (s, 1 H), 7.39 (s, 1 H), 7.47 (s, 1 H), 7.74 (q, J=8.48 Hz, 4 H); Calcd for C30H37F6NO2 (M+H) 558.27, Found 558.2.

EXAMPLE 35

4-Methyl-2-[4'-trifluoromethyl-5-(6-trifluoromethyl-piperidin-3-yl)-biphenyl-3-yl]-pentanoic acid

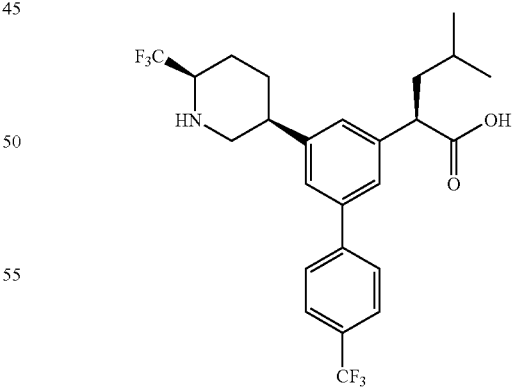

Compound 25b-1 was hydrolyzed following the same hydrolyzation procedure as in the preparation of Example 11 to give the title compound (Stereochemistry was tentatively assigned); 1H NMR (400 MHz, MeOD) δ ppm 0.94 (dd, J=6.60, 2.69 Hz, 6 H), 1.51 (dt, J=13.27, 6.69 Hz, 1 H), 1.68 (ddd, J=13.69, 7.21, 6.97 Hz, 1 H), 1.91-2.02 (m, 5 H), 2.86-2.94 (m, 1 H), 2.99-3.08 (m, 1 H), 3.09-3.17 (m, 1 H), 3.44 (dt, J=9.23, 4.55 Hz, 1 H), 3.73 (t, J=7.83 Hz, 1 H), 7.35-7.42 (m, 1 H), 7.50 (d, J=17.36 Hz, 2 H), 7.71-7.80 (m, 4 H); Calcd for C25H27F6NO2 (M+H) 488.19, Found 488.1.

EXAMPLE 36

4-Methyl-2-[4'-trifluoromethyl-5-(6-trifluoromethyl-piperidin-3-yl)-biphenyl-3-yl]-pentanoic acid

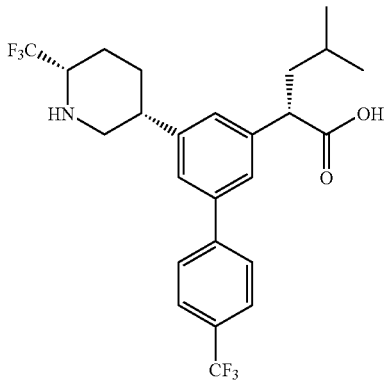

Compound 25b-2 was hydrolyzed following the same hydrolyzation procedure as in the preparation of Example 11 to give the title compound (Stereochemistry was tentatively assigned); 1H NMR (400 MHz, MeOD) δ ppm 0.90-0.98 (m, 6 H), 1.51 (dt, J=13.39, 6.63 Hz, 1 H), 1.59-1.70 (m, 2 H), 1.78-1.88 (m, 1 H), 1.97-2.12 (m, 3 H), 2.76-2.86 (m, 2 H), 3.20 (d, J=7.83 Hz, 1 H), 3.36 (ddd, J=1 1.43, 7.28, 2.57 Hz, 1 H), 3.73 (t, J=7.83 Hz, 1 H), 7.29 (s, 1 H), 7.44 (s, 1 H), 7.49 (s, 1 H), 7.71-7.81 (m, 4); Calcd for C25H27F6NO2 (M+H) 488.19, Found 488.1.

EXAMPLE 37

(R*) 4-Methyl-2-(4'-trifluoromethyl-5-{1-[1-(4-trifluoromethyl-phenyl)-propyl]-piperidin-3-yl}-biphenyl-3-yl)-pentanoic acid; (R* refers to the stereochemistry as draw not determined)

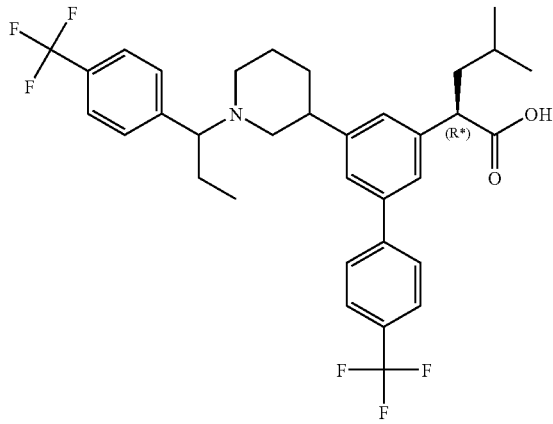

a) 1-(4-Trifluoromethyl-phenyl)-propan-1-ol

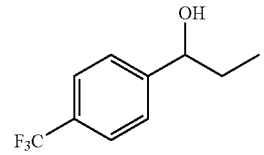

To 4-trifluoromethylpropiophenone (1.0 g, 5.0 mmol) in MeOH (25 mL, 0.20 M), was added NaBH4 (187 mg, 5.0 mmol). After 3 hours at RT, the reaction was concentrated in vacuo, partitioned between H2O and CH2Cl2, dried, filtered and concentrated to give the title compound as a white solid (0.97 g, 96%). 1H NMR (300 MHz, CHLOROFORM-D) δ ppm 0.93 (t, J=7.54 Hz, 3 H) 1.71-1.85 (m, 2 H) 1.85-1.92 (m, 1 H) 4.69 (td, J=6.41, 3.39 Hz, 1 H) 7.44-7.50 (m, 2 H) 7.61 (d, J=8.29 Hz, 2 H).

b) Methanesulfonic acid 1-(4-trifluoromethyl-phenyl)-propyl ester

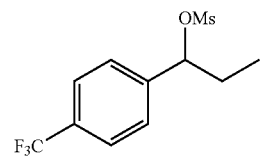

To a solution of compound 37a from the above reaction (918 mg, 4.5 mmol) in anhydrous CH2Cl2 (30 mL, 0.15 M) at 0° C. was added triethylamine (2.54 mL, 18 mmol), and methanesulfonylchloride (1.0 mL, 13.5 mmol). The cold bath was removed and the reaction stirred at RT. Once complete, the reaction was quenched with 1N HCl, diluted with H2O and extracted. The organics were washed with H2O and brine, dried, filtered and concentrated to give the title compound as a yellow oil. 1H NMR (300 MHz, CHLOROFORM-D) δ ppm 0.98 (t, J=7.35 Hz, 3 H) 1.92 (ddd, J=13.47, 7.16, 6.88 Hz, 1 H) 2.08 (dt, J=14.41, 7.30 Hz, 1 H) 2.80 (s, 3 H) 5.48-5.54 (m, 1 H) 7.50 (d, J=8.29 Hz, 2 H) 7.67 (d, J=7.91 Hz, 2 H)

c) 4-Methyl-2-(4'-trifluoromethyl-5-{1-[1-(4-trifluoromethyl-phenyl)-propyl]-piperidin-3-yl}-biphenyl-3-yl)-pentanoic acid ethyl ester

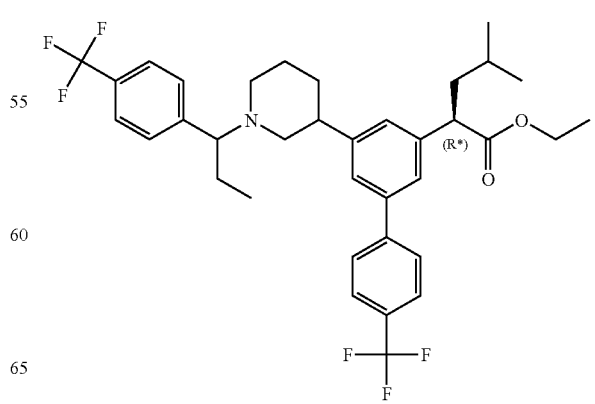

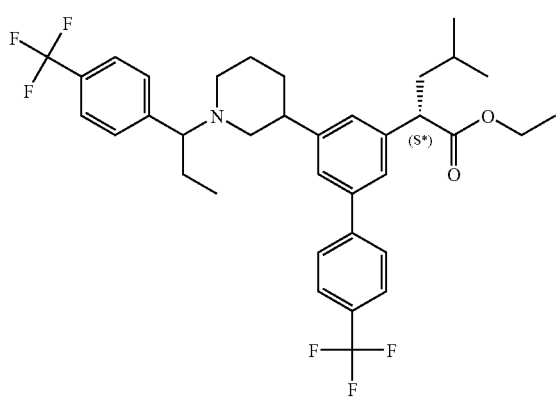

To a solution of compound 37b obtained from the above reaction in DMF (4 mL) was added compound 33b (1.3 g, 4.5 mmol) and $Cs_2CO_3$ (2.0 g, 6.0 mmol). After stirring 17 hours at RT, the reaction was poured into EtOAc, washed with $NaHCO_3$, $H_2O$ (3×) and brine, dried, filtered and concentrated to give a yellow oil. Purification via silica gel chromatography employing the Isco purification system gave two mixtures of diastereomers. The stereochemistry of the alpha-chain (C-2) of two diastereomer are tentatively assigned as shown; Compound A: $^1$H NMR (300 MHz, CHLOROFORM-D) δ ppm 0.80 (t, J=6.97 Hz, 3 H) 0.87-0.96 (m, 6 H) 1.24 (t, J=6.97 Hz, 3 H) 1.43-1.67 (m, 4 H) 1.95-2.10 (m, 5 H) 2.40-2.60 (m, 3 H) 3.35-3.60 (m, 3 H) 3.69 (dd, J=8.29, 6.78 Hz, 1 H) 4.05-4.21 (m, 2 H) 7.15 (d, J=4.90 Hz, 1 H) 7.29 (d, J=1.88 Hz, 2 H) 7.47 (s, 2 H) 7.57-7.76 (m, 6 H); Calc'd for $C_{36}H_{41}F_6NO_2$ $(M+H)^+$ 633.71, Found 634.3. Compound B: $^1$H NMR (300 MHz, CHLOROFORM-D) δ ppm 0.73 (t, J=7.16 Hz, 1 H) 0.85-0.96 (m, 7 H) 1.18-1.28 (m, 3 H) 1.44-2.2 (m, 9 H) 2.88-2.96 (m, 4 H) 3.32-3.98 (m, 4 H) 4.06-4.22 (m, 2 H) 7.29 (s, 1 H) 7.41 (s, 1 H) 7.40-7.71 (m, 9 H); Calc'd for $C_{36}H_{41}F_6NO_2$ $(M+H)^+$ 633.71, Found 634.3.

d) (R*) 4-Methyl-2-(4'-trifluoromethyl-5-{1-[1-(4-trifluoromethyl-phenyl)-propyl]-piperidin-3-yl}-biphenyl-3-yl)-pentanoic acid

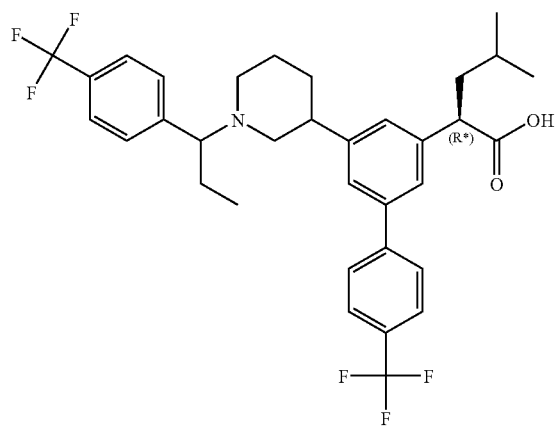

Compound A, obtained from the above reaction (125 mg, 0.197 mmol) in EtOH (10 mL) and 2M KOH (0.4 mL, 0.79 mmol) was heated to 78° C. for 2 hours, then cooled and concentrated in vacuo for 30 minutes. The concentrate was diluted with $CH_2Cl_2$ and $H_2O$; adjusting the pH to ~7 with 10% citric acid, the organics were extracted 3× with $CH_2Cl_2$, dried and filtered. Purification via silica gel chromatography employing the Isco purification system gave the product as an oil. $^1$H NMR (300 MHz, MeOD) δ ppm 0.61 (t, J=7.16 Hz, 3 H) 0.79-0.89 (m, 6 H) 1.44-1.71 (m, 6 H) 1.91-2.20(m, 3 H) 2.82-2.43 (m, 2 H) 2.75-2.89 (m, 1 H) 3.09 (d, J =10.17 Hz, 1H) 3.32 (d, J=8.67 Hz, 1 H) 3.53-3.64 (m, 1 H) 3.88 (td, J=7.35, 3.77 Hz, 1 H) 7.18-7.27 (m, 2 H) 7.43-7.52 (m, 3 H) 7.55-7.66 (m, 6 H); Calc'd for $C_{34}H_{37}F_6NO_2$ $(M+H)^+$ 605.65, Found 606.2.

The oil was concentrated with 1N HCl/Ether to provide the title compound as the HCl salt.

EXAMPLE 38

(S*) 4-Methyl-2-(4'-trifluoromethyl-5-{1-[1-(4-trifluoromethyl-phenyl)-propyl]-piperidin-3-yl}-biphenyl-3-yl)-pentanoic acid

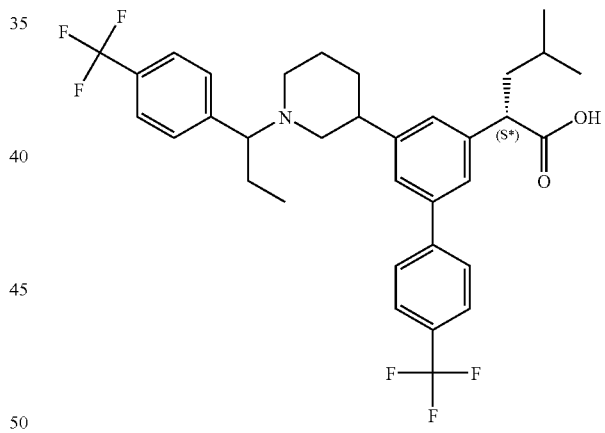

Compound B, prepared from Example 37, step (c) (200 mg, 0.316 mmol) in EtOH (15 mL) and 2M KOH (0.6 mL, 1.26 mmol) was heated to 78° C. for 2 hours, cooled and concentrated in vacuo for 30 minutes. The concentrate was diluted with $CH_2Cl_2$ and $H_2O$; adjusted to pH ~7 with 10% citric acid, and the organics were extracted 3× with $CH_2Cl_2$, dried and filtered. Purification via silica gel chromatography employing the Isco purification system gave the product as an oil. $^1$H NMR (300 MHz, MeOD) δ ppm 0.61 (t, J=7.35 Hz, 3 H) 0.82-0.90 (m, 6 H) 1.45-1.61 (m, 6 H) 1.91-2.03 (m, 2 H) 2.06-2.13 (m, 1 H) 2.25-2.39 (m, 2 H) 2.79-2.90 (m, 1 H) 3.07 (d, J=11.30 Hz, 1 H) 3.34 (d, J=10.17 Hz, 1 H) 3.53-3.66 (m, 1 H) 3.78-3.89 (m, 1 H) 7.20-7.28 (m, 2 H) 7.45-7.53 (m, 3 H) 7.57-7.68 (m, 6 H);

Calc'd for $C_{34}H_{37}F_6NO_2$ $(M+H)^+$ 605.65, Found 606.2.

The oil was concentrated with 1N HCl/Ether to provide the title compound as the HCl salt.

EXAMPLE 39

2-[5-(1-Methanesulfonyl-piperidin-3-yl)-4'-trifluoromethyl-biphenyl-3-yl]-4-methyl-pentanoic acid

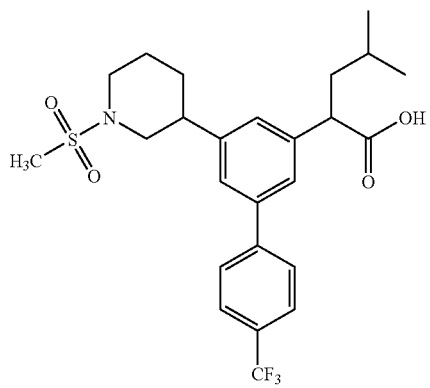

a) 2-[5-(1-Methanesulfonyl-piperidin-3-yl)-4'-trifluoromethyl-biphenyl-3-yl]-4-methyl-pentanoic acid ethyl ester

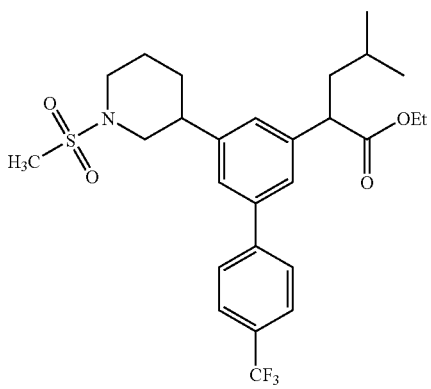

To a solution of compound 33b, 4-Methyl-2-(5-piperidin-3-yl-4'-trifluoromethyl-biphenyl-3-yl)-pentanoic acid ethyl ester (833 mg, 1.86 mmol) in anhydrous $CH_2Cl_2$ (27 ml) was added methanesulfonyl chloride (0.95 ml, 12.2 mmol) and Triethylamine (2.34 ml, 16.3 mmol). The reaction stirred at room temperature for 2 hours, was diluted with dichlormethane and washed with sat. $NaHCO_3$, and brine, dried and filtered to give a yellow oil. Purification by silica gel chromatography (Isco) gave the product as an off white solid, (662 mg, 68%). Calcd for $C_{27}H_{34}FNO_4S$ (M+H) 525.62, Found 526.3 b) 2-[5-(1-Methanesulfonyl-piperidin-3-yl)-4'-trifluoromethyl-biphenyl-3-yl]-4-methyl-pentanoic acid To a solution of compound 39a, 2-[5-(1-Methanesulfonyl-piperidin-3-yl)-4'-trifluoromethyl-biphenyl-3-yl]-4-methyl-pentanoic acid ethyl ester (70.0 mg, 0.133 mmol) in EtOH (6.5 ml) was added 2M KOH (0.027 ml, 0.53 mmol). The reaction was heated to 78° C. for 3 hours, cooled to room temperature, and concentrated in vacuo. Purification via Gilson HPLC, gave the product as a white lyophilate. (53.4 mg, 81%) 1H NMR (300 MHz, MeOD) δ ppm 0.85 (dd, J=6.59, 1.70 Hz, 6 H) 1.42 (dt, J=13.28, 6.74 Hz, 1 H) 1.56-1.71 (m, 3 H) 1.79-1.87 (m, 1 H) 1.92 (dd, J=13.56, 7.16 Hz, 2 H) 2.69-2.85 (m, 5 H) 3.19-3.23 (m, 2 H) 3.61-3.72 (m, 3 H) 7.23 (s, 1 H) 7.42 (d, J=1.51 Hz, 2 H) 7.62-7.74 (m, 4 H) Calcd for $C_{25}H_{30}F_3NO_4S$ (M+H) 497.57, Found 498.3.

EXAMPLE 40

4-Methyl-2-{4'-trifluoromethyl-5-[1-(3-trifluoromethyl-benzenesulfonyl)-piperidin-3-yl]-biphenyl-3-yl}-pentanoic acid

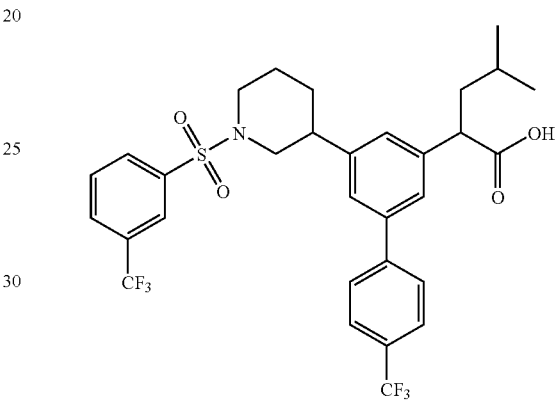

a) 4-Methyl-2-{4'-trifluoromethyl-5-[1-(3-trifluoromethyl-benzenesulfonyl)-piperidin-3-yl]-biphenyl-3-yl}-pentanoic acid ethyl ester

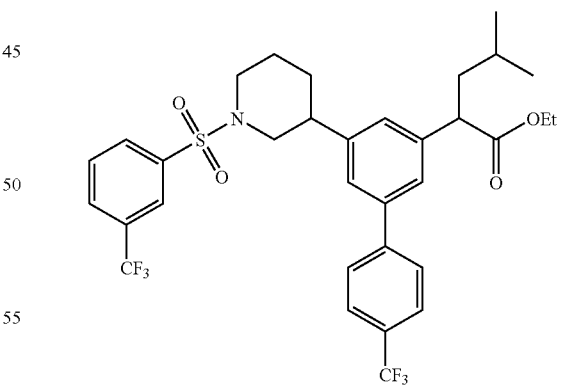

To a solution of compound 33b, 4-Methyl-2-(5-piperidin-3-yl-4'-trifluoromethyl-biphenyl-3-yl)-pentanoic acid ethyl ester (42 mg, 0.094mmol) in anhydrous $CH_2Cl_2$ (5 ml) was added 3-(Trifluoromethyl)benzene sulfonyl chloride (22.5 μl, 0.14 mmol) and diisopropylethylamine (32.7 μl, 0.19 mmol). The reaction stirred at room temperature overnight, was diluted with EtOAc and washed with sat. $NaHCO_3$, and brine, dried and filtered. Purification by silica gel chromatography (Isco) gave the desired product, (48.5 mg, 79%). Calcd for C33H35F6NO4S (M+H) 655.69, Found 656.2.

b) 4-Methyl-2-{4'-trifluoromethyl-5-[1-(3-trifluoromethyl-benzenesulfonyl)-piperidin-3-yl]-biphenyl-3-yl}-pentanoic acid To a solution of 40a, 4-Methyl-2-{4'-trifluoromethyl-5-[1-(3-trifluoromethyl-benzenesulfonyl)-piperidin-3-yl]-biphenyl-3-yl}-pentanoic acid ethyl ester (47.0 mg, 0.072 mmol) in EtOH (4.0 ml) was added 2M KOH (.36 ml, 0.72 mmol). The reaction was heated to 78° C. for 2 hours, cooled to room temperature, and concentrated in vacuo. Purification via Gilson HPLC, gave the product as a white lyophilate. (31.8 mg, 71%) 1H NMR (300 MHz, MeOD) δ ppm 0.84 (d, J=6.41 Hz, 6 H) 1.36-1.47 (m, J=13.42, 6.97, 6.76, 6.76 Hz, 1 H) 1.50-1.64 (m, J=16.81, 7.11, 3.77, 3.58 Hz, 2 H) 1.76-1.91 (m, 3 H) 2.43 (t, J=10.93 Hz, 2 H) 2.78-2.89 (m, 1 H) 3.63 (t, J=7.72 Hz, 1 H) 3.69-3.78 (m, 2 H) 7.16 (s, 1 H) 7.38 (d, J=19.59 Hz, 2 H) 7.61-7.77 (m, 5 H) 7.88-7.99 (m, 3 H) Calcd for C31H31F6NO4S (M+H) 627.64, Found 628.0.

EXAMPLE 41

2-{5-[1-(Isoquinoline-5-sulfonyl)-piperidin-3-yl]-4'-trifluoromethyl-biphenyl-3-yl}-4-methyl-pentanoic acid

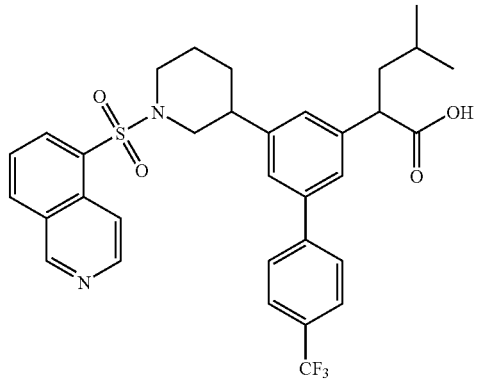

a) 2-{5-[1-(Isoquinoline-5-sulfonyl)-piperidin-3-yl]-4'-trifluoromethyl-biphenyl-3-yl}-4-methyl-pentanoic acid ethyl ester

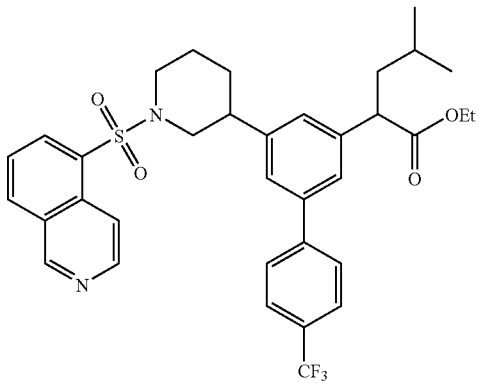

To a solution of compound 33b, 4-Methyl-2-(5-piperidin-3-yl-4'-trifluoromethyl-biphenyl-3-yl)-pentanoic acid ethyl ester (48.0 mg, 0.106mmol) in anhydrous dichloromethane (4 ml) was added isoquinoline -5-sulfonyl chloride (42.1 mg, 0.16 mmol) and DIEA (37.0 µl, 0.21 mmol). The reaction stirred at room temperature over 72 hours, was diluted with dichloromethane and washed with sat. NaHCO3, and brine, dried and filtered. Purification by silica gel chromatography (Isco) gave the desired product, (60.0 mg, 88%). Calcd for C35H37F3N2O4S (M+H) 638.74, Found 639.3.

b) 2-{5-[1-(Isoquinoline-5-sulfonyl)-piperidin-3-yl]-4'-trifluoromethyl-biphenyl-3-yl}-4-methyl-pentanoic acid To a solution of compound 41a, 2-{5-[1-(Isoquinoline-5-sulfonyl)-piperidin-3-yl]-4'-trifluoromethyl-biphenyl-3-yl}-4-methyl-pentanoic acid ethyl ester (59.0 mg, 0.092 mmol) in EtOH (4.6 ml) was added 2M KOH (0.46 ml, 0.92 mmol). The reaction was heated to 78° C. for 2 hours, cooled to room temperature, and concentrated in vacuo. Purification via Gilson HPLC, gave the product (35.7 mg, 63%) 1H NMR (300 MHz, MeOD) δ ppm 0.79-0.86 (m, 6 H) 1.33-1.46 (m, J=13.21, 6.78, 6.65, 6.65, 6.65 Hz, 1 H) 1.49-1.64 (m, 3 H) 1.76-1.92 (m, 3 H) 2.64-2.72 (m, 1 H) 2.74-2.81 (m, 2 H) 3.62 (t, J=7.91 Hz, 1 H) 3.86 (d, J=10.55 Hz, 2 H) 7.13 (s, 1 H) 7.31 (s, 1 H) 7.40 (s, 1 H) 7.61-7.69 (m, 4 H) 8.00 (t, J=7.72 Hz, 1 H) 8.57-8.66 (m, 3 H) 8.99 (d, J=5.65 Hz, 1 H) 9.73 (s, 1 H) Calcd for C33H33F3N2O4S (M+H) 610.69, Found 611.2.

EXAMPLE 42

4-Methyl-2-{4'-trifluoromethyl-5-[1-(2-trifluoromethyl-benzenesulfonyl)-piperidin-3-yl]-biphenyl-3-yl}-pentanoic acid

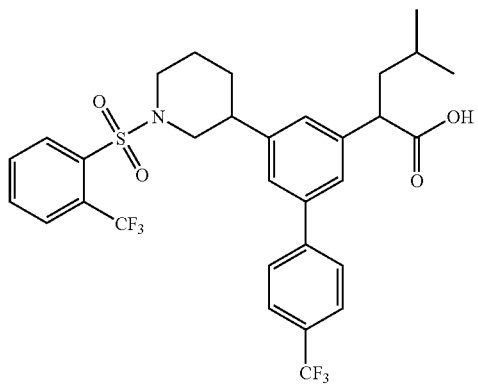

a) 4-Methyl-2-{4'-trifluoromethyl-5-[1-(2-trifluoromethyl-benzenesulfonyl)-piperidin-3-yl]-biphenyl-3-yl}-pentanoic acid ethyl ester

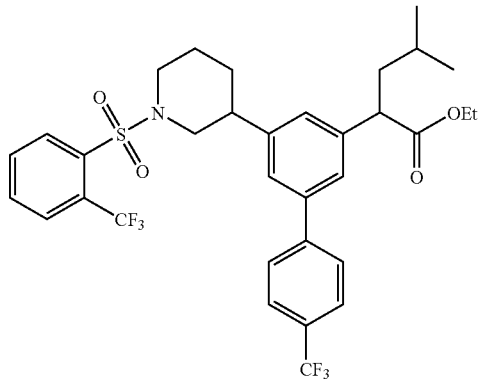

To a solution of compound 33b, 4-Methyl-2-(5-piperidin-3-yl-4'-trifluoromethyl-biphenyl-3-yl)-pentanoic acid ethyl ester (30.5 mg, 0.07mmol) in anhydrous CH$_2$Cl$_2$ (4 ml) was added 2-(Trifluoromethyl)benzene sulfonyl chloride (25.0 mg, 0.10 mmol) and diisopropylethylamine (24 µl, 0.14 mmol). The reaction stirred at room temperature 3 hours, was diluted with EtOAc and washed with sat. NaHCO$_3$, and brine, dried and filtered. Purification by silica gel chromatography (Isco) gave the desired product, (35.4 mg, 79%). Calcd for C33H35F6NO4S (M+H) 655.69, Found 656.2.

b) 4-Methyl-2-{4'-trifluoromethyl-5-[1-(2-trifluoromethyl-benzenesulfonyl)-piperidin-3-yl]-biphenyl-3-yl}-pentanoic acid To a solution of compound 42a, 4-Methyl-2-{4'-trifluoromethyl-5-[1-(2-trifluoromethyl-benzenesulfonyl)-piperidin-3-yl]-biphenyl-3-yl}-pentanoic acid ethyl ester (34.0 mg, 0.052 mmol) in EtOH (2.6 ml) was added 2M KOH (0.26 ml, 0.52 mmol). The reaction was heated to 78° C. for 1.5 hours, cooled to room temperature, and concentrated in vacuo. Purification via Gilson HPLC, gave the product as a white lyophilate. (17.3 mg, 53%) 1HNMR(300 MHz, MeOD) δ ppm0.79-0.87 (m, 6 H) 1.41 (dt,J=13.28, 6.74 Hz, 1 H) 1.53-1.69 (m, 3 H) 1.79 (dd, J=5.84, 2.83 Hz, 1 H) 1.84-1.96 (m, 2 H) 2.71-2.84 (m, 3 H) 3.64 (t, J=7.72 Hz, 1 H) 3.79 (d, J=6.03 Hz, 2 H) 7.18 (s, 1H) 7.38 (d, J=16.58 Hz, 2 H) 7.62-7.76 (m, 6 H) 7.85-7.90 (m, 1 H) 7.99-8.04 (m, 1 H) Calcd for C31H31F6NO4S (M+H) 627.64, Found 628.3.

EXAMPLE 43

4-Methyl-2-{4'-trifluoromethyl-5-[1-(4-trifluoromethyl-benzoyl)-piperidin-3-yl]-biphenyl-3-yl}-pentanoic acid

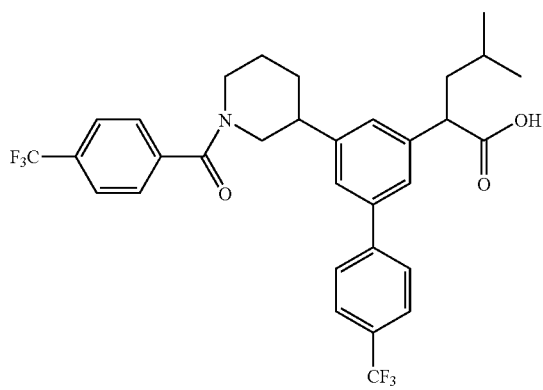

a) 4-Methyl-2-{4'-trifluoromethyl-5-[1-(4-trifluoromethyl-benzoyl)-piperidin-3-yl]-biphenyl-3-yl}-pentanoic acid ethyl ester

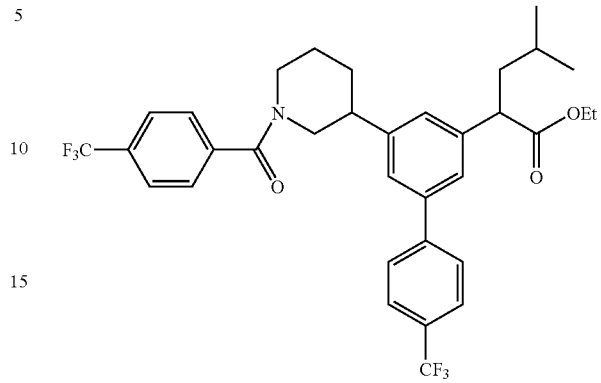

To a solution of compound 33b, 4-Methyl-2-(5-piperidin-3-yl-4'-trifluoromethyl-biphenyl-3-yl)-pentanoic acid ethyl ester) (51 mg, 0.11 mmol) in CH$_3$CN (5 ml) was added 4-(Trifluoromethyl)benzoyl chloride (35.6 mg, 0.17 mmol) and diisopropylethylamine (40 µl, 0.23 mmol). The reaction was microwaved at 130° C. for 10 minutes, was diluted with EtOAc and washed with brine, sat. NaHCO$_3$, and brine, dried and filtered. Purification by silica gel chromatography (Isco) gave the desired product, (62 mg, 87%). Calcd for C34H35F6NO3 (M+H) 619.64, Found 620.4.

b) 4-Methyl-2-{4'-trifluoromethyl-5-[1-(4-trifluoromethyl-benzoyl)-piperidin-3-yl]-biphenyl-3-yl}-pentanoic acid To a solution of compound 43a, 4-Methyl-2-{4'-trifluoromethyl-5-[1-(4-trifluoromethyl-benzoyl)-piperidin-3-yl]-biphenyl-3-yl}-pentanoic acid ethyl ester 60.0 mg, 0.097 mmol) in EtOH (4.8 ml) was added 2M KOH (0.48 ml, 0.48 mmol). The reaction was heated to 78° C. for 1.5 hours, cooled to room temperature, and concentrated in vacuo. Purification via Gilson HPLC, gave the product as a white lyophilate, (21.7 mg, 38%). 1H NMR (300 MHz, MeOD) δ ppm 0.88-0.96 (m, 6 H) 1.42-2.15 (m, 6 H) 2.70-3.24 (m, 3 H) 3.66-3.80 (m, 3 H) 4.68-7.71 (m, 1 H) 7.17 (s, 1 H) 7.32-7.81 (m, 10 H), Calcd for C32H31F6NO3 (M+H) 591.58, Found 592.3.

EXAMPLE 44

4-Methyl-2-{5-[1-(4-pyrrol-1-yl-benzyl)-piperidin-3-yl]-4'-trifluoromethyl-biphenyl-3-yl}-pentanoic acid

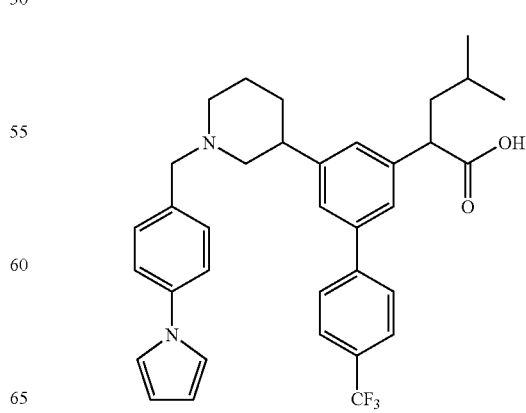

111 a) 4-Methyl-2-{5-[1-(4-pyrrol-1-yl-benzyl)-piperidin-3-yl]-4'-trifluoromethyl-biphenyl-3-yl}-pentanoic acid ethyl ester

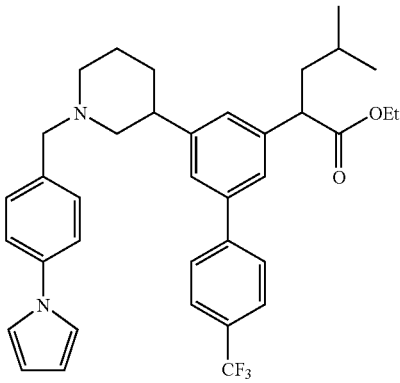

To a solution of compound 33b, 4-Methyl-2-(5-piperidin-3-yl-4'-trifluoromethyl-biphenyl-3-yl)-pentanoic acid ethyl ester (44.4 mg, 0.10 mmol) in CH$_3$CN (5 ml) was added 1-[4-Bromomethyl) phenyl]-H-pyrrole) (35.1 mg, 0.15 mmol) and diisopropylethylamine (35 μl, 0.20 mmol). The reaction was microwaved at 150° C. for 1 hour, then continued at room temperature overnight, then diluted with EtOAc and washed with brine, sat. NaHCO$_3$, and brine, dried and filtered. Purification by silica gel chromatography (Isco) gave the desired product, (56 mg, 94%). Calcd for C37H41F3N2O2 (M+H) 602.73, Found 603.5 b) 4-Methyl-2-{5-[1-(4-pyrrol-1-yl-benzyl)-piperidin-3-yl]-4'-trifluoromethyl-biphenyl-3-yl}-pentanoic acid To compound 44a, 4-Methyl-2-{5-[1-(4-pyrrol-1-yl-benzyl)-piperidin-3-yl]-4'-trifluoromethyl-biphenyl-3-yl}-pentanoic acid ethyl ester (56.2, 0.09 mmol) in EtOH (5 ml) was added 2M KOH (0.5 ml, 0.93 mmol). The reaction was heated to 78° C. for 1.5 hours, cooled to room temperature, and concentrated in vacuo. Purification via Gilson HPLC, salt exchange with 1N HCl (aqueous) gave the product as a white lyophilate, (32 mg, 56% ). 1H NMR (300 MHz, MeOD) δ ppm 0.89-0.97 (m, 6 H) 1.50 (dt, J=13.28, 6.74 Hz, 1 H) 1.67 (dt, J=13.47, 6.64 Hz, 1 H) 1.89-2.03 (m, 3 H) 2.05-2.15 (m, 2 H) 3.06-3.22 (m, 2 H) 3.52-3.63 (m, 2 H) 3.76 (t, J=7.72 Hz, 1 H) 4.39 (d, J=2.64 Hz, 2 H) 6.29-6.33 (m, 2 H) 7.23-7.26 (m, 2 H) 7.33 (s, 1 H) 7.54 (d, J=19.97 Hz, 2 H) 7.61 (s, 4 H) 7.78 (q, J=8.41 Hz, 4 H), Calcd for C35H37F3N2O2 (M+H) 574.68, Found 575.4.

EXAMPLE 45

2-{5-[1-(3-Fluoro-5-trifluoromethyl-benzyl)-piperidin-3-yl]-4'-trifluoromethyl-biphenyl-3-yl}-4-methyl-pentanoic acid

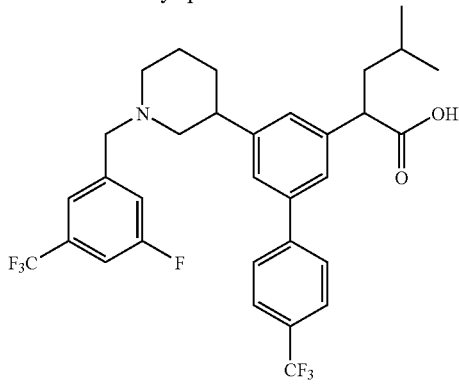

112 a) 2-{5-[1-(3-Fluoro-5-trifluoromethyl-benzyl)-piperidin-3-yl]-4'-trifluoromethyl-biphenyl-3-yl}-4-methyl-pentanoic acid

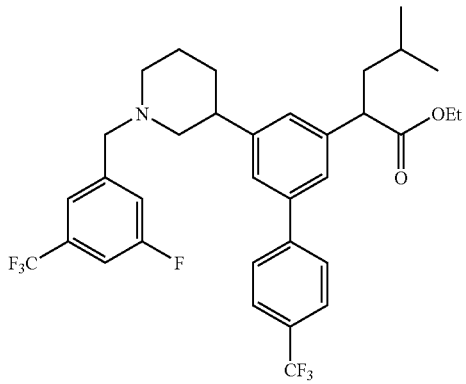

To a solution of compound 33b, 4-Methyl-2-(5-piperidin-3-yl-4'-trifluoromethyl-biphenyl-3-yl)-pentanoic acid ethyl ester (44.6 mg, 0.10 mmol) in CH$_3$CN (5 ml) was added 3-Fluoro-5-trifluoromethyl benzyl bromide) (77 mg, 0.3 mmol) and diisopropylethylamine (35 μl, 0.20 mmol). The reaction was microwaved at 130° C. for 10 minutes, then diluted with EtOAc and washed with brine, sat. NaHCO$_3$, and brine, dried and filtered. Purification by silica gel chromatography (Isco) gave the desired product, (53 mg, 85%). Calcd for C34H36F7N1O2 (M+H) 623.64, Found 624.3 b) 2-{5-[1-(3-Fluoro-5-trifluoromethyl-benzyl)-piperidin-3-yl]-4'-trifluoromethyl-biphenyl-3-yl}-4-methyl-pentanoic acid To compound 45a, 2-{5-[1-(3-Fluoro-5-trifluoromethyl-benzyl)-piperidin-3-yl]-4'-trifluoromethyl-biphenyl-3-yl}-4-methyl-pentanoic acid (53.3 mg, 0.085 mmol) in EtOH (4.3 ml) was added 2M KOH (0.43 ml, 0.85 mmol). The reaction was heated to 78° C. for 1 hour, cooled to room temperature, and concentrated in vacuo. Purification via Gilson HPLC, salt exchange with 1N HCl (aqueous) gave the product as a white lyophilate, (34 mg, 63%). 1H NMR (300 MHz, MeOD) δ ppm 0.90-0.97 (m, 6 H) 1.50 (dt, J=13.28, 6.74 Hz, 1 H) 1.68 (dt, J=13.66, 6.92 Hz, 1 H) 1.89-2.04 (m, 2 H) 2.05-2.15 (m, 2 H) 3.06-3.36 (m, 3 H) 3.50-3.64 (m, 2 H) 3.77 (t, J=7.72 Hz, 1 H) 4.41-4.56 (m, 3 H) 7.34 (s, 1 H) 7.55 (d, J=18.46 Hz, 2 H) 7.67 (t, J=8.29 Hz, 2 H) 7.78 (q, J=8.29 Hz, 5 H), Calcd for C32H32F7NO2 (M+H) 595.59, Found 596.4.

EXAMPLE 46

4-Methyl-2-[5-(1-naphthalen-2-ylmethyl-piperidin-3-yl)-4'-trifluoromethyl-biphenyl-3-yl]-pentanoic acid

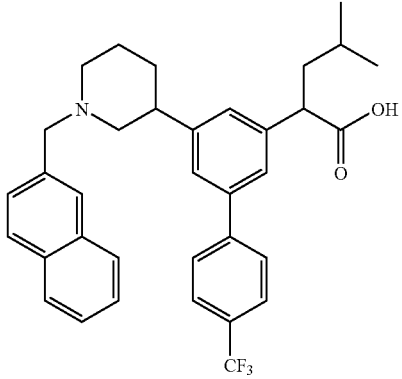

113 a) 4-Methyl-2-[5-(1-naphthalen-2-ylmethyl-piperidin-3-yl)-4'-trifluoromethyl-biphenyl-3-yl]-pentanoic acid ethyl ester

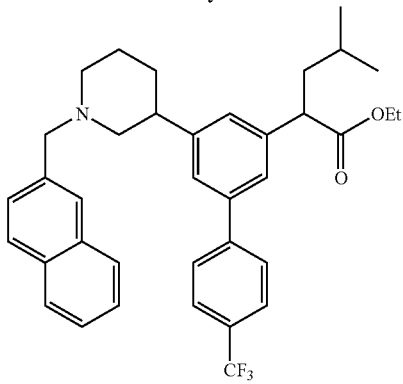

To a solution of compound 33b, 4-Methyl-2-(5-piperidin-3-yl-4'-trifluoromethyl-biphenyl-3-yl)-pentanoic acid ethyl ester (44.4 mg, 0.10 mmol) in $CH_3CN$ (5 ml) was added 2-Bromomethyl napthalene) (33 mg, 0.15 mmol) and diisopropylethylamine (35 µl, 0.20 mmol). The reaction was microwaved at 130° C. for 10 minutes, then diluted with EtOAc and washed with brine, sat. $NaHCO_3$, and brine, dried and filtered. Purification by silica gel chromatography (Isco) gave the desired product as a clear oil, (51 mg, 87%). Calcd for $C_{37}H_{40}F_3NO_2$ (M+H) 587.71, Found 588.5.

b) 4-Methyl-2-[5-(1-naphthalen-2-ylmethyl-piperidin-3-yl)-4'-trifluoromethyl-biphenyl-3-yl]-pentanoic acid To compound 46a, 4-Methyl-2-[5-(1-naphthalen-2-ylmethyl-piperidin-3-yl)-4'-trifluoromethyl-biphenyl-3-yl]-pentanoic acid ethyl ester (48.4 mg, 0.082mmol) in EtOH (4.1 ml) was added 2M KOH (0.41 ml, 0.82 mmol). The reaction was heated to 78° C. for 1.5 hour, cooled to room temperature, and concentrated in vacuo. Purification via Gilson HPLC, salt exchange with 1N HCl (aqueous) gave the product as a white lyophilate, (27 mg, 56%). 1HNMR (300 MHz, MeOD) δ ppm 0.88-0.96 (m, 7 H) 1.41-1.52 (m, J=6.59, 6.59, 6.59, 6.59 Hz, 1 H) 1.61-1.70 (m, J=7.06, 6.74, 6.74, 2.45 Hz, 1 H) 1.89-2.02 (m, 3 H) 2.04-2.14 (m, 2 H) 3.08-3.05 (m, 3 H) 3.52-3.67 (m, 2 H) 3.75 (t, J=7.91 Hz, 1 H) 4.47-4.61 (m, 2 H) 7.32 (s, 1 H) 7.49-7.64 (m, 5 H) 7.77 (q, J=8.29 Hz, 4 H) 7.91-8.02 (m, 3 H) 8.07 (s, 1 H), Calcd for $C_{32}H_{32}F_7NO_2$ (M+H) 559.66, Found 560.4.

EXAMPLE 47

4-Methyl-2-{5-[1-(4-trifluoromethoxy-benzyl)-piperidin-3-yl]-4'-trifluoromethyl-biphenyl-3-yl}-pentanoic acid

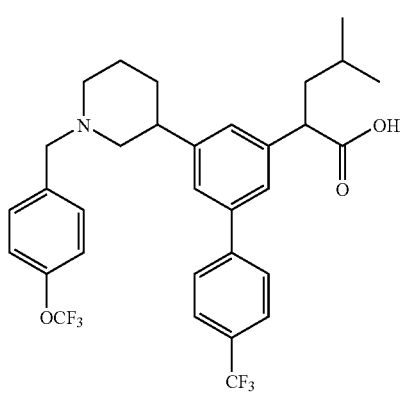

114 a) 4-Methyl-2-{5-[1-(4-trifluoromethoxy-benzyl)-piperidin-3-yl]-4'-trifluoromethyl-biphenyl-3-yl}-pentanoic acid ethyl ester

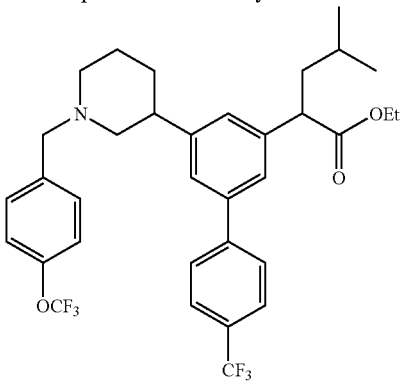

To a solution of compound 33b 4-Methyl-2-(5-piperidin-3-yl-4'-trifluoromethyl-biphenyl-3-yl)-pentanoic acid ethyl ester (60.8 mg, 0.136 mmol) in $CH_3CN$ (5 ml) was added 4-Trifluoromethoxybenzylbromide) (33 µl, 0.20 mmol) and diisopropylethylamine (47 µl, 0.27 mmol). The reaction was microwaved at 130° C. for 10 minutes, then diluted with EtOAc and washed with brine, sat. $NaHCO_3$, and brine, dried and filtered. Purification by silica gel chromatography (Isco) gave the desired product as a clear oil, (69.7 mg, 83%). Calcd for $C_{34}H_{37}F_6NO_3$ (M+H) 621.65, Found 622.3 b) 4-Methyl-2-{5-[1-(4-trifluoromethoxy-benzyl)-piperidin-3-yl]-4'-trifluoromethyl-biphenyl-3-yl}-pentanoic acid To compound 47a, 4-Methyl-2-{5-[1-(4-trifluoromethoxy-benzyl)-piperidin-3-yl]-4'-trifluoromethyl-biphenyl-3-yl}-pentanoic acid ethyl ester (67.3 mg, 0.10 mmol) in EtOH (5.2 ml) was added 2M KOH (0.52 ml, 1.04 mmol). The reaction was heated to 78° C. for 1.5 hour, cooled to room temperature, and concentrated in vacuo. Purification via Gilson HPLC, salt exchange with 1N HCl (aqueous) gave the product as a white lyophilate, (41 mg, 63%). 1H NMR (300 MHz, MeOD) δ ppm 0.90-0.96 (m, 6 H) 1.50 (tt, J=13.38, 6.78 Hz, 1 H) 1.67 (dt, J=13.66, 6.92 Hz, 1 H) 1.88-2.03 (m, 3 H) 2.08 (d, J=17.33 Hz, 2 H) 3.03-3.14 (m, 1 H) 3.14-3.25 (m, 1 H) 3.49-3.62 (m, 2 H) 3.76 (t, J=7.72 Hz, 1 H) 4.34-4.47 (m, 2 H) 7.32 (s, 1 H) 7.42 (d, J=8.29 Hz, 2 H) 7.50 (s, 1 H) 7.57 (s, 1 H) 7.66 (d, J=8.67 Hz, 2 H) 7.78 (q, J=8.41 Hz, 4 H), Calcd for $C_{32}H_{33}F_6NO_3$ (M+H) 593.60, Found 594.3.

EXAMPLE 48

2-(5-{1-[4-(4-Fluoro-phenoxy)-benzyl]-piperidin-3-yl}-4'-trifluoromethyl-biphenyl-3-yl)-4-methyl-pentanoic acid

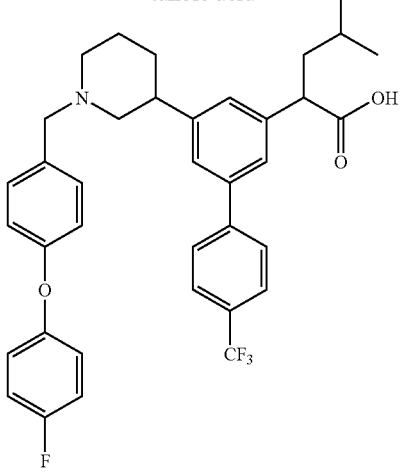

a) 2-(5-{1-[4-(4-Fluoro-phenoxy)-benzyl]-piperidin-3-yl}-4'-trifluoromethyl-biphenyl-3-yl)-4-methyl-pentanoic acid ethyl ester

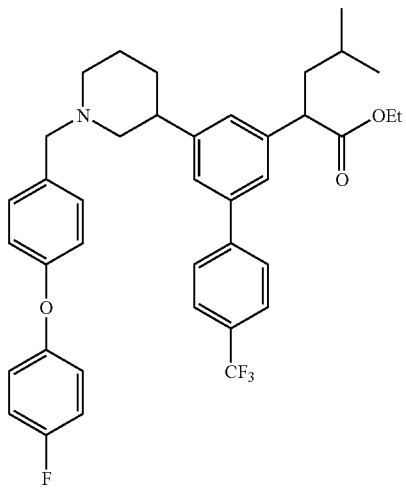

To a solution of compound 33b, 4-Methyl-2-(5-piperidin-3-yl-4'-trifluoromethyl-biphenyl-3-yl)-pentanoic acid ethyl ester (46.4 mg, 0.104 mmol) in $CH_3CN$ (5 ml) was added 3-(4-fluorophenoxybenzylbromide) (43.7 mg, 0.16 mmol) and diisopropylethylamine (36 µl, 0.21 mmol). The reaction was microwaved at 130° C. for 10 minutes, then diluted with EtOAc and washed with brine, sat. $NaHCO_3$, and brine, dried and filtered. Purification by silica gel chromatography (Isco) gave the desired product, (57 mg, 85%). Calcd for $C_{39}H_{41}F_4NO_3$ (M+H) 647.74, Found 648.5.

b) 2-(5-{1-[4-(4-Fluoro-phenoxy)-benzyl]-piperidin-3-yl}-4'-trifluoromethyl-biphenyl-3-yl)-4-methyl-pentanoic acid To compound 48a, 2-(5-{1-[4-(4-Fluoro-phenoxy)-benzyl]-piperidin-3-yl}-4'-trifluoromethyl-biphenyl-3-yl)-4-methyl-pentanoic acid ethyl ester (52.3 mg, 0.08 mmol) in EtOH (5.0 ml) was added 2M KOH (0.40 ml, 0.8 mmol). The reaction was heated to 78° C. for 3 hour, cooled to room temperature, and concentrated in vacuo. Purification via Gilson HPLC, salt exchange with 1N HCl (aqueous) gave the product as a white lyophilate, (41 mg, 76%). 1H NMR (400 MHz, MeOD) δ ppm 0.90-0.96 (m, 6 H) 1.51 (ddd, J=13.08, 6.72, 6.60 Hz, 1 H) 1.68 (dt, J=13.76, 6.94 Hz, 1 H) 1.88-1.93 (m, 2 H) 1.95-2.03 (m, 1 H) 2.11 (s, 2 H) 3.06 (d, J=2.93 Hz, 2 H) 3.22 (t, J=12.96 Hz, 1 H) 3.48-3.57 (m, 2 H) 3.77 (t, J=7.70 Hz, 1 H) 4.33 (s, 2 H) 7.00-7.10 (m, 5 H) 7.14 (d, J=1.96 Hz, 1 H) 7.24-7.34 (m, 2 H) 7.44-7.50 (m, 2 H) 7.58 (s, 1 H) 7.74-7.83 (m, 4 H), Calcd for $C_{37}H_{37}F_4NO_3$ (M+H) 619.69, Found 620.4.

EXAMPLE 49

2-[5-(1-Benzo[1,2,3]thiadiazol-6-ylmethyl-piperidin-3-yl)-4'-trifluoromethyl-biphenyl-3-yl]-4-methyl-pentanoic acid

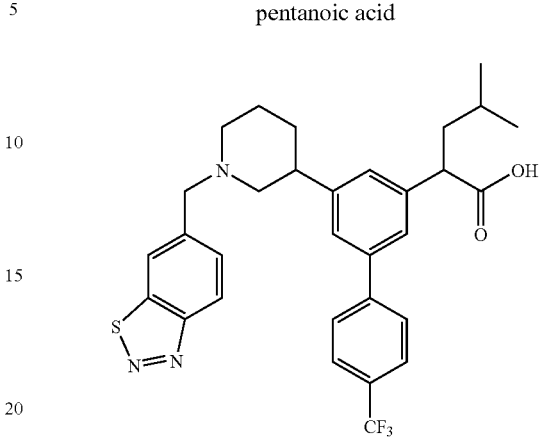

a) 2-[5-(1-Benzo [1,2,3]thiadiazol-6-ylmethyl-piperidin-3-yl)-4'-trifluoromethyl-biphenyl-3-yl]-4-methyl-pentanoic acid ethyl ester

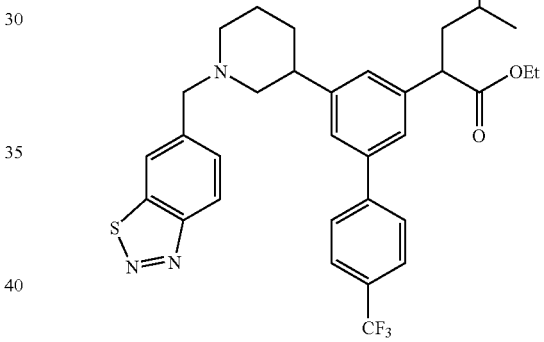

To a solution of compound 33b, 4-Methyl-2-(5-piperidin-3-yl-4'-trifluoromethyl-biphenyl-3-yl)-pentanoic acid ethyl ester (59.3 mg, 0.133 mmol) in $CH_3CN$ (5 ml) was added 5Bromomethyl-benzo 1,2,3 thiadiazole (45.5 mg, 0.20 mmol) and diisopropylethylamine (46 µl, 0.27 mmol). The reaction was microwaved at 130° C. for 10 minutes, then diluted with EtOAc and washed with brine, sat. $NaHCO_3$, and brine, dried and filtered. Purification by silica gel chromatography (Isco) gave the desired product, (70 mg, 89%). Calcd for $C_{33}H_{36}F_3N_3O_2S$ (M+H) 595.72, Found 597.3.

b) 2-[5-(1-Benzo [1,2,3]thiadiazol-6-ylmethyl-piperidin-3-yl)-4'-trifluoromethyl-biphenyl-3-yl]-4-methyl-pentanoic acid To compound 49a, 2-[5-(1-Benzo[1,2,3]thiadiazol-6-ylmethyl-piperidin-3-yl)-4'-trifluoromethyl-biphenyl-3-yl]-4-methyl-pentanoic acid ethyl ester (67.0 mg, 0.11 mmol) in EtOH (5.0 ml) was added 2M KOH (0.56 ml, 1.1 mmol). The reaction was heated to 78° C. for 3 hour, cooled to room temperature, and concentrated in vacuo. Purification via Gilson HPLC, salt exchange with 1N HCl (aqueous) gave the product as a white lyophilate, (46 mg, 68%). 1H NMR (400 MHz, MeOD) δ ppm 0.89-0.96 (m, 6 H) 1.44-1.55 (m, 1 H)

1.63-1.71 (m, 1 H) 1.92-2.04 (m, 3 H) 2.13 (s, 2 H) 3.12-3/23 (m, 2 H) 3.32-3.39 (m, 1 H) 3.60-3.67 (m, 2 H) 3.76 (t, J=7.83 Hz, 1 H) 4.62-4.71 (m, 1 H) 7.33 (s, 1 H) 7.51 (s, 1 H) 7.57 (s, 1 H) 7.73-7.82 (m, 4 H) 7.90-7.96 (m, 1 H) 8.40 (d, J=8.31 Hz, 1 H) 8.87 (s, 1 H) Calcd for C31H32F3N3O2S (M+H) 567.67, Found 568.3.

EXAMPLE 50

4-Methyl-2-{5-[1-(3-methyl-3H-benzotriazol-5-ylmethyl)-piperidin-3-yl]-4'-trifluoromethyl-biphenyl-3-yl}-pentanoic acid

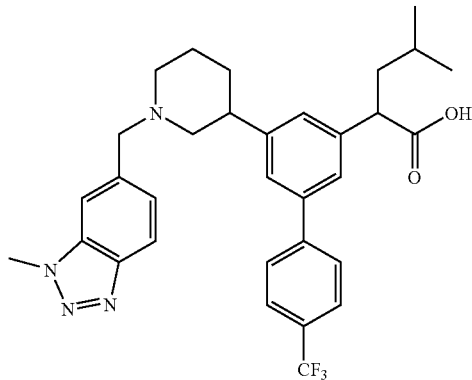

a) 4-Methyl-2-{5-[1-(3-methyl-3H-benzotriazol-5-ylmethyl)-piperidin-3-yl]-4'-trifluoromethyl-biphenyl-3-yl}-pentanoic acid ethyl ester

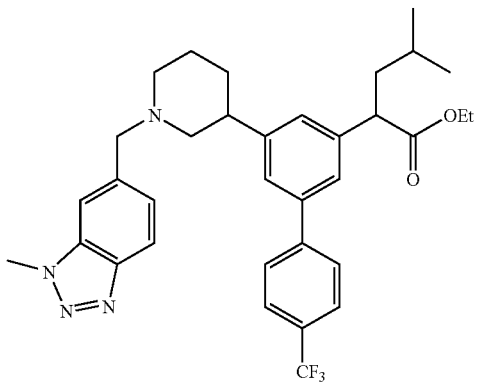

To a solution of compound 33b, 4-Methyl-2-(5-piperidin-3-yl-4'-trifluoromethyl-biphenyl-3-yl)-pentanoic acid ethyl ester (52.6 mg, 0.118 mmol) in CH$_3$CN (5 ml) was added 5-(Bromomethyl)-1-methyl-1H-1,2,3-benzotriazole (40.0 mg, 0.18 mmol), diisopropylethylamine (41 µl, 0.24 mmol) and DMF)(0.3 ml) to solubolize. The reaction was microwaved at 130° C. for 40 minutes, then at 150° C. for 1 hour 10 min. The reaction was diluted with EtOAc and washed with brine, sat. NaHCO$_3$, and brine, dried and filtered. Purification by silica gel chromatography (Isco) gave the desired product, (67 mg, 96%). Calcd for C33H39F3NO4 (M+H) 592.69, Found 593.4.

b) 4-Methyl-2-{5-[1-(3-methyl-3H-benzotriazol-5-ylmethyl)-piperidin-3-yl]-4'-trifluoromethyl-biphenyl-3-yl}-pentanoic acid To compound 50a, 4-Methyl-2-{5-[1-(3-methyl-3H-benzotriazol-5-ylmethyl)-piperidin-3-yl]-4'-trifluoromethyl-biphenyl-3-yl}-pentanoic acid ethyl ester (59.0 mg, 0.10 mmol) in EtOH (5.0 ml) was added 2M KOH (0.50 ml, 1.0 mmol). The reaction was heated to 78° C. for 2 hour, cooled to room temperature, and concentrated in vacuo. Purification via Gilson HPLC, salt exchange with 1N HCl (aqueous) gave the product as a white lyophilate, (32 mg, 53%). 1H NMR (400 MHz, MeOD) δ ppm 0.89-0.97 (m, 6 H) 1.49 (dt, J=13.39, 6.63 Hz, 1 H) 1.62-1.70 (m, J=13.72, 7.09, 6.94, 2.32 Hz, 1 H) 1.90-2.02 (m, 3 H) 2.11 (s, 2 H) 3.11-3.20 (m, 2 H) 3.30-3.50 (m, 1H) 3.57 (s, 2 H) 4.75 (t, J=7.70 Hz, 1 H) 4.33-4.37 (m, 3 H) 4.53-4.62 (m, 2 H) 7.32 (s, 1 H) 7.50 (s, 1 H) 7.56 (s, 1 H) 7.72-7.81 (m, 5 H) 7.90 (d, J=8.56 Hz, 1 H) 8.23 (s, 1 H) Calcd for C32H35F3NO4 (M+H) 564.64, Found 565.3.

EXAMPLE 51

2-{5-[1-(4-Methoxy-3-trifluoromethyl-benzyl)-piperidin-3-yl]-4'-trifluoromethyl-biphenyl-3-yl}-4-methyl-pentanoic acid

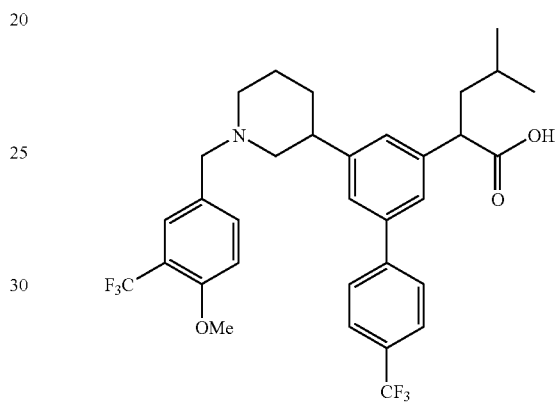

a) 2-{5-[1-(4-Methoxy-3-trifluoromethyl-benzyl)-piperidin-3-yl]-4'-trifluoromethyl-biphenyl-3-yl}-4-methyl-pentanoic acid ethyl ester

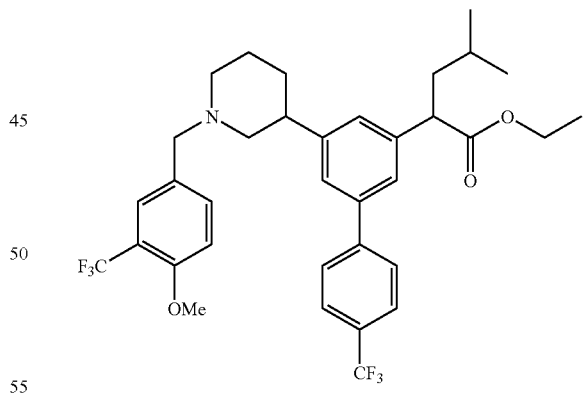

To a solution of compound 33b, 4-Methyl-2-(5-piperidin-3-yl-4'-trifluoromethyl-biphenyl-3-yl)-pentanoic acid ethyl ester (58.8 mg, 0.13 mmol) in CH$_3$CN (5 ml) was added 4-Bromomethyl-1-methoxy-2-trifluoromethyl-benzene (53.0 mg, 0.20 mmol), and diisopropylethylamine (46 µl, 0.26 mmol). The reaction was microwaved at 130° C. for 10 minutes. The reaction was diluted with EtOAc and washed with brine, sat. NaHCO$_3$, and brine, dried and filtered. Purification by silica gel chromatography (Isco) gave the desired product, (64 mg, 77%). Calcd for C35H39F6NO3 (M+H) 635.68, Found 636.5.

b) 2-{5-[1-(4-Methoxy-3-trifluoromethyl-benzyl)-piperidin-3-yl]-4'-trifluoromethyl-biphenyl-3-yl}-4-methyl-pentanoic acid To compound 51a, 2-{5-[1-(4-Methoxy-3-trifluoromethyl-benzyl)-piperidin-3-yl]-4'-trifluoromethyl-biphenyl-3-yl}-4-methyl-pentanoic acid ethyl ester (62.0 mg, 0.10 mmol) in EtOH (5.0 ml) was added 2M KOH (0.50 ml, 1.0 mmol). The reaction was heated to 78° C. for 3 hour, cooled to room temperature, and concentrated in vacuo. Purification via Gilson HPLC, salt exchange with 1N HCl (aqueous) gave the product as a white lyophilate, (45.5 mg, 71%). 1H NMR (300 MHz, MeOD) δ ppm 0.95 (d, J=6.41 Hz, 6 H) 1.49 (dq, J=13.33, 6.61 Hz, 1 H) 1.67 (ddd, J=13.75, 7.16, 6.97 Hz, 1 H) 1.89-2.14 (m, 6 H) 3.00-3.14 (m, 1 H) 3.14-3.26 (m, 2 H) 3.47-3.60 (m, 2 H) 3.76 (t, J=7.72 Hz, 1 H) 3.94 (s, 3 H) 4.30-4.43 (m, 2 H) 7.27-7.34 (m, 2 H) 7.50 (s, 1 H) 7.58 (s, 1 H) 7.72-7.83 (m, 5 H) Calcd for $C_{33}H_{35}F_6NO_3$ (M+H) 607.63, Found 608.4.

EXAMPLE 52

2-{5-[1-(3,5-Di-tert-butyl-benzyl)-piperidin-3-yl]-4'-trifluoromethyl-biphenyl-3-yl}-4-methyl-pentanoic acid

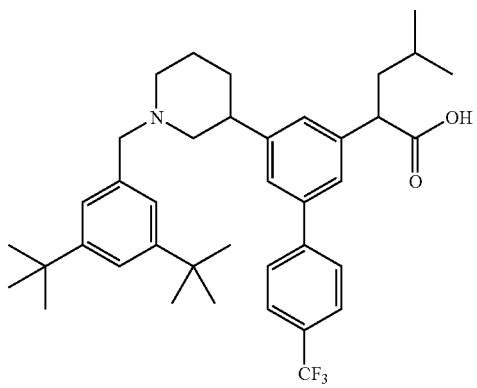

a) 2-{5-[1-(3,5-Di-tert-butyl-benzyl)-piperidin-3-yl]-4'-trifluoromethyl-biphenyl-3-yl}-4-methyl-pentanoic acid ethyl ester

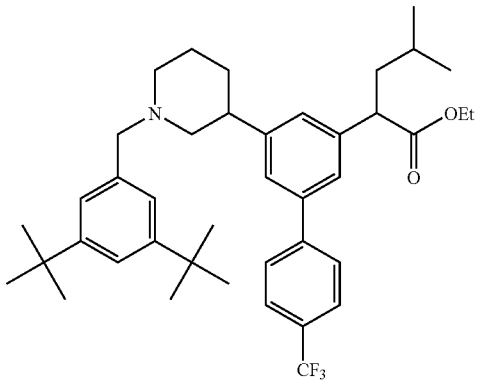

To a solution of compound 33b, 4-Methyl-2-(5-piperidin-3-yl-4'-trifluoromethyl-biphenyl-3-yl)-pentanoic acid ethyl ester (84 mg, 0.19 mmol) in $CH_3CN$ (5 ml) was added 1-Bromomethyl-3,5-di-tert-butyl-benzene (80.0 mg, 0.28 mmol), and diisopropylethylamine (66 μl, 0.38 mmol). The reaction was microwaved at 130° C. for 10 minutes. The reaction was diluted with EtOAc and washed with brine, sat. $NaHCO_3$, and brine, dried and filtered. Purification by silica gel chromatography (Isco) gave the desired product, (109 mg, 85%). Calcd for $C_{41}H_{54}F_3NO_2$ (M+H) 649.87, Found 650.5 b) 2-{5-[1-(3,5-Di-tert-butyl-benzyl)-piperidin-3-yl]-4'-trifluoromethyl-biphenyl-3-yl}-4-methyl-pentanoic acid To compound 52a, 2-{5-[1-(3,5-Di-tert-butyl-benzyl)-piperidin-3-yl]-4'-trifluoromethyl-biphenyl-3-yl}-4-methyl-pentanoic acid ethyl ester (85.3 mg, 0.13mmol) in EtOH (6.6 ml) was added 2M KOH (0.66 ml, 1.3 mmol). The reaction was heated to 78° C. for 1 hour, cooled to room temperature, and concentrated in vacuo. Purification via Gilson HPLC, salt exchange with 1N HCl (aqueous) gave the product as a white lyophilate, (50.0 mg, 58%). 1H NMR (300 MHz, MeOD) δ ppm 0.95 (d, J=6.41 Hz, 6 H) 1.34 (s, 18 H) 1.40-1.56 (m, 1H) 1.61-1.71 (m, 1 H) 1.89-2.14 (m, 5 H) 3.01-3.25 (, 3 H) 3.50-3.61 (m, 2 H) 3.73-3.78 (m, 1H) 4.29-4.40 (m, 2 H) 7.30-7.39 (m, 2 H) 7.48 (s, 1 H) 7.57 (d, J=1.88 Hz, 2 H) 7.73-7.82 (m, 4 H) Calcd for $C_{39}H_{50}F_3NO_2$ (M+H) 621.82, Found 622.5.

EXAMPLE 53

2-{5-[1-(3,5-Bis-trifluoromethyl-benzyl)-piperidin-3-yl]-4'-trifluoromethyl-biphenyl-3-yl}-4-methyl-pentanoic acid

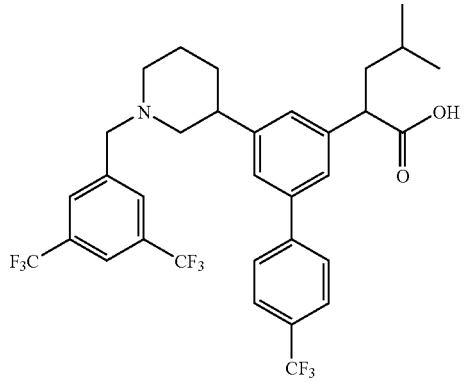

121 a) 2-{5-[1-(3,5-Bis-trifluoromethyl-benzyl)-piperidin-3-yl]-4'-trifluoromethyl-biphenyl-3-yl}-4-methyl-pentanoic acid ethyl ester

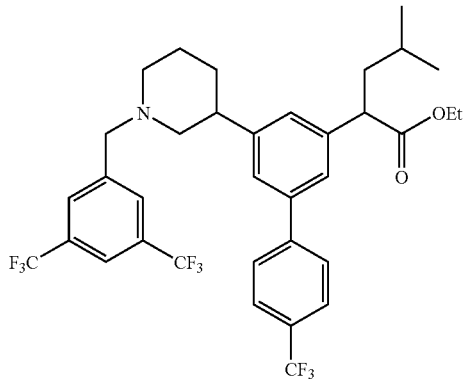

To a solution of compound 33b, 4-Methyl-2-(5-piperidin-3-yl-4'-trifluoromethyl-biphenyl-3-yl)-pentanoic acid ethyl ester (85 mg, 0.19 mmol) in CH$_3$CN (5 ml) was added 1-Bromomethyl-3,5-bis-trifluoromethyl-benzene (88.0 mg, 0.29 mmol), and diisopropylethylamine (66 µl, 0.38 mmol). The reaction was microwaved at 130° C. for 10 minutes. The reaction was diluted with EtOAc and washed with brine, sat. NaHCO$_3$, and brine, dried and filtered. Purification by silica gel chromatography (Isco) gave the desired product, (109 mg, 85%). Calcd for C35H36F9NO2 (M+H) 673.65, Found 675.4 b) 2-{5-[1-(3,5-Bis-trifluoromethyl-benzyl)-piperidin-3-yl]-4'-trifluoromethyl-biphenyl-3-yl}-4-methyl-pentanoic acid To compound 53a, 2-{5-[1-(3,5-Bis-trifluoromethyl-benzyl)-piperidin-3-yl]-4'-trifluoromethyl-biphenyl-3-yl}-4-methyl-pentanoic acid ethyl ester (106.5 mg, 0.16 mmol) in EtOH (7.9 ml) was added 2M KOH (0.79 ml, 1.6 mmol). The reaction was heated to 78° C. for 1 hour, cooled to room temperature, and concentrated in vacuo. Purification via Gilson HPLC, salt exchange with 1N HCl (aqueous) gave the product as a white lyophilate, (72.3 mg, 67%). 1H NMR (300 MHz, MeOD) δ ppm 0.94 (dd, J=6.22, 2.07 Hz, 6 H) 1.50 (dt, J=13.47, 6.64 Hz, 1 H) 1.67 (ddd, J=13.75, 7.16, 6.97 Hz, 1 H) 1.89-2.04 (m, 3 H) 2.06-2.14 (m, 2 H) 3.11-3.19 (m, 2 H) 3.33-3.43 (m, 1H) 3.51-3.56 (m, 1 H) 3.61-3.65 (m, 1 H) 3.77 (t, J=7.72 Hz, 1 H) 4.49-4.64 (m, 2 H) 7.34 (s, 1 H) 7.55 (d, J=18.09 Hz, 2 H) 7.78 (q, J=8.54 Hz, 4 H) 8.16 (s, 1 H) 8.25 (s, 2 H) Calcd for C33H32F9NO2 (M+H) 645.60, Found 646.3.

EXAMPLE 54

2-[5-(1-Benzhydryl-piperidin-3-yl)-4'-trifluoromethyl-biphenyl-3-yl]-4-methyl-pentanoic acid

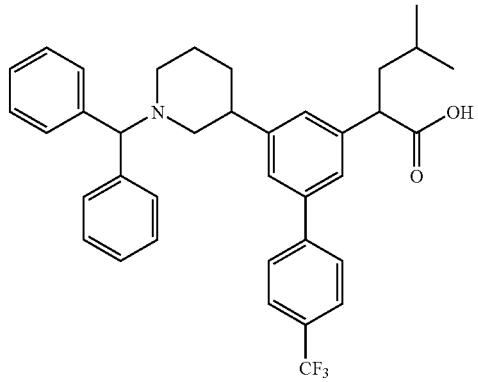

122 a) 2-[5-(1-Benzhydryl-piperidin-3-yl)-4'-trifluoromethyl-biphenyl-3-yl]-4-methyl-pentanoic acid ethyl ester

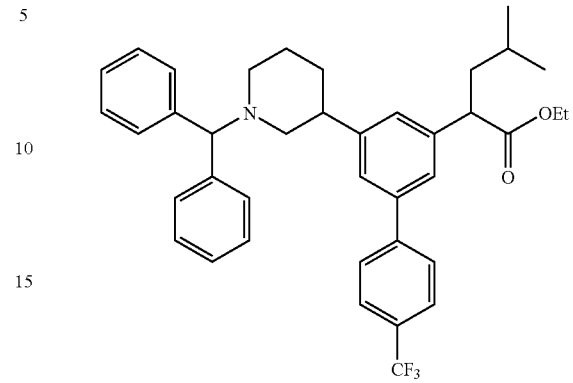

To a solution of compound 33b, 4-Methyl-2-(5-piperidin-3-yl-4'-trifluoromethyl-biphenyl-3-yl)-pentanoic acid ethyl ester (58 mg, 0.13 mmol) in CH$_3$CN (5 ml) was added α-Bromodiphenyl methane (48.0 mg, 0.19 mmol), and diisopropylethylamine (45 µl, 0.26 mmol). The reaction was microwaved at 130° C. for 10 minutes. The reaction was diluted with EtOAc and washed with brine, sat. NaHCO$_3$, and brine, dried and filtered. Purification by silica gel chromatography (Isco) gave the desired product, (39 mg, 49%). Calcd for C39H42F3NO2 (M+H) 613.75, Found 614.4 c) 2-[5-(1-Benzhydryl-piperidin-3-yl)-4'-trifluoromethyl-biphenyl-3-yl]-4-methyl-pentanoic acid To compound 54a, 2-[5-(1-Benzhydryl-piperidin-3-yl)-4'-trifluoromethyl-biphenyl-3-yl]-4-methyl-pentanoic acid ethyl ester (37.8 mg, 0.06 mmol) in EtOH (3.1 ml) was added 2M KOH (0.31 ml, 0.62 mmol). The reaction was heated to 78° C. for 3 hour, cooled to room temperature, and concentrated in vacuo. Purification via Gilson HPLC, salt exchange with 1N HCl (aqueous) gave the product as a white lyophilate, (30 mg, 79%). 1H NMR (300 MHz, MeOD) δ ppm 0.87-0.94 (m, 6 H) 1.37-1.49 (m, J=13.47, 6.64, 6.64, 6.41 Hz, 1 H) 1.63 (dq, J=13.80, 6.95 Hz, 1 H) 1.91-2.01 (m, 3 H) 2.03-2.63 (m, 4 H) 3.05-3.20 (m, 2 H) 3.40-3.55 (m, 1 H) 3.71 (t, J=7.35 Hz, 1 H) 5.43-5.49 (m, 1H) 7.23 (s, 1 H) 7.39-7.55 (m, 8 H) 7.63-7.78 (m, 8 H) Calcd for C37H38F3NO2 (M+H) 585.7, Found 586.3.

EXAMPLE 55

2-{5-[1-(3,4-Difluoro-phenyl)-piperidin-3-yl]-4'-trifluoromethyl-biphenyl-3-yl}-4-methyl-pentanoic acid

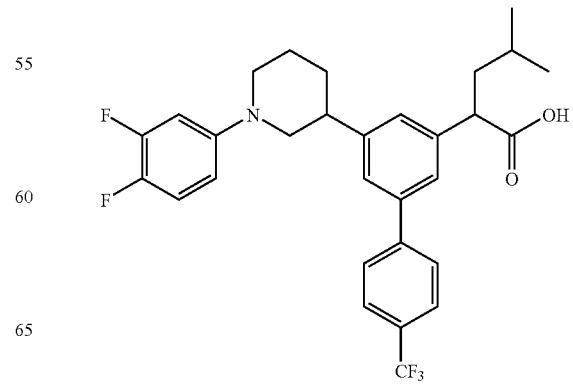

123 a) 2-{5-[1-(3,4-Difluoro-phenyl)-piperidin-3-yl]-4'-trifluoromethyl-biphenyl-3-yl}-4-methyl-pentanoic acid ethyl ester

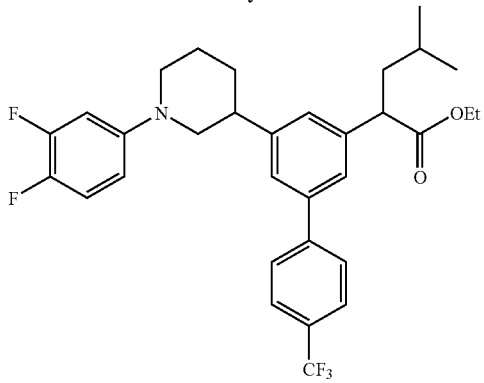

To a solution of compound 33b, 4-Methyl-2-(5-piperidin-3-yl-4'-trifluoromethyl-biphenyl-3-yl)-pentanoic acid ethyl ester (110 mg, 0.25 mmol) in dimethylsulfoxide (0.2 ml) was added L-proline (4.4 mg, 0.04 mmol), potassium carbonate (52.5 mg, 0.38 mmol), and copper iodine (3.6 mg, 0.02 mmol). The reaction was degassed under nitrogen and 1,2-difluoro-4-iodobenzene (45.4 mg, 0.19 mmol), was added, the reaction was again degassed and then heated to 90° C. The reaction was stirred over 48 hours. The reaction was partitioned between EtOAc/$H_2O$, washed with $H_2O$ (3×) and brine (1×). Purification by silica gel chromatography (Isco) gave the desired product, (39 mg, 37%). Calcd for C32H34F5NO2 (M+H) 559.60, Found 560.4.

b) 2-{5-[1-(3,4-Difluoro-phenyl)-piperidin-3-yl]-4'-trifluoromethyl-biphenyl-3-yl}-4-methyl-pentanoic acid This compound was synthesized using a similar procedure as Example 33 step (d). 1H NMR (400 MHz, MeOD) δ ppm 0.95 (dd, J=6.60, 2.20 Hz, 6 H) 1.53 (dt, J=13.27, 6.69 Hz, 1 H) 1.68 (ddd, J=13.51, 7.21, 6.91 Hz, 1 H) 1.78 (dd, J=11.86, 3.55 Hz, 1 H) 1.89 (s, 1 H) 1.94-2.06 (m, 3 H) 2.96 (s, 1 H) 2.98-3.07 (m, 2 H) 3.68 (s, 2 H) 3.76 (t, J=7.83 Hz, 1 H) 6.81-6.91(m, 2 H) 7.01-7.09 (m, 1 H) 7.11-7.14 (m, 1H)) 7.35 (s, 1H) 7.50-7.53 (m, 2 H) 7.72-7.76 (m, 2 H) 7.79-7.83 (m, 2 H) Calcd for C30H30F5NO2 (M+H) 531.56, Found 532.3.

EXAMPLE 56

(R*) 4-Methyl-2-(5-{1-[4-methyl-1-(4-trifluoromethyl-phenyl)-pentyl]-piperidin-3-yl}-4'-trifluoromethyl-biphenyl-3-yl)-pentanoic acid

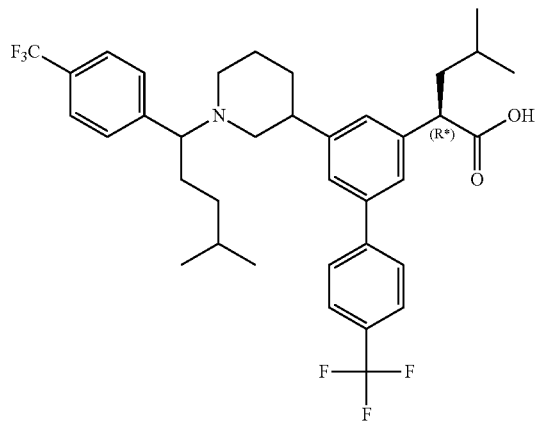

124 a) 4-Methyl-2-(5-{1-[4-methyl-1-(4-trifluoromethyl-phenyl)-pentyl]-piperidin-3-yl}-4'-trifluoromethyl-biphenyl-3-yl)-pentanoic acid ethyl ester

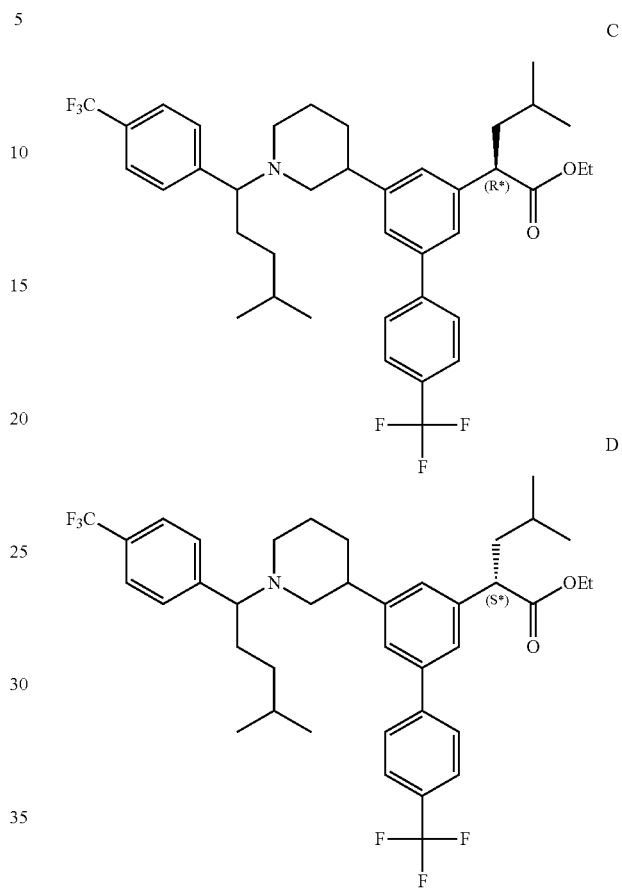

Compound 33b (341 mg, 0.762 mmol), 4-(trifluoromethyl) benzaldehyde (107 μL, 0.800 mmol), and benzotriazole (95.3 mg. 0.800 mmol) in toluene (4 mL) were combined and heated at reflux in a dean stark condenser for 18 hours. The cooled residue was concentrated, and pumped for several hours. The residue was dissolved in $CH_2Cl_2$ (8.0 mL, 0.1M), cooled to an internal temperature of <10° C., and 3-methyl-butylzinc (4.6 mL, 2.3 mmol) was added while maintaining the <10° C. temperature. After 45 minutes, the bath was removed and the reaction continued at RT overnight. The reaction mixture was cooled to 0° C., quenched with sat. $NH_4Cl$ (5.6 mL) and then stirred for 30 minutes before being diluted with $CH_2Cl_2/H_2O$. The solution was filtered through a pad of celite, extracted with $CH_2Cl_2$ (3×), dried, filtered and concentrated in vacuo. Purification via silica gel chromatography employing the Isco purification system gave the compounds as two diastereomers. The stereochemistry of the alpha-side chain of the two diastereomers are tentatively assigned as shown C (R*) and D (S*).

Compound C: $^1$H NMR (400 MHz, CHLOROFORM-D) δ ppm 0.82 (dd, J=6.60, 3.18 Hz, 6 H) 0.93 (d, J=6.60 Hz, 6 H) 1.19-1.28 (m, 3 H) 1.43-1.53 (m, 2 H) 1.60-1.68 (m, 2 H) 1.71-1.79 (m, 2 H) 1.81-2.05 (m, 9 H) 2.85-2.94 (m, 1 H) 3.05-3.08 (m, 1H) 3.40 (dd, J=9.17, 5.26 Hz, 1 H) 3.65-3.71 (m, 1 H) 4.05-4.21 (m, 2H) 7.19 (s, 1 H) 7.29-7.34 (m, 3 H) 7.39 (s, 1 H) 7.56 (d, J=8.31 Hz, 2 H) 7.64-7.70 (m, 4 H). Calc'd for $C_{39}H_{47}F_6NO_2$ (M+H)$^+$ 675.79, Found 676.5.

Compound D: ¹H NMR (400 MHz, CHLOROFORM-D) δ ppm 0.83 (dd, J=6.60, 2.69 Hz, 6 H) 0.87-0.94 (m, 6 H) 1.21 (t, J=7.21 Hz, 3 H) 1.36-1.52 (m, 4H) 1.64 (dt, J=13.69, 6.85 Hz, 1 H) 1.70-1.82 (m, 4 H) 1.87-1.96 (m, 3 H) 1.98-2.05 (m, 2 H) 2.76-2.81 (m, 1 H) 2.91-2.99 (m, 2 H) 3.44 (dd, J=9.05, 5.14 Hz, 1 H) 3.64-3.69 (m, 1 H) 4.05-4.18 (m, 2 H) 7.15 (s, 1 H) 7.29-7.38 (m, 4 H) 7.55 (d, J=8.07 Hz, 2 H) 7.62-7.69 (m, 4 H). Calc'd for $C_{39}H_{47}F_6NO_2$ (M+H)⁺ 675.79, Found 676.5.

b) (R*) 4-Methyl-2-(5-{1-[4-methyl-1-(4-trifluoromethyl-phenyl)-pentyl]-piperidin-3-yl}-4'-trifluoromethyl-biphenyl-3-yl)-pentanoic acid A mixture of Compound C, (67 mg, 0.099 mmol) in EtOH (5.5 mL) and 2M KOH (0.5 mL, 0.99 mmol) was heated to reflux for 3 hours, cooled, and concentrated in vacuo. Purification via Gilson Preparative HPLC, subsequent salt exchange with 1N HCl, followed by lyophilization gave the title compound as the HCl salt.

¹H NMR (400 MHz, MeOD) δ ppm 0.50-0.61 (m, 1 H) 0.64 (dd, J=6.60, 1.22 Hz, 6 H) 0.73 (d, J=6.36 Hz, 6 H) 0.83-0.93 (m, 1 H) 1.27-1.39 (m, 2 H) 1.41-1.48 (m, 2 H) 1.59-1.90 (m, 4 H) 2.05-2.14 (m, 2 H) 2.6-2.8 (m, 2 H) 3.00-3.10 (m, 1 H) 3.28-3.31 (m, 1 H) 3.54 (t, J=7.70 Hz, 2 H) 3.60 (d, J=11.9 Hz, 1H) 4.21-4.24 (m, 1 H) 7.09 (s, 1 H) 7.28 (s, 1 H) 7.35 (s, 1 H) 7.51-7.59 (m, 5 H) 7.63 (d, J=8.07 Hz, 2 H). Calc'd for $C_{37}H_{43}F_6NO_2$ (M+H)⁺ 647.32, Found 648.5.

EXAMPLE 57

(S*) 4-Methyl-2-(5-{1-[4-methyl-1-(4-trifluoromethyl-phenyl)-pentyl]-piperidin-3-yl}-4'-trifluoromethyl-biphenyl-3-yl)-pentanoic acid

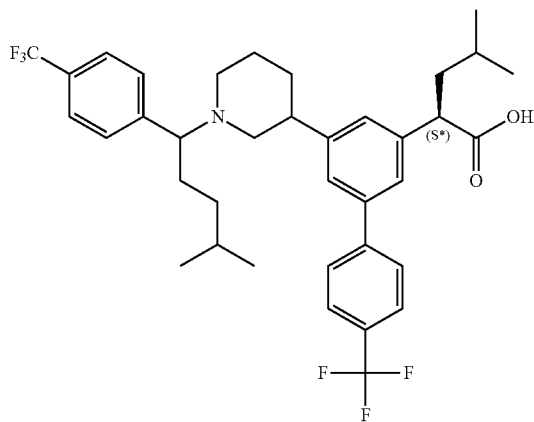

A mixture of Compound D, prepared in Example 56, step (a) (75.4 mg, 0.112 mmol) in EtOH (5.6 mL) and 2M KOH (0.6 mL, 1.12 mmol) was heated to reflux for 3 hours, cooled, and concentrated in vacuo. Purification via Gilson Preparative HPLC, subsequent salt exchange with 1N HCl, followed by lyophilization gave the title compound as the HCl salt.

¹H NMR (400 MHz, MeOD) δ ppm 0.74-0.82 (m, 1 H) 0.86 (dd, J=6.60, 3.42 Hz, 7 H) 0.90-0.95 (m, 6 H) 1.06-1.16 (m, 1 H) 1.47 (dt, J=13.39, 6.63 Hz, 1 H) 1.58 (ddd, J=13.08, 6.72, 6.60 Hz, 1 H) 1.84 (s, 1 H) 1.93-2.05 (m, 3 H) 2.08 (s, 2 H) 2.30 (dd, J=10.52, 5.14 Hz, 2 H) 2.91-3.02 (m, 2 H) 3.12-3.21 (m, 1 H) 3.45-3.52 (m, 1 H) 3.74 (t, J=7.83 Hz, 1 H) 3.82 (s, 1 H) 4.48 (dd, J=11.00, 4.16 Hz, 1 H) 7.27 (s, 1 H) 7.46 (s, 1 H) 7.55 (s, 1 H) 7.73-7.84 (m, 8 H). Calc'd for $C_{37}H_{43}F_6NO_2$ (M+H)⁺ 647.32, Found 648.5.

EXAMPLE 58

4-Methyl-2-[5-(1-phenyl-piperidin-3-yl)-4'-trifluoromethyl-biphenyl-3-yl]-pentanoic acid

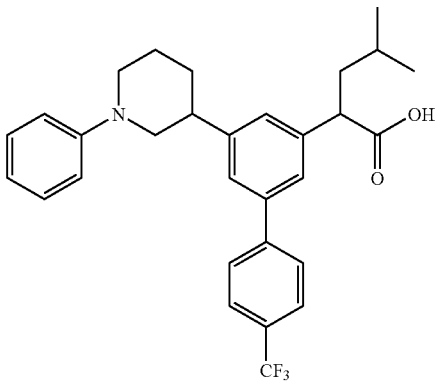

a) 4-Methyl-2-[5-(1-phenyl-piperidin-3-yl)-4'-trifluoromethyl-biphenyl-3-yl]-pentanoic acid ethyl ester

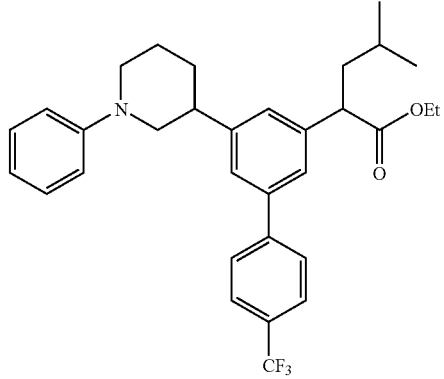

This compound was synthesized using a similar procedure as Example 55 step (a) with iodobenzene. Calcd for C32H34F3NO2 (M+H) 523.63, Found 524.4.

b) 4-Methyl-2-[5-(1-phenyl-piperidin-3-yl)-4'-trifluoromethyl-biphenyl-3-yl]-pentanoic acid This compound was synthesized using a similar procedure as Example 55 step (b). 1H NMR (300 MHz, CHLOROFORM-D) δ ppm 0.93 (t, J=6.78 Hz, 6 H) 1.19-1.30 (m, 3 H) 1.60-1.72 (m, 2 H) 1.89 (dd, J=6.97, 3.58 Hz, 2 H) 2.04 (ddd, J=13.38, 8.48, 6.78 Hz, 2 H) 2.75-2.89 (m, 2 H) 2.98 (d, J=12.06 Hz, 1 H) 3.68-3.83 (m, 3 H) 4.07-4.22 (m, 2 H) 6.84 (t, J=7.35 Hz, 1 H) 6.97 (d, J=7.91 Hz, 2 H) 7.22-7.28 (m, 1H)

7.40 (d, J=16.58 Hz, 2 H) 7.65-7.72 (m, 4 H) Calcd for C30H32F3NO2 (M+H) 531.56, Found 532.3.

EXAMPLE 59

4-Methyl-2-{4'-trifluoromethyl-5-[1-(4-trifluoromethyl-phenyl)-piperidin-3-yl]-biphenyl-3-yl}-pentanoic acid

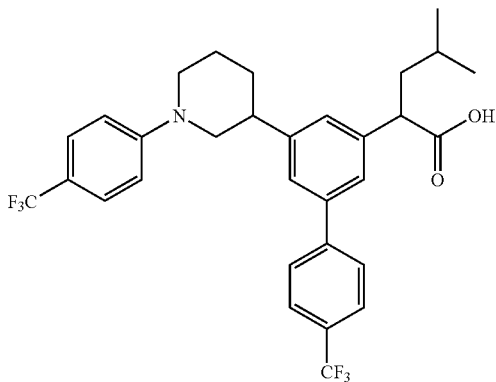

a) 4-Methyl-2-{4'-trifluoromethyl-5-[1-(4-trifluoromethyl-phenyl)-piperidin-3-yl]-biphenyl-3-yl}-pentanoic acid ethyl ester

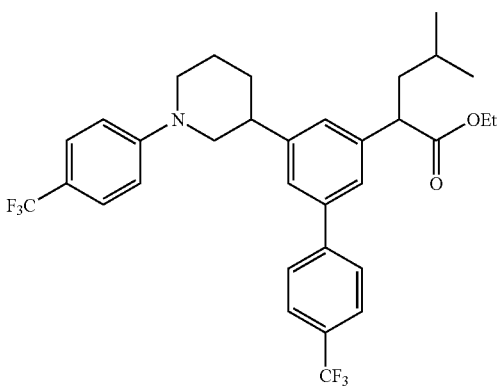

To a solution of compound 33b, 4-Methyl-2-(5-piperidin-3-yl-4'-trifluoromethyl-biphenyl-3-yl)-pentanoic acid ethyl ester (35 mg, 0.08 mmol) in toluene (1.0 ml), 1-Iodo-4-trifluoromethyl-benzene (11.4 µl, 0.08 mmol), racemic-2-Ditbutylphosphino-1-1'binapthyl (14 mg, 0.035 mmol), and sodium t-butoxide ((10.0 mg, 0.01 mmol) were added and the reaction was bubbled with nitrogen for 20 minutes. The reaction was degassed with nitrogen and Pd (II) OAc) 8.0 mg, 0.01 mmol) was added. The reaction was microwaved at 120° C. for 30 minutes. The reaction was concentrated in vacuo, and purified by silica gel chromatography to give the product as a yellow oil (17 mg, 22%). Calcd for C33H35F6NO2 (M+H) 591.63, Found 592.3 b) 4-Methyl-2-{4'-trifluoromethyl-5-[1-(4-trifluoromethyl-phenyl)-piperidin-3-yl]-biphenyl-3-yl}-pentanoic acid.

This compound was synthesized using a similar procedure as Example 55 step (b). 1H NMR (300 MHz, MeOD) δ ppm 0.80-0.87 (m, 6 H) 1.21 (m, 2 H) 1.41-1.45 (m, 1 H) 1.56-1.61 (m, 1 H) 1.83-2.09 (m, 5 H) 3.04-3.17 (m, 1 H) 3.31-3.58 (m, 1 H) 3.78-3.83 (m, 2 H) 7.28-7.31 (m, 3 H) 7.44-7.45 (m, 2 H) 7.54-7.66 (m, 2 H) 7.66-7.74s (s, 4 H) Calcd for C31H31F6NO2 (M+H) 563.77, Found 564.3.

EXAMPLE 60

(R)-2-{5-[2-(3-Methoxy-propyl)-piperidin-1-yl]-4'-trifluoromethyl-biphenyl-3-yl}-4-methyl-pentanoic acid

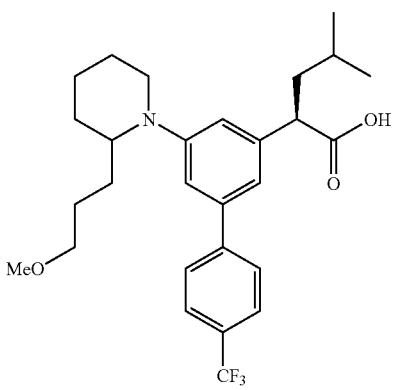

a) (R)-2-{5-[2-(3-Methoxy-propyl)-piperidin-1-yl]-4'-trifluoromethyl-biphenyl-3-yl}-4-methyl-pentanoic acid methyl ester

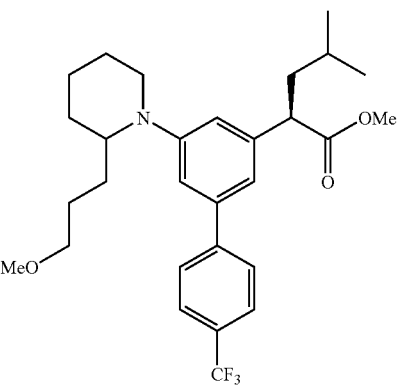

To a solution of (R)-4-methyl-2-(5-trifluoromethanesulfonyloxy-4'-trifluoromethyl-biphenyl-3-yl)-pentanoic acid methyl ester (1 g-methyl ester) (210 mg, 0.42 mmol) in toluene (2.5 mL) in a sealed tube was added racemic-2-(di-t-butylphosphino)-1,1'-binaphthyl (50 mg, 0.13 mmol), Pd(OAc)₂ (94 mg, 0.42 mmol), 2-(3-methyoxy-propyl)-piperidine (93 mg, 0.59 mmol). The system was flushed with nitrogen. To this was added NaO'Bu (61 mg, 0.63 mmol) and heated to 100° C. for 2 h. The reaction was cooled to room temperature and quenched by slow addition of water. The mixture was extracted with EtOAc (3×20 mL). The organic phase was washed with saturated NaHCO₃ solution and brine. The organic fraction was dried (MgSO₄) and concentrated in vacuo. The crude mixture was purified by ISCO column chromatography to obtain (R)-2-{5-[2-(3-methoxy-propyl)-piperidin-1-yl]-4'-trifluoromethyl-biphenyl-3-yl}-4-methyl-pentanoic acid methyl ester. Calcd for C29H38F3NO3 (M+H) 506.61, Found 506.38.

b) (R)-2-{5-[2-(3-Methoxy-propyl)-piperidin-1-yl]-4'-trifluoromethyl-biphenyl-3-yl}-4-methyl-pentanoic acid To a solution of (R)-2-{5-[2-(3-methoxy-propyl)-piperidin-1-yl]-4'-trifluoromethyl-biphenyl-3-yl}-4-methyl-pentanoic acid methyl ester (18 mg, 0.04 mmol) in MeOH (1 mL) was added 3N NaOH (0.200 mL) and heated to 60° C. for 14 h. The reaction was concentrated in vacuo to remove MeOH. The thick liquid was acidified to pH=2 by 2N HCl. The resulting acidic solution was extracted with EtOAc. The organic fraction was dried (MgSO$_4$) and concentrated in vacuo. The crude mixture was purified by Gilson reverse phase column chromatography to obtain (R)-2-{5-[2-(3-methoxy-propyl)-piperidin-1-yl]-4'-trifluoromethyl-biphenyl-3-yl}-4-methyl-pentanoic acid.

$^1$H-NMR (MeOD-d$_4$): δ 0.87 (d, 6H), 1.31-1.51 (m, 6H), 1.67 (m, 3H), 1.92 (m, 4H), 2.17 (d, 1H), 3.06 (s, 3H), 3.14 (t, 2H), 3.53-3.69 (m, 2H), 3.80 (m, 2H), 7.54 (s, 1H), 7.70-7.80 (m, 6H); Calcd for C28H36F3NO2 (M+H) 492.59, Found 492.3

EXAMPLE 61

4-Methyl-2-{4'-trifluoromethyl-5-[1-(4-trifluoromethyl-benzenesulfonyl)-piperidin-3-yl]-biphenyl-3-yl}-pentanoic acid

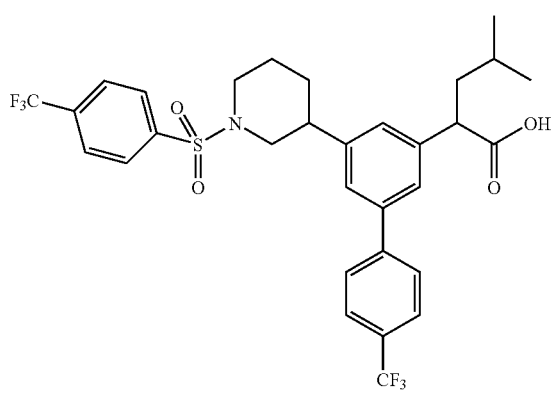

a) 4-Methyl-2-{4'-trifluoromethyl-5-[1-(4-trifluoromethyl-benzenesulfonyl)-piperidin-3-yl]-biphenyl-3-yl}-pentanoic acid ethyl ester

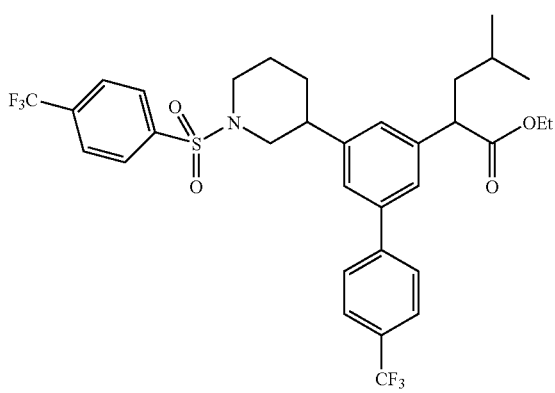

To a solution of compound 33b, 4-Methyl-2-(5-piperidin-3-yl-4'-trifluoromethyl-biphenyl-3-yl)-pentanoic acid ethyl ester (56 mg, 0.12 mmol) in anhydrous dimethylformamide (0.8 ml) was added Trifluoromethyl benzene sulfonyl chloride (46 mg, 0.19 mmol) and cesium carbonate (101 mg, 0.31 mmol). The reaction stirred at room temperature for 4 hours, was diluted with EtOAc and washed with sat. NaHCO$_3$, H$_2$O (3×) and brine, dried then filtered. Purification by silica gel chromatography (Isco) gave the product as clear oil, (44 mg, 54%). Calcd for C33H35F6NO4S (M+H) 655.69, Found 656.2 b) 4-Methyl-2-{4'-trifluoromethyl-5-[1-(4-trifluoromethyl-benzenesulfonyl)-piperidin-3-yl]-biphenyl-3-yl}-pentanoic acid This compound was synthesized using a similar procedure as Example 55 step (b). 1H NMR (400 MHz, MeOD) δ ppm 0.83 (td, J=6.85, 2.69 Hz, 6 H) 1.40 (dt, J=13.27, 6.69 Hz, 1 H) 1.50-1.60 (m, 2 H) 1.67 (d, J=3.91 Hz, 1 H) 1.81-1.90 (m, 2 H) 2.42 (q, J=11.57 Hz, 2 H) 2.84 (s, 1 H) 3.64 (t, J=7.70 Hz, 1 H) 3.73 (s, 2 H) 7.17 (s, 1 H) 7.36 (s, 1 H) 7.41 (s, 1 H) 7.61-7.71 (m, 4 H) 7.81-7.90 (m, 4 H)

Calcd for C31H31F6NO4S (M+H) 627.64, Found 628.3.

EXAMPLE 62

4-Methyl-2-{5-[1-(3-methyl-butyl)-piperidin-3-yl]-4'-trifluoromethyl-biphenyl-3-yl}-pentanoic acid

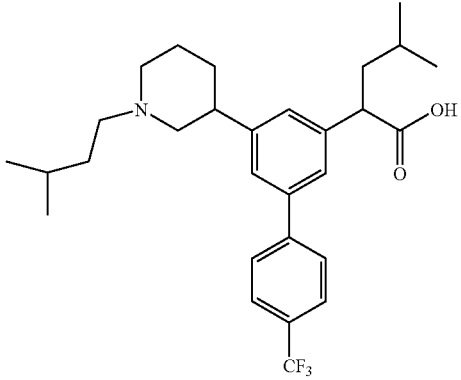

a) 4-Methyl-2-{5-[1-(3-methyl-butyl)-piperidin-3-yl]-4'-trifluoromethyl-biphenyl-3-yl}-pentanoic acid ethyl ester

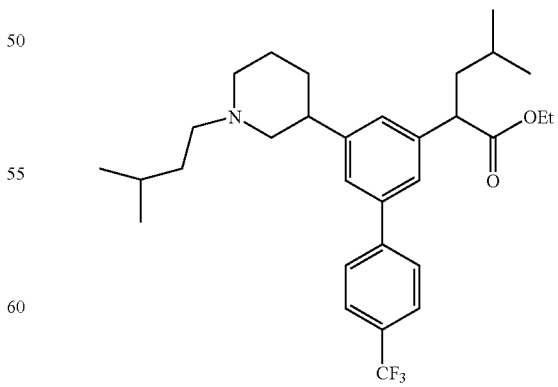

This compound was synthesized using a similar procedure as Example 61 step (a). Calcd for C31H42F3NO2 (M+H) 517.67, Found 518.2 b) 4-Methyl-2-{5-[1-(3-methyl-butyl)-piperidin-3-yl]-4'-trifluoromethyl-biphenyl-3-yl}-pentanoic acid This compound was synthesized using a similar procedure as Example 55 step (b). 1H NMR (300 MHz, MeOD) δ ppm 0.81-0.92 (m, 12 H) 1.42 (dt, J=13.19, 6.59 Hz, 1 H) 1.53-1.62 (m, 4 H) 1.78-1.85 (m, 1 H) 1.87-2.03 (m, 3 H) 2.88-2.98 (m, 1 H) 3.00-3.15 (m, 4 H) 3.50-3.61 (m, 2 H) 3.68 (t, J=7.72 Hz, 1 H) 7.25 (s, 1 H) 7.46 9d, J=15.07 Hz, 2 H) 7.64-7.75 (m, 4 H) Calcd for C29H38F3NO2 (M+H) 489.61, Found 490.2.

EXAMPLE 63 AND EXAMPLE 64

(S*)-4-Methyl-2-(4'-trifluoromethyl-5-{1-[1-(4-trifluoromethyl-phenyl)-ethyl]-piperidin-3-yl}-biphenyl-3-yl)-pentanoic acid

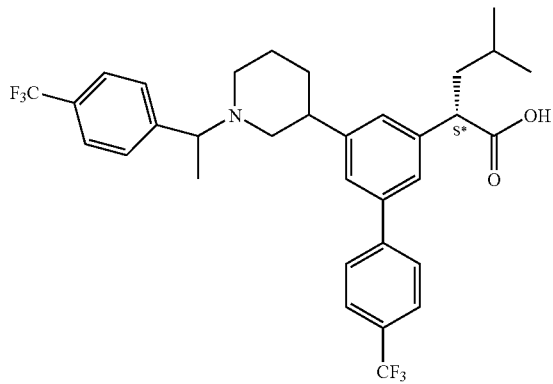

a) 4-Methyl-2-(4'-trifluoromethyl-5-{1-[1-(4-trifluoromethyl-phenyl)-ethyl]-piperidin-3-yl}-biphenyl-3-yl)-pentanoic acid ethyl ester

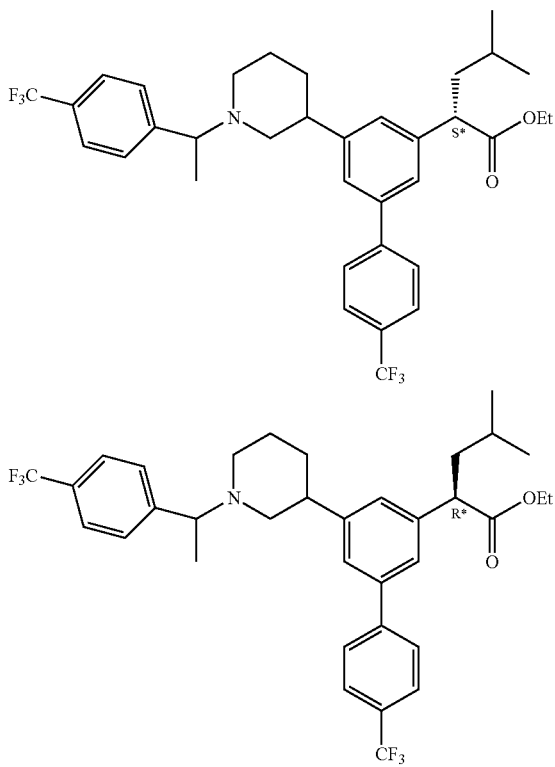

To compound 33b, 4-Methyl-2-(5-piperidin-3-yl-4'-trifluoromethyl-biphenyl-3-yl)-pentanoic acid ethyl ester (75 mg, 0.17 mmol), was added 4-Trifluoromethylacetophenonne (34 mg, 0.18 mmol), and titanium isopropoxide (76 mg), 0.27 mmol) under argon at room temperature. After 3 hours, add methanol ((0.76 ml), followed by sodium borohydride (10 mg, 0.27 mmol). After 5 minutes, the reaction was quenched with 0.1 N NaOH, filtered through celite and washed with dichloromethane. The solution was concentrated in vacuo, then diluted with dichloromethane, and washed with NaHCO3, and brine, and dried over magnesium sulfate. The reaction was concentrated in vacuo, and purified by silica gel chromatography to give two diastereomeric mixtures (S* and R*, tentative assignments); Calcd for C35H39F6NO2 (M+H) 619.68, Found 520.4 b) (S*)-4-Methyl-2-(4'-trifluoromethyl-5-{1-[1-(4-trifluoromethyl-phenyl)-ethyl]-piperidin-3-yl}-biphenyl-3-yl)-pentanoic acid The S* isomer ethyl ester, as prepared above, was hydrolyzed using a similar procedure as Example 55 step (b) to give the title compound. 1H NMR (400 MHz, MeOD) δ ppm 0.97 (dd, J=6.60, 1.71 Hz, 6 H) 1.49-1.58 (m, 1 H) 1.66-1.74 (m, 1 H) 1.81-1.87 (m, 4 H) 1.96 (s, 1 H) 2.00-2.10 (m, 3 H) 2.95 (s, 1 H) 3.15 (t, J=12.10 Hz, 1 H) 3.27 (s, 1 H) 3.42 (s, 1 H) 3.79 (t, J=7.83 Hz, 2 H) 4.64 (d, J=7.09 Hz, 1 H) 7.36 (s, 1 H) 7.55 (s, 1 H) 7.61 (s, 1 H) 7.76-7.86 (m, 8 H) 7.87 (s, 1 H) Calcd for C33H35F6NO2 (M+H) 591.63, Found 592.2.

EXAMPLE 64

(R*)-4-Methyl-2-(4'-trifluoromethyl-5-{1-[1-(4-trifluoromethyl-phenyl)-ethyl]-piperidin-3-yl}-biphenyl-3-yl)-pentanoic acid

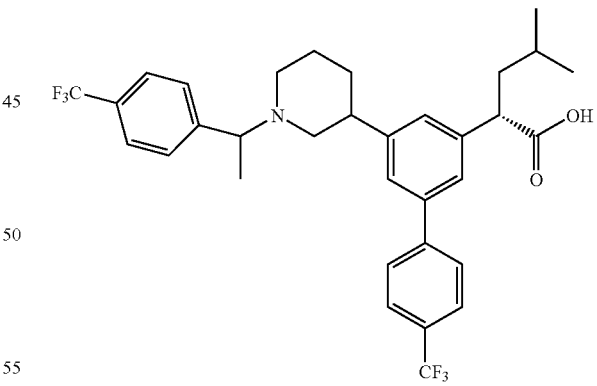

The R* isomer ethyl ester obtained from Example 63, step (a) was hydrolyzed using a similar procedure as Example 55 step (b) to give the title compound; 1H NMR (300 MHz, MeOD) δ ppm 0.89-0.98 (m, 6 H) 1.48 (ddd, J=13.09, 6.97, 6.69 Hz, 1 H) 1.58-1.73 (m, J=10.36, 7.25, 7.06, 3.20 Hz, 1 H) 1.85 (d, J=7.16 Hz, 5 H) 1.94-2.10 (m, 3 H) 2.20 (s, 1 H) 3.04-3.18 (m, 2 H) 3.41 (d, J=9.80 Hz, 1 H) 3.75 (t, J=7.91 Hz, 2 H) 4.69 (q, J=7.16 Hz, 1 H) 7.28 (s, 1 H) 7.48 (s, 1 H) 7.56 (s, 1 H) 7.74-7.86 (m, 8 H) Calcd for C33H35F6NO2 (M+H) 591.63, Found 592.2.

EXAMPLE 65

4-Methyl-2-{4'-trifluoromethyl-5-[1-(4-trifluoromethyl-benzyl)-piperidin-3-yl]-biphenyl-3-yl}-pentanoic acid

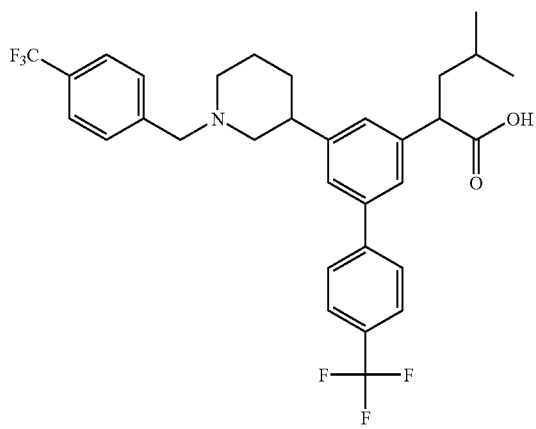

a) 4-Methyl-2-{4'-trifluoromethyl-5-[1-(4-trifluoromethyl-benzyl)-piperidin-3-yl]-biphenyl-3-yl}-pentanoic acid ethyl ester

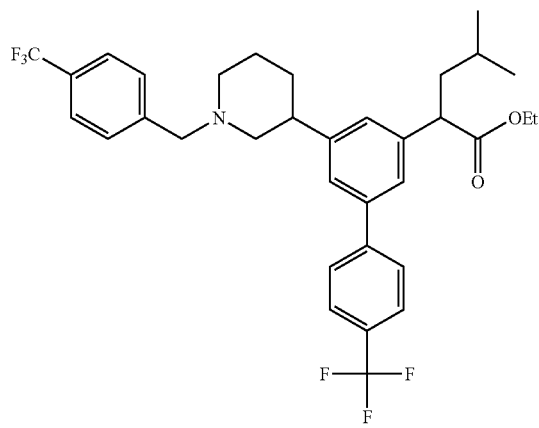

Compound 26b (357 mg, 0.800 mmol), 4-(trifluoromethyl) benzaldehyde (146 mg, 0.838 mmol), and benzotriazole (100 mg. 0.838 mmol) in toluene (4 mL, ) were combined and heated to reflux in a dean stark condenser for 22 hours. The reaction mixture solvent was carefully removed on a rotary evaporator and the residue was re-dissolved in THF and cooled to −10° C. To the cold stirred solution was added 3-methyl butyl zinc bromide (4.8 mL, 0.1M in THF obtained from Aldrich) dropwise. The reaction mixture was allowed to stir in the cold bath for 1 h, at room temperature overnight, and was quenched with sat. $NH_4Cl$ solution. The mixture was diluted with $CH_2Cl_2/H_2O$ and was filtered through a celite pad, extracted with $CH_2Cl_2$ (3×), dried, filtered and concentrated in vacuo. The residue was purified via silica gel chromatography employing the Isco purification system to give the title compound as a brown oil. (Note: The reaction did not give the desired product, compound 37a shown in Example 37, instead the reductive amination product with 4-(trifluomethylbenzaldehyde. It was possibly due to the bad zinc bromide reagent obtained from Aldrich). $^1$H NMR (300 MHz, CHLOROFORM-D) δ ppm 0.92 (d, J=6.78 Hz, 6 H) 1.18- 1.25 (m, 3 H) 1.51-1.54 (m, 2 H) 1.60-1.70 (m, 3H) 1.78-2.16 (m, 4 H) 2.85-3.00 (m, 3 H) 3.59 (s, 2 H) 3.68 (dd, J=8.48, 6.97 Hz, 1 H) 4.05-4.20 (m, 2 H) 7.21 (s, 1 H) 7.29-7.33 (m, 1 H) 7.36-7.50 (m, 3 H) 7.52-7.59 (m, 2 H) 7.60-7.72 (m, 4 H) Calc'd for $C_{34}H_{37}F_6NO_2$ (M+H)$^+$ 605.65, Found 606.3 b) 4-Methyl-2-{4'-trifluoromethyl-5-[1-(4-trifluoromethyl-benzyl)-piperidin-3-yl]-biphenyl-3-yl}-pentanoic acid Compound 36a (67 mg, 0.111 mmol) in EtOH (5.5 mL) and 2M KOH (0.6 mL, 1.1 mmol) was heated to reflux for 2 hours, cooled, and concentrated in vacuo for 30 minutes. The concentrate was diluted with $CH_2Cl_2$ and $H_2O$; adjusted to pH ~7 with 10% citric acid, and the organics were extracted 3× with $CH_2Cl_2$, dried and filtered. Purification via silica gel chromatography employing the Isco purification system followed by lyophilization gave the title compound. $^1$H NMR (300 MHz, MeOD) δ ppm 0.96 (d, J=6.41 Hz, 6 H) 1.50-1.81 (m, 4 H) 1.88-2.07 (m, 3 H) 2.44-2.63 (m, 2 H) 2.95-3.03 (m, 1 H) 3.13-3.25 (m, 2 H) 3.66-3.74 (m, 1 H) 3.89-4.02 (m, 2 H) 7.33 (d, J=3.77 Hz, 1 H) 7.41 (s, 1 H) 7.54 (s, 1 H) 7.61-7.76 (m, 6 H) 7.78-7.82 (m, 2 H).
Calc'd for $C_{32}H_{33}F_6NO_2$ (M+H)$^+$ 577.60, Found 578.3.

EXAMPLE 66

2-[5-(1-Ethyl-piperidin-3-yl)-4'-trifluoromethyl-biphenyl-3-yl]-4-methyl-pentanoic acid

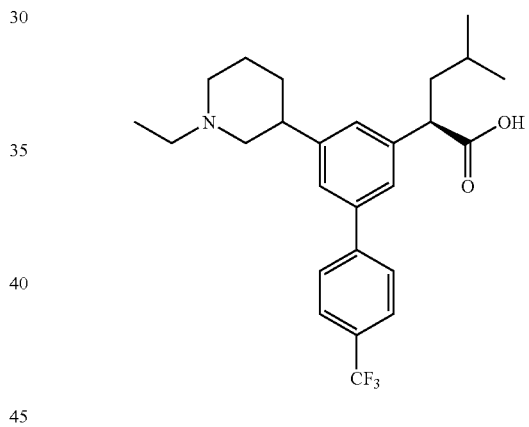

a) 2-[5-(1-Ethyl-piperidin-3-yl)-4'-trifluoromethyl-biphenyl-3-yl]-4-methyl-pentanoic acid ethyl ester

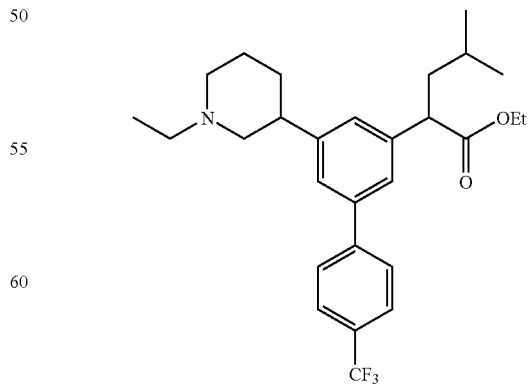

To a solution of compound 33b, 4-Methyl-2-(5-piperidin-3-yl-4'-trifluoromethyl-biphenyl-3-yl)-pentanoic acid ethyl ester (47 mg, 0.11 mmol), and 4-Trifluoromethylacetophenone (20 mg, 0.11 mmol), in 1,2 dichloroethane (0.7 ml) was added sodium acetoxyborohydride (29 mg, 0.14 mmol) and acetic acid (6.6 µl, 0.12 mmol). The reaction stirred at room temperature with little product. The reaction was heated at 50° C., then reflux over 48 hours. The solution was concentrated in vacuo, and purified by silica gel chromatography to give the above pictured by product. Calcd for C28H36F3NO2 (M+H) 475.59, Found 476.4.

b) 2-[5-(1-Ethyl-piperidin-3-yl)-4'-trifluoromethyl-biphenyl-3-yl]-4-methyl-pentanoic acid This compound was synthesized using a similar procedure as Example 55 step (b). 1H NMR (300 MHz, MeOD) δ ppm 0.97 (d, J=6.41 Hz, 6 H) 1.40 (t, J=7.35 Hz, 3 H) 1.54-1.56 (m, 1 H) 1.70-1.86 (m, 1 H) 1.91-2.13 (m, 5 H) 2.68 (s, 2 H) 3.02-3.27 (m, 4 H) 3.63-3.80 (m, 2 H) 7.37 (s, 1H) 7.60 (s, 2 H) 7.81 (d, J=11.30 Hz, 4 H) Calcd for C26H32F3NO2 (M+H) 447.53, Found 448.2.

EXAMPLE 67

2-[5-(1-Benzyl-piperidin-3-yl)-4'-trifluoromethyl-biphenyl-3-yl]-4-methyl-pentanoic acid

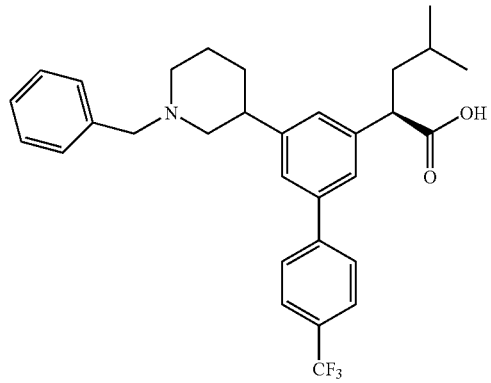

a) 2-[5-(1-Benzyl-piperidin-3-yl)-4'-trifluoromethyl-biphenyl-3-yl]-4-methyl-pentanoic acid ethyl ester

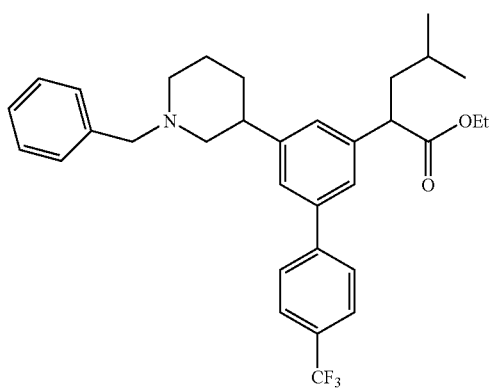

This compound was synthesized using a similar procedure as Example 66 step (a). Calcd for C33H38F3NO2 (M+H) 537.66, Found 538.2.

b) 2-[5-(1-Benzyl-piperidin-3-yl)-4'-trifluoromethyl-biphenyl-3-yl]-4-methyl-pentanoic acid This compound was synthesized using a similar procedure as Example 55 step (b). 1H NMR (300 MHz, MeOD) δ ppm 0.80-0.88 (m, 6 H) 1.06-1.19 (m, 1H) 1.40-1.54 (m, 2 H) 1.57-1.67-(m, 2 H) 1.71-1.85 (m, 2 H) 1.88-1.98 (m, 1 H) 2.58-2.76 (m, 4 H) 2.81-2.93 (m, 1 H) 3.53-3.61 (m, 1 H) 3.94-4.06 (m, 2 H) 7.22-7.38 (m, 7 H) 7.48 (d, J=4.14 Hz, 1 H) 7.59-7.71 (m, 4 H) Calcd for C31H34F3NO2 (M+H) 509.60, Found 510.1.

EXAMPLE 68

4-Methyl-2-(5-piperidin-4-yl-4'-trifluoromethyl-biphenyl-3-yl)-pentanoic acid

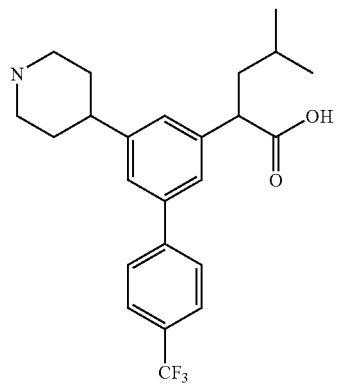

a) 4-Methyl-2-(5-pyridin-4-yl-4'-trifluoromethyl-biphenyl-3-yl)-pentanoic acid ethyl ester

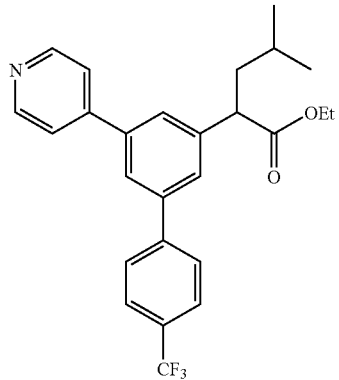

A mixture of 4-methyl-2-(5-trifluoromethanesulfonyloxy-4'-trifluoromethyl-biphenyl-3-yl)-pentanoic acid ethyl ester (1g) (2.0 g, 3.90 mol), pyridine-4-boronic acid (540 mg, 4.39 mol), 1,2-dimethoxyethane (8 mL) and aqueous Na2CO3 (2 M, 1.93 mL, 3.90 mol) was mechanically stirred while purging N2 at room temperature for 10 min. To this system was added Pd(Ph3)4 (75 mg, 0.06 mmol) and heated to reflux (95° C.) for 2 h. Added another portion of Pd(Ph3)4 (75 mg, 0.06 mmol) and heated to reflux (95° C.) for further 2 h. The red-brown mixture was diluted with EtOAc (25 mL) and washed with saturated aqueous NaHCO3 solution (3×50 mL) and brine (2×50 mL). The organic fraction was dried (Na2SO4) and concentrated in vacuo. The crude mixture was purified by ISCO column chromatography to obtain 4-methyl-2-(5-pyridin-4-yl-4'-trifluoromethyl-biphenyl-3-yl)-pentanoic acid ethyl ester.

¹H-NMR (CDCl₃): δ 0.95 (d, 6H), 1.25 (t, 3H), 1.56 (m, 1H), 1.75 (m, 1H), 2.06 (m, 1H), 3.80 (t, 1H), 4.15 (m, 2H), 7.56 (dd, 2H), 7.63 (d, 2H), 7.73 (m, 5H), 8.70 (dd, 2H); Calcd for C26H26F3NO2 (M+H) 442.49, Found 442.67 b) 4-Methyl-2-(5-piperidin-4-yl-4'-trifluoromethyl-biphenyl-3-yl)-pentanoic acid ethyl ester

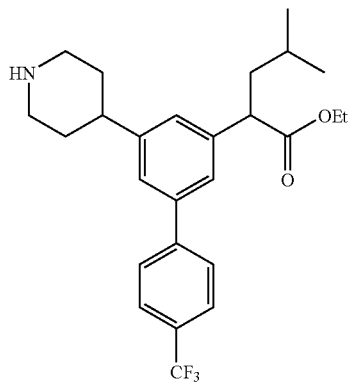

To a solution of 4-methyl-2-(5-pyridin-4-yl-4'-trifluoromethyl-biphenyl-3-yl)-pentanoic acid ethyl ester (1.15 g, 2.61 mmol) in MeOH (50 mL) was added 4N HCl (0.717 mL, 2.88 mmol) and stand for 5 minutes. To this solution was added PtO₂ (25 mg). The suspension was stirred for 10 minute and filtered through celite. To the filtrate was added another portion of PtO₂ (25 mg). The black suspension was hydrogenated at 40 psi overnight. The suspension was re-filtered. To the filtrate was added another portion of PtO₂ (25 mg) and 4N HCl (0.100 mL). The black suspension was hydrogenated at 40 psi for 2 days. The mixture was filtered through celite and the solvent was removed in vacuo. The crude mixture was purified by ISCO column chromatography to obtain a mixture of 4-methyl-2-(5-piperidin-4-yl-4'-trifluoromethyl-biphenyl-3-yl)-pentanoic acid methyl ester and 4-methyl-2-(5-piperidin-4-yl-4'-trifluoromethyl-biphenyl-3-yl)-pentanoic acid ethyl ester. Calcd for C25H30F3NO2 (M+H) 434.51, Found 434.23 (methyl ester) and Calcd for C26H32F3NO2 (M+H) 448.53, Found 448.43 (ethyl ester).

c) 4-Methyl-2-(5-piperidin-4-yl-4'-trifluoromethyl-biphenyl-3-yl)-pentanoic acid To a solution of a mixture of 4-methyl-2-(5-piperidin-4-yl-4'-trifluoromethyl-biphenyl-3-yl)-pentanoic acid ethyl ester and methyl ester (43 mg, 0.10 mmol) in MeOH (1 mL) was added 3N NaOH (0.10 mL) and heated to 50° C. for 2 h. The reaction was concentrated in vacuo to remove MeOH. The thick liquid was acidified to pH=2 by 2N HCl. The resulting acidic solution was extracted with EtOAc. The organic fraction was dried (MgSO₄) and concentrated in vacuo. The crude mixture was purified by Gilson reverse phase column chromatography to obtain 4-methyl-2-(5-piperidin-4-yl-4'-trifluoromethyl-biphenyl-3-yl)-pentanoic acid.

¹H-NMR (DMSO-d₆): δ 0.89 (d, 6H), 1.43 (m, 1H), 1.61 (m, 1H), 1.83-2.05 (m, 5H), 2.87-3.09 (m, 3H), 3.41 (m, 2H), 3.71 (t, 1H), 7.26 (s, 1H), 7.45 (s, 1H), 7.53 (s, 1H), 7.85 (dd, 4H), 8.77 (bs, 1H), 12.38 (bs, 1H); Calcd for C24H28F3NO2 (M+H) 420.48, Found 420.3

EXAMPLE 69

4-Methyl-2-{5-[1-(4-methyl-pent-2-enyl)-piperidin-4-yl]-4'-trifluoromethyl-biphenyl-3-yl}-pentanoic acid

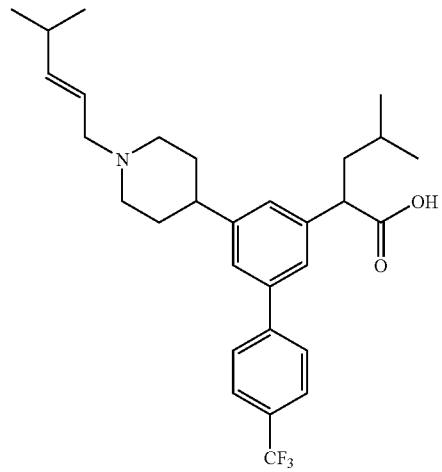

a) 4-Methyl-2-{5-[1-(4-methyl-pent-2-enyl)-piperidin-4-yl]-4'-trifluoromethyl-biphenyl-3-yl}-pentanoic acid ethyl ester

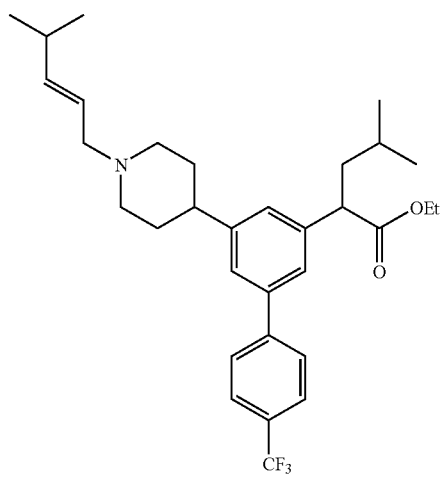

To a solution of a mixture of 4-methyl-2-(5-piperidin-4-yl-4'-trifluoromethyl-biphenyl-3-yl)-pentanoic acid ethyl ester and methyl ester (68b) (60 mg, 0.13 mmol) in 1,2-dichloroethane (2.0 mL) was added 4-methyl-pent-2-enal (15 mg, 0.15 mmol) and sodiumtriacetoxyborohydride (37 mg, 0.17 mmol). The mixture was stirred for 2 h at room temperature. The reaction was quenched with water and extracted with dichloromethane. The organic was washed with saturated aqueous NaHCO₃ solution and brine. The organic fraction was dried (MgSO₄) and concentrated in vacuo. The crude mixture contained 4-methyl-2-{5-[1-(4-methyl-pent-2-enyl)-piperidin-4-yl]-4'-trifluoromethyl-biphenyl-3-yl}-pentanoic acid ethyl and methyl ester. Calcd for C31H40F3NO2 (M+H) 516.65, Found 516.30 (methyl ester) and Calcd for C32H42F3NO2 (M+H) 530.68, Found 531.24 (ethyl ester).

b) 4-Methyl-2-{5-[1-(4-methyl-pent-2-enyl)-piperidin-4-yl]-4'-trifluoromethyl-biphenyl-3-yl}-pentanoic acid To a solution of a mixture of 4-methyl-2-{5-[1-(4-methyl-pent-2-enyl)-piperidin-4-yl]-4'-trifluoromethyl-biphenyl-3-yl}-pentanoic acid ethyl and methyl ester (20 mg, 0.10 mmol) in MeOH (1 mL) was added 3N NaOH (0.75 mL) and heated to 50° C. for 2 h. The reaction was concentrated in vacuo to remove MeOH. The thick liquid was acidified to pH=2 by 2N HCl. The resulting acidic solution was extracted with EtOAc. The organic fraction was dried (MgSO₄) and concentrated in vacuo. The crude mixture was purified by Gilson reverse phase column chromatography to obtain 4-methyl-2-{5-[1-(4-methyl-pent-2-enyl)-piperidin-4-yl]-4'-trifluoromethyl-biphenyl-3-yl}-pentanoic acid.

¹H-NMR (MeOD-d₄): δ 0.85 (dd, 6H), 0.98 (d, 6H), 1.41 (m, 1H), 1.58 (m, 1H), 1.91 (m, 3H), 2.10 (bd, 2H), 2.35 (m, 1H), 2.85-3.07 (m, 3H), 3.55 (bd, 2H), 3.65 (m, 3H), 5.49 (m, 1H), 5.97 (dd, 1H), 7.22 (s, 1H), 7.37 (s, 1H), 7.43 (s, 1H), 7.86 (dd, 4H);); Calcd for C30H38F3NO2 (M+H) 502.62, Found 502.4

EXAMPLE 70

2-{5-[1-(3-Fluoro-5-trifluoromethyl-benzyl)-piperidin-4-yl]-4'-trifluoromethyl-biphenyl-3-yl}-4-methyl-pentanoic acid

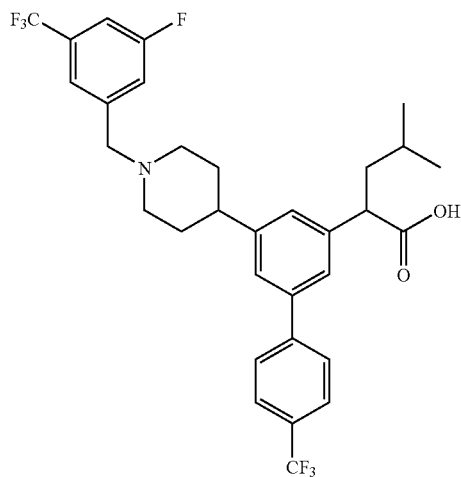

a) 2-{5-[1-(3-Fluoro-5-trifluoromethyl-benzyl)-piperidin-4-yl]-4'-trifluoromethyl-biphenyl-3-yl}-4-methyl-pentanoic acid ethyl ester

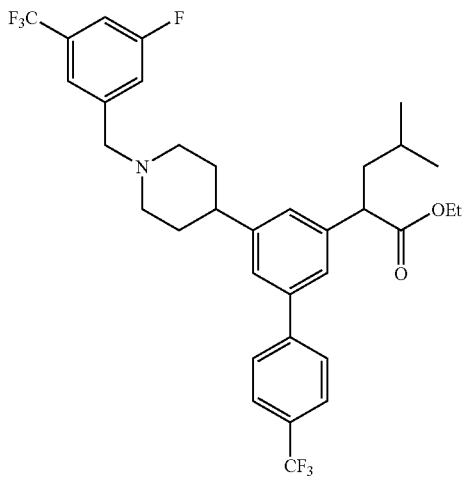

To a solution of a mixture of 4-methyl-2-{5-piperidin-4-yl-4'-trifluoromethyl-biphenyl-3-yl)-pentanoic acid ethyl ester and methyl ester (68b) (40 mg, 0.09 mmol) in 1,2-dichloroethane (2.0 mL) was added 3-fluoro-5-trifluoromethyl-benzaldehyde (19 mg, 0.10 mmol) and sodiumtriacetoxyborohydride (25 mg, 0.12 mmol). The mixture was stirred for 14 h at room temperature. The reaction was quenched with water and extracted with dichloromethane. The organic was washed with saturated aqueous NaHCO₃ solution and brine. The organic fraction was dried (MgSO₄) and concentrated in vacuo. The crude mixture contained 2-{5-[1-(3-fluoro-5-trifluoromethyl-benzyl)-piperidin-4-yl]-4'-trifluoromethyl-biphenyl-3-yl}-4-methyl-pentanoic acid ethyl ester and methyl ester. Calcd for C33H34F7NO2 (M+H) 610.62, Found 610.30 (methyl ester) and Calcd for C34H36F7NO2 (M+H) 624.64, Found 624.24 (ethyl ester).

b) 2-{5-[1-(3-Fluoro-5-trifluoromethyl-benzyl)-piperidin-4-yl]-4'-trifluoromethyl-biphenyl-3-yl}-4-methyl-pentanoic acid To a solution of a mixture of 2-{5-[1-(3-fluoro-5-trifluoromethyl-benzyl)-piperidin-4-yl]-4'-trifluoromethyl-biphenyl-3-yl}-4-methyl-pentanoic acid ethyl ester and methyl ester (38 mg, 0.06 mmol) in MeOH (1 mL) was added 3N NaOH (0.750 mL) and heated to 60° C. for 2 h. The reaction was concentrated in vacuo to remove MeOH. The thick liquid was acidified to pH=2 by 2N HCl. The resulting acidic solution was extracted with EtOAc. The organic fraction was dried (MgSO₄) and concentrated in vacuo. The crude mixture was purified by Gilson reverse phase column chromatography to obtain 2-{5-[1-(3-fluoro-5-trifluoromethyl-benzyl)-piperidin-4-yl]-4'-trifluoromethyl-biphenyl-3-yl}-4-methyl-pentanoic acid. ¹H-NMR (MeOD-d₄): δ 0.84 (d, 6H), 1.41 (m, 1H), 1.57 (m, 1H), 1.88-1.93 (m, 3H), 2.09 (m, 2H), 2.92 (t, 1H), 3.14 (t, 1H), 3.52 (m, 2H), 3.65 (t, 1H), 4.40 (s, 2H), 7.21 (s, 1H), 7.36 (s, 1H), 7.42 (s, 1H), 7.56-7.69 (m, 7H); Calcd for C32H32F7NO2 (M+H) 596.59, Found 596.40

EXAMPLE 71

4-Methyl-2-(5-{1-[4-methyl-1-(4-trifluoromethyl-phenyl)-pentyl]-piperidin-4-yl}-4'-trifluoromethyl-biphenyl-3-yl)-pentanoic acid

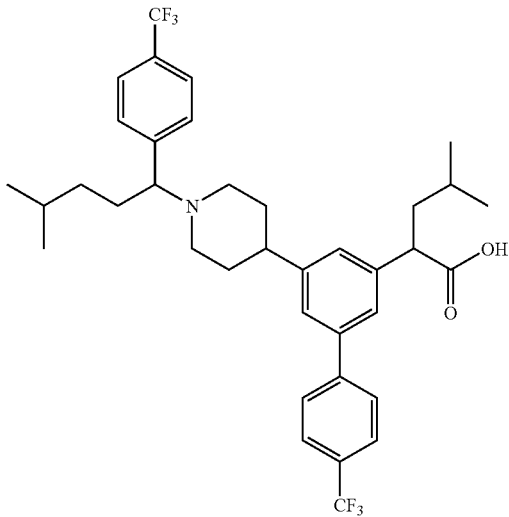

a) 4-Methyl-2-(5-{1-[4-methyl-1-(4-trifluoromethyl-phenyl)-pentyl]-piperidin-4-yl}-4'-trifluoromethyl-biphenyl-3-yl)-pentanoic acid ethyl ester.

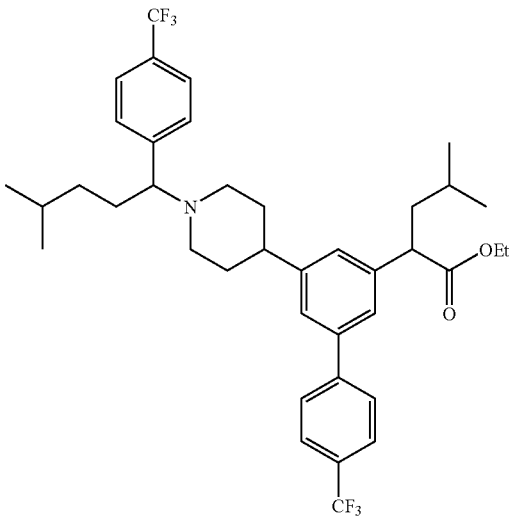

To a solution of a mixture of 4-methyl-2-(5-piperidin-4-yl-4'-trifluoromethyl-biphenyl-3-yl)-pentanoic acid ethyl ester and methyl ester (68b) (54 mg, 0.12 mmol) in toluene (1.0 mL) was added 4-trifluoromethyl-benzaldehyde (0.017 mL, 0.13 mmol) and 1H-benzotriazole (16 mg, 0.13 mmol). The mixture was heated at 130° C. for 18 h under Dean-Stark condition. The reaction mixture was concentrated in vacuo and dried in the pump for 4 h. The resulting thick yellow oil was dissolved in dichloromethane (1 mL) and cooled to 8° C. To this cold solution was added 3-methylbutylzincbromide (0.5 M in THF, 0.720 mL, 0.36 mmol) drop-wise maintaining the internal temperature below 10° C. The resulting solution was stirred at 10° C. for 1 h and at room temperature for 24 h. To this incomplete reaction mixture was added another equivalent of 3-methylbutylzincbromide (0.5 M in THF, 0.240 mL, 0.12 mmol) and stirred for 2 more days. The reaction was quenched with saturated aqueous NH4Cl solution and diluted with dichlorometane. The organic was washed with H2O, dried over (MgSO4) and concentrated in vacuo. The crude mixture was purified by ISCO column chromatography to obtain a mixture of 4-methyl-2-(5-{1-[4-methyl-1-(4-trifluoromethyl-phenyl)-pentyl]-piperidin-4-yl}-4'-trifluoromethyl-biphenyl-3-yl)-pentanoic acid ethyl ester and methyl ester. Calcd for C38H45F6NO2 (M+H) 662.76, Found 662.4 (methyl ester) and Calcd for C39H47F6NO2 (M+H) 676.79, Found 676.79 (ethyl ester).

b) 4-Methyl-2-(5-{1-[4-methyl-1-(4-trifluoromethyl-phenyl)-pentyl]-piperidin-4-yl}-4'-trifluoromethyl-biphenyl-3-yl)-pentanoic acid To a solution of a mixture of 4-methyl-2-(5-{1-[4-methyl-1-(4-trifluoromethyl-phenyl)-pentyl]-piperidin-4-yl}-4'-trifluoromethyl-biphenyl-3-yl)-pentanoic acid ethyl ester and methyl ester (56 mg, 0.09 mmol) in MeOH (1 mL) was added 3N NaOH (0.060 mL) and heated to 50° C. for 2 h. The reaction was concentrated in vacuo to remove MeOH. The thick liquid was acidified to pH=2 by 2N HCl. The resulting acidic solution was extracted with EtOAc. The organic fraction was dried (MgSO4) and concentrated in vacuo. The crude mixture was purified by ISCO column chromatography to obtain 4-methyl-2-(5-{1-[4-methyl-1-(4-trifluoromethyl-phenyl)-pentyl]-piperidin-4-yl}-4'-trifluoromethyl-biphenyl-3-yl)-pentanoic acid.

$^1$H-NMR (DMSO-d$_6$): δ 0.78 (m, 1H), 0.86 (d, 6H), 0.88 (d, 6H), 1.00 (m, 1H), 1.42 (m, 1H), 1.57 (m, 2H), 1.83-2.10 (m, 5H), 2.22 (bs, 2H), 2.85 (bs, 4H), 3.70 (t, 1H), 3.81 (bd, 1H), 4.57 (bs, 1H), 7.22 (s, 1H), 7.41 (s, 1H), 7.53 (s, 1H), 7.78-7.99 (m, 8H), 9.82 (s, 1H); Calcd for C37H43F6NO2 (M+H) 648.73, Found 648.5

EXAMPLE 72

4-Methyl-2-{4'-trifluoromethyl-5-[1-(4-trifluoromethyl-phenyl)-piperidin-4-yl]-biphenyl-3-yl}-pentanoic acid

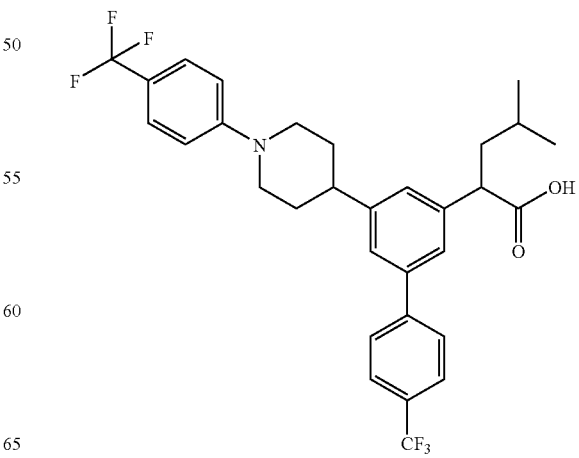

a) 4-Methyl-2-{4'-trifluoromethyl-5-[1-(4-trifluoromethyl-phenyl)-piperidin-4-yl]-biphenyl-3-yl}-pentanoic acid ethyl ester.

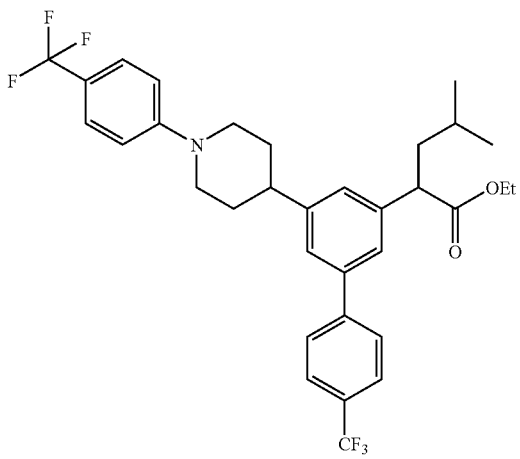

To a solution of a mixture of 4-methyl-2-(5-piperidin-4-yl-4'-trifluoromethyl-biphenyl-3-yl)-pentanoic acid ethyl ester and methyl ester (68b) (75 mg, 0.17 mmol) in toluene (1.0 mL) was added Pd$_2$(dba)$_3$ (1.6 mg, 0.0017 mmol), racemic-2-(di-t-butylphosphino)-1,1'-binaphthyl (0.7 mg, 0.0017 mmol), 1-bromo-4-trifluoromethyl-benzene (38 mg, 0.17 mmol) and sodium tert-butoxide (22 mg, 0.23 mmol). The mixture was heated, in a sealed-tube, to reflux for 3.5 h. The reaction was quenched with H$_2$O at room temperature and extracted with EtOAc (3×10 mL). The organic was washed with brine (2×10 mL), dried (MgSO$_4$) and concentrated in vacuo. The crude mixture was purified by ISCO column chromatography to obtain 4-methyl-2-{4'-trifluoromethyl-5-[1-(4-trifluoromethyl-phenyl)-piperidin-4-yl]-biphenyl-3-yl}-pentanoic acid ethyl ester and methyl ester. Calcd for C32H33F6NO2 (M+H) 578.60, Found 578.4 (methyl ester) and Calcd for C33H35F6NO2 (M+H) 592.63, Found 592.31 (ethyl ester).

b) 4-Methyl-2-{4'-trifluoromethyl-5-[1-(4-trifluoromethyl-phenyl)-piperidin-4-yl]-biphenyl-3-yl}-pentanoic acid To a solution of a mixture of 4-methyl-2-{4'-trifluoromethyl-5-[1-(4-trifluoromethyl-phenyl)-piperidin-4-yl]-biphenyl-3-yl}-pentanoic acid ethyl ester and methyl ester (69 mg, 0.12 mmol) in MeOH (2 mL) was added 3N NaOH (0.100 mL) and heated to 50° C. for 14 h. The reaction was concentrated in vacuo to remove MeOH. The thick liquid was acidified to pH=2 by 2N HCl. The resulting acidic solution was extracted with EtOAc. The organic fraction was dried (MgSO$_4$) and concentrated in vacuo. The crude mixture was purified by Gilson reverse phase column chromatography to obtain 4-methyl-2-{4'-trifluoromethyl-5-[1-(4-trifluoromethyl-phenyl)-piperidin-4-yl]-biphenyl-3-yl}-pentanoic acid. $^1$H-NMR (DMSO-d$_6$): δ 0.88 (d, 6H), 1.44 (m, 1H), 1.60 (m, 1H), 1.69-1.99 (m, 5H), 2.92 (m, 4H), 3.68 (m, 2H), 4.02 (d, 2H), 7.10 (s, 1H), 7.13 (s, 1H), 7.29 (s, 1H), 7.51 (m, 4H), 7.85 (dd, 4H); Calcd for C31H31F6NO2 (M+H) 564.57, Found 564.3

EXAMPLE 73

2-[5-(1,1-Dimethyl-piperidin-4-yl)-4'-trifluoromethyl-biphenyl-3-yl]-4-methyl-pentanoic acid

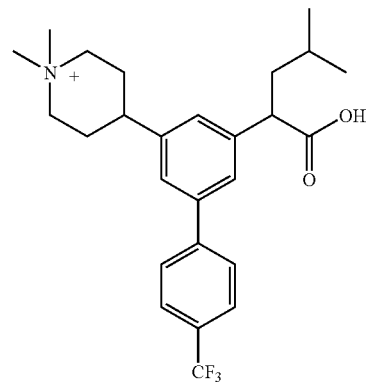

a) 2-[5-(1,1-Dimethyl-piperidin-4-yl)-4'-trifluoromethyl-biphenyl-3-yl]-4-methyl-pentanoic acid ethyl ester

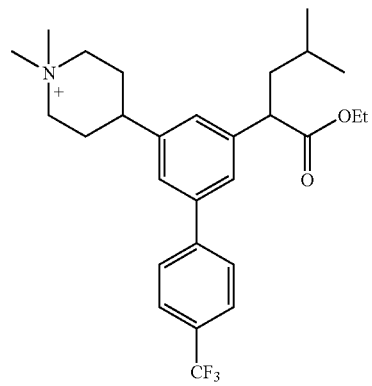

To a solution of a mixture of 4-methyl-2-(5-piperidin-4-yl-4'-trifluoromethyl-biphenyl-3-yl)-pentanoic acid ethyl ester and methyl ester (68b) (61 mg, 0.14 mmol) in N,N-dimethylformamide (1.0 mL) was added Cs$_2$CO$_3$ (91 mg, 0.28 mmol) and iodomethane (0.013 mL, 0.21 mmol). The mixture was stirred for 2 h at room temperature. The reaction was diluted with EtOAC (10 mL) and washed with saturated aqueous NaHCO$_3$ solution, brine and water. The organic fraction was dried (MgSO$_4$) and concentrated in vacuo. The crude mixture contained 2-[5-(1,1-dimethyl-piperidin-4-yl)-4'-trifluoromethyl-biphenyl-3-yl]-4-methyl-pentanoic acid ethyl ester and methyl ester. Calcd for C27H35F3NO2 (M+H) 463.57, Found 463.30 (methyl ester) and Calcd for C28H37F3NO2 (M+H) 477.59, Found 477.4 (ethyl ester).

b) 2-[5-(1,1-Dimethyl-piperidin-4-yl)-4'-trifluoromethyl-biphenyl-3-yl]-4-methyl-pentanoic acid To a solution of a mixture of 2-[5-(1,1-dimethyl-piperidin-4-yl)-4'-trifluoromethyl-biphenyl-3-yl]-4-methyl-pentanoic acid ethyl ester and methyl ester (67 mg, 0.14 mmol) in MeOH (1 mL) was added 3N NaOH (0.21 mL) and heated to 50° C. for 2 h. The reaction was concentrated in vacuo to remove MeOH. The thick liquid was acidified to pH=2 by 2N HCl. The resulting acidic solution was extracted with EtOAc. The organic fraction was dried (MgSO$_4$) and concentrated in vacuo. The crude mixture was purified by Gilson reverse phase column chromatography to obtain 2-[5-(1,1-dimethyl-piperidin-4-yl)-4'-trifluoromethyl-biphenyl-3-yl]-4-methyl-pentanoic acid.

$^1$H-NMR (DMSO-d$_6$): δ 0.89 (dd, 6H), 1.44 (m, 1H), 1.62 (m, 1H), 1.97 (m, 3H), 2.18 (m, 2H), 2.88 (m, 1H), 3.20 (s, 3H), 3.22 (s, 3H), 3.52 (m, 4H), 3.72 (t, 1H), 7.37 (s, 1H), 7.55 (s, 1H), 7.65 (s, 1H), 7.87 (dd, 4H), 12.38 (bs, 1H); Calcd for C26H33F3NO2 (M+H) 449.54, Found 449.2 mmol) and sodiumtriacetoxyborohydride (33 mg, 0.16 mmol). The mixture was stirred for 14 h at room temperature. The reaction was quenched with water and extracted with dichloromethane. The organic was washed with saturated aqueous NaHCO$_3$ solution and brine. The organic fraction was dried (MgSO$_4$) and concentrated in vacuo. The crude mixture was purified by ISCO column chromatography to obtain 2-[5-(1-cyclohexyl-piperidin-4-yl)-4'-trifluoromethyl-biphenyl-3-yl]-4-methyl-pentanoic acid ethyl ester and methyl ester. Calcd for C31H40F3NO2 (M+H) 516.65, Found 516.3 (methyl ester) and Calcd for C32H42F3NO2 (M+H) 530.68, Found 530.2 (ethyl ester).

EXAMPLE 74

2-[5-(1-Cyclohexyl-piperidin-4-yl)-4'-trifluoromethyl-biphenyl-3-yl]-4-methyl-pentanoic acid

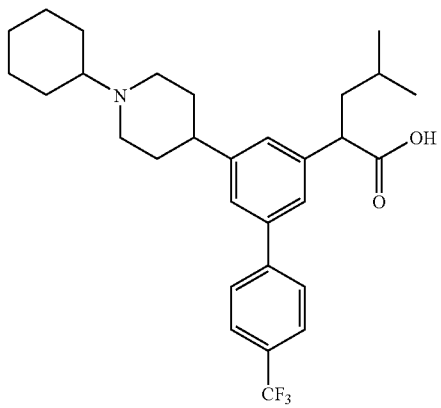

a) 2-[5-(1-Cyclohexyl-piperidin-4-yl)-4'-trifluoromethyl-biphenyl-3-yl]-4-methyl-pentanoic acid ethyl ester

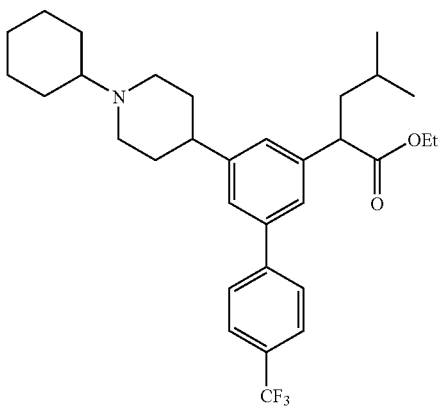

To a solution of a mixture of 4-methyl-2-(5-piperidin-4-yl-4'-trifluoromethyl-biphenyl-3-yl)-pentanoic acid ethyl ester and methyl ester (68b) (55 mg, 0.12 mmol) in 1,2-dichloroethane (1.0 mL) was added cyclohexanone (0.014 mL, 0.14 b) 2-[5-(1-Cyclohexyl-piperidin-4-yl)-4'-trifluoromethyl-biphenyl-3-yl]-4-methyl-pentanoic acid To a solution of a mixture of 2-[5-(1-cyclohexyl-piperidin-4-yl)-4'-trifluoromethyl-biphenyl-3-yl]-4-methyl-pentanoic acid ethyl ester and methyl ester (50 mg, 0.09 mmol) in MeOH (1 mL) was added 3N NaOH (0.100 mL) and heated to 50° C. for 2 h. The reaction was concentrated in vacuo to remove MeOH. The thick liquid was acidified to pH=2 by 2N HCl. The resulting acidic solution was extracted with EtOAc. The organic fraction was dried (MgSO$_4$) and concentrated in vacuo. The crude mixture was purified by Gilson reverse phase column chromatography to obtain 2-[5-(1-cyclohexyl-piperidin-4-yl)-4'-trifluoromethyl-biphenyl-3-yl]-4-methyl-pentanoic acid. $^1$H-NMR (DMSO-d$_6$): δ 0.82 (d, 6H), 1.00-1.45 (m, 6H), 1.54 (m, 2H), 1.74-2.06 (m, 9H), 2.83-3.22 (m, 4H), 3.46 (bd, 2H), 3.63 (t, 1H), 7.20 (s, 1H), 7.39 (s, 1H), 7.47 (s, 1H), 7.78 (dd, 4H), 12.35 (bs, 1H); Calcd for C30H38F3NO2 (M+H) 502.62, Found 502.4

EXAMPLE 75

2-{5-[1-(3,5-Difluoro-benzyl)-piperidin-4-yl]-4'-trifluoromethyl-biphenyl-3-yl}-4-methyl-pentanoic acid

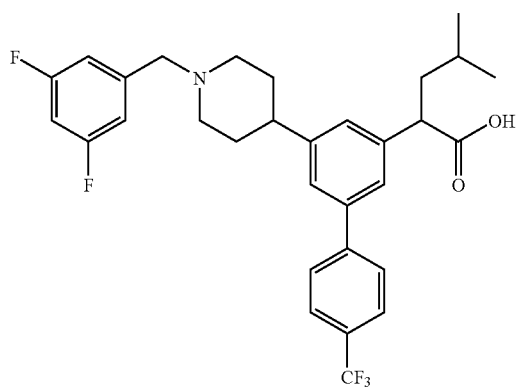

a) 2-{5-[1-(3,5-Difluoro-benzyl)-piperidin-4-yl]-4'-trifluoromethyl-biphenyl-3-yl}-4-methyl-pentanoic acid ethyl ester

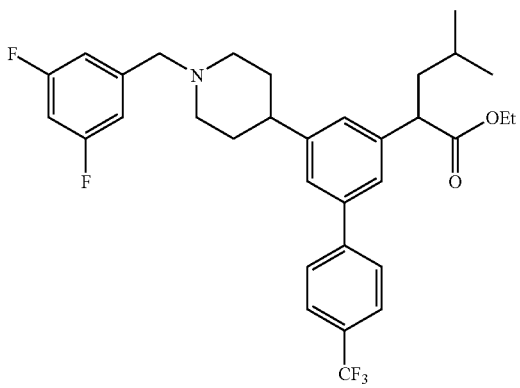

To a solution of a mixture of 4-methyl-2-(5-piperidin-4-yl-4'-trifluoromethyl-biphenyl-3-yl)-pentanoic acid ethyl ester and methyl ester (68b) (50 mg, 0.11 mmol) in 1,2-dichloroethane (1.0 mL) was added 3,5-difluorobenzaldehyde (0.014 mL, 0.12 mmol) and sodiumtriacetoxyborohydride (31 mg, 0.14 mmol). The mixture was stirred for 2 h at room temperature. The reaction was quenched with water and extracted with dichloromethane. The organic was washed with saturated aqueous NaHCO$_3$ solution and brine. The organic fraction was dried (MgSO$_4$) and concentrated in vacuo. The crude mixture contained 2-{5-[1-(3,5-difluoro-benzyl)-piperidin-4-yl]-4'-trifluoromethyl-biphenyl-3-yl}-4-methyl-pentanoic acid ethyl ester and methyl ester. Calcd for C32H34F5NO2 (M+H) 560.61, Found 560.3 (methyl ester) and Calcd for C33H36F5NO2 (M+H) 574.64, Found 574.2 (ethyl ester).

b) 2-{5-[1-(3,5-Difluoro-benzyl)-piperidin-4-yl]-4'-trifluoromethyl-biphenyl-3-yl}-4-methyl-pentanoic acid To a solution of a mixture of 2-{5-[1-(3,5-difluoro-benzyl)-piperidin-4-yl]-4'-trifluoromethyl-biphenyl-3-yl}-4-methyl-pentanoic acid ethyl ester and methyl ester (63 mg, 0.11 mmol) in MEOH (1 mL) was added 3N NAOH (0.100 mL) and heated to 50° C. for 4 h. The reaction was concentrated in vacuo to remove MEOH. The thick liquid was acidified to pH=2 by 2N HCl. The resulting acidic solution was extracted with EtOAc. The organic fraction was dried (MgSO$_4$) and concentrated in vacuo. The crude mixture was purified by Gilson reverse phase column chromatography to obtain 2-{5-[1-(3,5-difluoro-benzyl)-piperidin-4-yl]-4'-trifluoromethyl-biphenyl-3-yl}-4-methyl-pentanoic acid. $^1$H-NMR (DMSO-d$_6$): δ 0.82 (d, 6H), 1.36 (m, 1H), 1.53 (m, 1H), 1.88 (m, 5H), 2.94 (m, 4H), 3.42 (m, 1H), 3.63 (t, 1H), 4.32 (s, 2H), 7.19 (s, 1H), 7.33 (m, 3H), 7.39 (s, 1H), 7.46 (s, 1H), 7.78 (dd, 4H), 12.35 (bs, 1H); Calcd for C31H32F5NO2 (M+H) 546.58, Found 546.3

EXAMPLE 76

4-Methyl-2-{5-[1-(3-methyl-butyl)-piperidin-4-yl]-4'-trifluoromethyl-biphenyl-3-yl}-pentanoic acid

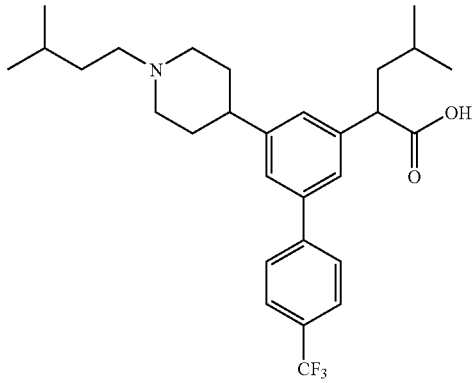

a) 4-Methyl-2-{5-[1-(3-methyl-butyl)-piperidin-4-yl]-4'-trifluoromethyl-biphenyl-3-yl}-pentanoic acid ethyl ester

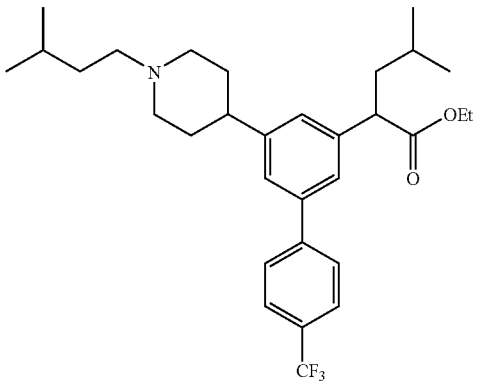

To a solution of a mixture of 4-methyl-2-(5-piperidin-4-yl-4'-trifluoromethyl-biphenyl-3-yl)-pentanoic acid ethyl ester and methyl ester (68b) (57 mg, 0.13 mmol) in N,N-dimethylformamide (1.0 mL) was added Cs$_2$CO$_3$ (85 mg, 0.26 mmol) and 1-iodo-3-methyl-butane (0.025 mL, 0.19 mmol). The mixture was stirred for 2 h at room temperature. The reaction was diluted with EtOAC (10 mL) and washed with saturated aqueous NaHCO$_3$ solution, brine and water. The organic fraction was dried (MgSO$_4$) and concentrated in vacuo. The crude mixture was purified by ISCO column chromatography to obtain 4-methyl-2-{5-[1-(3-methyl-butyl)-piperidin-4-yl]-4'-trifluoromethyl-biphenyl-3-yl}-pentanoic acid ethyl ester and methyl ester. Calcd for C30H40F3NO2 (M+H) 504.64, Found 504.4 (methyl ester) and Calcd for C31H42F3NO2 (M+H) 518.67, Found 518.7 (ethyl ester).

b) 4-Methyl-2-{5-[1-(3-methyl-butyl)-piperidin-4-yl]-4'-trifluoromethyl-biphenyl-3-yl}-pentanoic acid To a solution of a mixture of 4-methyl-2-{5-[1-(3-methyl-butyl)-piperidin-4-yl]-4'-trifluoromethyl-biphenyl-3-yl}- pentanoic acid ethyl ester and methyl ester (67 mg, 0.13 mmol) in MeOH (1 mL) was added 3N NaOH (0.130 mL) and heated to 50° C. for 2 h. The reaction was concentrated in vacuo to remove MeOH. The thick liquid was acidified to pH=2 by 2N HCl. The resulting acidic solution was extracted with EtOAc. The organic fraction was dried (MgSO$_4$) and concentrated in vacuo. The crude mixture was purified by Gilson reverse phase column chromatography to obtain 4-methyl-2-{5-[1-(3-methyl-butyl)-piperidin-4-yl]-4'-trifluoromethyl-biphenyl-3-yl}-pentanoic acid.

$^1$H-NMR (DMSO-d$_6$): δ 0.89 (dd, 6H), 0.92 (dd, 6H) 1.44 (m, 1H), 1.61 (m, 4H), 1.93 (m, 1H), 2.04 (m, 4H), 2.84-3.12 (m, 6H), 3.54 (m, 1H), 3.71 (m, 1H), 7.28 (s, 1H), 7.49 (s, 1H), 7.54 (s, 1H), 7.86 (dd, 4H); Calcd for C29H38F3NO2 (M+H) 490.61, Found 490.4

EXAMPLE 77

4-Methyl-2-{5-[1-(4-methyl-pentyl)-piperidin-4-yl]-4'-trifluoromethyl-biphenyl-3-yl}-pentanoic acid

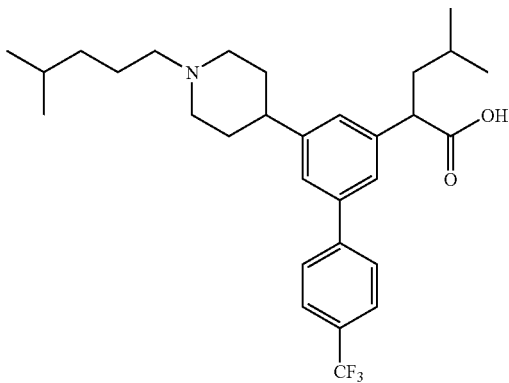

a) 4-Methyl-2-{5-[1-(4-methyl-pentyl)-piperidin-4-yl]-4'-trifluoromethyl-biphenyl-3-yl}-pentanoic acid ethyl ester

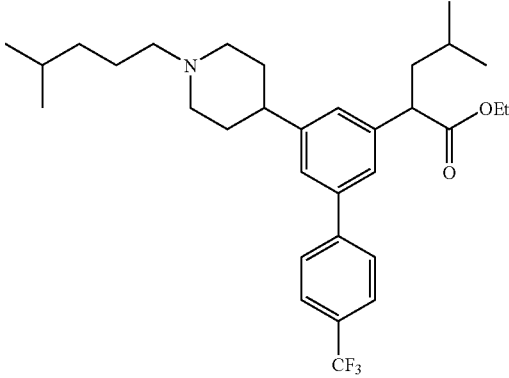

A solution of a mixture of 4-methyl-2-{5-[1-(4-methyl-pent-2-enyl)-piperidin-4-yl]-4'-trifluoromethyl-biphenyl-3-yl}-pentanoic acid ethyl ester and methyl ester (69a) (25 mg, 0.05 mmol) in MeOH (2.0 mL) was flushed with N$_2$. To this was added 10% Pd/C (5 mg). The suspension was hydrogenated at 20 psi for 4 h at room temperature. It was filtered through celite and the solid was washed with EtOAc. The filtrate was dried (MgSO$_4$) and concentrated in vacuo to obtain 4-methyl-2-{5-[1-(4-methyl-pentyl)-piperidin-4-yl]-4'-trifluoromethyl-biphenyl-3-yl}-pentanoic acid ethyl ester and methyl ester. Calcd for C31H42F3NO2 (M+H) 518.67, Found 518.3 (methyl ester) and Calcd for C32H44F3NO2 (M+H) 532.69, Found 532.4 (ethyl ester).

b) 4-Methyl-2-{5-[1-(4-methyl-pentyl)-piperidin-4-yl]-4'-trifluoromethyl-biphenyl-3-yl}-pentanoic acid To a solution of a mixture of 4-methyl-2-{5-[1-(4-methyl-pentyl)-piperidin-4-yl]-4'-trifluoromethyl-biphenyl-3-yl}-pentanoic acid ethyl ester and methyl ester (26 mg, 0.05 mmol) in MeOH (1 mL) was added 3N NaOH (0.100 mL) and heated to 50° C. for 2 h. The reaction was concentrated in vacuo to remove MeOH. The thick liquid was acidified to pH=2 by 2N HCl. The resulting acidic solution was extracted with EtOAc. The organic fraction was dried (MgSO$_4$) and concentrated in vacuo. The crude mixture was purified by Gilson reverse phase column chromatography to obtain 4-methyl-2-{5-[1-(4-methyl-pentyl)-piperidin-4-yl]-4'-trifluoromethyl-biphenyl-3-yl}-pentanoic acid.

$^1$H-NMR (MeOD-d$_4$): δ 0.86 (m, 12H), 1.20 (q, 2H), 1.42 (m, 1H), 1.57 (m, 2H), 1.70 (m, 2H), 1.92 (m, 3H), 2.09 (m, 2H), 2.91 (m, 1H), 3.03 (m, 4H), 3.63 (m, 3H), 7.22 (s, 1H), 7.37 (s, 1H), 7.43 (s, 1H), 7.68 (dd, 4H); Calcd for C30H40F3NO2 (M+H) 504.64, Found 504.5

EXAMPLE 78

4-Methyl-2-{4'-trifluoromethyl-5-[1-(4-trifluoromethyl-benzyl)-piperidin-4-yl]-biphenyl-3-yl}-pentanoic acid

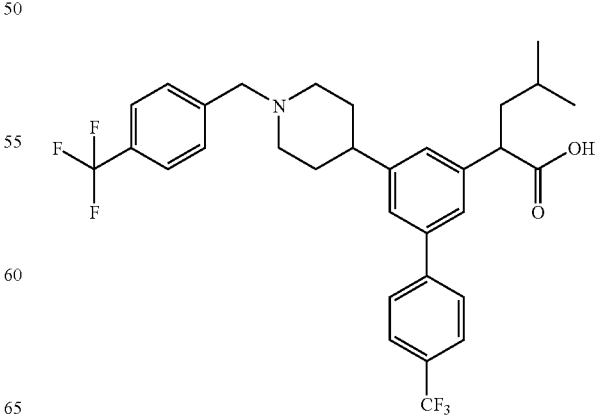

a) 4-Methyl-2-{4'-trifluoromethyl-5-[1-(4-trifluoromethyl-benzyl)-piperidin-4-yl]-biphenyl-3-yl}-pentanoic acid ethyl ester

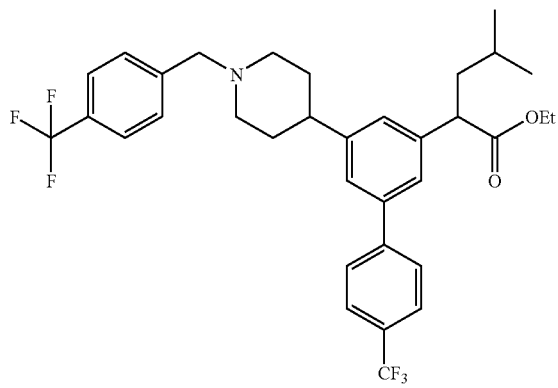

To a solution of a mixture of 4-methyl-2-(5-piperidin-4-yl-4'-trifluoromethyl-biphenyl-3-yl)-pentanoic acid ethyl ester and methyl ester (68b) (57 mg, 0.13 mmol) in 1,2-dichloroethane (1.0 mL) was added 4-trifluoromethyl-benzaldehyde (0.019 mL, 0.14 mmol) and sodiumtriacetoxyborohydride (35 mg, 0.17 mmol). The mixture was stirred for 2 h at room temperature. The reaction was quenched with water and extracted with dichloromethane. The organic was washed with saturated aqueous $NaHCO_3$ solution and brine. The organic fraction was dried ($MgSO_4$) and concentrated in vacuo. The crude mixture was purified by ISCO column chromatography to obtain a mixture of 4-methyl-2-{4'-trifluoromethyl-5-[1-(4-trifluoromethyl-benzyl)-piperidin-4-yl]-biphenyl-3-yl}-pentanoic acid ethyl ester and methyl ester. Calcd for $C_{33}H_{35}F_6NO_2$ (M+H) 592.63, Found 592.30 (methyl ester) and Calcd for $C_{34}H_{37}F_6NO_2$ (M+H) 606.65, Found 606.30 (ethyl ester).

b) 4-Methyl-2-{4'-trifluoromethyl-5-[1-(4-trifluoromethyl-benzyl)-piperidin-4-yl]-biphenyl-3-yl}-pentanoic acid To a solution of a mixture of 4-methyl-2-{4'-trifluoromethyl-5-[1-(4-trifluoromethyl-benzyl)-piperidin-4-yl]-biphenyl-3-yl}-pentanoic acid ethyl ester and methyl ester (56 mg, 0.09 mmol) in MeOH (1 mL) was added 3N NaOH (0.060 mL) and heated to 50° C. for 2 h. The reaction was concentrated in vacuo to remove MeOH. The thick liquid was acidified to pH=2 by 2N HCl. The resulting acidic solution was extracted with EtOAc. The organic fraction was dried ($MgSO_4$) and concentrated in vacuo. The crude mixture was purified by ISCO column chromatography to obtain 4-methyl-2-{4'-trifluoromethyl-5-[1-(4-trifluoromethyl-benzyl)-piperidin-4-yl]-biphenyl-3-yl}-pentanoic acid.

$^1$H-NMR (DMSO-$d_6$): δ 0.88 (d, 6H), 1.42 (m, 1H), 1.60 (m, 1H), 1.92 (m, 1H), 2.01 (bs, 4H), 2.80-3.51 (m, 5H), 3.69 (t, 1H), 4.10 (bs, 1H), 4.47 (bs, 1H), 7.26 (s, 1H), 2.01 (bs, 1H), 7.52 (s, 1H), 7.86 (m, 8H); Calcd for $C_{32}H_{33}F_6NO_2$ (M+H) 578.60, Found 578.4

EXAMPLE 79

2-{5-[4-(3,4-Difluoro-phenyl)-piperazin-1-yl]-4'-trifluoromethyl-biphenyl-3-yl}-4-methyl-pentanoic acid

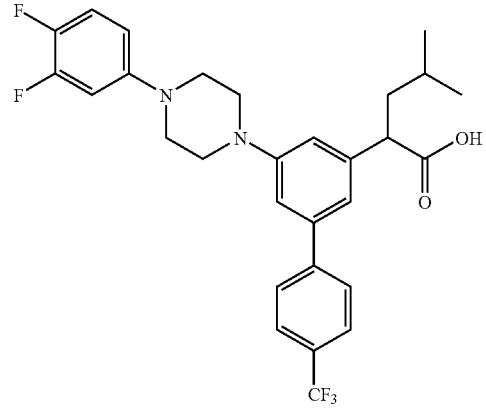

A mixture of compound 1 g (100 mg, 0.195 mmol), 1-(3,4-difluoro-phenyl)-piperazine (38.7 mg, 0.198 mmol), $Pd(OAc)_2$ (14 mg, 0.062 mmol), racemic-2-(di-t-butylphosphino)-1,1'-binaphthyl (48 mg, 0.12 mmol) and NaOt-Bu (22.6 mg, 0.235 mmol) in toluene (2 mL) was heated at 85° C. under microwave irradiation (150° C., 300W, 250 psi) for 30 min. After cooling to room temperature, the solution was partitioned between EtOAc and $H_2O$. The organic layer was dried ($Na_2SO_4$), concentrated and purified by column chromatography to give an ester intermediate.

The above intermediate was hydrolyzed following the same hydrolyzation procedure as in Example 11 to give the title compound; 1H NMR (400 MHz, MeOD) δ ppm 0.86 (dd, J=6.60, 2.93 Hz, 6H), 1.44 (ddd, J=13.33, 6.85, 6.72 Hz, 1 H), 1.60 (ddd, J=13.82, 7.09, 6.97 Hz, 1 H), 1.86-1.94 (m, 1 H), 3.20-3.28 (m, 4 H), 3.34-3.38 (m, 3 H), 3.39 (s, 1 H), 3.65 (t, J=7.83 Hz, 1 H), 6.68-6.72 (m, 1 H), 6.85 (ddd, J=13.45, 6.85, 2.93 Hz, 1 H), 7.00-7.08 (m, 2 H), 7.13-7.20 (m, 2 H), 7.62-7.72 (m, 4 H); Calcd for $C_{29}H_{29}F_5N_2O_2$ (M+H) 533.54, Found 533.3.

EXAMPLE 80

4-Methyl-2-{4'-trifluoromethyl-5-[4-(3-trifluoromethyl-phenyl)-piperazin-1-yl]-biphenyl-3-yl}-pentanoic acid

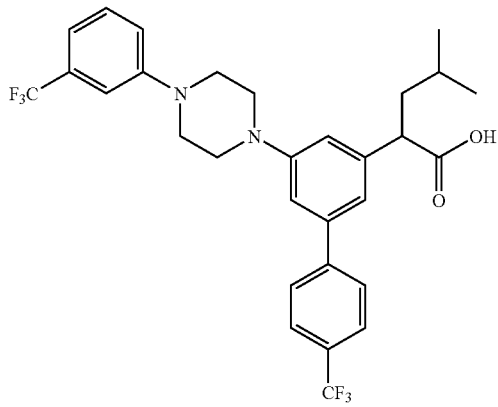

Replacing 1-(3,4-difluoro-phenyl)-piperazine with 1-(3-trifluoromethyl-phenyl)-piperazine following the same coupling and saponification procedure as in Example 79 gave the title compound; 1H NMR (400 MHz, MeOD) δ ppm 0.88 (dd, J=6.60, 2.93 Hz, 6 H), 1.47 (dt, J=13.39, 6.63 Hz, 1 H), 1.62 (ddd, J=13.69, 7.21, 6.97 Hz, 1 H), 1.86-1.97 (m, 1 H), 3.33-3.42 (m, 8 H), 3.67 (t, J=7.83 Hz, 1 H), 7.04 (d, J=7.58 Hz, 1 H), 7.08 (s, 1 H), 7.14-7.21 (m, 4 H), 7.35 (t, J=8.31 Hz, 1 H), 7.62-7.73 (m, 4 H); Calcd for C30H30F6N2O2 (M+H) 565.22, Found 565.3.

EXAMPLE 81

4-Methyl-2-{4'-trifluoromethyl-5-[4-(4-trifluoromethyl-phenyl)-piperazin-1-yl]-biphenyl-3-yl}-pentanoic acid

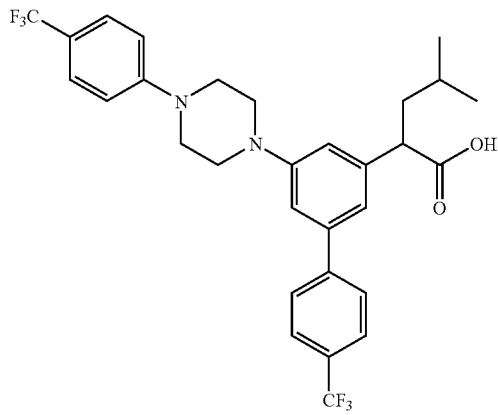

Replacing 1-(3,4-difluoro-phenyl)-piperazine with 1-(4-trifluoromethyl-phenyl)-piperazine following the same coupling and saponification procedure as in Example 79 gave the title compound; 1H NMR (400 MHz, MeOD) δ ppm 0.86-0.97 (m, 6 H), 1.40-1.52 (m, 1 H), 1.62 (ddd, J=13.63, 7.09, 6.91 Hz, 1 H), 1.87-1.99 (m, 1 H), 3.30-3.55 (m, 8 H), 3.65 (t, J=7.83 Hz, 1 H), 7.02-7.07 (m, 2 H), 7.07-7.19 (m, 3 H), 7.43 (d, J=8.80 Hz, 2 H), 7.64-7.76 (m, 4 H); Calcd for C30H30F6N2O2 (M+H) 565.22, Found 565.2.

EXAMPLE 82

4-Methyl-2-(5-piperazin-1-yl-4'-trifluoromethyl-biphenyl-3-yl)-pentanoic acid

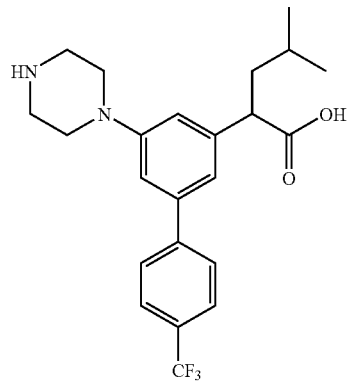

Replacing 1-(3,4-difluoro-phenyl)-piperazine with piperazine following the same coupling and saponification procedure as in Example 79 gave the title compound; 1H NMR (400 MHz, MeOD) δ ppm 0.97 (dd, J=6.60, 2.93 Hz, 6 H), 1.49-1.59 (m, 1 H), 1.68-1.75 (m, 1 H), 1.95-2.06 (m, 1 H), 3.40-3.45 (m, 4 H), 3.49-3.54 (m, 4 H), 3.73 (t, J=7.83 Hz, 1 H), 7.08 (s, 1 H), 7.22 (dd, J=4.03, 1.83 Hz, 2 H), 7.74-7.83 (m, 4 H); Calcd for C23H27F3N2O2 (M+H) 421.20, Found 421.2.

EXAMPLE 83

4-Methyl-2-{5-[2-(2-methyl-benzyl)-piperidin-1-yl]-4'-trifluoromethyl-biphenyl-3-yl}-pentanoic acid

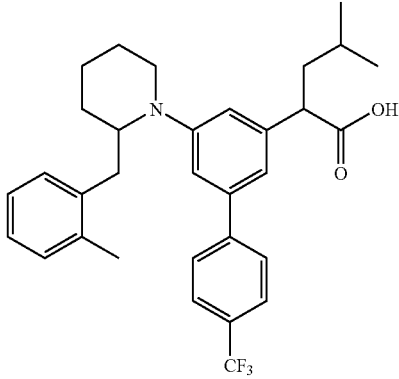

a) 4-Methyl-2-{5-[2-(2-methyl-benzyl)-piperidin-1-yl]-4'-trifluoromethyl-biphenyl-3-yl}-pentanoic acid ethyl ester

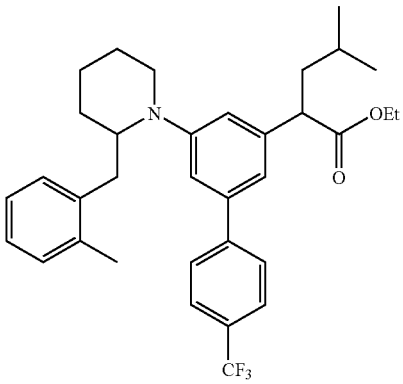

To a solution of 4-methyl-2-(5-trifluoromethanesulfonyloxy-4'-trifluoromethyl-biphenyl-3-yl)-pentanoic acid ethyl ester (1g) (190 mg, 0.37 mmol) in toluene (2.5 mL) in a sealed tube was added racemic-2-(di-t-butylphosphino)-1,1'-binaphthyl (44 mg, 0.11 mmol), Pd(OAc)₂ (83 mg, 0.37 mmol), 2-(2-methyl-benzyl)-piperidine (98 mg, 0.52 mmol). The system was flushed with nitrogen. To this was added NaO$^t$Bu (53 mg, 0.56 mmol) and heated to 100° C. for 1 h. The reaction was cooled to room temperature and quenched by slow addition of water. The mixture was extracted with EtOAc (3×20 mL). The organic phase was washed with saturated NaHCO₃ solution and brine. The organic fraction was dried (MgSO₄) and concentrated in vacuo. The crude mixture was purified by ISCO column chromatography to obtain 4-methyl-2-{5-[2-(2-methyl-benzyl)-piperidin-1-yl]-4'-trifluoromethyl-biphenyl-3-yl}-pentanoic acid ethyl ester. Calcd for C34H40F3NO2 (M+H) 552.68, Found 552.41.

b) 4-Methyl-2-{5-[2-(2-methyl-benzyl)-piperidin-1-yl]-4'-trifluoromethyl-biphenyl-3-yl}-pentanoic acid To a solution of 4-methyl-2-{5-[2-(2-methyl-benzyl)-piperidin-1-yl]-4'-trifluoromethyl-biphenyl-3-yl}-pentanoic acid ethyl ester (12 mg, 0.02 mmol) in MeOH (1 mL) was added 3N NaOH (0.200 mL) and heated to 60° C. for 14 h. The reaction was concentrated in vacuo to remove MeOH. The thick liquid was acidified to pH=2 by 2N HCl. The resulting acidic solution was extracted with EtOAc. The organic fraction was dried (MgSO$_4$) and concentrated in vacuo. The crude mixture was purified by Gilson reverse phase column chromatography to obtain 4-methyl-2-{5-[2-(2-methyl-benzyl)-piperidin-1-yl]-4'-trifluoromethyl-biphenyl-3-yl}-pentanoic acid.

$^1$H-NMR (MeOD-d$_4$): δ 0.88 (m, 6H), 1.47 (m, 1H), 1.67 (m, 3H), 1.82-2.00 (m, 5H), 2.02 (s, 3H), 2.58-2.73 (m, 2H), 3.65 (m, 2H), 3.81 (t, 1H), 4.02 (m, 1H), 6.89 (m, 1H), 6.99 (m, 3H), 7.73 (m, 7H); Calcd for C32H36F3NO2 (M+H) 524.63, Found 524.3 b) (R)-4-Methyl-2-[5-(2-phenethyl-piperidin-1-yl)-4'-trifluoromethyl-biphenyl-3-yl]-pentanoic acid To a solution of (R)-4-methyl-2-[5-(2-phenethyl-piperidin-1-yl)-4'-trifluoromethyl-biphenyl-3-yl]-pentanoic acid methyl ester (14 mg, 0.03 mmol) in MeOH (2 mL) was added 1N NaOH (0.100 mL) and heated to 60° C. for 2 h. The reaction was concentrated in vacuo to remove MeOH. The thick liquid was acidified to pH=2 by 2N HCl. The resulting acidic solution was extracted with EtOAc. The organic fraction was dried (MgSO$_4$) and concentrated in vacuo. The crude mixture was purified by Gilson reverse phase column chromatography to obtain (R)-4-methyl-2-[5-(2-phenethyl-piperidin-1-yl)-4'-trifluoromethyl-biphenyl-3-yl]-pentanoic acid. $^1$H-NMR (MeOD-d$_4$): δ 0.84 (m, 6H), 1.40 (m, 1H), 1.60-1.76 (m, 5H), 1.93 (m, 4H), 2.28-2.41 (m, 2H), 2.59 (m, 1H), 3.56-3.73 (m, 3H), 3.78 (q, 1H), 6.85 (s, 1H), 6.87 (s, 1H), 6.98 (m, 1H), 7.04 (m, 2H), 7.47-7.57 (m, 2H), 7.71 (s, 5H); Calcd for C32H36F3NO2 (M+H) 524.63, Found 524.3

Biological Activity

Screening of the Compounds of the Invention for γ-Secretase-Modulating Activity

Screening was carried out using SKNBE2 cells carrying the APP 695—wild type, grown in DMEM/NUT-mix F12 (HAM) provided by Gibco (cat no. 31330-38) containing 5% Serum/Fe supplemented with 1% non-essential amino acids.

Cells were grown to near confluency.

The screening was performed using the assay as described in Citron et al (1997) Nature Medicine 3: 67.

Examples of the γ-secretase modulating activity of representative products of the invention are shown in the following table.

| # | Structure | Chemical name | EC$_{50}$ μM | % inhibition @ 1 uM |
|---|---|---|---|---|
| 1 | 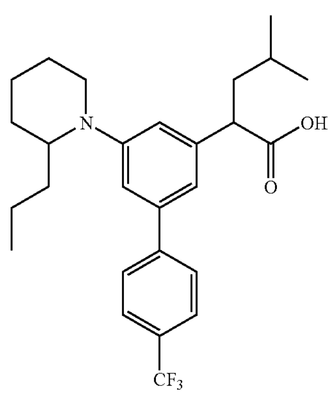 | 4-Methyl-2-[5-(2-propyl-piperidin-1-yl)-4'-trifluoromethyl-biphenyl-3-yl]-pentanoic acid | 0.43 | |
| 2 | 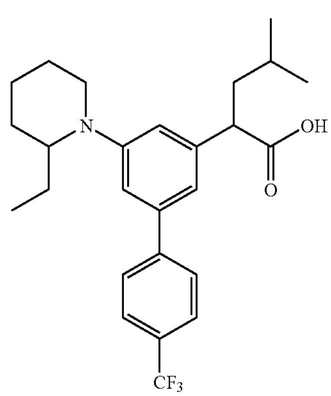 | 2-[5-(2-Ethyl-piperidin-1-yl)-4'-trifluoromethyl-biphenyl-3-yl]-4-methyl-pentanoic acid | — | 45 |

-continued

| # | Structure | Chemical name | EC$_{50}$ μM | % inhibition @ 1 uM |
|---|---|---|---|---|
| 3 | 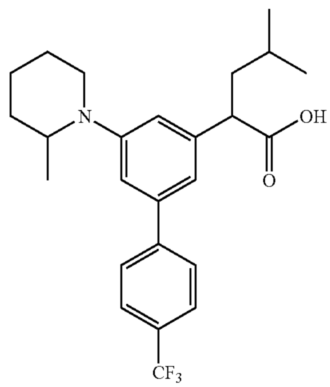 | 4-Methyl-2-[5-(2-methyl-piperidin-1-yl)-4'-trifluoromethyl-biphenyl-3-yl]-pentanoic acid | — | 23 |
| 4 | 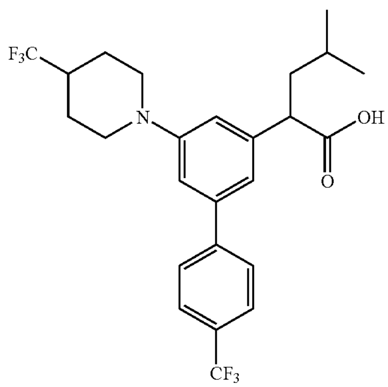 | 4-Methyl-2-[4'-trifluoromethyl-5-(4-trifluoromethyl-piperidin-1-yl)-biphenyl-3-yl]-pentanoic acid | 0.44 | |
| 5 | 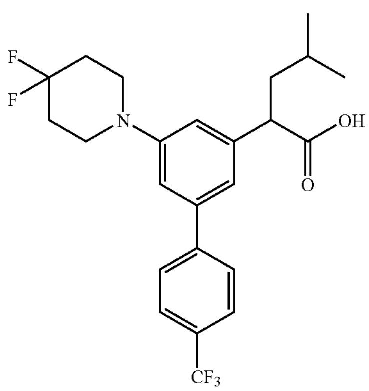 | 2-[5-(4,4-Difluoro-piperidin-1-yl)-4'-trifluoromethyl-biphenyl-3-yl]-4-methyl-pentanoic acid | — | 8 |
| 6 | 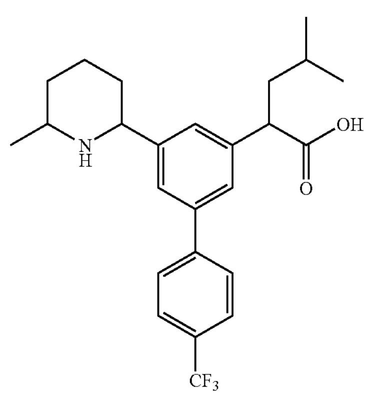 | 4-Methyl-2-[5-(6-methyl-piperidin-2-yl)-4'-trifluoromethyl-biphenyl-3-yl]-pentanoic acid | — | 0 |

-continued

| # | Structure | Chemical name | EC$_{50}$ μM | % inhibition @ 1 uM |
|---|---|---|---|---|
| 7 | 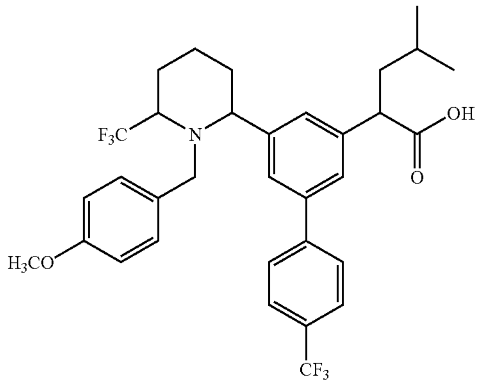 | 2-{5-[1-(4-Methoxy-benzyl)-6-trifluoromethyl-piperidin-2-yl]-4'-trifluoromethyl-biphenyl-3-yl}-4-methyl-pentanoic acid | — | 70 |
| 8 | 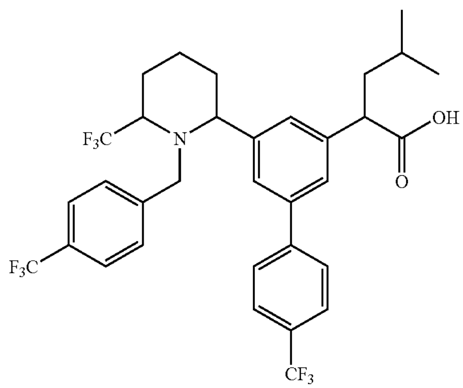 | 4-Methyl-2-{4'-trifluoromethyl-5-[6-trifluoromethyl-1-(4-trifluoromethyl-benzyl)-piperidin-2-yl]-biphenyl-3-yl}-pentanoic acid | 0.31 | |
| 9 | 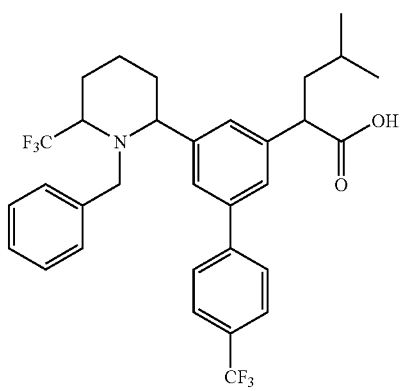 | 2-[5-(1-Benzyl-6-trifluoromethyl-piperidin-2-yl)-4'-trifluoromethyl-biphenyl-3-yl]-4-methyl-pentanoic acid | 0.45 | |
| 10 | 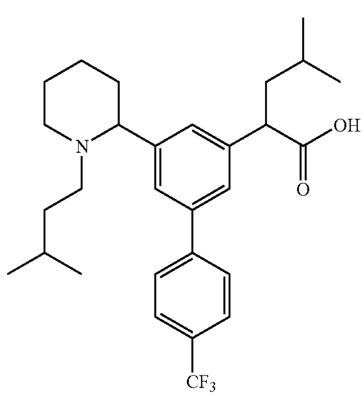 | 4-Methyl-2-{5-[1-(3-methyl-butyl)-piperidin-2-yl]-4'-trifluoromethyl-biphenyl-3-yl}-pentanoic acid | | 34 |

| # | Structure | Chemical name | EC$_{50}$ μM | % inhibition @ 1 uM |
|---|---|---|---|---|
| 11 | 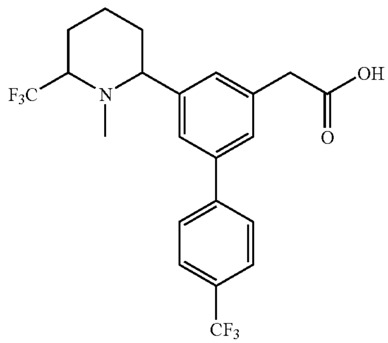 | [5-(1-Methyl-6-trifluoromethyl-piperidin-2-yl)-4'-trifluoromethyl-biphenyl-3-yl]-acetic acid | | 23 |
| 12 | 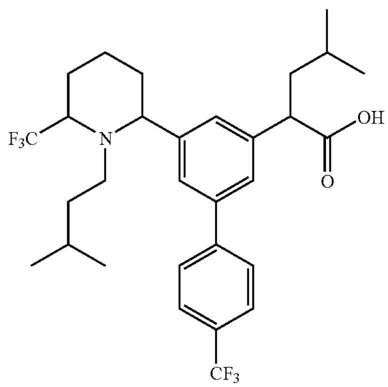 | 4-Methyl-2-{5-[1-(3-methyl-butyl)-6-trifluoromethyl-piperidin-2-yl]-4'-trifluoromethyl-biphenyl-3-yl}-pentanoic acid | 0.11 | |
| 13 | 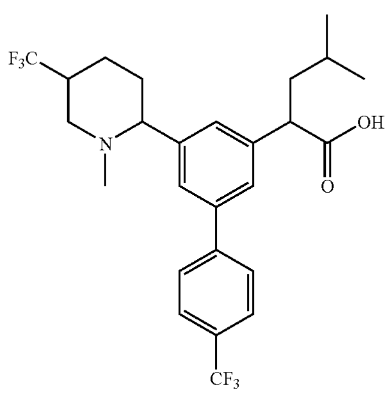 | 4-Methyl-2-[4'-trifluoromethyl-5-(5-trifluoromethyl-piperidin-2-yl)-biphenyl-3-yl]-pentanoic acid | | 30 |
| 14 | 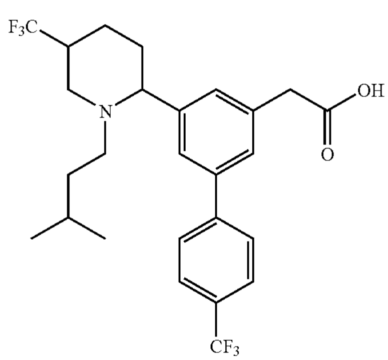 | {5-[1-(3-Methyl-butyl)-5-trifluoromethyl-piperidin-2-yl]-4'-trifluoromethyl-biphenyl-3-yl}-acetic acid | 0.72 | |

| # | Structure | Chemical name | EC$_{50}$ μM | % inhibition @ 1 uM |
|---|---|---|---|---|
| 15 | 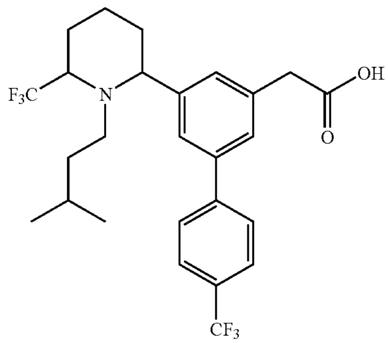 | {5-[1-(3-Methyl-butyl)-6-trifluoromethyl-piperidin-2-yl]-4'-trifluoromethyl-biphenyl-3-yl}-acetic acid | 0.6 | |
| 16 | 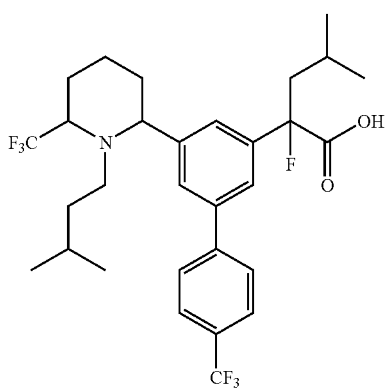 | 2-Fluoro-4-methyl-2-{5-[1-(3-methyl-butyl)-6-trifluoromethyl-piperidin-2-yl]-4'-trifluoromethyl-biphenyl-3-yl}-pentanoic acid | | 0 |
| 17 | 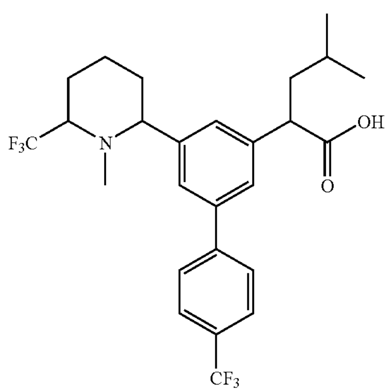 | 4-Methyl-2-[5-(1-methyl-6-trifluoromethyl-piperidin-2-yl)-4'-trifluoromethyl-biphenyl-3-yl]-pentanoic acid | 0.42 | |
| 18 | 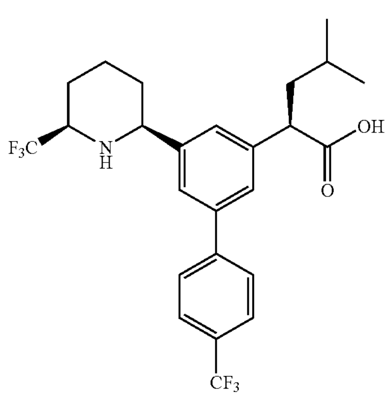 | (R)4-Methyl-2-[4'-trifluoromethyl-5-(6-trifluoromethyl-piperidin-2-yl)-biphenyl-3-yl]-pentanoic acid | 0.59 | |

| # | Structure | Chemical name | EC$_{50}$ μM | % inhibition @ 1 uM |
|---|---|---|---|---|
| 19 | 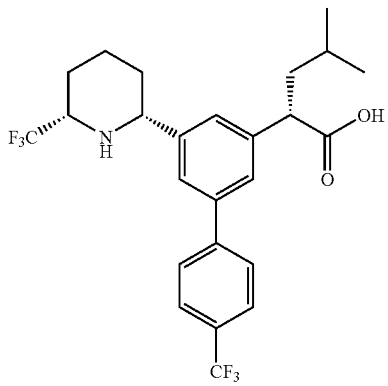 | (S) 4-Methyl-2-[4'-trifluoromethyl-5-(6-trifluoromethyl-piperidin-2-yl)-biphenyl-3-yl]-pentanoic acid | | 48 |
| 20 | 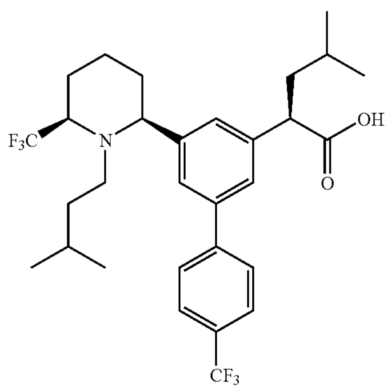 | (R) 4-Methyl-2-{5-[1-(3-methyl-butyl)-6-trifluoromethyl-piperidin-2-yl]-4'-trifluoromethyl-biphenyl-3-yl}-pentanoic acid | 0.16 | |
| 21 | 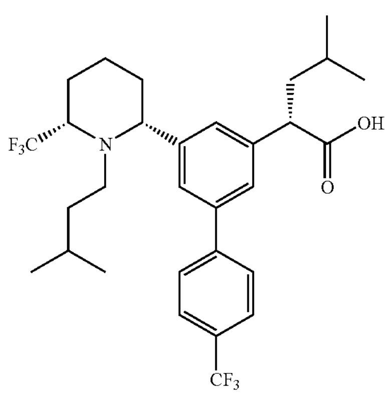 | (S) 4-Methyl-2-{5-[1-(3-methyl-butyl)-6-trifluoromethyl-piperidin-2-yl]-4'-trifluoromethyl-biphenyl-3-yl}-pentanoic acid | 0.29 | |
| 22 | 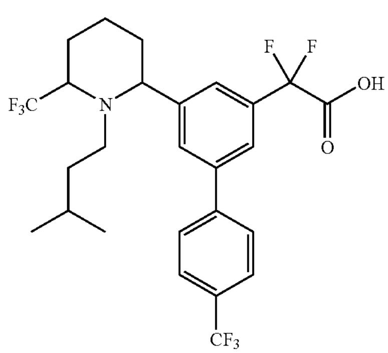 | Difluoro-{5-[1-(3-methyl-butyl)-6-trifluoromethyl-piperidin-2-yl]-4'-trifluoromethyl-biphenyl-3-yl}-acetic acid | | 35 |

-continued

| # | Structure | Chemical name | EC$_{50}$ μM | % inhibition @ 1 uM |
|---|---|---|---|---|
| 23 | 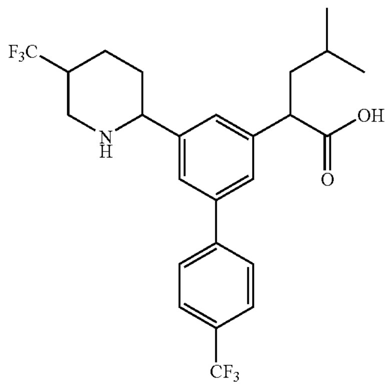 | 4-Methyl-2-[4'-trifluoromethyl-5-(5-trifluoromethyl-piperidin-2-yl)-biphenyl-3-yl]-pentanoic acid | | 30 |
| 24 | 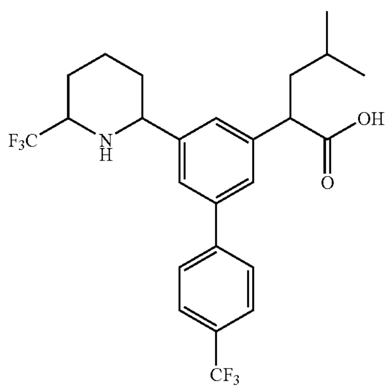 | 4-Methyl-2-[4'-trifluoromethyl-5-(6-trifluoromethyl-piperidin-2-yl)-biphenyl-3-yl]-pentanoic acid | 0.7 | |
| 25 | 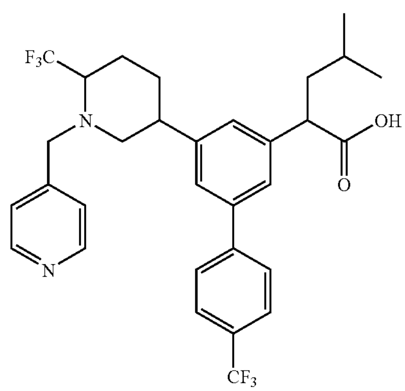 | 4-Methyl-2-[5-(1-pyridin-4-ylmethyl-6-trifluoromethyl-piperidin-3-yl)-4'-trifluoromethyl-biphenyl-3-yl]-pentanoic acid | | 23 |
| 26 | 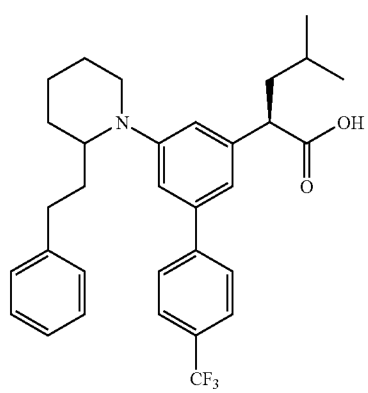 | (R)-4-Methyl-2-[5-(2-phenethyl-piperidin-1-yl)-4'-trifluoromethyl-biphenyl-3-yl]-pentanoic acid | | |

-continued

| # | Structure | Chemical name | EC$_{50}$ μM | % inhibition @ 1 uM |
|---|---|---|---|---|
| 27 | 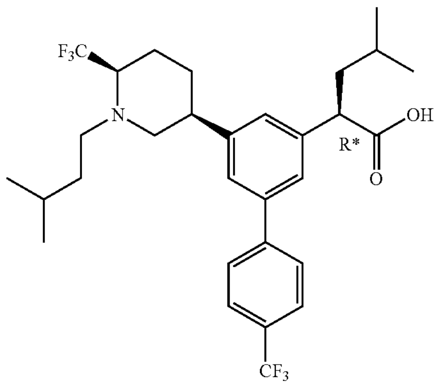 | (R*) 4-Methyl-2-{5-[1-(3-methyl-butyl)-6-trifluoromethyl-piperidin-3-yl]-4'-trifluoromethyl-biphenyl-3-yl}-pentanoic acid | 0.43 | |
| 28 | 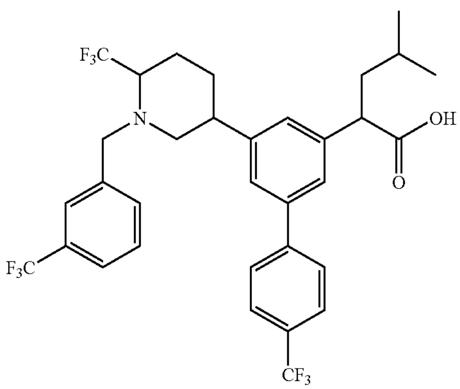 | 4-Methyl-2-{4'-trifluoromethyl-5-[6-trifluoromethyl-1-(3-trifluoromethyl-benzyl)-piperidin-3-yl]-biphenyl-3-yl}-pentanoic acid | | 68 |
| 29 | 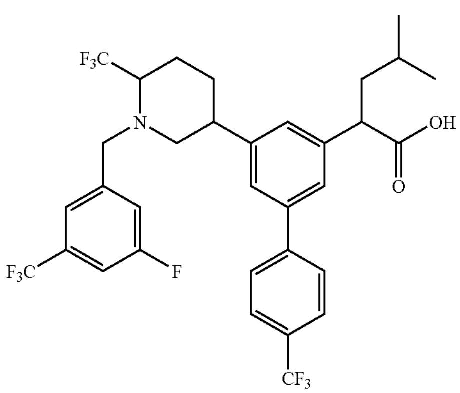 | 2-{5-[1-(3-Fluoro-5-trifluoromethyl-benzyl)-6-trifluoromethyl-piperidin-3-yl]-4'-trifluoromethyl-biphenyl-3-yl}-4-methyl-pentanoic acid | 0.48 | |
| 30 | 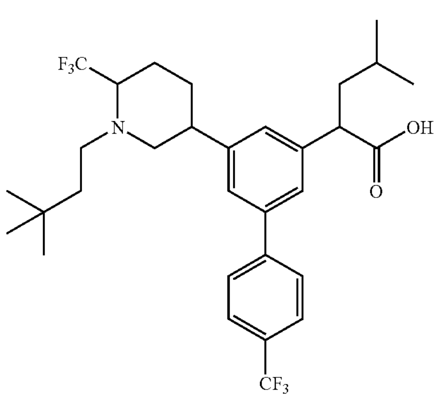 | 2-{5-[1-(3,3-Dimethyl-butyl)-6-trifluoromethyl-piperidin-3-yl]-4'-trifluoromethyl-biphenyl-3-yl}-4-methyl-pentanoic acid | 0.37 | |

| # | Structure | Chemical name | EC$_{50}$ μM | % inhibition @ 1 uM |
|---|---|---|---|---|
| 31 | 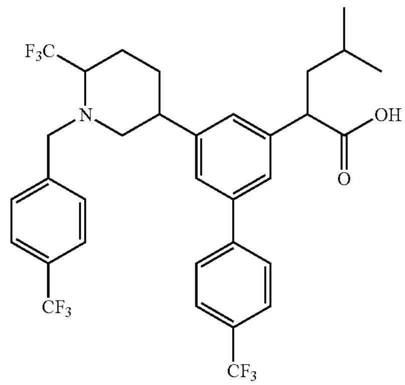 | 4-Methyl-2-{4'-trifluoromethyl-5-[6-trifluoromethyl-1-(4-trifluoromethyl-benzyl)-piperidin-3-yl]-biphenyl-3-yl}-pentanoic acid | 0.3 | |
| 32 | 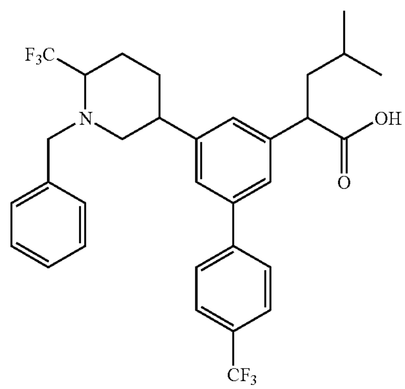 | 2-[5-(1-Benzyl-6-trifluoromethyl-piperidin-3-yl)-4'-trifluoromethyl-biphenyl-3-yl]-4-methyl-pentanoic acid | 0.37 | |
| 33 | 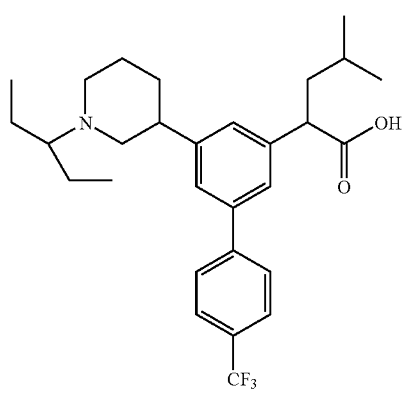 | 2-{5-[1-(1-Ethyl-propyl)-piperidin-3-yl]-4'-trifluoromethyl-biphenyl-3-yl}-4-methyl-pentanoic acid | | 22 |
| 34 | 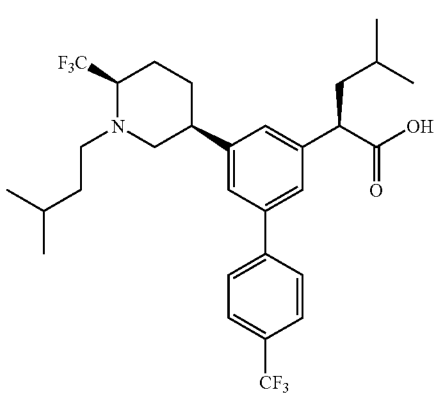 | (R*) 4-Methyl-2-{5-[1-(3-methyl-butyl)-6-trifluoromethyl-piperidin-3-yl]-4'-trifluoromethyl-biphenyl-3-yl}-pentanoic acid | 0.21 | |

-continued

| # | Structure | Chemical name | EC$_{50}$ μM | % inhibition @ 1 uM |
|---|---|---|---|---|
| 35 | 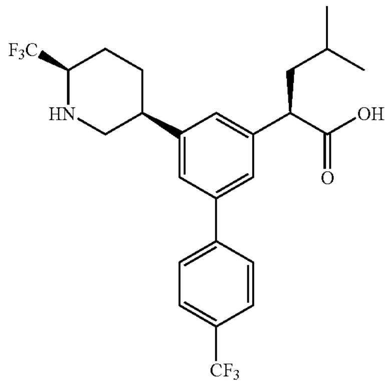 | (R*) 4-Methyl-2-[4'-trifluoromethyl-5-(6-trifluoromethyl-piperidin-3-yl)-biphenyl-3-yl]-pentanoic acid | | 8 |
| 36 | 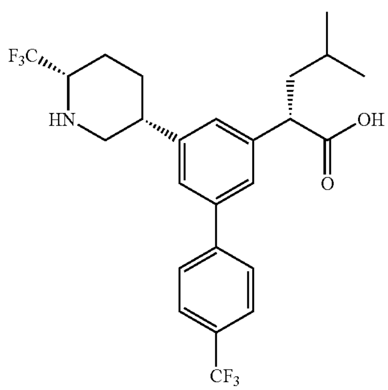 | (S*) 4-Methyl-2-[4'-trifluoromethyl-5-(6-trifluoromethyl-piperidin-3-yl)-biphenyl-3-yl]-pentanoic acid | | 40 |
| 37 | 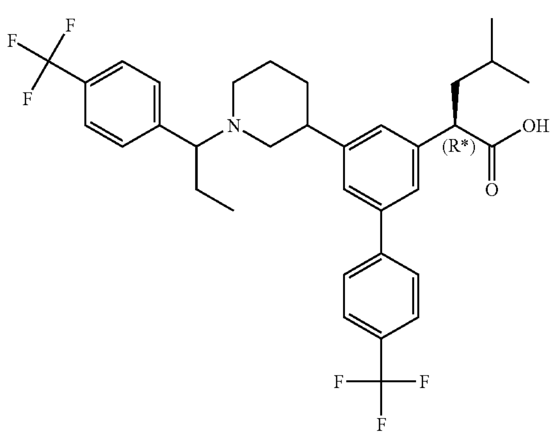 | (R*) 4-Methyl-2-(4'-trifluoromethyl-5-{1-[1-(4-trifluoromethyl-phenyl)-propyl]-piperidin-3-yl}-biphenyl-3-yl)-pentanoic acid | 0.41 | |

| # | Structure | Chemical name | EC$_{50}$ μM | % inhibition @ 1 uM |
|---|-----------|---------------|--------------|---------------------|
| 38 | 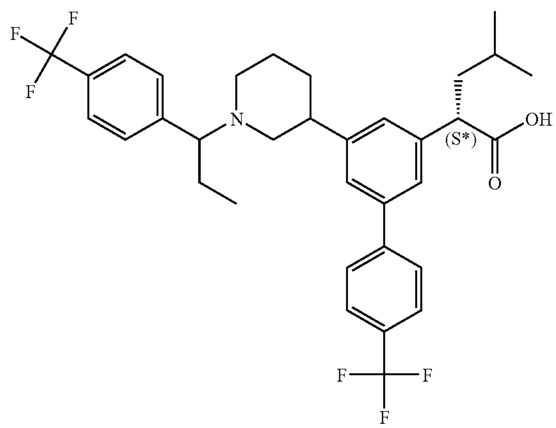 | (S*) 4-Methyl-2-(4'-trifluoromethyl-5-{1-[1-(4-trifluoromethyl-phenyl)propyl]-piperidin-3-yl}-biphenyl-3-yl)-pentanoic acid | 0.59 | |
| 39 | 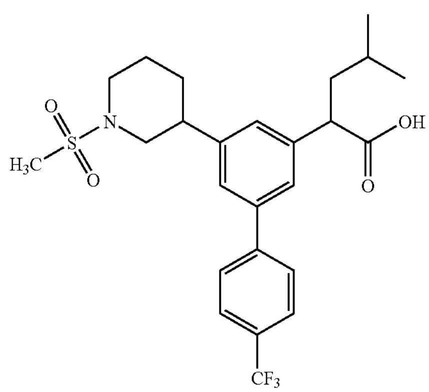 | 2-[5-(1-Methanesulfonyl-piperidin-3-yl)-4'-trifluoromethyl-biphenyl-3-yl]-4-methyl-pentanoic acid | | |
| 40 | 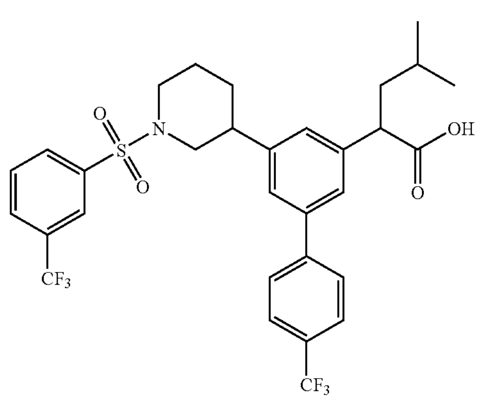 | 4-Methyl-2-{4'-trifluoromethyl-5-[1-(3-trifluoromethyl-benzenesulfonyl)-piperidin-3-yl]-biphenyl-3-yl}-pentanoic acid | | 70 |

| # | Structure | Chemical name | EC$_{50}$ μM | % inhibition @ 1 uM |
|---|---|---|---|---|
| 41 | 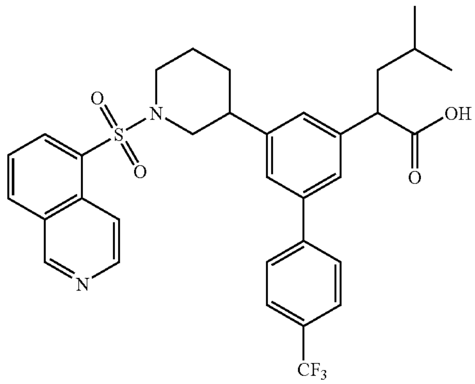 | 2-{5-[1-(Isoquinoline-5-sulfonyl)-piperidin-3-yl]-4'-trifluoromethyl-biphenyl-3-yl}-4-methyl-pentanoic acid | | 70 |
| 42 | 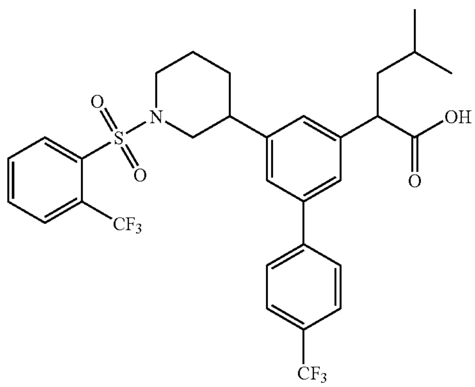 | 4-Methyl-2-{4'-trifluoromethyl-5-[1-(2-trifluoromethyl-benzenesulfonyl)-piperidin-3-yl]-biphenyl-3-yl}-pentanoic acid | | 63 |
| 43 | 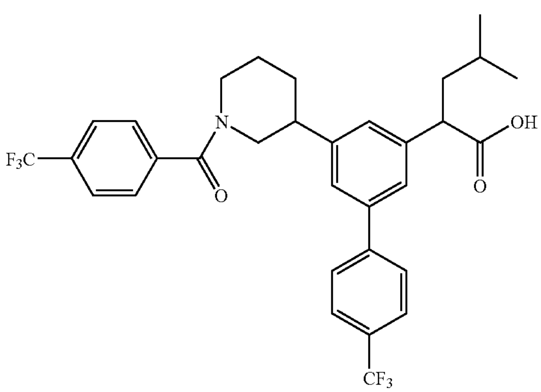 | 4-Methyl-2-{4'-trifluoromethyl-5-[1-(4-trifluoromethyl-benzoyl)-piperidin-3-yl]-biphenyl-3-yl}-pentanoic acid | | 55 |
| 44 | 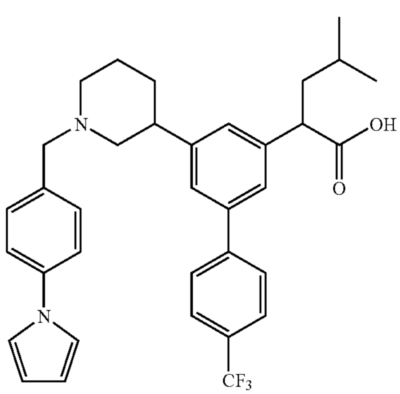 | 4-Methyl-2-{5-[1-(4-pyrrol-1-yl-benzyl)-piperidin-3-yl]-4'-trifluoromethyl-biphenyl-3-yl}-pentanoic acid | | 46 |

| # | Structure | Chemical name | EC$_{50}$ μM | % inhibition @ 1 uM |
|---|---|---|---|---|
| 45 | 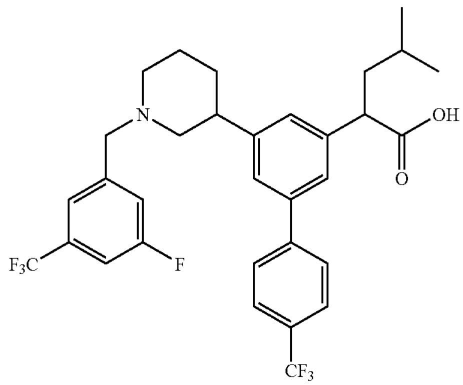 | 2-{5-[1-(3-Fluoro-5-trifluoromethyl-benzyl)-piperidin-3-yl]-4'-trifluoromethyl-biphenyl-3-yl}-4-methyl-pentanoic acid | 0.31 | |
| 46 | 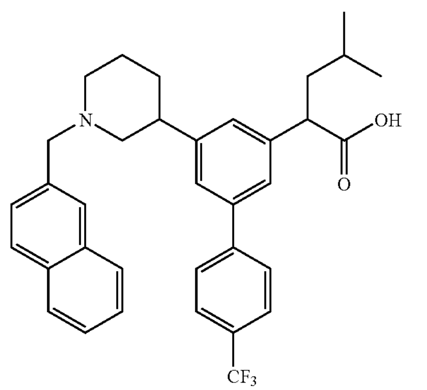 | 4-Methyl-2-[5-(1-naphthalen-2-ylmethyl-piperidin-3-yl)-4'trifluoromethyl-biphenyl-3-yl]-pentanoic acid | | 57 |
| 47 | 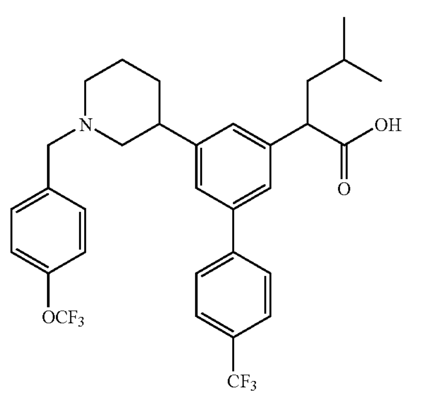 | 4-Methyl-2-{5-[1-(4-trifluoromethoxy-benzyl)-piperidin-3-yl]-4'-trifluoromethyl-biphenyl-3-yl}-pentanoic acid | | 61 |

| # | Structure | Chemical name | EC$_{50}$ μM | % inhibition @ 1 uM |
|---|---|---|---|---|
| 48 | 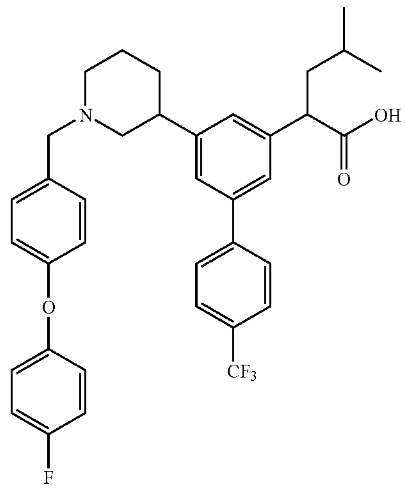 | 2-(5-{1-[4-(4-Fluoro-phenoxy)-benzyl]-piperidin-3-yl}-4'-trifluoromethyl-biphenyl-3-yl)-4-methyl-pentanoic acid | | 59 |
| 49 | 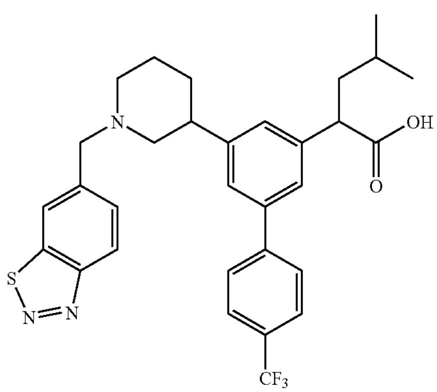 | 2-[5-(1-Benzo[1,2,3]thiadiazol-6-ylmethyl-piperidin-3-yl)-4'-trifluoromethyl-biphenyl-3-yl]-4-methyl-pentanoic acid | | 54 |
| 50 | 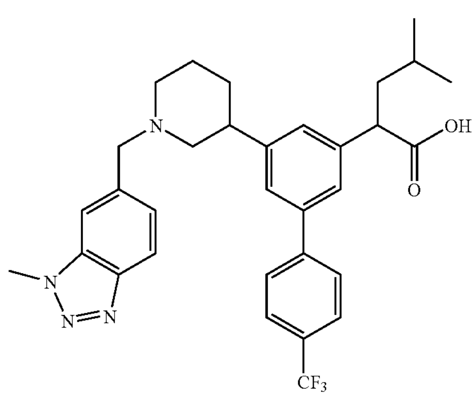 | 4-Methyl-2-{5-[1-(3-methyl-3H-benzotriazol-5-ylmethyl)-piperidin-3-yl]-4'-trifluoromethyl-biphenyl-3-yl}-pentanoic acid | | 17 |

| # | Structure | Chemical name | EC$_{50}$ μM | % inhibition @ 1 uM |
|---|---|---|---|---|
| 51 | 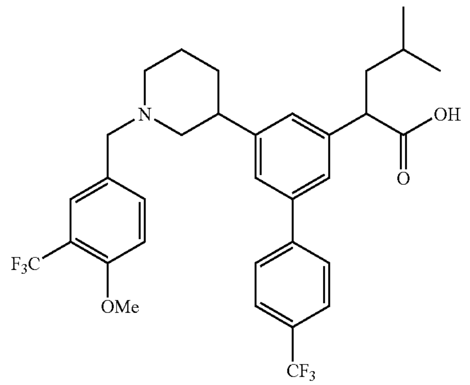 | 2-{5-[1-(4-Methoxy-3-trifluoromethyl-benzyl)-piperidin-3-yl]-4'-trifluoromethyl-biphenyl-3-yl}-4-methyl-pentanoic acid | | 48 |
| 52 | 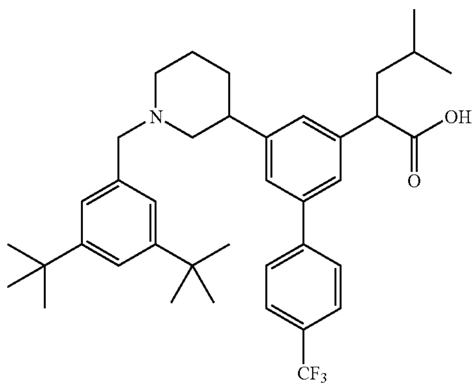 | 2-{5-[1-(3,5-Di-tert-butyl-benzyl)-piperidin-3-yl]-4'-trifluoromethyl-biphenyl-3-yl}-4-methyl-pentanoic acid | | 58 |
| 53 | 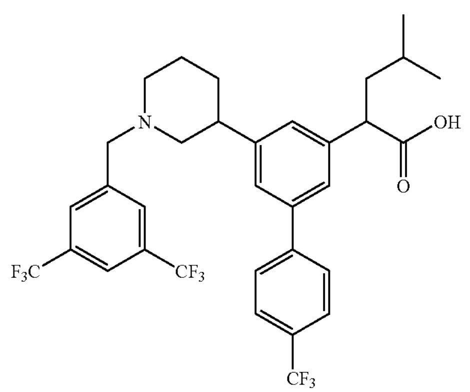 | 2-{5-[1-(3,5-Bis-trifluoromethyl-benzyl)-piperidin-3-yl]-4'-trifluoromethyl-biphenyl-3-yl}-4-methyl-pentanoic acid | | 57 |
| 54 | 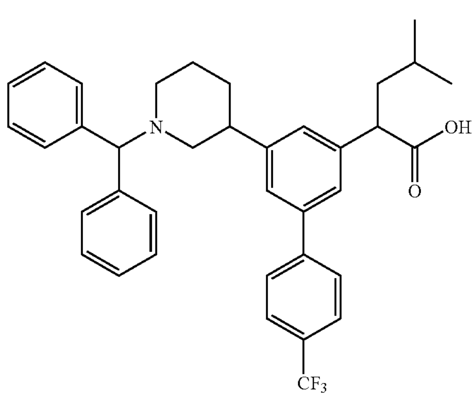 | 2-[5-(1-Benzhydryl-piperidin-3-yl)-4'-trifluoromethyl-biphenyl-3-yl]-4-methyl-pentanoic acid | | 80 |

| # | Structure | Chemical name | EC$_{50}$ μM | % inhibition @ 1 uM |
|---|---|---|---|---|
| 55 | 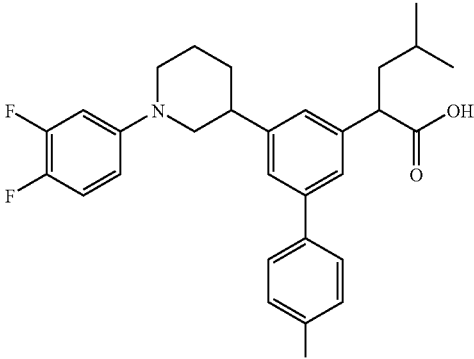 | 2-{5-[1-(3,4-Difluoro-phenyl)-piperidin-3-yl]-4'-trifluoromethyl-biphenyl-3-yl}-4-methyl-pentanoic acid | | 45 |
| 56 | 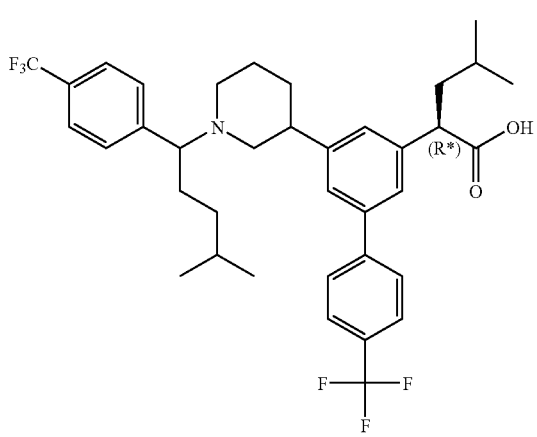 | (R*) 4-Methyl-2-(5-{1-[4-methyl-1-(4-trifluoromethyl-phenyl)-pentyl]-piperidin-3-yl}-4'-trifluoromethyl-biphenyl-3-yl)-pentanoic acid | | 75 |
| 57 | 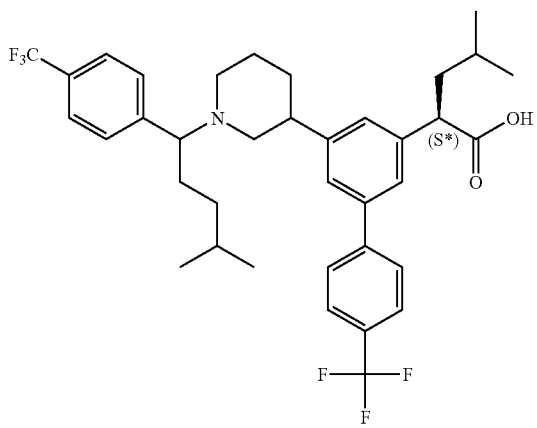 | (S*) 4-Methyl-2-(5-{1-[4-methyl-1-(4-trifluoromethyl-phenyl)-pentyl]-piperidin-3-yl}-4'-trifluoromethyl-biphenyl-3-yl)-pentanoic acid | 0.45 | |

| # | Structure | Chemical name | EC$_{50}$ μM | % inhibition @ 1 uM |
|---|---|---|---|---|
| 58 | 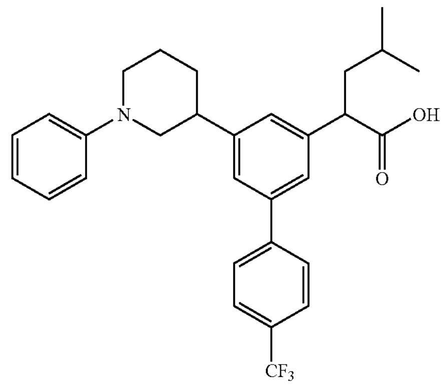 | 4-Methyl-2-[5-(1-phenyl-piperidin-3-yl)-4'-trifluoromethyl-biphenyl-3-yl]-pentanoic acid | | 40 |
| 59 | 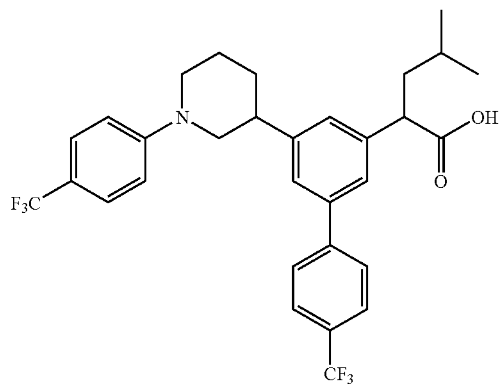 | 4-Methyl-2-{4'-trifluoromethyl-5-[1-(4-trifluoromethyl-phenyl)-piperidin-3-yl]-biphenyl-3-yl}-pentanoic acid | | 37 |
| 60 | 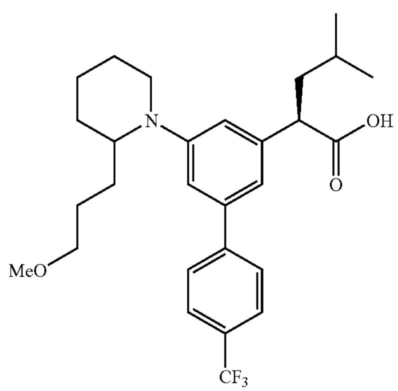 | (R)-2-{5-[2-(3-Methoxy-propyl)-piperidin-1-yl]-4'-trifluoromethyl-biphenyl-3-yl}-4-methyl-pentanoic acid | | 52 |
| 61 | 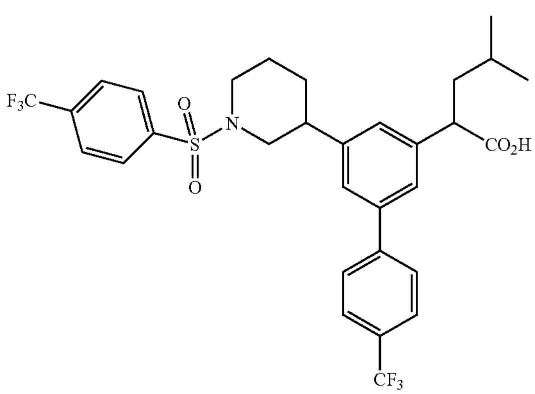 | 4-Methyl-2-{4'-trifluoromethyl-5-[1-(4-trifluoromethyl-benzenesulfonyl)-piperidin-3-yl]-biphenyl-3-yl}-pentanoic acid | 0.44 | |

| # | Structure | Chemical name | EC$_{50}$ μM | % inhibition @ 1 uM |
|---|-----------|---------------|--------------|---------------------|
| 62 | 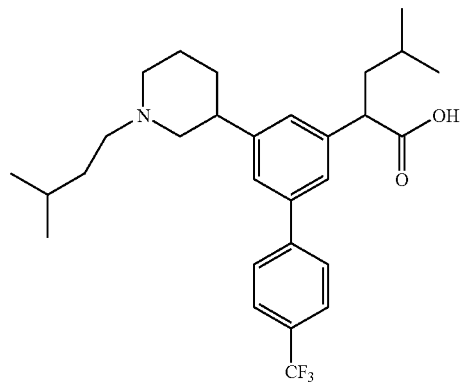 | 4-Methyl-2-{5-[1-(3-methyl-butyl)-piperidin-3-yl]-4'-trifluoromethyl-biphenyl-3-yl}-pentanoic acid | | 5 |
| 63 | 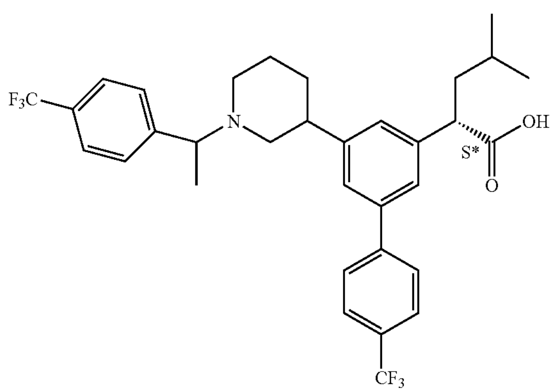 | (S*) 4-Methyl-2-(4'-trifluoromethyl-5-{1-[1-(4-trifluoromethyl-phenyl)-ethyl]-piperidin-3-yl}-biphenyl-3-yl)-pentanoic acid | | 44 |
| 64 | 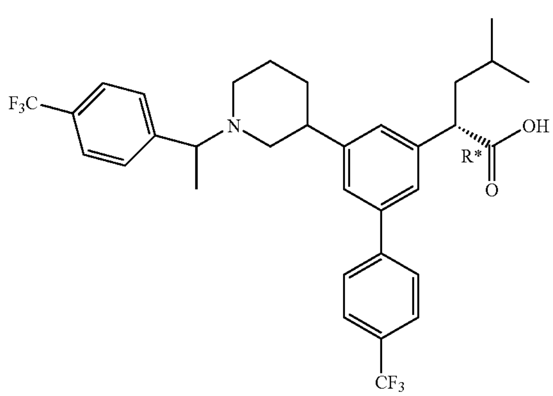 | (R*) 4-Methyl-2-(4'-trifluoromethyl-5-{1-[1-(4-trifluoromethyl-phenyl)-ethyl]-piperidin-3-yl}-biphenyl-3-yl)-pentanoic acid | | 41 |

| # | Structure | Chemical name | EC$_{50}$ μM | % inhibition @ 1 uM |
|---|---|---|---|---|
| 65 | 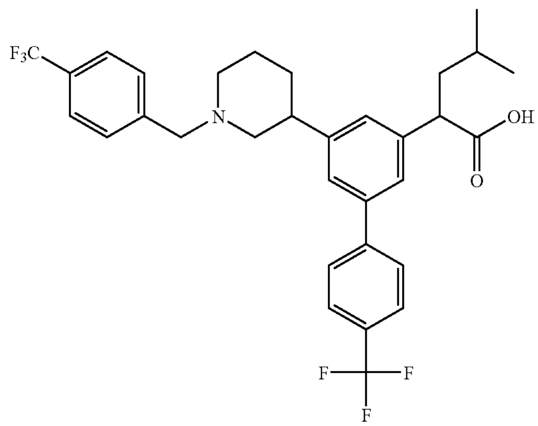 | 4-Methyl-2-{4'-trifluoromethyl-5-[1-(4-trifluoromethyl-benzyl)-piperidin-3-yl]-biphenyl-3-yl}-pentanoic acid | 0.51 | |
| 66 | 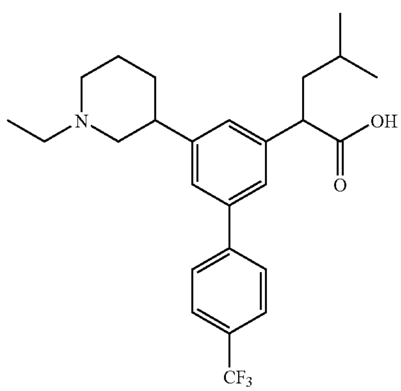 | 2-[5-(1-Ethyl-piperidin-3-yl)-4'-trifluoromethyl-biphenyl-3-yl]-4-methyl-pentanoic acid | | 0 |
| 67 | 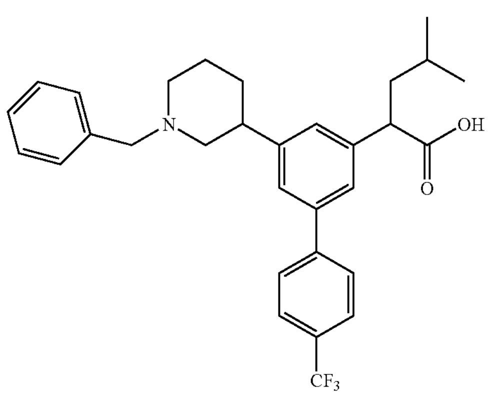 | 2-[5-(1-Benzyl-piperidin-3-yl)-4'-trifluoromethyl-biphenyl-3-yl]-4-methyl-pentanoic acid | 2.17 | 49 |

| # | Structure | Chemical name | EC$_{50}$ μM | % inhibition @ 1 uM |
|---|---|---|---|---|
| 68 | 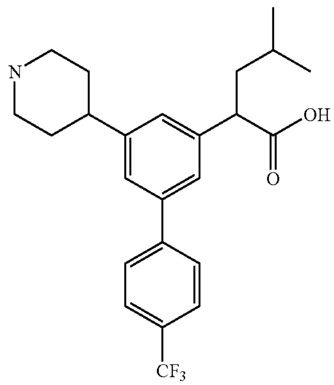 | 4-Methyl-2-(5-piperidin-4-yl-4'-trifluoromethyl-biphenyl-3-yl)-pentanoic acid | | 2 |
| 69 | 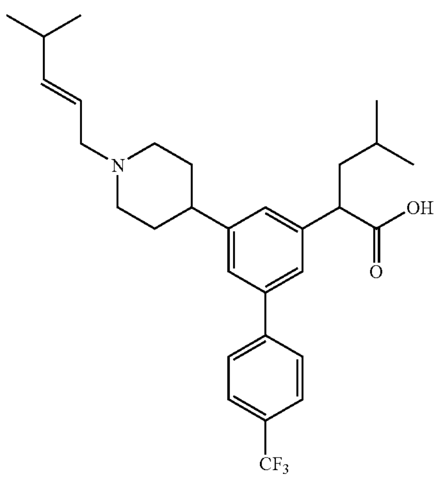 | 4-Methyl-2-{5-[1-(4-methyl-pent-2-enyl)-piperidin-4-yl]-4'-trifluoromethyl-biphenyl-3-yl}-pentanoic acid | | 8 |
| 70 | 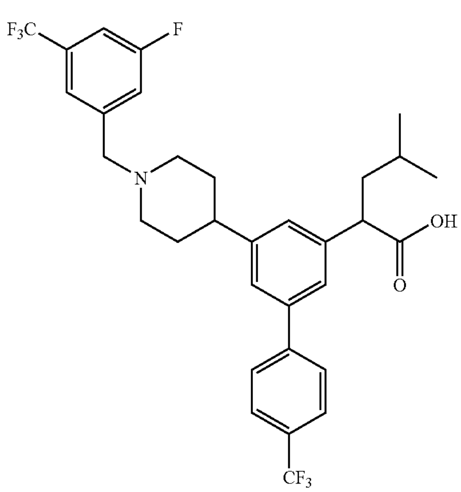 | 2-{5-[1-(3-Fluoro-5-trifluoromethyl-benzyl)-piperidin-4-yl]-4'-trifluoromethyl-biphenyl-3-yl}-4-methyl-pentanoic acid | | 47 |

| # | Structure | Chemical name | EC$_{50}$ μM | % inhibition @ 1 uM |
|---|---|---|---|---|
| 71 | 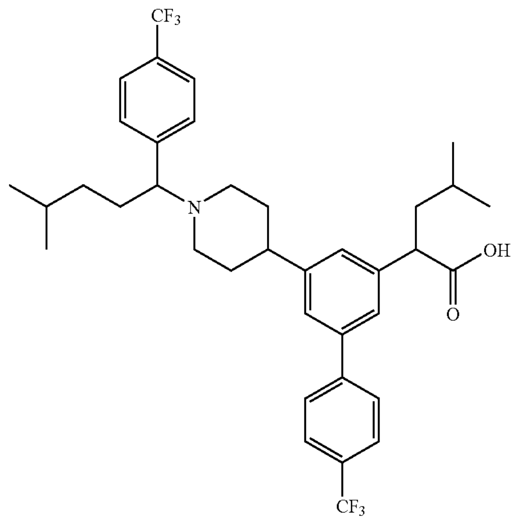 | 4-Methyl-2-(5-{1-[4-methyl-1-(4-trifluoromethyl-phenyl)-pentyl]-piperidin-4-yl}-4'-trifluoromethyl-biphenyl-3-yl)-pentanoic acid | | 51 |
| 72 | 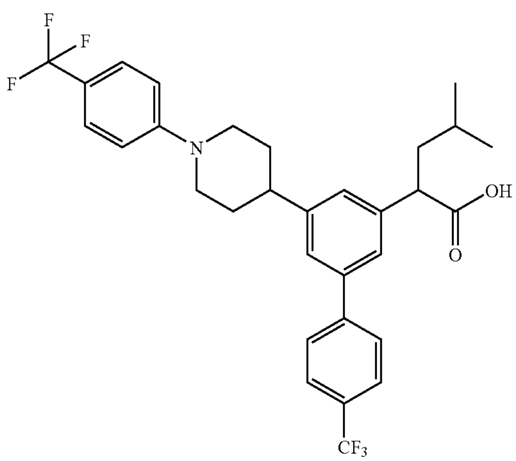 | 4-Methyl-2-{4'-trifluoromethyl-5-[1-(4-trifluoromethyl-phenyl)-piperidin-4-yl]-biphenyl-3-yl}-pentanoic acid | | 6 |
| 73 | 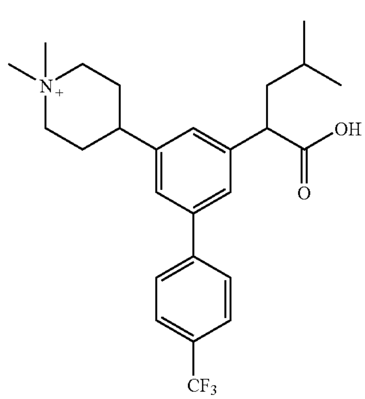 | 2-[5-(1,1-Dimethyl-piperidin-4-yl)-4'-trifluoromethyl-biphenyl-3-yl]-4-methyl-pentanoic acid. | | 9 |

| # | Structure | Chemical name | EC$_{50}$ μM | % inhibition @ 1 uM |
|---|---|---|---|---|
| 74 | 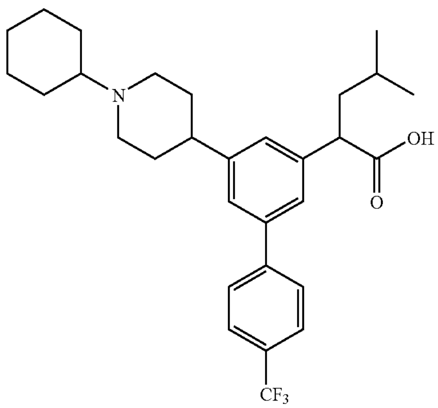 | 2-[5-(1-Cyclohexyl-piperidin-4-yl)-4'-trifluoromethyl-biphenyl-3-yl]-4-methyl-pentanoic acid | | 4 |
| 75 | 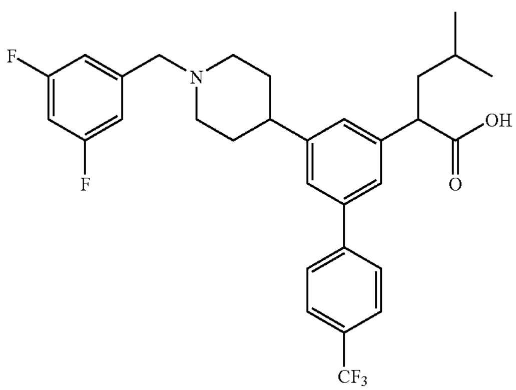 | 2-{5-[1-(3,5-Difluoro-benzyl)-piperidin-4-yl]-4'-trifluoromethyl-biphenyl-3-yl}-4-methyl-pentanoic acid | | 46 |
| 76 | 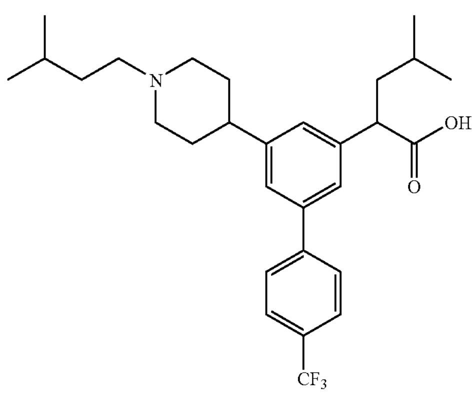 | 4-Methyl-2-{5-[1-(3-methyl-butyl)-piperidin-4-yl]-4'-trifluoromethyl-biphenyl-3-yl}-pentanoic acid | | 11 |
| 77 | 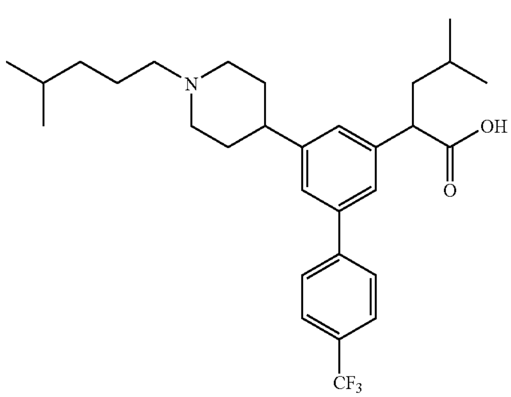 | 4-Methyl-2-{5-[1-(4-methyl-pentyl)-piperidin-4-yl]-4'-trifluoromethyl-biphenyl-3-yl}-pentanoic acid | | 36 |

-continued

| # | Structure | Chemical name | EC$_{50}$ μM | % inhibition @ 1 uM |
|---|-----------|---------------|--------------|---------------------|
| 78 | 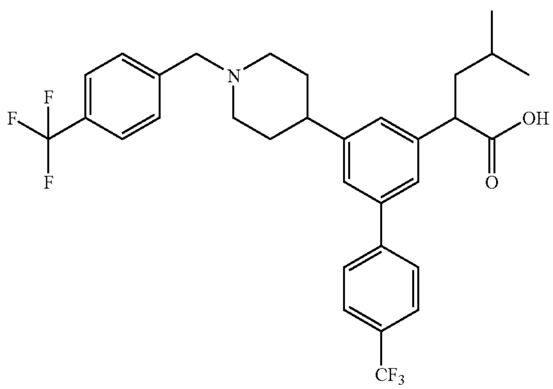 | 4-Methyl-2-{4'-trifluoromethyl-5-[1-(4-trifluoromethyl-benzyl)-piperidin-4-yl]-biphenyl-3-yl}-pentanoic acid | | 35 |
| 79 | 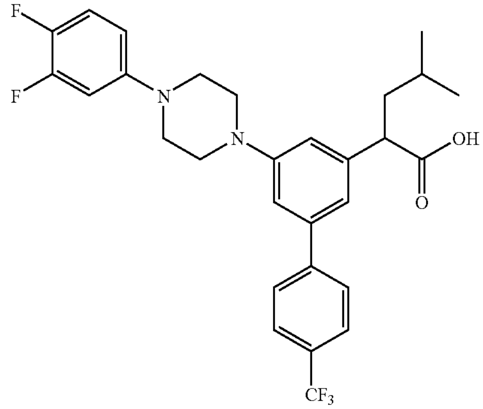 | 2-{5-[4-(3,4-Difluoro-phenyl)-piperazin-1-yl]-4'-trifluoromethyl-biphenyl-3-yl}-4-methyl-pentanoic acid | | 28 |
| 80 | 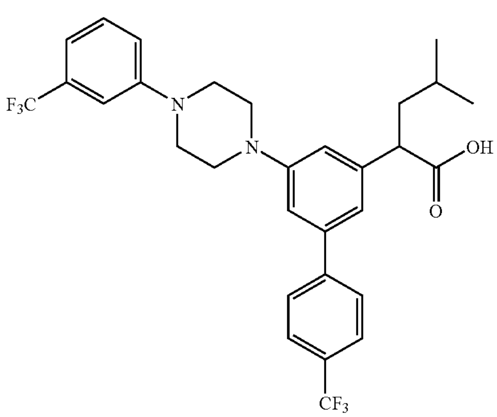 | 4-Methyl-2-{4'-trifluoromethyl-5-[4-(3-trifluoromethyl-phenyl)-piperazin-1-yl]-biphenyl-3-yl}-pentanoic acid | | 35 |

| # | Structure | Chemical name | EC$_{50}$ μM | % inhibition @ 1 uM |
|---|-----------|---------------|--------------|---------------------|
| 81 | 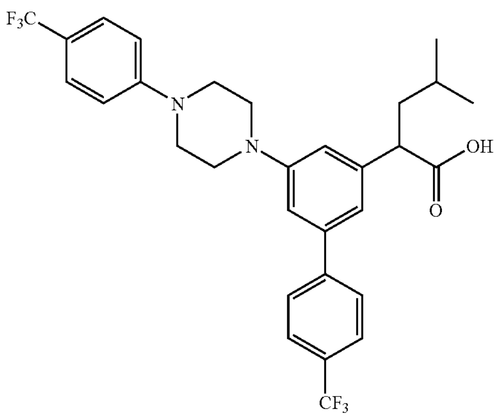 | 4-Methyl-2-{4'-trifluoromethyl-5-[4-(4-trifluoromethyl-phenyl)-piperazin-1-yl]-biphenyl-3-yl}-pentanoic acid | | 63 |
| 82 | 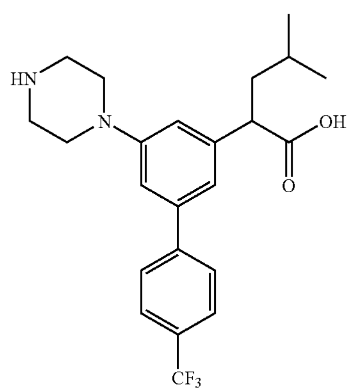 | 4-Methyl-2-(5-piperazin-1-yl-4'-trifluoromethyl-biphenyl-3-yl)-pentanoic acid | | 5 |
| 83 | 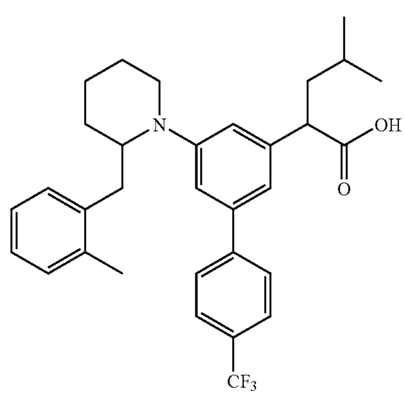 | 4-Methyl-2-{5-[2-(2-methyl-benzyl)-piperidin-1-yl]-4'-trifluoromethyl-biphenyl-3-yl}-pentanoic acid | | 44 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All publications disclosed in the above specification are hereby incorporated by reference in full.

The invention claimed is:
1. A compound having the general Formula (I)

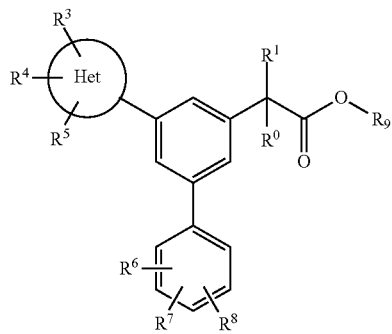

wherein

is:

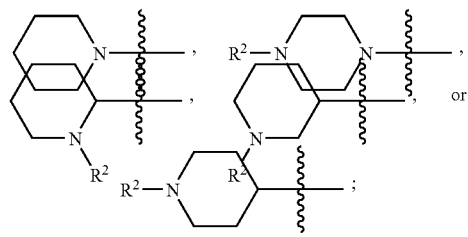

$R^0$ is H or F;
$R^1$ is selected from the group consisting of H, F, alkyl selected from the group $CH_3$, $C_2H_5$, i-$C_3H_7$, n-$C_3H_7$, i-$C_4H_9$, n-$C_4H_9$, sec-$C_4H_9$, tert-$C_4H_9$; alkenyl selected from $C_2H_3$, i-$C_3H_5$, n-$C_3H_5$, n-$C_4H_7$, i-$C_4H_7$, sec-$C_4H_7$; wherein said alkyl and alkenyl groups are optionally substituted with one, two, or three substituents independently selected from the group consisting of F, Cl, Br, I and $CF_3$;
$R^2$ is selected from the group consisting of H, cyclohexyl,

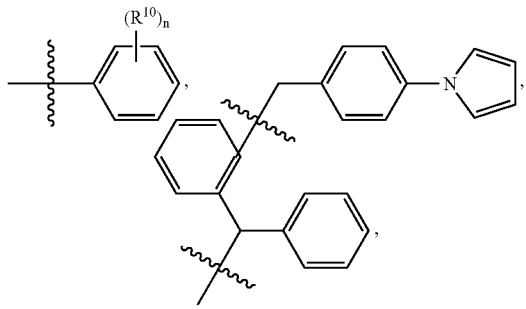

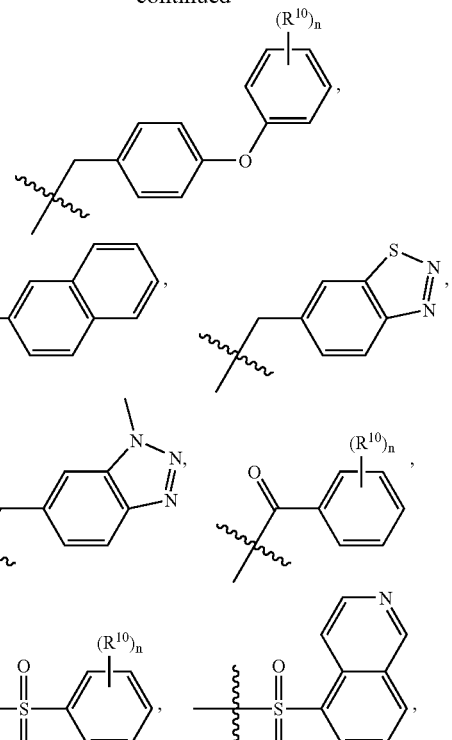

$SO_2CH_3$, alkyl selected from the group consisting of $CH_3$, $C_2H_5$, i-$C_3H_7$, n-$C_3H_7$, i-$C_4H_9$, n-$C_4H_9$, sec-$C_4H_9$, tert-$C_4H_9$, $CH_2CH_2CH(CH_3)_2$, $CH_2CH_2CH_2CH(CH_3)_2$, $CH_2CH_2C(CH_3)_3$, $CH(CH_2CH_3)_2$, and $C(O)CH_2CH(CH_3)_2$; alkenyl selected from the group consisting of $C_2H_3$, i-$C_3H_5$, n-$C_3H_5$, n-$C_4H_7$, i-$C_4H_7$, sec-$C_4H_7$, and $CH_2CH=CHCH(CH_3)_2$; wherein said alkyl and alkenyl groups are optionally substituted with F, Cl, Br, I, $CF_3$, -heteroaryl-$(R^{10})_n$, or

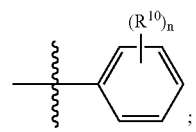

wherein $R^{10}$ is $CF_3$, $OCF_3$, H, F, Cl, $OCH_3$, $C_{(1-4)}$alkyl, or CN; and n is 1, 2, or 3; alternatively, $R^2$ can be two $C_{(1-4)}$alkyl groups, so that their attached nitrogen is quaternized;
$R^3$ is H,

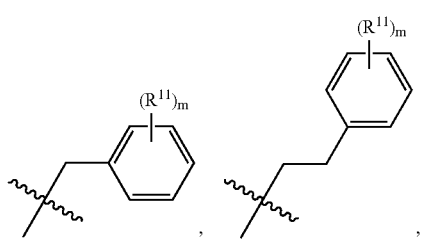

or $C_{(1-4)}$alkyl-$R^{11}$; wherein $R^{11}$ is $CF_3$, $OCF_3$, H, F, Cl, $OCH_3$, $C_{(1-4)}$alkyl, or CN; and m is 1, 2, or 3;

$R^6$ is selected from the group consisting of H, F, Cl, Br, I, CN, OH, C(O)N($C_{(1-4)}$alkyl)$_2$, S(O)$_2C_{(1-4)}$alkyl, SO$_2$N($C_{(1-4)}$alkyl)$_2$, S(O)N($C_{(1-4)}$alkyl)$_2$, N($C_{(1-4)}$alkyl)S(O)$_2C_{(1-4)}$alkyl, N($C_{(1-4)}$alkyl)S(O)$C_{(1-4)}$alkyl, S(O)$_2C_{(1-4)}$alkyl, N($C_{(1-4)}$alkyl)S(O)$_2$N($C_{(1-4)}$alkyl)$_2$, S$C_{(1-4)}$alkyl, N($C_{(1-4)}$alkyl)$_2$, N($C_{(1-4)}$alkyl)C(O)$C_{(1-4)}$alkyl, N($C_{(1-4)}$alkyl)C(O)N($C_{(1-4)}$alkyl)$_2$, N($C_{(1-4)}$alkyl)C(O)O$C_{(1-4)}$alkyl, OC(O) N($C_{(1-4)}$alkyl)$_2$, C(O)$C_{(1-4)}$alkyl, $C_1$-$C_4$-alkyl, and $C_1$-$C_4$-alkoxy; wherein said alkyl and alkoxy are optionally substituted with one, two, or three substituents selected from the group consisting of F, Cl, Br, and I;

$R^4$, $R^5$, $R^7$, and $R^8$ are independently selected from the group consisting of CF$_3$, H, F, Cl, OCH$_3$, $C_{(1-4)}$alkyl, and CN;

$R^9$ is H or alkenyl selected from $C_2H_3$, i-$C_3H_5$, n-$C_3H_5$, n-$C_4H_7$, i-$C_4H_7$, sec-$C_4H_7$; wherein said alkyl and alkenyl groups are optionally substituted with one, two, or three substituents independently selected from the group consisting of F, Cl, Br, I and CF$_3$;

or a pharmaceutically acceptable salts thereof.

2. A compound of claim 1 wherein $R^1$ is selected from the group consisting of H, F, alkyl selected from the group CH$_3$, C$_2$H$_5$, i-C$_3$H$_7$, n-C$_3$H$_7$, i-C$_4$H$_9$, n-C$_4$H$_9$, sec-C$_4$H$_9$, and tert-C$_4$H$_9$; and alkenyl selected from C$_2$H$_3$, i-C$_3$H$_5$, n-C$_3$H$_5$, n-C$_4$H$_7$, i-C$_4$H$_7$, and sec-C$_4$H$_7$;

$R^2$ is selected from the group consisting of H, cyclohexyl,

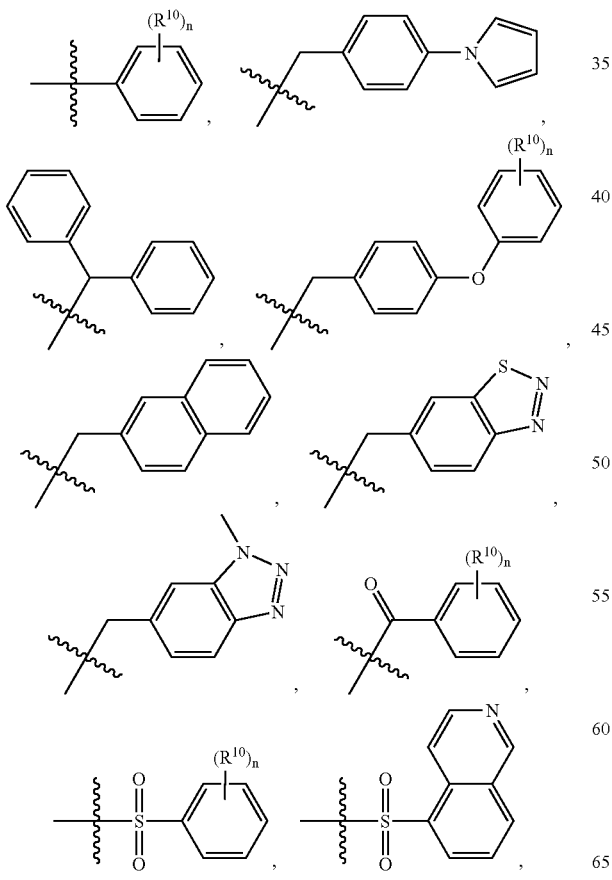

SO$_2$CH$_3$, alkyl selected from the group consisting of CH$_3$, C$_2$H$_5$, i-C$_3$H$_7$, n-C$_3$H$_7$, i-C$_4$H$_9$, n-C$_4$H$_9$, sec-C$_4$H$_9$, tert-C$_4$H$_9$, CH$_2$CH$_2$CH(CH$_3$)$_2$, CH$_2$CH$_2$CH$_2$CH(CH$_3$)$_2$, CH$_2$CH$_2$C(CH$_3$)$_3$, CH(CH$_2$CH$_3$)$_2$, and C(O)CH$_2$CH(CH$_3$)$_2$; alkenyl selected from the group consisting of C$_2$H$_3$, i-C$_3$H$_5$, n-C$_3$H$_5$, n-C$_4$H$_7$, i-C$_4$H$_7$, sec-C$_4$H$_7$, and CH$_2$CH=CHCH(CH$_3$)$_2$; wherein said alkyl and alkenyl groups are optionally substituted with F, Cl, Br, I, CF$_3$,

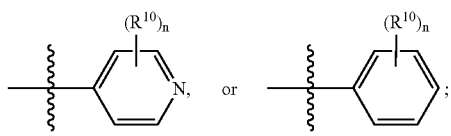

wherein $R^{10}$ is CF$_3$, OCF$_3$, H, F, Cl, OCH$_3$, $C_{(1-4)}$alkyl, or CN; and n is 1, 2, or 3; alternatively, $R^2$ can be two $C_{(1-4)}$alkyl groups, so that their attached nitrogen is quaternized;

$R^4$, $R^5$, $R^6$, $R^7$, and $R^8$ are independently selected from the group consisting of CF$_3$, H, F, Cl, OCH$_3$, $C_{(1-4)}$alkyl, and CN;

$R^9$ is H;

or a pharmaceutically acceptable salts thereof.

3. A compound of claim 2 wherein $R^3$ is H,

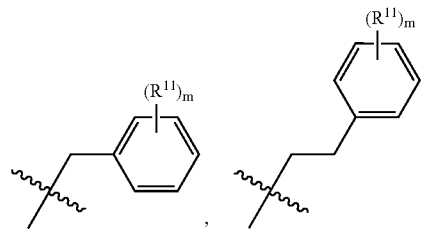

or $C_{(1-4)}$alkyl-$R^{11}$; wherein $R^{11}$ is CF$_3$, OCF$_3$, H, F, Cl, OCH$_3$, $C_{(1-4)}$alkyl, or CN; and m is 1, 2, or 3;

$R^4$, $R^5$, $R^6$, $R^7$, and $R^8$ are H, CF$_3$, Cl, and F;

or a pharmaceutically acceptable salts thereof.

4. A compound of claim 3 wherein $R^2$ is selected from the group consisting of H, cyclohexyl,

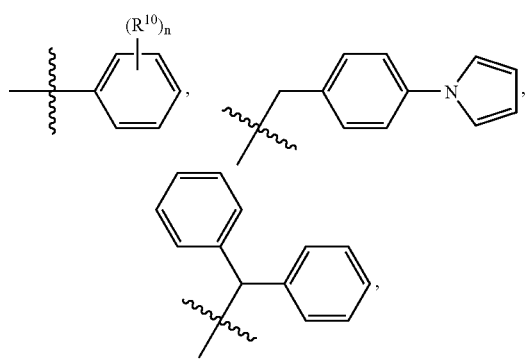

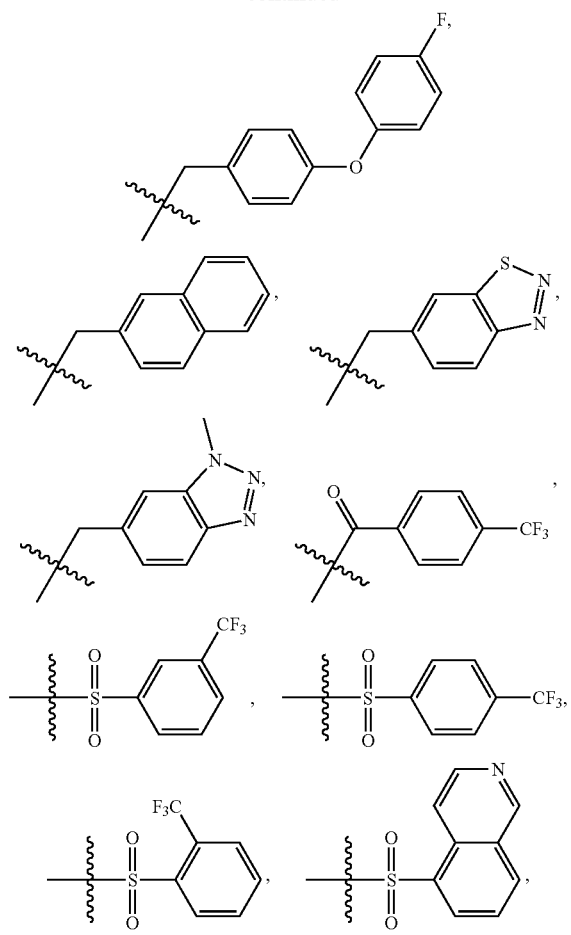

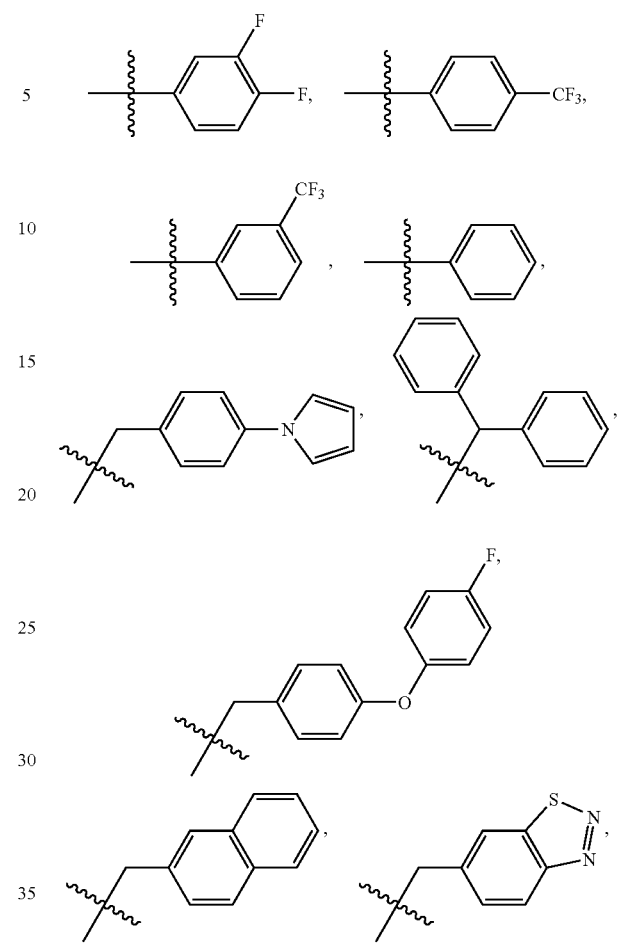

SO$_2$CH$_3$, alkyl selected from the group consisting of CH$_3$, C$_2$H$_5$, i-C$_3$H$_7$, n-C$_3$H$_7$, i-C$_4$H$_9$, n-C$_4$H$_9$, sec-C$_4$H$_9$, tert-C$_4$H$_9$, CH$_2$CH$_2$CH(CH$_3$)$_2$, CH$_2$CH$_2$CH$_2$CH(CH$_3$)$_2$, CH$_2$CH$_2$C(CH$_3$)$_3$, CH(CH$_2$CH$_3$)$_2$, and C(O)CH$_2$CH(CH$_3$)$_2$; alkenyl selected from the group consisting of C$_2$H$_3$, i-C$_3$H$_5$, n-C$_3$H$_5$, n-C$_4$H$_7$, i-C$_4$H$_7$, sec-C$_4$H$_7$, and CH$_2$CH=CHCH(CH$_3$)$_2$; wherein said alkyl and alkenyl groups are optionally substituted with F, Cl, Br, I, CF$_3$,

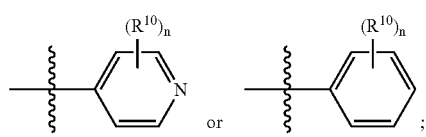

wherein

R$^{10}$ is CF$_3$, OCF$_3$, H, F, Cl, OCH$_3$, C$_{(1-4)}$alkyl, or CN; and n is 1, 2, or 3; alternatively, R$^2$ can be two C$_{(1-4)}$alkyl groups, so that their attached nitrogen is quaternized;

R$^9$ is H;

or a pharmaceutically acceptable salts thereof.

5. A compound of claim 1 wherein

R$^1$ is H, F, or CH$_2$CH(CH$_3$)$_2$;

R$^2$ is selected from the group consisting of H, cyclohexyl,

SO$_2$CH$_3$, CH$_2$CH=CHCH(CH$_3$)$_2$, alkyl selected from the group consisting of CH$_3$, C$_2$H$_5$, i-C$_3$H$_7$, n-C$_3$H$_7$, i-C$_4$H$_9$, n-C$_4$H$_9$, sec-C$_4$H$_9$, tert-C$_4$H$_9$, CH$_2$CH$_2$CH(CH$_3$)$_2$, CH$_2$CH$_2$CH$_2$CH(CH$_3$)$_2$, CH$_2$CH$_2$C(CH$_3$)$_3$, and CH(CH$_2$CH$_3$)$_2$; wherein said alkyl is optionally substituted with F, Cl, Br, I, CF$_3$,

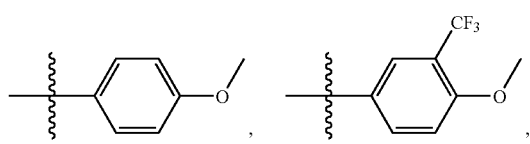
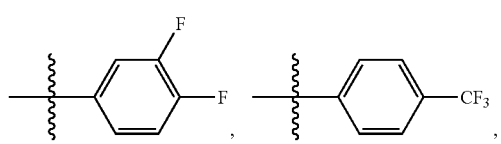
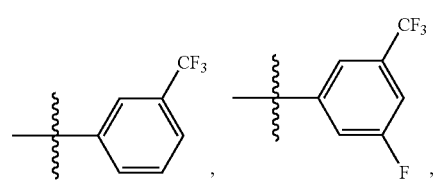
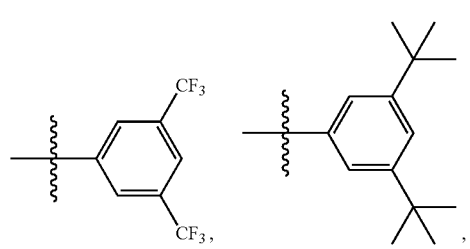
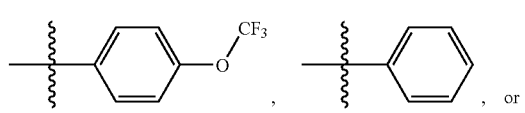, or
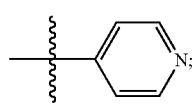
alternatively, $R^2$ can be two $C_{(1-4)}$alkyl groups, so that their attached nitrogen is quaternized;
$R^3$ is H,
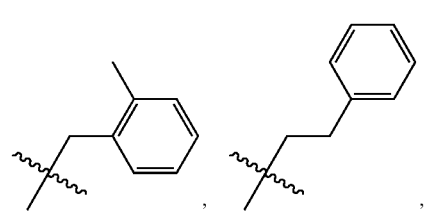
$CF_3$, $CH_3$, $CH_2CH_3$, $CH_2CH_2CH_3$, or $(CH_2)_3OCH_3$;
$R^4$ and $R^5$ are H;
$R^6$ is $CF_3$;
$R^7$ and $R^8$ are H;
$R^9$ is H;
or an esters, and pharmaceutically acceptable salts thereof.
6. A compound selected from the group consisting of:
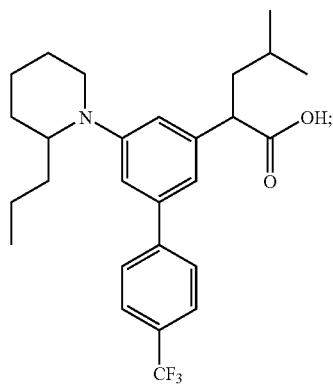
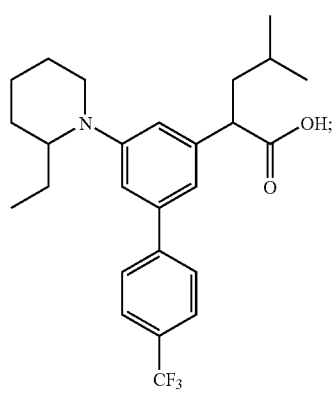
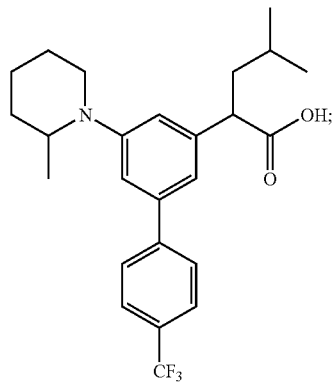
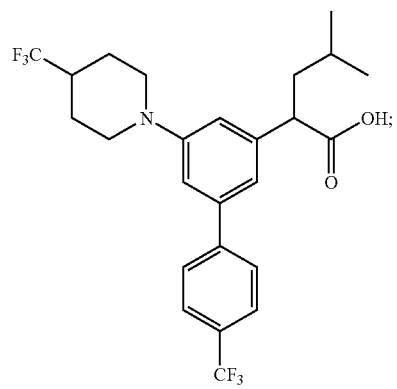

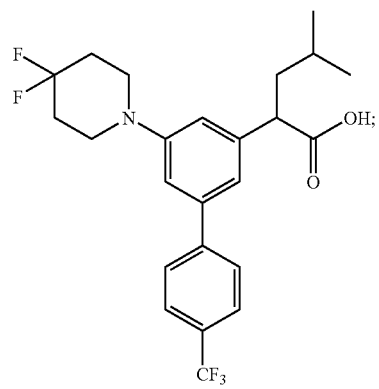
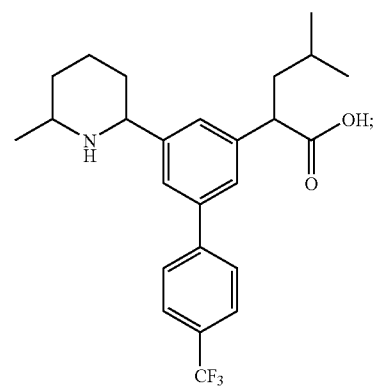
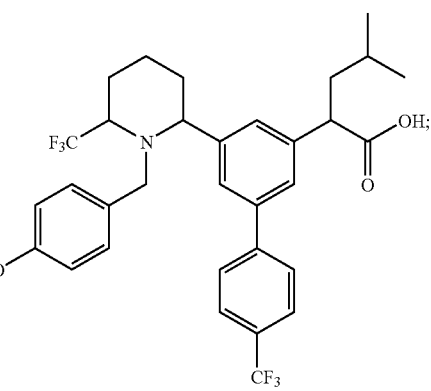
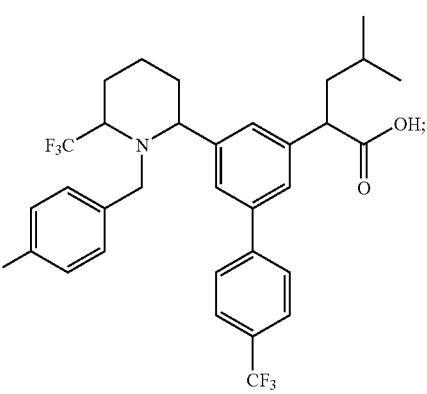
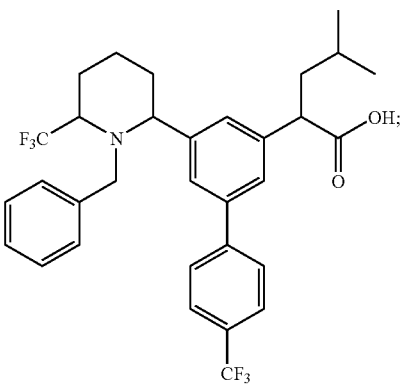
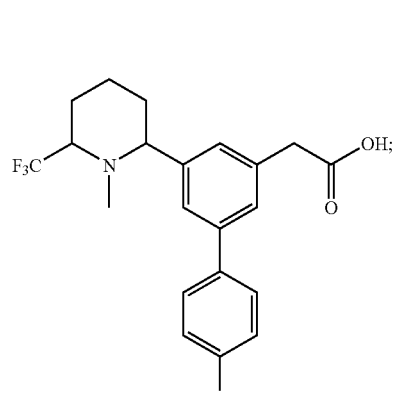
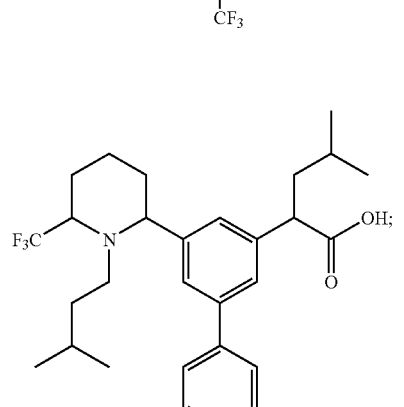

213
-continued
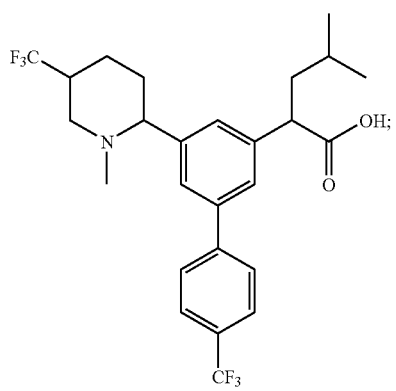
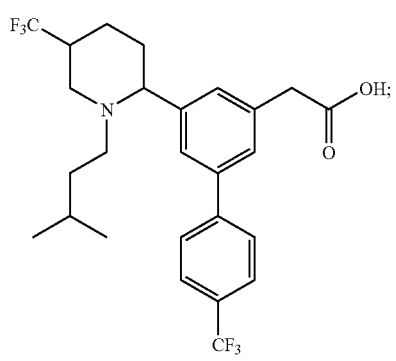
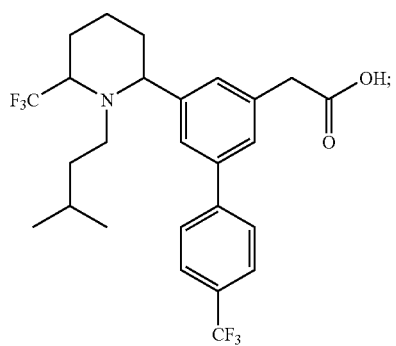
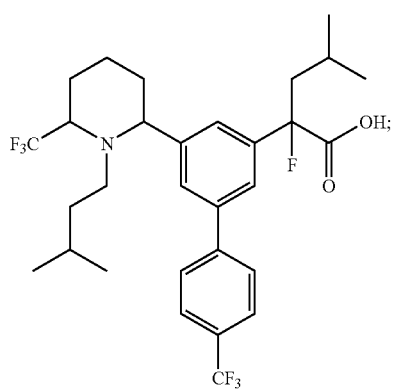
214
-continued
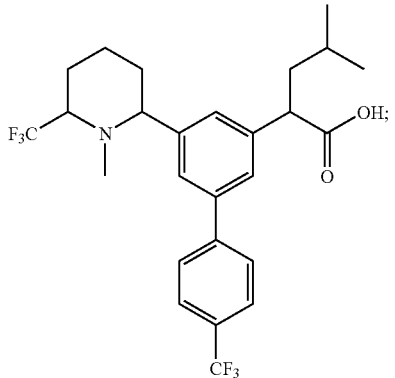
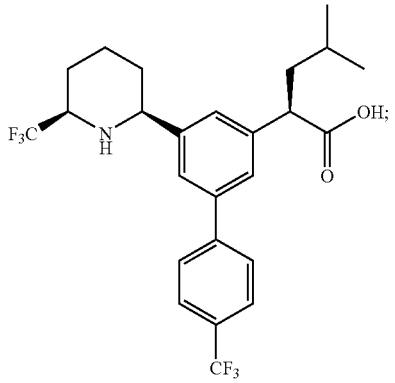
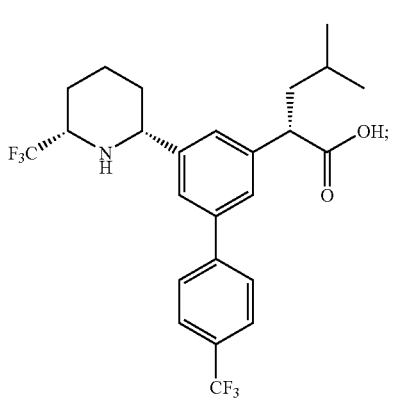
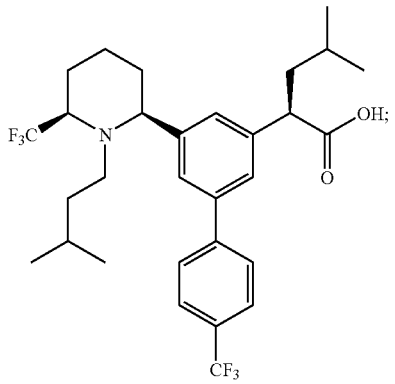

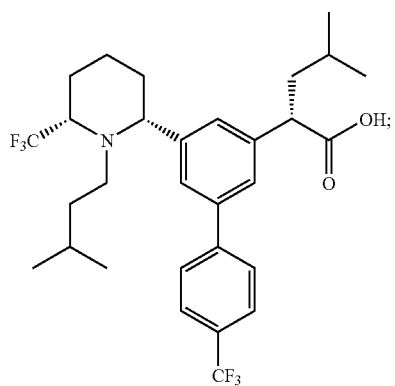
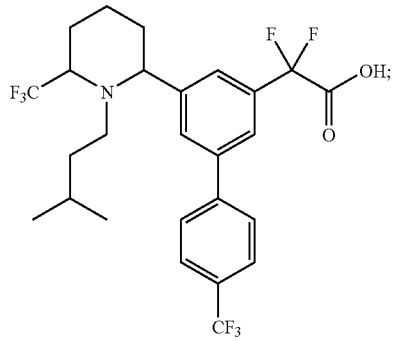
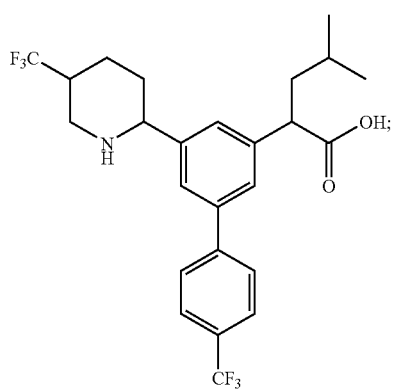
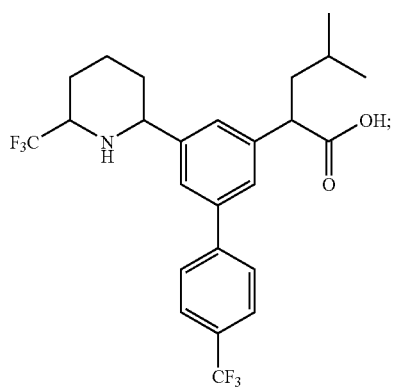
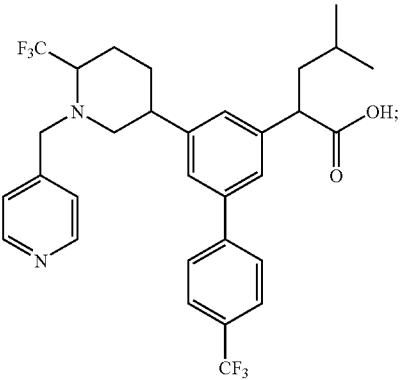
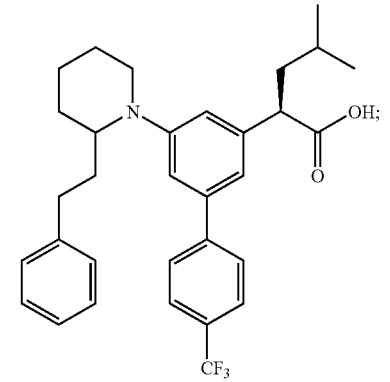
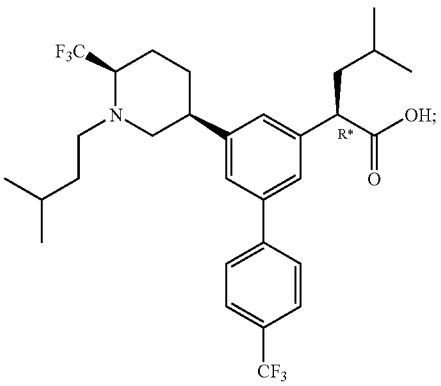
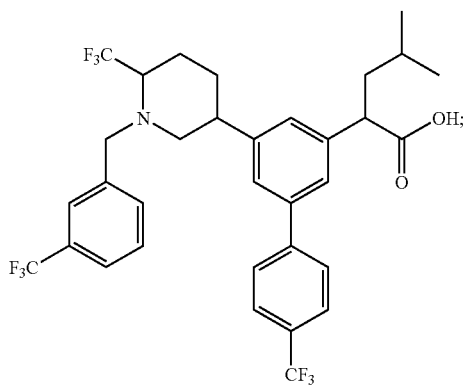

217
-continued
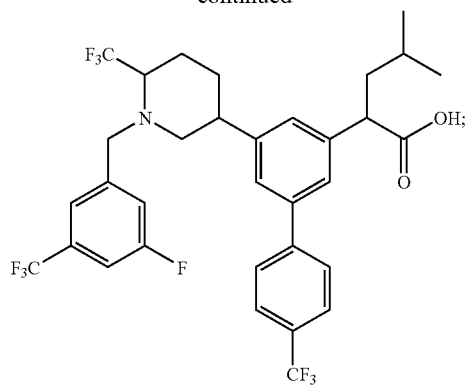
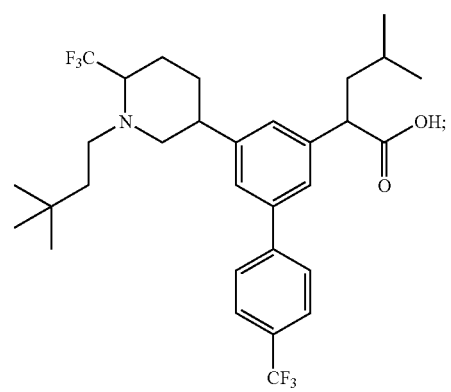
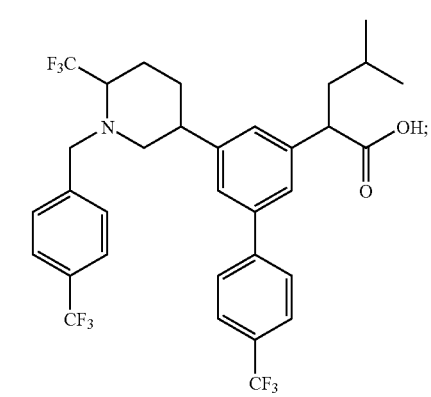
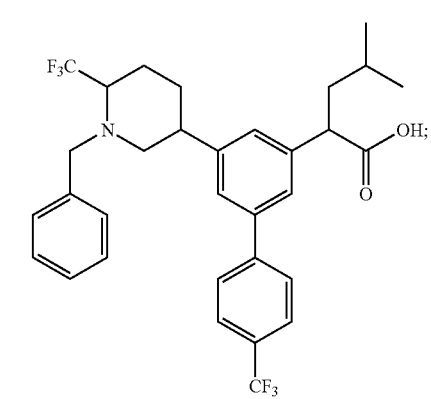
218
-continued
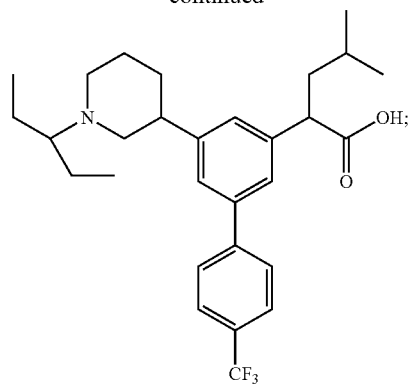
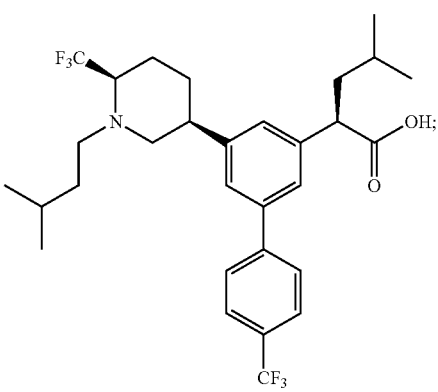
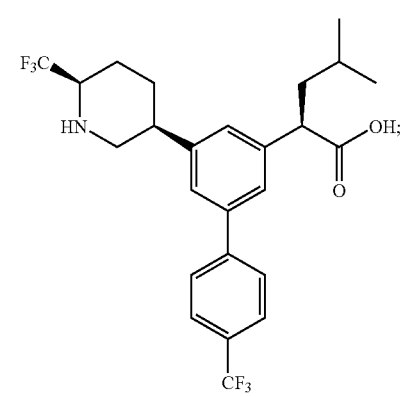
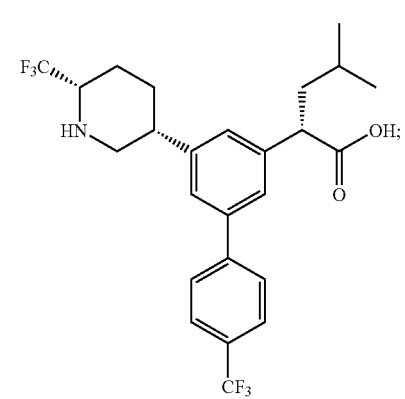

219
-continued
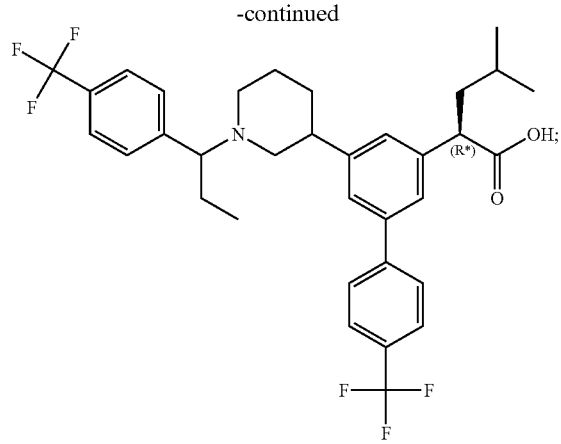
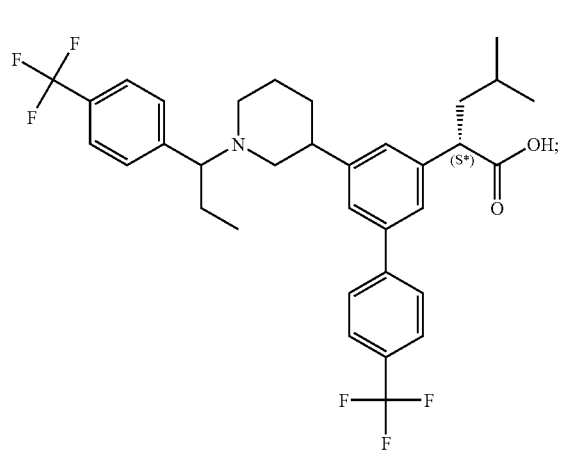
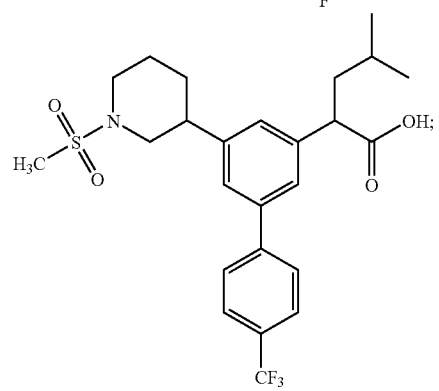
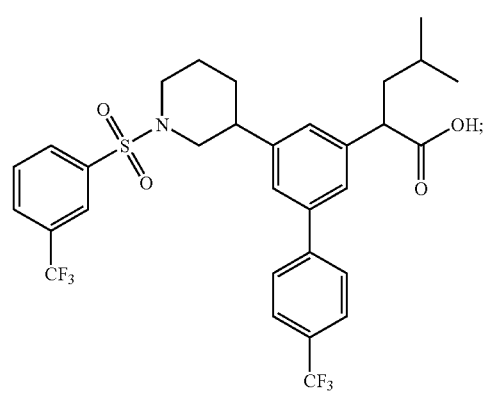
220
-continued
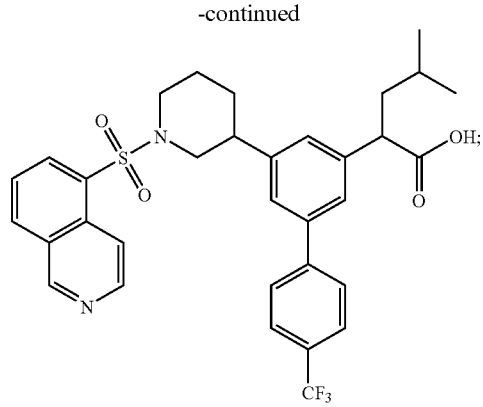
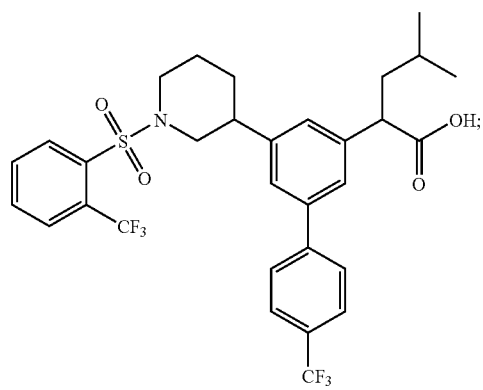
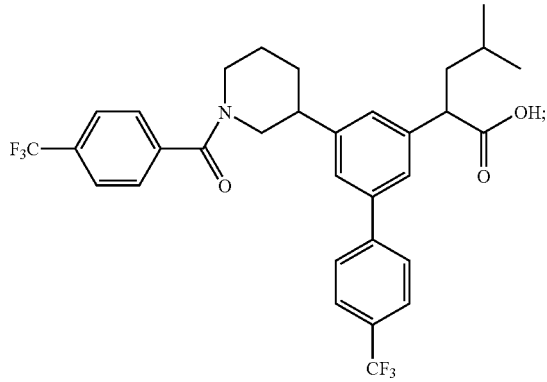
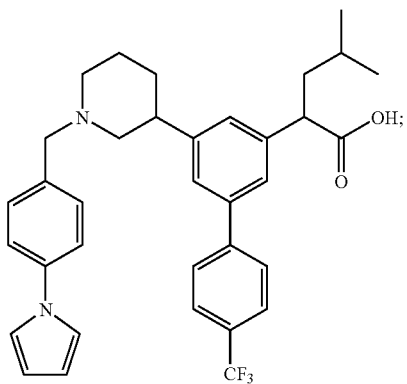

221
-continued
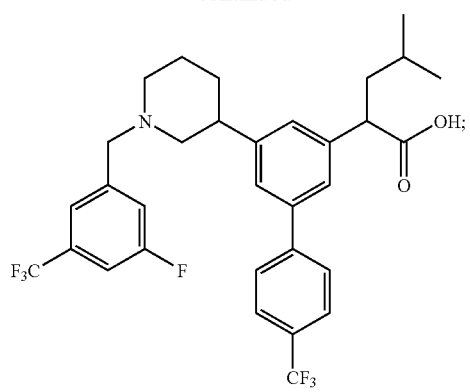
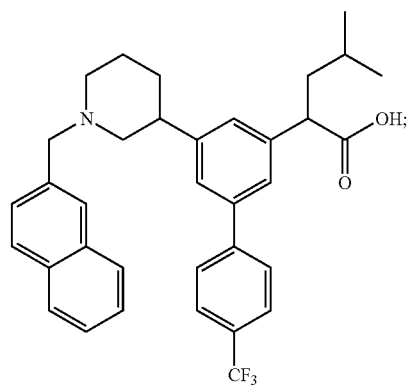
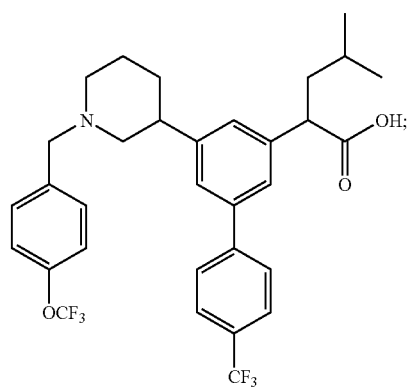
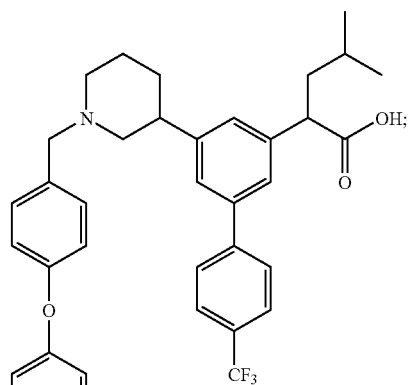
222
-continued
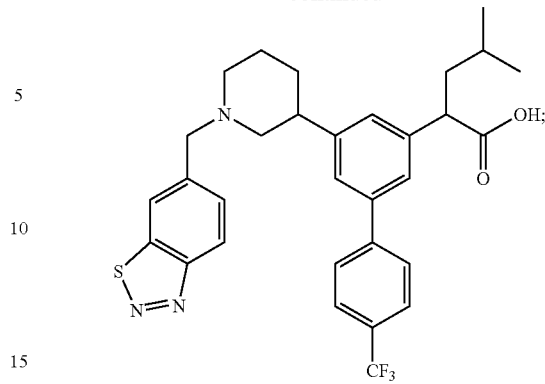
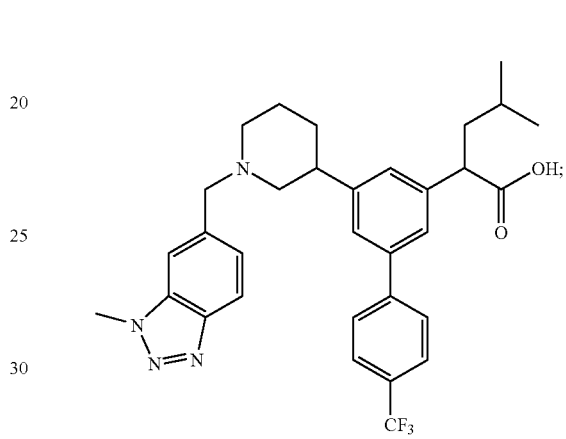
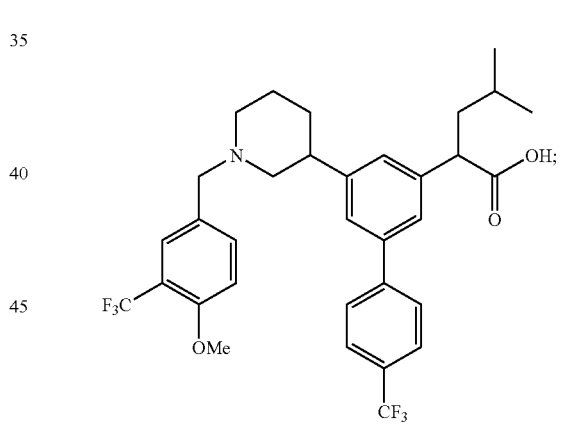
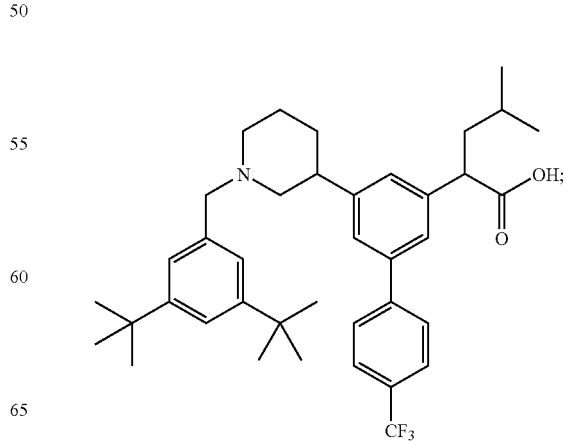

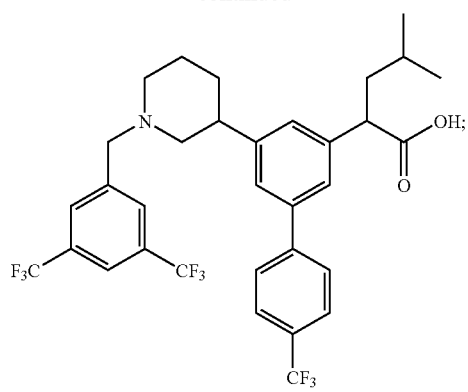
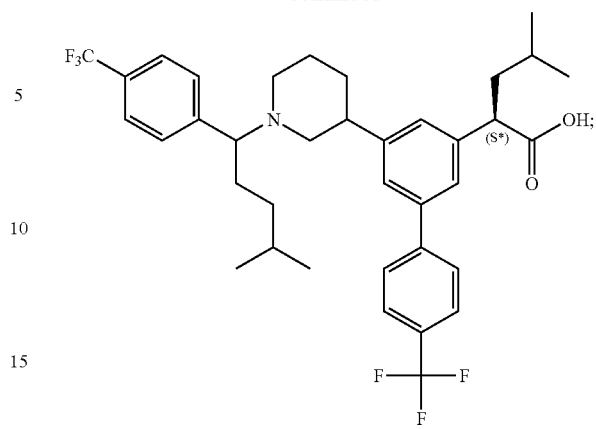
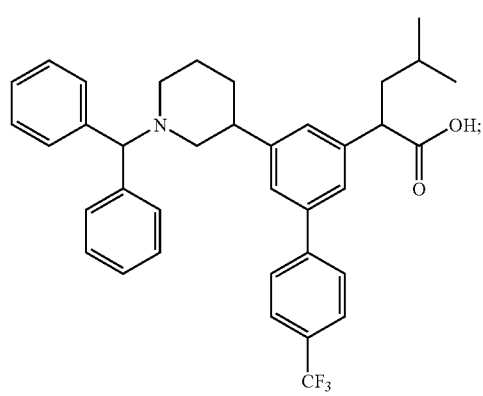
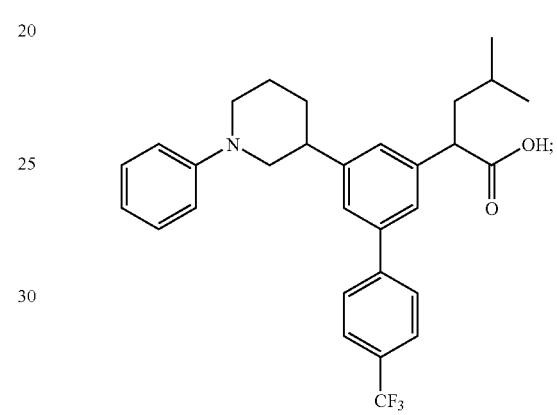
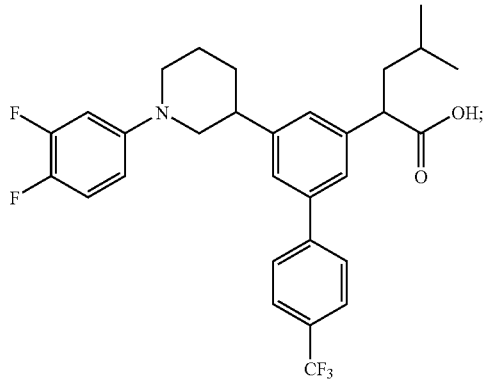
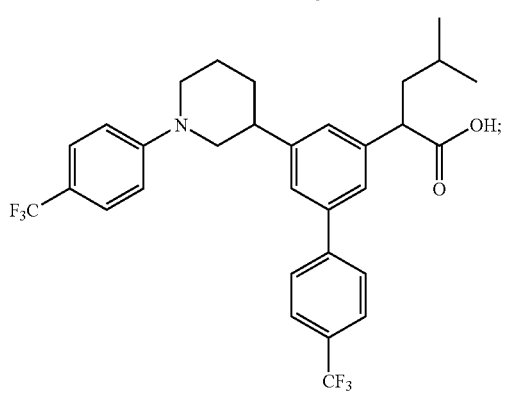
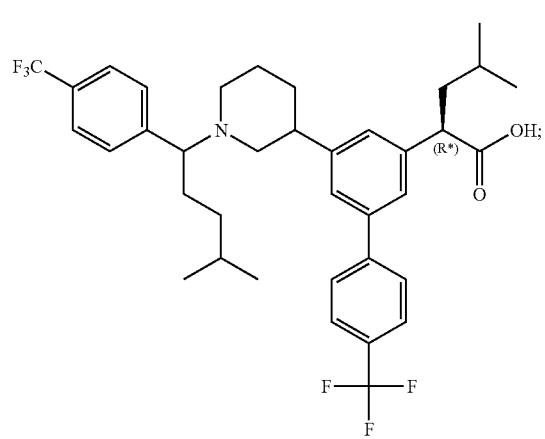
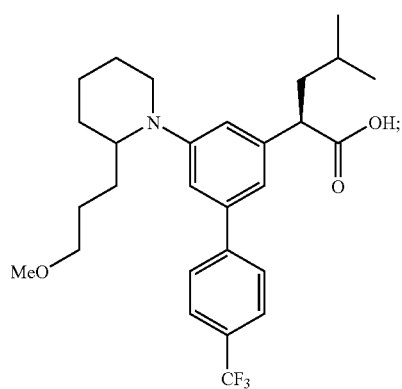

225
-continued
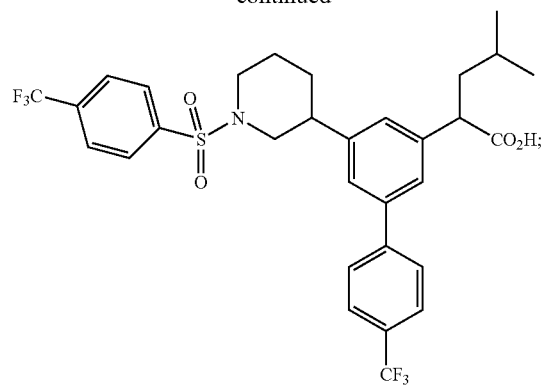
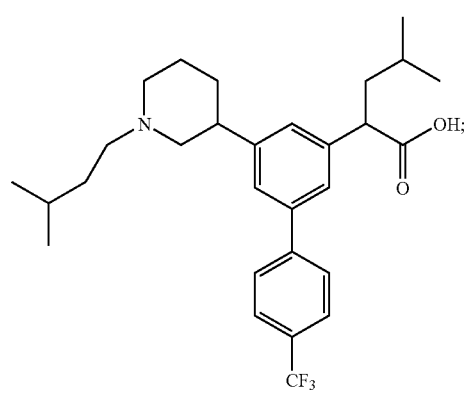
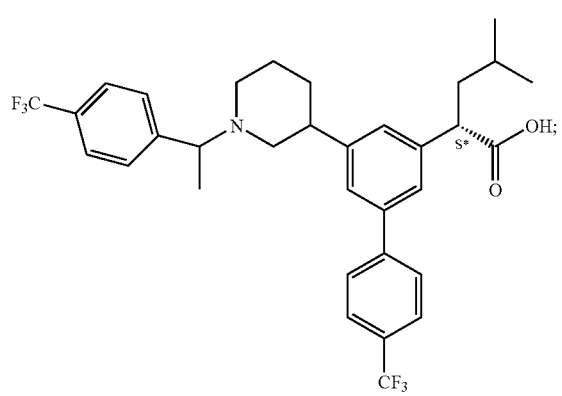
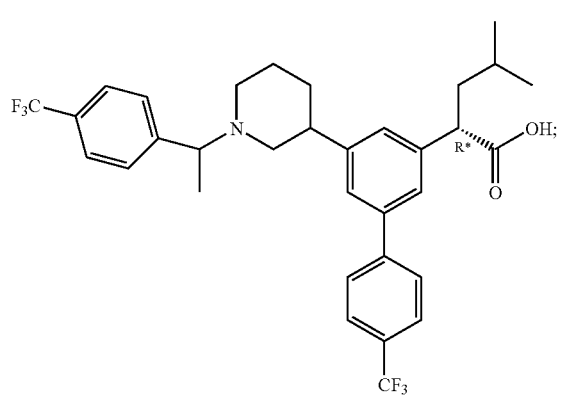
226
-continued
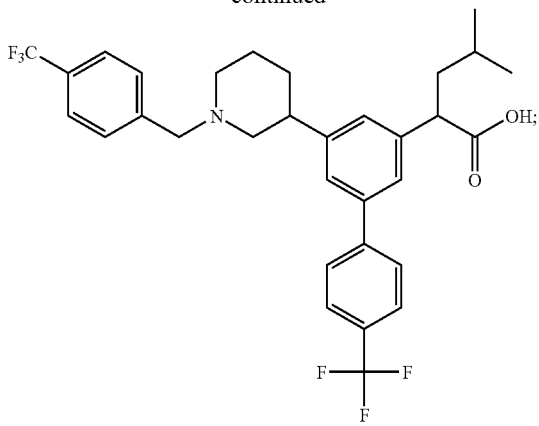
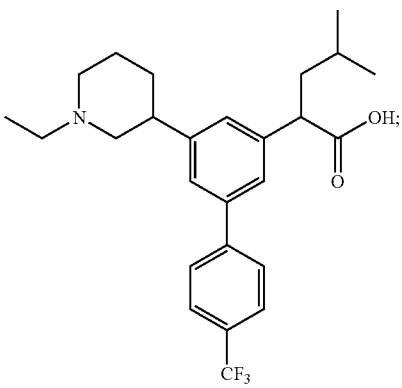
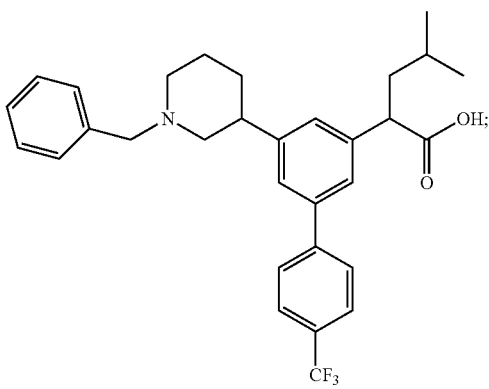
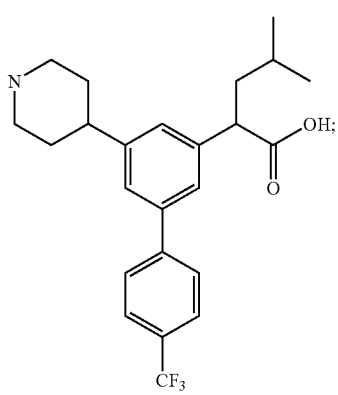

227
-continued
228
-continued
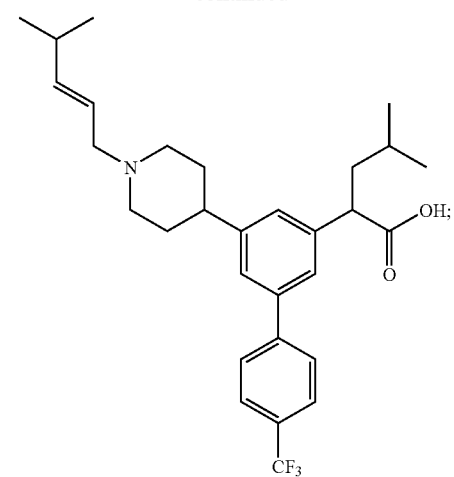
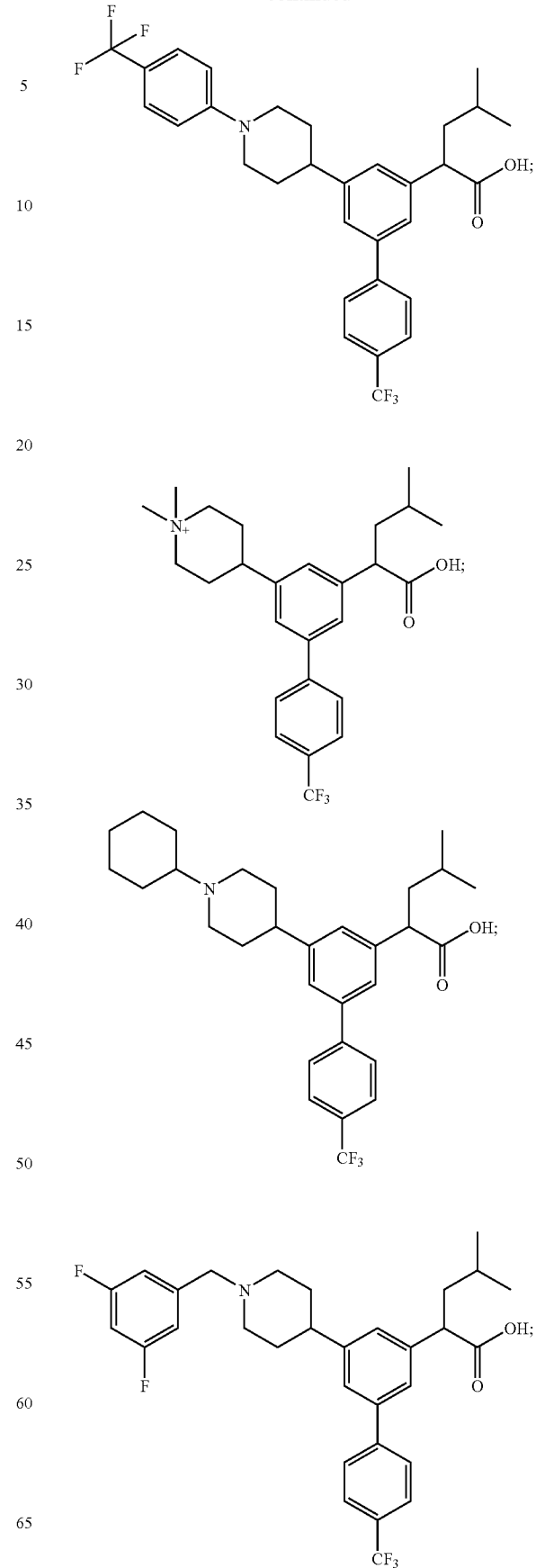

-continued
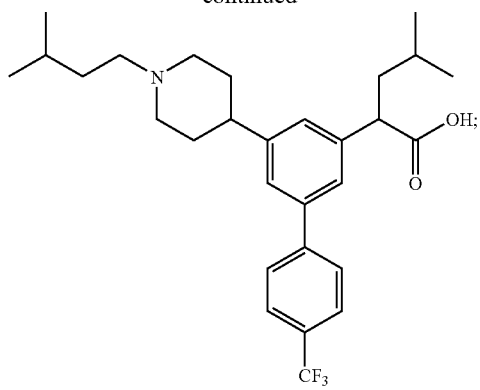
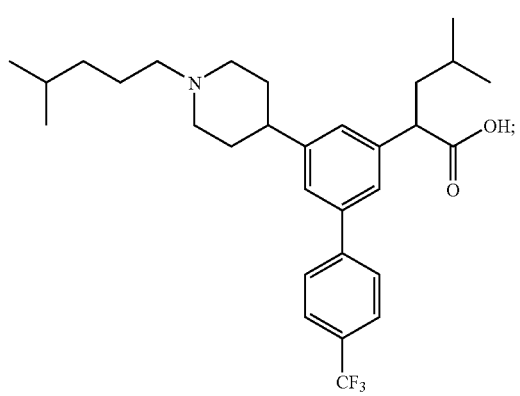
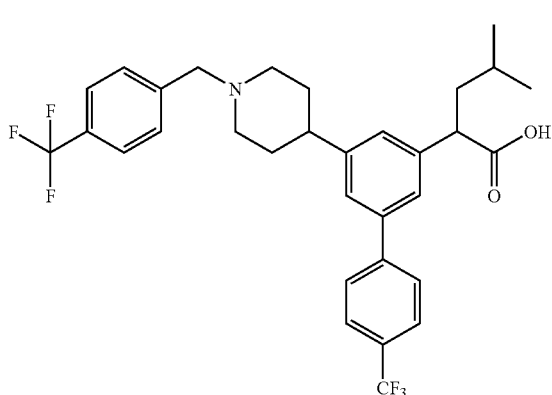
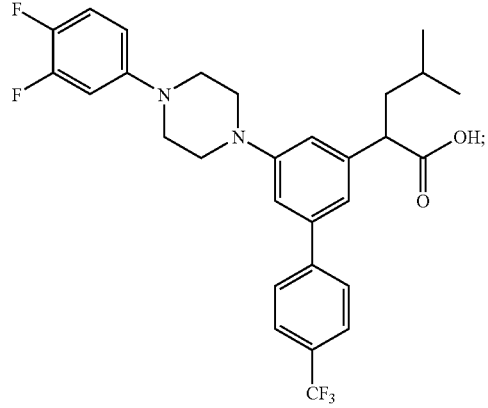
-continued
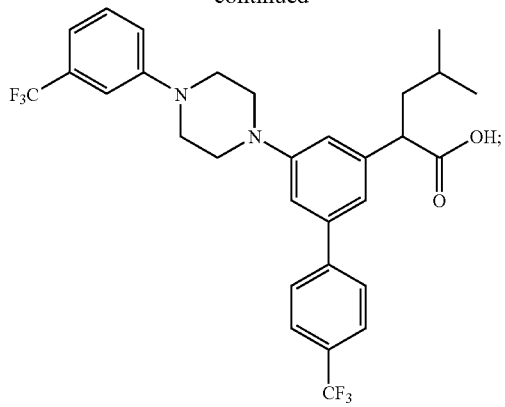
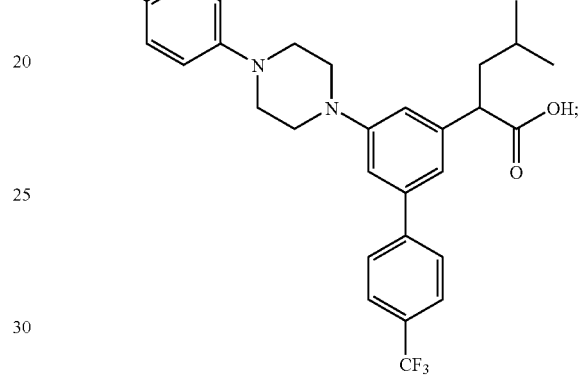
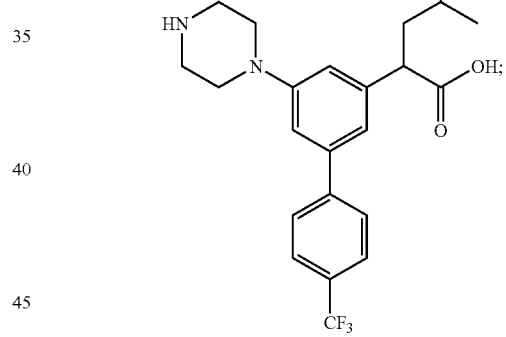
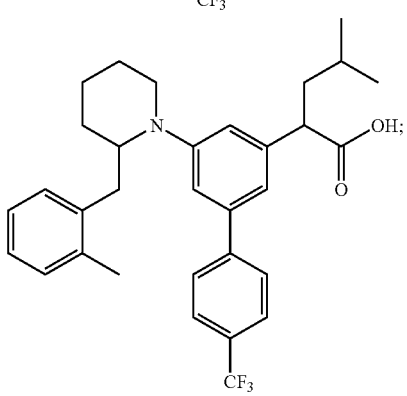
or an ester or pharmaceutically acceptable salts thereof.
7. A pharmaceutical composition comprising a compound according to any of claims 1 to 6 in admixture with an inert carrier.
* * * * *